US007951819B2

(12) United States Patent
Niculescu-Duvaz et al.

(10) Patent No.: US 7,951,819 B2
(45) Date of Patent: *May 31, 2011

(54) IMIDAZO[4, 5-B]PYRIDIN-2-ONE AND OXAZOLO[4, 5-B] PYRIDIN-2-ONE COMPOUNDS AND ANALOGS THEREOF AS CANCER THERAPEUTIC COMPOUNDS

(75) Inventors: Dan Niculescu-Duvaz, Sutton (GB);
Caroline Joy Springer, Sutton (GB);
Richard Malcolm Marais, London (GB); Harmen Dijkstra, Maarssen (NL); Delphine Menard, Sutton (GB);
Ion Niculescu-Duvaz, Sutton (GB);
Lawrence Davies, Sutton (GB); Arnaud Nourry, Sutton (GB)

(73) Assignees: Cancer Research Technology Limited, London (GB); The Institute of Cancer Research: Royal Cancer Hospital, London (GB); Astex Therapeutics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/298,325

(22) PCT Filed: Apr. 26, 2007

(86) PCT No.: PCT/GB2007/001534
§ 371 (c)(1),
(2), (4) Date: Oct. 24, 2008

(87) PCT Pub. No.: WO2007/125330
PCT Pub. Date: Nov. 8, 2007

(65) Prior Publication Data
US 2009/0325945 A1 Dec. 31, 2009

Related U.S. Application Data

(60) Provisional application No. 60/745,633, filed on Apr. 26, 2006.

(30) Foreign Application Priority Data

Apr. 26, 2006 (GB) .................................. 0608268.9

(51) Int. Cl.
*A01N 43/42* (2006.01)
*A01N 43/40* (2006.01)
*A01N 43/52* (2006.01)
*A61K 31/44* (2006.01)
*A61K 31/415* (2006.01)
*C07D 513/02* (2006.01)
*C07D 515/02* (2006.01)
*C07D 403/02* (2006.01)

(52) U.S. Cl. ........ 514/303; 514/341; 514/395; 546/118; 548/314.7

(58) Field of Classification Search ................ 514/303, 514/341, 395; 546/118; 548/314.7
See application file for complete search history.

(56) References Cited

U.S. PATENT DOCUMENTS

| 4,666,828 | A | 5/1987 | Gusella |
| 4,683,202 | A | 7/1987 | Mullis |
| 4,801,531 | A | 1/1989 | Frossard |
| 5,192,659 | A | 3/1993 | Simons |
| 5,272,057 | A | 12/1993 | Smulson |
| 5,521,073 | A | 5/1996 | Davis et al. |
| 5,877,020 | A | 3/1999 | Alitalo |
| 5,879,672 | A | 3/1999 | Davis et al. |
| 5,882,864 | A | 3/1999 | An et al. |
| 6,030,831 | A | 2/2000 | Godowski et al. |
| 6,218,529 | B1 | 4/2001 | An et al. |
| 6,258,809 | B1 | 7/2001 | Parthasarathi et al. |
| 6,492,529 | B1 | 12/2002 | Kapadia et al. |
| 2004/0082583 | A1 | 4/2004 | Cheung et al. |

FOREIGN PATENT DOCUMENTS

| JP | 56065863 | 6/1981 |
| JP | 57038777 | 3/1982 |
| WO | WO 99/16438 | 4/1999 |
| WO | WO 99/21859 | 5/1999 |
| WO | WO 01/36383 | 5/2001 |
| WO | WO 01/46196 | 6/2001 |
| WO | WO 03/056036 | 7/2003 |
| WO | WO 2004/014300 | 2/2004 |
| WO | WO 2006/003378 | 1/2006 |
| WO | WO 2006/024834 | 3/2006 |
| WO | WO 2006/043090 | 4/2006 |

OTHER PUBLICATIONS

Adams, R.H. et al, 1999, "Roles of ephrinB ligands and EphB receptors in cardiovascular development: demarcation of arterial/venous domains, vascular morphogenesis, and sprouting angiogenesis", Genes Dev., vol. 13, pp. 295-306. Ananthanarayanan, C., et al, 1988, "Reaction of azides in presence of aluminium chloride", Indian Journal of Chemistry, Section B, vol. 27B, pp. 156-157.
Angerer, L.M., et al, 1987, "Demonstration of tissue-specific gene expression by in situ hybridization", Methods in Enzymology, vol. 152, pp. 649-661.
Auvray, P., et al, 1988, "Preparation and nucleophilic substitution of (E)-1-bromo-2-phenylsulfonyl-2-alkenes and 3-acetoxy-2-phenylsulfonyl-1-alkenes", Tetrahedron, vol. 44, pp. 6095-6106.
Avenoza, A., et al, 1995, "New efficient synthesis of 4-amino-3-arylphenols", Synthesis, pp. 671-674.
Ballesteros, P., et al, 1987, "Study of the catalytic properties of tris (3,6-dioxaheptyl) amine (TDA-1) in heteroaromatic nucleophilic substitution of chloropyridines and their N-oxides", Tetrahedron, vol. 43, pp. 2557-2564.

(Continued)

*Primary Examiner* — San-ming Hui
*Assistant Examiner* — Paul Zarek
(74) *Attorney, Agent, or Firm* — Michael Best & Friedrich LLP

(57) ABSTRACT

The present invention pertains to certain imidazo[4,5-b]pyridin-2-one and oxazolo[4,5 b]pyridin-2-one compounds and analogs thereof, which, inter alia, inhibit RAF (e.g., B RAF) activity, inhibit cell proliferation, treat cancer, etc. The present invention also pertains to pharmaceutical compositions comprising such compounds, and the use of such compounds and compositions, both in vitro and in vivo, to inhibit RAF (e.g., B-RAF) activity, to inhibit receptor tyrosine kinase (RTK) activity, to inhibit cell proliferation, and in the treatment of diseases and conditions that are ameliorated by the inhibition of RAF, RTK, etc., proliferative conditions such as cancer (e.g., colorectal cancer, melanoma), etc.

46 Claims, No Drawings

OTHER PUBLICATIONS

Bhatt, D.J., et al, 1980, "Preparation of N'-2-phenyl-4-quinolinoyl-N3-aryl thioureas", J. Instit. Chem. (India), vol. 52, pp. 113-114.

Bianchi, M., et al, 1981, "Compounds with antiulcer and antisecretory activity", Eur. J. Med. Chem., vol. 16, pp. 321-326.

Borthakur, N., et al, 1995, "New direct synthesis of thioamides from carboxylic acids", Tetrahedron Letters, vol. 36, pp. 6745-6746.

Broekhof, N., et al, 1981, "Novel applications of α-aminosubstituted diphenylphosphine oxides. The conversion of aldehydes into α-aminomethylketones", Tetrahedron Letters, vol. 22, pp. 2799-2802.

Brooks, P.C., et al, 1994, "Integrin αvβ3 antagonists promote tumor regression by inducing apoptosis of angiogenic blood vessels", Cell, vol. 79, pp. 1157-1164.

Brose, M.S., et al, 2002, "BRAF and RAS mutations in human lung cancer and melanoma", Cancer Research, vol. 62, pp. 6997-7000.

Bruckner, K., et al, 1997, "Tyrosine phosphorylation of transmembrane ligands for Eph receptors", Science, vol. 275, pp. 1640-1643.

Bruder, J.T., et al, 1992, "Serum-, TPA-, and Ras-induced expression from Ap-1/Ets-driven promotors requires Raf-1 kinase", Genes & Development, vol. 6, pp. 545-556.

Cantrell, D.A., 2003, "GTPases and T cell activation", Immunological Reviews, vol. 192, pp. 122-130.

Chan, A.C., et al, 1996, "Regulation of antigen receptor signal tgransdu8ction by protein tyrosine kinases", Current Opin. Immunol., vol. 8, pp. 394-401.

Clare, B.W., et al, 2001, "Protease inhibitors: synthesis of a series of bacterial collagenase inhibitors of the sulfonyl amino acyl hydroxamate type", J. Med. Chem., vol. 44, pp. 2253-2258.

Cohen, Y., et al, 2003, "Lack of BRAF mutation in primary uveal melanoma", Invest. Ophthalmol. Vis. Sci., vol. 44, pp. 2876-2878.

Colville-Nash, P.R., et al, 1992, "Angiogenesis and rheumatoid arthritis: pathogenic and therapeutic implications", Annals of the Rheum. Dis., vol. 51, pp. 919-925.

Comins, D.L., et al, 1994, "Grignard addition to 1-acyl salts of chiral 4-alkoxypyridines. A new enantioselective preparation of 2-alkyl-2,3-dihydro-4-pyridones", Tetrahedron Letters, vol. 35, pp. 7343-7346.

Cooper, J.A., 1994, "Membrane-associated tyrosine kinases as molecular switches", Sem. Cell Biology, vol. 5, pp. 377-387.

Correia, J., 1978, "Reaction of phenylglyoxal with aniline under acidic conditions", J. Org. Chem., vol. 43, pp. 3394-3396.

Courtneidge, S.A., et al, 1993, "The Src family of protein tyrosine kinases: regulation and functions", Development 1993 Supplement, pp. 57-64.

Cowley, S., et al, 1994, "Activation of MAP kinase kinase is necessary and sufficient for PC12 differentiation and for transformation of NIH 3T3 cells", Cell, vol. 77, pp. 841-852.

Davies, H., et al, 2002, "Mutations of the BRAF gene in human cancer", Nature, vol. 417, pp. 949-954.

Davis, S., et al, 1996, "Isolation of angiopoietin-1, a ligand for the TIE2 receptor, by secretion-trap expression cloning", Cell, vol. 87, pp. 1161-1169.

Denekamp, J., 1993, "Review article: angiogenesis, neovascular proliferation and vascular pathophysiology as targets for cancer therapy", British Journal of Radiology, vol. 66, pp. 181-196.

Dickson, B., et al, 1992, "Raf functions downstream of Ras1 in the sevenless signal transduction pathway", Nature, vol. 360, pp. 600-603.

Dubois, G.E., 1980, "Amination of aryl sufamate esters. A convenient general synthesis of aliphatic sulfamides", Journal of Organic Chemistry, vol. 45, pp. 5373-5375.

Fidler, I.J., et al, 1994, "The implications of angiogenesis for the biology and therapy of cancer metastasis", Cell, vol. 79, pp. 185-188.

Folkman, J., et al, 1992, "Angiogensis", Journal of Biol. Chem., vol. 267, pp. 10931-10934.

Folkman, J., 1992, "The role of angiogenesis in tumor growth", Cancer Biology, vol. 3, pp. 65-71.

Folkman, J., et al, 1995, "Angiogenesis in cancer, vascular, rheumatoid and other disease", Nature Medicine, vol. 1, pp. 27-31.

Folkman, J., 1997, "Angiogenesis and angiogenesis inhibition: an overview", Regulation of Angiogenesis, EXS, vol. 79, pp. 1-8.

Fourrey, J-L.,1987, "Preparation of stable 1,4-dihydropyrazines", J. Chem. Soc., Perkins Transactions 1: Org. & Bio. Chem., vol. 8, pp. 1841-1843.

Friedlander, et al, 1995, "Definition of two angiogenic pathways by distinct αv integrins", Science, vol. 270, pp. 1500-1502.

Gale, N. et al, 1999, "Growth factors acting via endothelial cell-specific receptor tyrosine kinases: VEGFs, angiopoietins, and ephrins in vascular development", Genes Dev., vol. 13, pp. 1055-1066.

Galons, H., et al, 1981, "Cyclisation indolique selon Bischler en presence d'acides de Lewis", J. Heterocyclic Chemistry, vol. 18, pp. 561-563 (in French, with partial English language translation).

Genot, E., et al, 2000, "Ras regulation and function in lymphocytes", Curr. Opin. Immunol., vol. 12, pp. 289-294.

Giannotti, D., et al, 1991, "New dibenzothiadiazepine derivatives with antidepressant activities", J. Med. Chem., vol. 34, pp. 1356-1362.

Giardina, G.A.M., et al, 1999, "Replacement of the quinoline system in 2-phenyl-4-quinolinecarboxamide NK-3 receptor antagonists", Il Farmaco, vol. 54, pp. 364-374.

Glinka, R., et al, 1991, "Synthesis and structure of new hetercyclic systems containing the sulfamide group", Pol. J. Chem., vol. 65, pp. 2053-2055.

Gorden, A., et al, 2003, "Analysis of BRAF and N-RAS mutations in metastatic malanoma tissues", Cancer Research, vol. 63, pp. 3955-3957.

Guarna, A., et al, 2002, "Synthesis of a new enantiopure bicyclic γ/δ-amino acid (BTKa) derived from tartaric acid and α-amino acetophenone", Tetrahedron, vol. 58, pp. 9865-9870.

Haesslein, J., et al, 2002, "Recent advances in cyclin-dependent kinase inhibition. Purine-based derivatives as anti-cancer agents. Roles and perspectives for the future", Curr. Top. Med. Chem, vol. 2, pp. 1037-1050.

Hammond, M., et al, 2003, "Structure-activity relationships in a series of NPY Y5 antagonists: 3-amido-9-ethylcarbazoles, core-modified analogues and amide isosteres", Bioorganic & Medicinal Chemistry Letters, vol. 13, pp. 1989-1992.

Helbling, P.M., et al, 2000, "The receptor tyrosine kinase EphB4 and ephrin-B ligands restrict angiogenic growth of embryonic veins in Xenopus laevis", Development, vol. 127, pp. 269-278.

Hirayama, F., et al, 2002, "Design, synthesis and biological activity of YM-60828 derivatives: potent and orally-bioavailable factor Xa inhibitors based on naphthaoanilide and naphthalensulfonanilide templates", Bioorganic & Medicinal Chemistry, vol. 10, pp. 2597-2610.

Holland, S.J., et al, 1996, "Bidirectional signalling through the EPH-family receptor Nuk and its transmembrane ligands", Nature, vol. 383, pp. 722-725.

Ingber, et al, 1990,"Synthetic analogues of fumagillin that inhibit angiogenesis and suppress tumour growth", Nature, vol. 348, pp. 555-557.

Ishii, A., et al, 1997, "First synthesis and reactivities of isolable dithiiranes and their 1-oxides", Bull. Chem. Soc. Jpn., vol. 70, pp. 509-523.

Itaya, T., et al, 1998, "Syntheses of the marine ascidian purine aplidiamine and its 9-beta-d-ribofuranoside", Tetrahedron Letters, vol. 39, pp. 4695-4696.

Janvier, P., et al, 2002, "Ammonium chloride-promoted four-component synthesis of pyrrolo[3-4-b]pyridin-5-one", J. American Chemical Society, vol. 124, pp. 2560-2567.

Johnson, C.R., et al, 1979, "Preparation and reactions of sulfonimidoyl chlorides", Journal of Organic Chemistry, vol. 44, pp. 2055-2061.

Jursic, B., 1988, "Synthetic application of micellar catalysis. Williamson's synthesis of ethers", Tetrahedron, vol. 44, pp. 6677-6680.

Kahlon, R., et al, 1992, "Angiogenesis in atherosclerosis", Can. J. Cardiol., vol. 8, pp. 60-64.

Kolch, W., et al, 1991, "Raf-1 protein kinase is required for growth of induced NIH/3T3 cells", Nature, vol. 349, pp. 426-428.

Lemonnier, J., et al, 2001, "Role of N-cadherin and protein kinase C in osteoblast gene activation inducted by the S252W fibroblast growth factor receptor 2 mutation in apert craniosynostosis", J. Bone & Min. Research, vol. 16, pp. 832-845.

Liu, W., et al, 2004, "Effects of overexpression of ephrin-B2 on tumour growth in human colorectal cancer", British Journal of Cancer, vol. 90, pp. 1620-1626.

Lozinskii, M.O., et al, 2002, "Alkylthio derivatives of the aminoketene S,N-acetals of heterocyclic β-dicarbonyl compounds: one stage synthesis and properties", Chemistry of Heterocyclic Compounds, vol. 38, pp. 1077-1080.

Mansour, S.J., et al, 1994, "Transformation of mammalian cells by constitutively active MAP kinase kinase", Science, vol. 265, pp. 966-970.

Marais, R., et al, 1997, "Differential regulation of Raf-1, A-Raf, and B-Raf by oncogenic Ras and tyrosine kinases", J. of Biol. Chem., vol. 272, pp. 4378-4383.

Mataloni, M., et al, 2003, "Synthesis of secondary amines by reduction of α-amidoalkylphenyl sulfones with sodium acetoxyborohbydride", Synlett, vol. 8, pp. 1129-1132.

Mcmahon, G., 2000, "VEGF receptor signaling in tumor angiogenesis", The Oncologist, vol. 5, pp. 3-10.

Messinger, P., et al, "Notiz zur synthese von α-amino- and α-amidosulfonen", Archive Der Pharmazie, 1974, vol. 307, pp. 653-655 (in German, with partial English language translation).

Meyers, G.A., et al, 1996, "FGFR2 Exon IIIa and IIIc mutations in Crouzon, Jackson-Weiss, and Pfeiffer syndromes: Evidence for Missense changes, insertions, and a deletion due to alternative RNA splicing", Am. J. Hum. Genet., vol. 58, pp. 491-498.

Mineo, T.C., et al, 2004, "Prognostic impact of VEGF, CD31, CD34, and CD105 expression and tumour vessel invasion after radical surgery for IB-IIA non-small cell lung cancer", J. Clin. Pathol., vol. 57, pp. 591-597.

Mohanta, P.K., et al, 2000, "1-(methyldithiocarbony)imidazole: a useful thiocarbonyl transfer reagent for synthesis of substituted thioureas", Tetrahedron, vol. 2000, pp. 629-637.

Moore, J.D., et al, 2003, "ROMP-generated oligomeric sulfonyl chlorides as versatile soluble scavenging agents", Organic Letters, vol. 5, pp. 105-107.

Mustonen, T., et al, 1995, "Endothelial receptor tyrosine kinases involved in angiogenesis", J. Cell Biol., vol. 129, pp. 895-898.

Nakamoto, M., et al, 2002, "Diverse roles for the Eph family of receptor tyrosine kinases in carcinogenesis", Micros. Res. and Tech., vol. 59, pp. 58-67.

O'Reilly, M.S., et al, 1994, "Angiostatin: A novel angiogenesis inhibitor that mediates the suppression of metastases by a Lewis lung carcinoma", Cell, vol. 79, pp. 315-328.

Orre, M., et al, 1999, "VEGF, VEGFR-1, VEGFR-2, microvessel density and endothelial cell proliferation in tumours of the ovary", Int. J. Cancer, vol. 84, pp. 101-108.

Ozawa, F., et al, 2001, "Growth factors and their receptors in pancreatic cancer", Teratog. Carcinog. & Mutagen., vol. 21, pp. 27-44.

Pabst, B., et al, 1999, "Analysis of K-*ras* mutations in pancreatic tissue after fine needle aspirates", Anticancer Research, vol. 19, pp. 2481-2484.

Parlow, J.J., et al, 2003, "Synthesis and crystal structures of substituted benzenes and benzoquinones as tissue factor VIIa inhibitors"; J. Med. Chem., vol. 46, pp. 4297-4312.

Partanen, J., et al, 1992, "A novel endothelial cell surface receptor tyrosine kinase with extracellular epidermal growth factor homology domains", Mol. Cell. Biol., vol. 12, pp. 1698-1707.

Partanen, J., et al, 1999, "Functions of Tie1 and Tie2 receptor tyrosine kinases in vascular development", Current Topics in Microbiol. Immunol., vol. 237, pp. 159-172.

Paulson, R.F., et al, 1995, "Receptor tyrosine kinases and the regulation of hematopoiesis", Semin. Immunol., vol. 7, pp. 267-277.

Peacock, D.J., et al, 1992, "Angiogenesis inhibition suppresses collagen arthritis", J. Exp. Med., vol. 175, pp. 1135-1138.

Peacock, D.J., et al, 1995, "A novel angiogenesis inhibitor suppresses rat adjuvant arthritis", Cell. Immun., vol. 160, pp. 178-184.

Peters, K.G., 1998, "Vascular endothelial growth factor and the angiopoietins", Circ. Res., vol. 83, pp. 342-343.

Pinedo, H.M., et al, 2000, "Translational research: The role of VEGF in tumor angiogenesis", The Oncologist, vol. 5, pp. 1-2.

Plomp, A.S., et al, 1998, "Pfeiffer syndrome type 2: Further delineation and review of the literature", Am. J. Med. Gen., vol. 75, pp. 245-251.

Powers, C.J., et al, 2000, "Fibroblast growth factors, their receptors and signaling", Endocrine-Related Cancer, vol. 7, pp. 165-197.

Prakash, O., et al, 1992, Indian Journal of Chemistry, Section B: Organic Chemistry Including Medicinal Chemistry, vol. 31B, pp. 349-350.

Prix, L., et al, 2002, "Diagnostic biochip array for fast and sensitive detection of K-*ras* mutations in stool", Clinical Chemistry, vol. 48, pp. 428-435.

Rajagopalan, H., et al, 2002, "RAF/RAS oncogenes and mismatch-repair status", Nature, vol. 418, p. 934.

Ramadas, K., et al, 1997, "LAC sulfur assisted synthesis of symmetrical thioureas", Synth. Comm., vol. 27, pp. 2255-2260.

Sarkis, G.Y., et al, 1985, "Synthesis and spectroscopic properties of some new N,N'-disubstituted thioureas of potential biological interest", J. Heterocyclic Chemistry, vol. 22, pp. 137-140.

Shaw, J.T., et al, 1980, "The preparation of 2,6-diaminopyrazine, 2,6-diazidopyrazine and some of their derivatives", J. Het. Chem., vol. 17, pp. 11-16.

Shiina, I., et al, 2003, "A new method for the synthesis of carboxamides and peptides using 1,1'-carbonyldioxydi[2(1$H$)-pyridone] (CDOP) in the absence of basic promoters", Tetrahedron Letters, vol. 44, pp. 1952-1955.

Shin, D., et al, 2001, "Expression of EphrinB2 identifies a stable genetic difference between arterial and venous vascular smooth muscle as well as endothelial cells, and marks subsets of microvessels at sites of adult neovascularization", Dev. Biol., vol. 230. pp. 139-150.

Singer, G., et al, 2003, "Mutations in BRAF and KRAS characterize the development of low-grade ovarian serous carcinoma", J. Nat. Can. Inst., vol. 95, pp. 484-486.

Srinivas, K.V.N.S., et al, 2003, "A highly convenient, efficient, and selective process for preparation of esters and amides from carboxylic acids using Fe3+-L-1- montmorillonite clay", Journal of Organic Chemistry, vol. 68, pp. 1165-1167.

Srivastava, P.K., et al, 1981, "Synthesis and antithyroid activity of some benzimidazolyl and benzenesulphonyl thiocarbamides", Current Science, vol. 50, pp. 305-307.

Suri, C., et al, 1996, "Requisite role of angiopoietin-1, a ligand for the TIE2 receptor, during embryonic angiogenesis", Cell, vol. 87, pp. 1171-1180.

Tang, X.X., et al, 1999, "High-level expression of EPHB6, EFNB2, and EFNB3 is associated with low tumor stage and high TrkA exp0ression in human neuroblastomas", Clin. Can. Res., vol. 5, pp. 1491-1496.

Tang, X.X., et al, 1999, "Coexpression of transcripts encoding EPHB receptor protein tyrosine kinases and their Ephrin-B ligands in human small cell lung carincoma1", Clin. Can. Res., vol. 5, pp. 455-460.

Tanga, M.J., et al, 2003, "Synthesis of two potential food mutagens", J. Heterocyclic Chemistry, vol. 40, pp. 569-573.

Taraboletti, G., et al, 1995, "Inhibition of angiogenesis and murine hemangioma growth by batimastat, a synthetic inhibitor of matrix metalloproteinases", J. Nat. Can. Instit., vol. 87, pp. 293-298.

Temple, C., et al, 1989, "New anticancer agents: alterations of the carbamate group of ethyl (5-amino-1,2-dihydro-3-phenylpyrido[3,4-*b*]pyrazin-7-yl) carbamates", J. Med. Chem., vol. 32, pp. 2363-2367.

Terao, Y., et al, 1977, "Synthesis of α-thio, α-sulfinyl, and α-sulfonyl-substituted nitrosamines", Chem. Pharm. Bull., vol. 25(11), pp. 2964-2968.

Thornber, C.W., 1979, "Isosterism and molecular modification in drug design", Chemical Society Reviews, vol. 8, No. 4, pp. 563-580.

Uchida, M., et al, 1985, "Studies on 2(1$H$)-quinolinone derivatives as gastric antiulcer active agents. 2-(4-chlorobenzoylamino)-3-[2(1$H$)-quinolinon-4-yl]propionic acid and related compounds", Chem. Pharm. Bull., vol. 33(9), pp. 3775-3786.

Wan, P.T.C., et al, 2004, "Mechanism of activation of the RAF-ERK signaling pathway by oncogenic mutations of B-RAF", Cell, vol. 116, pp. 855-867.

Wang, H.U., et al, 1998, "Molecular distinction and angiogenic interaction between embryonic arteries and veins revealed by ephrin-B2 and its receptor Eph-B4", Cell, vol. 93, pp. 741-753.

Wilks, A.F., 1990, "Structure and function of the protein tyrosine kinases", Progress in Growth Factor Research, vol. 2, pp. 97-111.

Yancopoulos, G.D., et al, 1998, "Vasculogenesis, angiogenesis, and growth factors: ephrins enter the fray at the border", Cell, vol. 93, pp. 661-664.

Yu, K., et al, 2000, "Loss of fibroblast growth factor receptor 2 ligand-binding specificity in Apert syndrome", Proc. Natl. Acad. Sci. U.S.A., vol. 97, pp. 14536-14541.

Zejc, A., et al, 1990, "Synthesis and anticonvulsant properties of some arylsuccinate methylpyridylimides", Pol. J. Pharmaceol. Pharm., vol. 42, pp. 69-77.

Zhou, Z-L., et al, 2001, "Synthesis and SAR of 5-, 6-, 7- and 8-aza analogues of 3-aryl-4-hydroxyquinolin-2(1$H$)-one as NMDA/ glycine site antagonists", Bioorganic & Medicinal Chemistry, vol. 9, pp. 2061-2071.

UK Search Report for GB 0423554.5 dated Feb. 23, 2005 (1 page).

International Search Report and Written Opinion for PCT/GB2005/ 004081 dated Feb. 2, 2006 (14 pages).

International Preliminary Report on Patentability for PCT/GB2005/ 004081 dated Apr. 24, 2007 (8 pages).

UK Search Report for GB 0608268.9 dated Aug. 9, 2006 (1 page).

International Search Report for PCT/GB2007/001534 dated Sep. 6, 2007 (4 pages).

International Preliminary Report on Patentability for PCT/GB2007/ 001534 dated Oct. 28, 2008 (10 pages).

IMIDAZO[4, 5-B]PYRIDIN-2-ONE AND OXAZOLO[4, 5-B] PYRIDIN-2-ONE COMPOUNDS AND ANALOGS THEREOF AS CANCER THERAPEUTIC COMPOUNDS

RELATED APPLICATIONS

This application is a national stage filing under 35 U.S.C. 371 of International Application No. PCT/GB2007/001534 filed 26 Apr. 2007, which is related to: United Kingdom patent application number 0608268.9 filed 26 Apr. 2006 and U.S. patent application No. 60/745,633 filed 26 Apr. 2006; the contents of each of which are incorporated herein by reference in their entirety.

TECHNICAL FIELD

The present invention pertains generally to the field of therapeutic compounds for treating proliferative conditions, cancer, etc., and more specifically to certain imidazo[4,5-b]pyridin-2-one and oxazolo[4,5-b]pyridin-2-one compounds and analogs thereof which, inter alia, inhibit RAF (e.g., B-RAF) activity. The present invention also pertains to pharmaceutical compositions comprising such compounds, and the use of such compounds and compositions, both in vitro and in vivo, to inhibit RAF (e.g., BRAF) activity, to inhibit receptor tyrosine kinase (RTK) activity, to inhibit cell proliferation, and in the treatment of diseases and conditions that are ameliorated by the inhibition of RAF, RTK, etc., proliferative conditions such as cancer (e.g., colorectal cancer, melanoma), etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

RAF, Proliferative Conditions, and Cancer

Mutations in genes that directly or indirectly control cell growth and differentiation are generally considered to be the main cause of cancer. Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation.

RAF is key downstream target for the ras GTPase and mediates the activation of the MAP kinase cascade consisting of raf-MEK-ERK. Activated ERK is a kinase that subsequently targets a number of proteins responsible for mediating, amongst other things, the growth, survival and transcriptional functions of the pathway. These include the transcription factors ELK1, C-JUN, the Ets family (including Ets 1, 2, and 7), and the FOS family. The ras-raf-MEK-ERK signal transduction pathway is activated in response to many cell stimuli including growth factors such as EGF, PDGF, KGF etc. Because the pathway is a major target for growth factor action, the activity of raf-MEK-ERK has been found to be upregulated in many factor dependent tumours. The observation that about 20% of all tumours have undergone an activating mutation in one of the ras proteins indicates that the pathway is more broadly important in tumorigenesis. There is growing evidence that activating mutations in other components of the pathway also occur in human tumours. This is true for RAF.

The RAF oncogene family includes three highly conserved genes termed A-RAF, B-RAF and C-RAF (also called Raf-1). RAF genes encode protein kinases that are thought to play important regulatory roles in signal transduction processes that regulate cell proliferation. RAF genes code for highly conserved serine-threonine-specific protein kinases, which are recruited to the plasma membrane following direct binding to the Ras small Guanine-nucleotide binding proteins and this is the initiating event in RAF activation. RAF proteins are part of a signal transduction pathway believed to consist of receptor tyrosine kinases, p21 Ras, RAF protein kinases, Mek1 (ERK activator or MAPKK) kinases and ERK (MAPK) kinases, which ultimately phosphorylate several cellular substrates, including transcription factors. Signaling through this pathway can mediate differentiation, proliferation or oncogenic transformation in different cellular contexts. Thus, RAF kinases are believed to play a fundamental role in the normal cellular signal transduction pathway, coupling a multitude of growth factors to their net effect, cellular proliferation. Because RAF proteins are direct downstream effectors of ras protein function, therapies directed against RAF kinases are believed to be useful in treatment of ras-dependent tumors.

The RAF kinases are differentially regulated and expressed; C-RAF is the most thoroughly characterized and is expressed in all organs and in all cell lines that have been examined. A-RAF and B-RAF also appear to be ubiquitous, but are most highly expressed in urogenital and brain tissues, respectively. Because B-RAF is highly expressed in neural tissues it was once thought to be limited to these tissues but it has since been found to be more widely expressed. Although all RAF proteins can bind to active Ras, B-raf is most strongly activated by oncogenic Ras, and may be the primary target of oncogenic Ras in transformed cells.

Recent evidence indicates that mutational activation of B-RAF is found in a number of different tumours including more than 65% of malignant melanomas, more than 10% of colorectal cancers (Davies, H., et al., 2002, *Nature*, Vol. 417, pp. 949-954; Rajagopalan, H. et al., 2002, *Nature*, Vol. 418, p. 934), ovarian cancers (Singer, G., et al., 2003, *J. Natl. Cancer Inst.*, Vol. 95, pp. 484-486) and papillary thyroid cancers (Brose, M., et al., 2002, *Cancer Res.*, Vol. 62, pp. 6997-7000;

Cohen, Y., et al., 2003, *Invest. Opthalmol. Vis. Sci.*, Vol. 44, pp. 2876-2878). A range of different B-RAF mutations have been identified in different tumours with the most common being a V600E mutation in the so-called activation loop of the kinase domain (Davies, H., et al., 2002, *Nature*, Vol. 417, pp. 949-954).

Other mutations of B-RAF found associated with human cancers may not necessarily activate B-RAF directly but do upregulate the activity of the ras-raf-MEK-ERK pathway by mechanisms which are not fully understood but may involve cross-talk with other RAF isoforms, such as A-RAF (Wan, P., et al., 2004, *Cell*, Vol. 116, pp. 855-867). In such cases, inhibition of RAF activity would remain a beneficial aim in cancer treatment.

In addition to link between B-RAF and certain cancers, there is a significant amount of evidence to indicate a more broad inhibition of RAF activity could be beneficial as an antitumour therapy. Blocking the pathway at the level of B-RAF would be effective at counteracting the upregulation of this pathway caused by tumourigenic ras mutations and also in tumours responding to growth factor action via this pathway. Genetic evidence in *Drosophila* and *C. elegans* indicates that RAF homologues are essential for ras dependent actions on differentiation (Dickson, B., et al., 1993, *Nature*, Vol. 360, pp. 600-603). Introduction of constitutively active MEK into NIH3T3 cells can have a transforming action whilst expression of dominant negative MEK proteins can suppress the tumourigenicity of ras transformed cell lines (Mansour, S. J., et al., 1994, *Science*, Vol. 265, pp. 966-970; Cowely, S., et al., 1994, *Cell*, Vol. 77, pp. 841-852). Expression of a dominant negative raf protein has also been found to inhibit ras dependent signalling as has suppression of raf expression using an antisense oligonucleotide construct (Koch, W., et al., 1991, *Nature*, Vol. 349, pp. 426-428; Bruder, T. T., et al., 1992, *Genes and Development*, Vol. 6, pp. 545-556).

This and other evidence suggests that inhibition of RAF (e.g., B-RAF) activity would be beneficial in the treatment of cancer, and that inhibition of RAF (e.g., B-RAF) activity could be particularly beneficial in those cancers containing a constitutively activated B-raf mutation.

The raf-MEK-ERK pathway functions downstream of many receptors and stimuli indicating a broad role in regulation of cell function. For this reason inhibitors of RAF may find utility in other disease conditions that are associated with upregulation of signalling via this pathway. The raf-MEK-ERK pathway is also an important component of the normal response of non-transformed cells to growth factor action. Therefore inhibitors of RAF may be of use in diseases where there is inappropriate or excessive proliferation of normal tissues. These include, but are not limited to glomerulonephritis and psoriasis. The cellular signalling pathway of which RAF is a part has also been implicated in inflammatory disorders characterized by T-cell proliferation (T-cell activation and growth), such as tissue graft rejection, endotoxin shock, and glomerular nephritis.

RAF (e.g., B-RAF) has been shown to be a valid therapeutic target in hyperproliferative disorders such as cancer. Activated versions of RAF (e.g., B-RAF) are able to transform mammalian cells, allowing them to take on the characteristics of cancer cells and the growth of these cells becomes dependent on the mutant RAF (e.g., B-RAF) protein. Inhibition of RAF (e.g., B-RAF) activity in human cancer cell lines that express the mutant forms of RAF (e.g., B-RAF) blocks their growth and ultimately induces their death.

Angiogenesis

Chronic proliferative diseases are often accompanied by profound angiogenesis, which can contribute to or maintain an inflammatory and/or proliferative state, or which leads to tissue destruction through the invasive proliferation of blood vessels. (Folkman, 1997, *EXS*, Vol. 79, pp. 1-81; Folkman, 1995, *Nature Medicine*, Vol. 1, pp. 27-31; Folkman and Shing, 1992, *J. Biol. Chem.*, Vol. 267, p. 10931.)

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, 1992, *Ann. Rhum. Dis.*, Vol. 51, p. 919). In diabetes (and in many different eye diseases), new vessels invade the macula or retina or other ocular structures, and may cause blindness (Brooks et al., 1994, *Cell*, Vol. 79, p. 1157). The process of atherosclerosis has been linked to angiogenesis (Kahlon et al., 1992, *Can. J. Cardiol.*, Vol. 8, p. 60). Tumor growth and metastasis have been found to be angiogenesis-dependent (Folkman, 1992, *Cancer Biol.*, Vol. 3, p. 65; Denekamp, 1993, *Br. J. Rad.*, Vol. 66, p. 181; Fidler and Ellis, 1994, *Cell*, Vol. 79, p. 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., 1994, *Cell*, Vol. 79, p. 315; Ingber et al., 1990, Nature, Vol. 348, p. 555), ocular diseases (Friedlander et al., 1995, *Science*, Vol. 270, p. 1500), arthritis (Peacock et al., 1992, *J. Exp. Med.*, Vol. 175, p. 1135; Peacock et al., 1995, *Cell. Immun.*, Vol. 160, p. 178) and hemangioma (Taraboletti et al., 1995, *J. Natl. Cancer Inst.*, Vol. 87, p. 293).

RTKs

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

FGFR

The fibroblast growth factor (FGF) family of signaling polypeptides regulates a diverse array of physiologic functions including mitogenesis, wound healing, cell differentiation and angiogenesis, and development. Both normal and malignant cell growth as well as proliferation are affected by changes in local concentration of these extracellular signaling molecules, which act as autocrine as well as paracrine factors. Autocrine FGF signaling may be particularly important in the progression of steroid hormone-dependent cancers and to a hormone independent state (Powers et al., 2000, *Endocr. Relat. Cancer*, Vol. 7, pp. 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa et al., 2001, *Teratog. Carcinog. Mutagen.*, Vol. 21, pp. 27-44).

The two prototypic members are acidic fibroblast growth factor (aFGF or FGF1) and basic fibroblast growth factors (bFGF or FGF2), and to date, at least twenty distinct FGF family members have been identified. The cellular response to FGFs is transmitted via four types of high affinity transmembrane tyrosine-kinase fibroblast growth factor receptors numbered 1 to 4 (FGFR-1 to FGFR-4). Upon ligand binding, the receptors dimerize and auto- or trans-phosphorylate specific cytoplasmic tyrosine residues to transmit an intracellular signal that ultimately reaches nuclear transcription factor effectors.

Disruption of the FGFR-1 pathway should affect tumor cell proliferation since this kinase is activated in many tumor types in addition to proliferating endothelial cells. The overexpression and activation of FGFR-1 in tumor-associated vasculature has suggested a role for these molecules in tumor angiogenesis.

FGFR-2 has high affinity for the acidic and/or basic fibroblast growth factors, as well as the keratinocyte growth factor ligands. FGFR-2 also propagates the potent osteogenic effects of FGFs during osteoblast growth and differentiation. Mutations in FGFR-2, leading to complex functional alterations, were shown to induce abnormal ossification of cranial sutures (craniosynostosis), implying a major role of FGFR signaling in intramembranous bone formation. For example, in Apert (AP) syndrome, characterized by premature cranial suture ossification, most cases are associated with point mutations engendering gain-of-function in FGFR-2 (Lemonnier et al., 2001, *J. Bone Miner. Res.*, Vol. 16, pp. 832-845).

Several severe abnormalities in human skeletal development, including Apert, Crouzon, Jackson-Weiss, Beare-Stevenson cutis gyrata, and Pfeiffer syndromes are associated with the occurrence of mutations in FGFR-2. Most, if not all, cases of Pfeiffer Syndrome (PS) are also caused by de novo mutation of the FGFR-2 gene (Meyers et al., 1996, *Am. J. Hum. Genet.*, Vol. 58, pp. 491-498; Plomp et al., 1998, *Am. J. Med. Genet.*, Vol. 75, 245-251), and it was recently shown that mutations in FGFR-2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of FGFR-2 (Yu et al., 2000, *Proc. Natl. Acad. Sci. U.S.A.*, Vol. 97, pp. 14536-14541).

Activating mutations of the FGFR-3 receptor tyrosine kinase such as chromosomal translocations or point mutations produce deregulated, constitutively active, FGFR-3 receptors which have been involved in multiple myeloma and in bladder and cervix carcinomas (Powers, C. J., et al., 2000, *Endocr. Rel. Cancer*, Vol. 7, p. 165). Accordingly, FGFR-3 inhibition would be useful in the treatment of multiple myeloma, bladder and cervix carcinomas.

VEGFR

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al., 2000, *The Oncologist*, Vol. 5 (90001), pp. 1-2). VEGFR(s) are protein tyrosine kinases (PTKs). PTKs catalyze the phosphorylation of specific tyrosyl residues in proteins involved in the regulation of cell growth and differentiation. (Wilks, A. F., 1990, *Progress in Growth Factor Research*, Vol. 2, pp. 97-111; Courtneidge, S. A., 1993, *Dev. Supp. I*, pp. 57-64; Cooper, J. A., 1994, *Semin. Cell Biol.*, Vol. 5(6), pp. 377-387; Paulson, R. F., 1995, *Semin. Immunol.*, Vol. 7(4), pp. 267-277; Chan, A. C., 1996, *Curr. Opin. Immunol.*, Vol. 8(3), pp. 394-401).

Three PTK receptors for VEGF have been identified: VEGFR-1 (Flt-1), VEGFR-2 (Flk-1 or KDR), and VEGFR-3 (Flt-4). These receptors are involved in angiogenesis and participate in signal transduction (Mustonen, T., et al., 1995, *J. Cell Biol.*, Vol. 129, pp. 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G., 2000, *The Oncologist*, Vol. 5(90001), pp. 3-10).

Inhibition at the kinase domain binding site of VEGFR-2 would block phosphorylation of tyrosine residues and serve to disrupt initiation of angiogenesis.

TIE

Angiopoieten 1 (Ang1), a ligand for the endothelium-specific receptor tyrosine kinase TIE-2 is a novel angiogenic factor (Davis et al., 1996, *Cell*, Vol. 87, pp. 1161-1169; Partanen et al., 1992, *Mol. Cell. Biol.*, Vol. 12, pp. 1698-1707; U.S. Pat. Nos. 5,521,073; 5,879,672; 5,877,020; and 6,030, 831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intra-chain disulfide bonds (Partanen et al., 1999, *Curr. Topics Microbiol. Immunol.*, Vol. 237, pp. 159-172). Unlike VEGF, which functions during the early stages of vascular development, Ang1 and its receptor TIE-2 function in the later stages of vascular development, i.e., during vascular remodelling (remodelling refers to formation of a vascular lumen) and maturation (Yancopoulos et al., 1998, *Cell*, Vol. 93, pp. 661-664; Peters, K. G., 1998, *Circ. Res.*, Vol. 83(3), pp. 342-343; Suri et al., 1996, *Cell*, Vol. 87, pp. 1171-1180).

Consequently, inhibition of TIE-2 would be expected to serve to disrupt remodelling and maturation of new vasculature initiated by angiogenesis thereby disrupting the angiogenic process.

Eph

The largest subfamily of receptor tyrosine kinases (RTKs), the Eph family, and their ligands (ephrins), play important roles in physiologic and pathologic vascular processes. Both the Ephs (receptors) and ephrins (ligands) are divided into two groups, A and B subfamilies (Eph Nomenclature Committee, 1997). The binding of ephrin ligands to Eph receptors is dependent on cell-cell interactions. The interactions of ephrins and Ephs have recently been shown to function via bi-directional signalling. The ephrins binding to Eph receptors initiate phosphorylation at specific tyrosine residues in the cytoplasmic domain of the Eph receptors. In response to Eph receptor binding, the ephrin ligand also undergoes tyrosine phosphorylation, so-called 'reverse' signalling (Holland, S. J., et al., 1996, *Nature*, Vol. 383, pp. 722-725; Bruckner et al., 1997, *Science*, Vol. 275, pp. 1640-1643).

Eph RTKs and their ephrin ligands play important roles in embryonic vascular development. Disruption of specific Eph receptors and ligands (including ephrin-B2) leads to defective vessel remodelling, organisation, and sprouting resulting in embryonic death (Wang, H. U., et al., 1998, *Cell*, Vol. 93, pp. 741-753; Adams, R. H., et al., 1999, *Genes Dev*, Vol. 13, pp. 295-306; Gale and Yancopoulos, 1999, *Genes Dev*, Vol. 13, pp. 1055-1066; Helbling, P. M., et al., 2000, *Development*, Vol. 127, pp. 269-278). Coordinated expression of the Eph/ephrin system determines the phenotype of embryonic vascular structures: ephrin-B2 is present on arterial endothelial cells (ECs), whereas EphB4 is present on venous ECs (Gale and Yancopoulos, 1999, *Genes Dev*, Vol. 13, pp. 1055-1066; Shin, D., et al., 2001, *Dev Biol*, Vol. 230, pp. 139-150). Recently, specific Ephs and ephrins have been implicated in tumour growth and angiogenesis.

The Ephs and ephrins have been found to be overexpressed in many human tumours. In particular, the role of EphB2 has been identified in small cell lung carcinoma (Tang, X. X., et al., 1999, *Clin Cancer Res*, Vol. 5, pp. 455-460), human neuroblastomas (Tang, X. X., et al., 1999, *Clin Cancer Res*, Vol. 5, pp. 1491-1496) and colorectal cancers (Liu, W., et al., 2004, *Brit. J. Canc.*, Vol. 90, pp. 1620-1626), and higher expression levels of Ephs and ephrins, including EphB2, have been found to correlate with more aggressive and metastatic tumours (Nakamoto, M. and Bergemann, A. D., 2002, *Microsc. Res Tech*, Vol. 59, pp. 58-67).

Consequently, inhibition of EphB2 would be expected to serve to disrupt angiogenesis, and in particular in certain tumours where over-expression occurs.

The inventors have discovered compounds that, e.g., inhibit RAF (e.g., B-RAF) activity and/or are useful in the treatment of, e.g., proliferative conditions, cancer, etc.

There is a recognized need for more and better treatments for proliferative conditions (e.g., cancer) which offer, for example, one or more the following benefits:

(a) improved activity;
(b) improved efficacy;
(c) improved specificity;
(d) reduced toxicity (e.g., cytotoxicity);
(e) complement the activity of other treatments (e.g., chemotherapeutic agents);
(f) reduced intensity of undesired side-effects;
(g) fewer undesired side-effects;
(h) simpler methods of administration (e.g., route, timing, compliance);
(i) reduction in required dosage amounts;
(j) reduction in required frequency of administration;
(k) increased ease of synthesis, purification, handling, storage, etc.;
(l) reduced cost of synthesis, purification, handling, storage, etc.

Thus, one aim of the present invention is the provision of active compounds that offer one or more of the above benefits.

SUMMARY OF THE INVENTION

One aspect of the invention pertains to active compounds, specifically, certain imidazo[4,5-b]pyridin-2-one and oxazolo[4,5-b]pyridin-2-one compounds and analogs thereof, as described herein.

Another aspect of the invention pertains to a composition (e.g., a pharmaceutical composition) comprising an active compound as described herein and a pharmaceutically acceptable carrier or diluent.

Another aspect of the present invention pertains to a method of inhibiting RAF (e.g., B-RAF) activity in a cell, in vitro or in vivo, comprising contacting the cell with an effective amount of an active compound, as described herein.

Another aspect of the present invention pertains to a method of inhibiting receptor tyrosine kinase (RTK) activity, such as FGFR, Tie, VEGFR and/or Eph activity, for example, FGFR-1, FGFR-2, FGFR-3, Tie2, VEGFR-2 and/or EphB2 activity, in a cell, in vitro or in vivo, comprising contacting the cell with an effective amount of an active compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting cells (or the cell) with an effective amount of an active compound, as described herein.

Another aspect of the present invention pertains to a method for the treatment comprising administering to a subject in need of treatment a therapeutically-effective amount of an active compound, as described herein, preferably in the form of a pharmaceutical composition.

Another aspect of the present invention pertains to an active compound as described herein for use in a method of treatment of the human or animal body by therapy.

Another aspect of the present invention pertains to use of an active compound, as described herein, in the manufacture of a medicament for use in treatment.

In one embodiment, the treatment is treatment of a disease or condition (e.g., cancer) that is characterised by the up-regulation and/or activation of RAF (e.g., B-RAF), and/or is ameliorated by the inhibition of RAF (e.g., B-RAF).

In one embodiment, the treatment is treatment of a disease or condition (e.g., cancer) that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of a disease or condition that is characterised by inappropriate, excessive, and/or undesirable angiogenesis.

In one embodiment, the treatment is treatment of a proliferative condition, e.g., cancer.

Another aspect of the present invention pertains to a kit comprising (a) an active compound, as described herein, preferably provided as a pharmaceutical composition and in a suitable container and/or with suitable packaging; and (b)

instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

One aspect of the present invention pertains to compounds which may be described as "imidazo[4,5-b]pyridin-2-one and oxazolo[4,5-b]pyridin-2-one compounds and analogs thereof", and their surprising and unexpected RAF (e.g., B-RAF) inhibitory, anti-proliferative, and anti-cancer properties.

Compounds

One aspect of the present invention pertains to compounds selected from compounds of the following formula, and pharmaceutically acceptable salts, solvates, amides, esters, ethers, N-oxides, chemically protected forms, and prodrugs thereof:

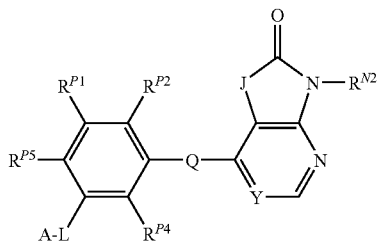

wherein:
J is independently —O— or —NR$^{N1}$—;
R$^{N1}$, if present, is independently —H or a group selected from:
 aliphatic saturated $C_{1-5}$alkyl,
 aliphatic $C_{2-5}$alkenyl,
 aliphatic $C_{2-5}$alkynyl,
 saturated $C_{3-6}$cycloalkyl,
 $C_{3-6}$cycloalkenyl;
 $C_6$carboaryl;
 $C_{5-6}$heteroaryl;
 $C_{5-6}$heterocyclic;
 and is independently unsubstituted or substituted;
R$^{N2}$ is independently —H or a group selected from:
 aliphatic saturated $C_{1-5}$alkyl,
 aliphatic $C_{2-5}$alkenyl,
 aliphatic $C_{2-5}$alkynyl,
 saturated $C_{3-6}$cycloalkyl,
 $C_{3-6}$cycloalkenyl;
 $C_6$carboaryl;
 $C_{5-6}$heteroaryl;
 $C_{5-6}$heterocyclic;
 and is independently unsubstituted or substituted;
Y is independently —CH= or —N=;
Q is independently —$(CH_2)_j$-M-$(CH_2)_k$— wherein:
 j is independently 0, 1 or 2;
 k is independently 0, 1, or 2;
 j+k is 0, 1, or 2;
 M is independently —O—, —S—, —NH—, —NMe-, or —CH$_2$—;
each of R$^{P1}$, R$^{P2}$, and R$^{P4}$ is independently —H or a group selected from:
 aliphatic saturated $C_{1-5}$alkyl;
 aliphatic $C_{2-5}$alkenyl;
 aliphatic $C_{2-5}$alkynyl;
 saturated $C_{3-6}$cycloalkyl;
 $C_{3-6}$cycloalkenyl;
 aliphatic saturated $C_{1-5}$haloalkyl;
 —C(=O)OR$^1$.
  wherein R$^1$ is —H, $C_{5-12}$aryl-$C_{1-7}$alkyl, $C_{5-12}$aryl, $C_{3-12}$heterocyclyl, or $C_{1-7}$alkyl;
 —OR$^2$ and —SR$^2$,
  wherein R$^2$ is —H, $C_{5-12}$aryl-$C_{1-7}$alkyl, $C_{5-12}$aryl, $C_{3-12}$heterocyclyl, or $C_{1-7}$alkyl;
 —C(=O)NR$^3$R$^4$,
  wherein each of R$^3$ and R$^4$ is independently —H; or $C_{5-12}$aryl-$C_{1-7}$alkyl, $C_{5-12}$aryl, $C_{3-12}$heterocyclyl, or $C_{1-7}$alkyl; or R$^3$ and R$^4$ taken together with the nitrogen atom to which they are attached form a ring having from 3 to 7 ring atoms;
 NR$^5$R$^6$
  wherein each of R$^5$ and R$^3$ is independently —H; or $C_{5-12}$aryl-$C_{1-7}$alkyl, $C_{5-12}$aryl, $C_{3-12}$heterocyclyl, or $C_{1-7}$alkyl; or R$^5$ and R$^6$ taken together with the nitrogen atom to which they are attached form a ring having from 3 to 7 ring atoms;
 —NR$^7$C(=O)R$^8$,
  wherein:
   R$^7$ is —H or $C_{1-3}$alkyl;
   R$^8$ is $C_{5-12}$aryl-$C_{1-7}$alkyl, $C_{5-12}$aryl, $C_{3-12}$heterocyclyl, or $C_{1-7}$alkyl;
 —S(=O)R$^9$ or —S(=O)$_2$R$^9$,
  wherein R$^9$ is $C_{1-7}$alkyl, $C_{5-12}$aryl, or $C_{5-12}$aryl-$C_{1-7}$alkyl;
 —F, —Cl, —Br, or —I;
 —CN;
 wherein each $C_{1-5}$alkyl, $C_{2-5}$alkenyl, $C_{2-5}$alkynyl, $C_{3-6}$cycloalkyl, $C_{3-6}$cycloalkenyl, $C_{5-12}$aryl-$C_{1-7}$alkyl, $C_{5-12}$aryl, $C_{3-12}$heterocyclyl, and $C_{1-7}$alkyl is independently unsubstituted or substituted;
and additionally R$^{P1}$ and R$^{P2}$ taken together may be —CH=CH—CH=CH—;
R$^{P5}$ is independently —H or a group selected from:
 aliphatic saturated $C_{1-5}$alkyl;
 aliphatic $C_{2-5}$alkenyl;
 aliphatic $C_{2-5}$alkynyl;
 saturated $C_{3-6}$cycloalkyl;
 $C_{3-6}$cycloalkenyl;
 aliphatic saturated $C_{1-5}$haloalkyl;
 —C(=O)OR$^1$,
  wherein R$^1$ is —H, $C_{5-12}$aryl-$C_{1-7}$alkyl, $C_{5-12}$aryl, $C_{3-12}$heterocyclyl, or $C_{1-7}$alkyl;
 —OR$^2$ and —SR$^2$,
  wherein R$^2$ is —H, $C_{5-12}$aryl-$C_{1-7}$alkyl, $C_{5-12}$aryl, $C_{3-12}$heterocyclyl, or $C_{1-7}$alkyl;
 —C(=O)NH$_2$, —C(=O)NHMe, —C(=O)NHEt, —C(=O)NMe$_2$, —C(=O)morpholino, —C(=O)piperidino, —C(=O)piperizino;

—NH₂, —NHMe, —NMe₂, —NHEt, —NEt₂, morpholino, piperidino, piperazino;
—NHC(=O)Me, —NMeC(=O)Me, —NHC(=O)Et, —NMeC(=O)Et;
—S(=O)R⁹ or —S(=O)₂R⁹,
wherein R⁹ is $C_{1-7}$alkyl, $C_{5-12}$aryl, or $C_{5-12}$aryl-$C_{1-7}$alkyl;
—F, —Cl, —Br, or —I;
—CN;
wherein each $C_{1-5}$alkyl, $C_{2-5}$alkenyl, $C_{2-5}$alkynyl, $C_{3-6}$cycloalkyl, $C_{3-6}$cycloalkenyl, $C_{5-12}$aryl-$C_{1-7}$alkyl, $C_{5-12}$aryl, $C_{3-12}$heterocyclyl, and $C_{1-7}$alkyl is independently unsubstituted or substituted;
and additionally $R^{P1}$ and $R^{P5}$ taken together may be —CH=CH—CH=CH—;

L is independently:
  a linker group formed by a chain of 2, 3, or 4 linker moieties; wherein:
    each linker moiety is independently —CH₂—, —NR^N—, —C(=X)—, or —S(=O)₂—;
    either: exactly one linker moiety is —NR^N—,
    or: exactly two linker moieties are —NR^N—;
    either: exactly one linker moiety is —C(=X)—, and no linker moiety is —S(=O)₂—,
    or: exactly one linker moiety is —S(=O)₂—, and no linker moiety is —C(=X)—;
    no two adjacent linker moieties are —NR^N—;
X is independently =O or =S;
each $R^N$ is independently —H, saturated aliphatic $C_{1-3}$alkyl, or aliphatic $C_{2-3}$alkenyl;
A is independently:
  $C_{6-14}$-carboaryl,
  $C_{5-14}$heteroaryl,
  $C_{3-12}$-carbocyclic,
  $C_{3-12}$heterocyclic;
  and is independently unsubstituted or substituted.

The compound may conveniently be described as "meta" because of the relative orientation of the groups -Q- and A-L-. For comparison, see, e.g., WO 2006/043090 A1 published 27 Apr. 2006.

The Group Y
  The group Y is independently —CH= or —N=.
  In one embodiment, Y is independently —CH=.
  In one embodiment, Y is independently —N=.

The Group J
  The group J is independently —O— or —NR^{N1}—.
  In one embodiment, J is independently —O—.
  In one embodiment, J is independently —NR^{N1}—.

The Bicyclic Aryl-One Group
  In one embodiment, the bicyclic aryl-one group is selected from:

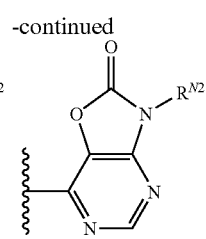

For example:

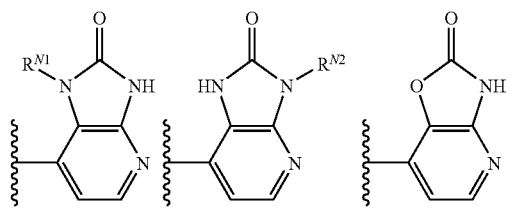

For example:

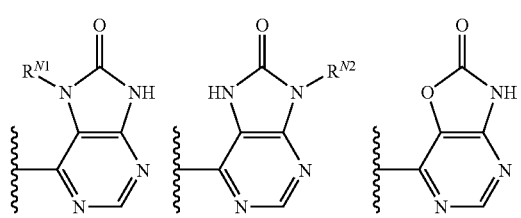

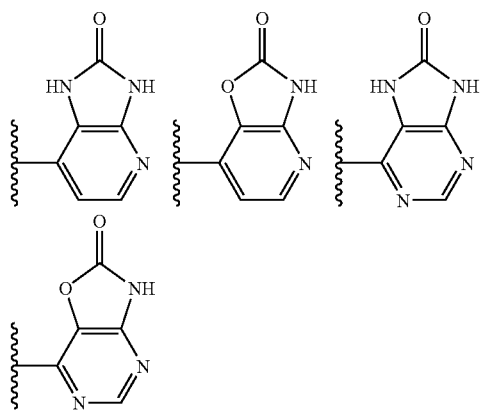

In one embodiment, the bicyclic aryl-one group is selected from:

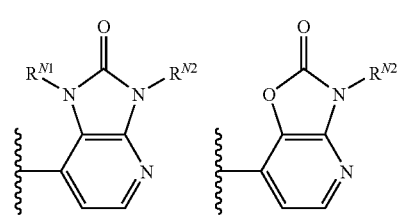

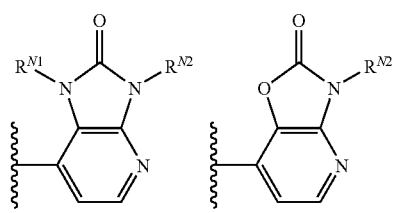

For example:

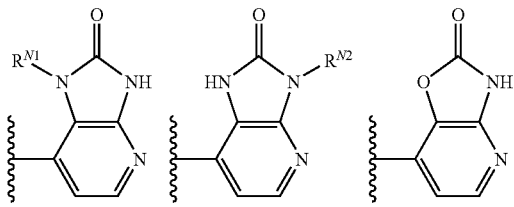

For example:

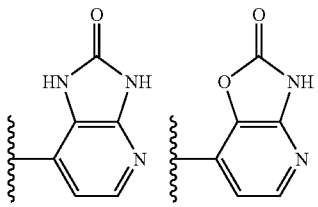

In one embodiment, the bicyclic aryl-one group is (a "1-(optionally substituted)-2-oxo-2,3-dihydro-1H-imidazo[4,5-b]pyridin-7-yl" group):

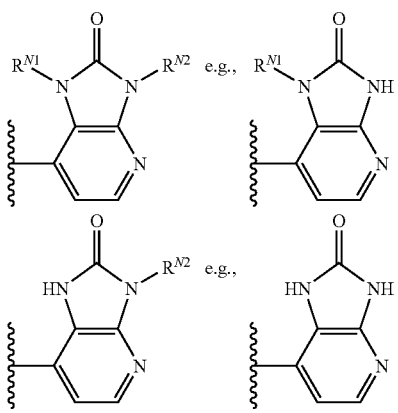

In one embodiment, the bicyclic aryl-one group is (a "2-oxo-2,3-dihydro-oxazolo[4,5-b]pyridin-7-yl" group):

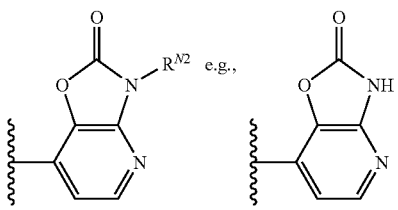

The Group $R^{N1}$

The group $R^{N1}$, if present, is independently —H or a group selected from:

aliphatic saturated $C_{1-5}$alkyl;
(e.g., -Me, -Et, -nPr, -iPr, -nBu, -iBu, -sBu, -tBu)
aliphatic $C_{2-5}$alkenyl;
(e.g., —CH=CH$_2$, —CH$_2$—CH=CH$_2$)
aliphatic $C_{2-5}$alkynyl;
(e.g., —C≡CH, —CH$_2$—C≡CH)
saturated $C_{3-6}$cycloalkyl;
(e.g., cyclopropyl, cyclobutyl, cyclopentyl, cyclohexyl)
$C_{3-6}$cycloalkenyl;
(e.g., cyclopropenyl, cyclobutenyl, cyclopentenyl, cyclohexenyl)
$C_6$carboaryl;
(e.g., phenyl)
$C_{5-6}$heteroaryl;
(e.g., pyridinyl, pyrazinyl, pyrimidinyl, pyridazinyl, furanyl, thiophenyl,
pyrrolyl, imidazolyl, pyrazolyl, oxazolyl, thiazolyl, thiadiazole) $C_{5-6}$heterocyclic;
(e.g., pyrrolidinyl, imidazolidinyl, pyrazolidinyl, piperidinyl, piperazinyl, tetrahydrofuranyl, tetrahydropyranyl, morpholinyl)
and is independently unsubstituted or substituted.

In one embodiment, $R^{N1}$, if present, is independently —H or a group selected from:
aliphatic saturated $C_{1-5}$alkyl;
(e.g., -Me, -Et, nPr, -iPr, -nBu, -iBu, -sBu, -tBu)
aliphatic $C_{2-5}$alkenyl;
(e.g., —CH=CH$_2$, —CH$_2$—CH=CH$_2$)
and is independently unsubstituted or substituted.

In one embodiment, $R^{N1}$, if present, is independently —H or aliphatic saturated $C_{1-3}$alkyl.

In one embodiment, $R^{N1}$, if present, is independently —H or -Me.

In one embodiment, $R^{N1}$, if present, is independently -Me.
In one embodiment, $R^{N1}$, if present, is independently —H.
Substituents on the Group $R^{N1}$ The group $R^{N1}$, if present, is independently unsubstituted or substituted.

In one embodiment, $R^{N1}$, if present, is independently unsubstituted.

In one embodiment, $R^{N1}$, if present, is independently substituted.

In one embodiment, $R^{N1}$, if present, is independently unsubstituted or substituted with one or more (e.g., 1, 2, or 3) substituents.

In one embodiment, the substituents on $R^{N1}$, if present, are selected from the substituents described under the heading "Substituents on the Group A" below.

In one embodiment, the substituents are selected from: (3) amido or thioamido; (4) acyl; (8) hydroxy; (9) ether; (14) amino; (18) sulfonyl; (22) $C_{5-20}$aryl; (23) $C_{3-20}$heterocyclyl; as described under the heading "Substituents on the Group A" below.

For example, in one embodiment, the substituents are selected from:
(3) —(C=O)NH$_2$, —(C=O)NMe$_2$, —(C=O)NEt$_2$,
—(C=O)N(iPr)$_2$, —(C=O)N(CH$_2$CH$_2$OH)$_2$;
—(C=O)-morpholino, —(C=O)NHPh, —(C=O)NHCH$_2$Ph;
(4) —C(=O)H, —(C=O)Me, —(C=O)Et, —(C=O)(tBu), —(C=O)-cHex, —(C=O)Ph; —(C=O)CH$_2$Ph;
(8) —OH;
(9) —OMe, —OEt, —O(iPr), —O(tBu), —OPh, —OCH$_2$Ph; —OCF$_3$, —OCH$_2$CF$_3$;
—OCH$_2$CH$_2$OH, —OCH$_2$CH$_2$OMe, —OCH$_2$CH$_2$OEt;
—OCH$_2$CH$_2$NH$_2$, —OCH$_2$CH$_2$NMe$_2$, —OCH$_2$CH$_2$N(iPr)$_2$;
—OPh-Me, —OPh-OH, —OPh-OMe, —OPh-F, —OPh-Cl, —OPh-Br, —OPh-I;

(14) —NH₂, —NHMe, —NHEt, —NH(iPr), —NMe₂, —NEt₂, —N(iPr)₂, —N(CH₂CH₂OH)₂;

—NHPh, —NHCH₂Ph; piperidino, piperazino, morpholino;

(18) —SO₂Me, —SO₂CF₃, —SO₂Et, —SO₂Ph, —SO₂PhMe, —SO₂CH₂Ph;

(22) -Ph, -Ph-Me, -Ph-OH, -Ph-OMe, -Ph-NH₂, -Ph-F, -Ph-Cl, -Ph-Br, -Ph-I;

pyridinyl, pyrazinyl, pyrimidinyl, pyridazinyl; furanyl, thiophenyl, pyrrolyl, imidazolyl, pyrazolyl, oxazolyl, thiazolyl, thiadiazolyl;

(23) pyrrolidinyl, imidazolidinyl, pyrazolidinyl, piperidinyl, piperazinyl, azepinyl, tetrahydrofuranyl, tetrahydropyranyl, morpholinyl, azetidinyl.

In one embodiment, the substituents are independently (optionally additionally) selected from those defined under the heading "Substituents on the Group A" below.

In one embodiment, the substituents are independently (optionally additionally) selected from those substituents exemplified under the heading "Some Preferred Embodiments."

Additional examples of $R^{N1}$ groups include —(CH₂)ₙ—R, wherein n is independently 1, 2, or 3, and R is independently —H or a substituent on $R^{N1}$, are described below.

Additional examples of $R^{N1}$ groups (here $R^{N1}$ is —(CH₂)ₙ—, n is independently 1, 2, or 3) substituted with (14) amino include the following (where R is, e.g., independently —H or $C_{1-3}$alkyl):

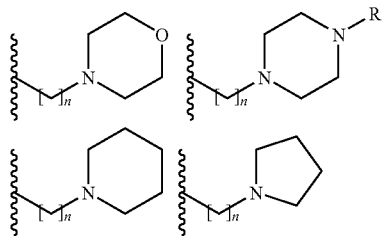

Additional examples of $R^{N1}$ groups (here $R^{N1}$ is —(CH₂)ₙ—, n is independently 1, 2, or 3) substituted with (23) $C_{3-20}$heterocyclyl include the following:

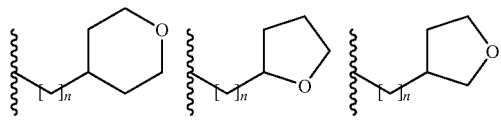

Additional examples of $R^{N1}$ groups (here $R^{N1}$ is —(CH₂)ₙ—, n is independently 1, 2, or 3) substituted with (9) ether include the following (where m is independently 0, 1, 2, or 3):

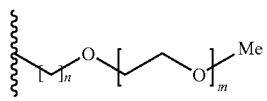

The Group $R^{N2}$

The group $R^{N2}$ is independently as defined for $R^{N1}$.

For example:

In one embodiment, $R^{N2}$ is independently —H or aliphatic saturated $C_{1-3}$alkyl.

In one embodiment, $R^{N2}$ is independently —H or -Me.

In one embodiment, $R^{N2}$ is independently -Me.

In one embodiment, $R^{N2}$ is independently —H, for example, as in:

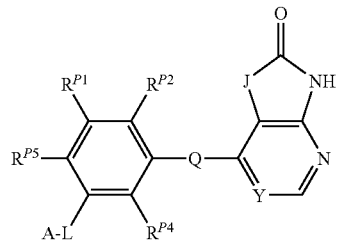

The Group Q

The group Q is independently —(CH₂)ⱼ-M-(CH₂)ₖ—, wherein:

j is independently 0, 1 or 2;
k is independently 0, 1, or 2;
j+k is 0, 1, or 2; and
M is independently —O—, —S—, —NH—, —NMe-, or —CH₂—.

In one embodiment, M is independently —O—, —S—, —NH—, or —NMe-.
In one embodiment, M is independently —O— or —S—.
In one embodiment, M is independently —O—.
In one embodiment, M is independently —S—.
In one embodiment, j is independently 0 or 1.
In one embodiment, j is independently 0.
In one embodiment, k is independently 0 or 1.
In one embodiment, k is independently 0.
In one embodiment, j+k is independently 0, 1, or 2.
In one embodiment, j+k is independently 0 or 1.
In one embodiment, j+k is independently 0.
In one embodiment, j+k is independently 1.
In one embodiment, j+k is independently 2.
In one embodiment, j is 0 and k is 0.
In one embodiment, Q is independently —O—.
In one embodiment, Q is independently —S—.

The Groups $R^{P1}$, $R^{P2}$, and $R^{P4}$

Each of $R^{P1}$, $R^{P2}$, and $R^{P4}$ is independently —H or a group selected from:

aliphatic saturated $C_{1-5}$alkyl;
(e.g., -Me, -Et, -nPr, -iPr, -nBu, -iBu, -sBu, -tBu)
aliphatic $C_{2-5}$alkenyl;
(e.g., —CH=CH₂, —CH₂—CH=CH₂)
aliphatic $C_{2-5}$alkynyl;
(e.g., —C≡CH, —CH₂—C≡CH)
saturated $C_{3-6}$cycloalkyl;
(e.g., cyclopropyl, cyclobutyl, cyclopentyl, cyclohexyl)
$C_{3-6}$cycloalkenyl;
(e.g., cyclopropenyl, cyclobutenyl, cyclopentenyl, cyclohexenyl)
aliphatic saturated $C_{1-5}$haloalkyl;
(e.g., —CF₃, —CH₂CF₃, —CF₂CF₃)
—C(=O)OR¹,
wherein R¹ is —H, $C_{5-12}$aryl-$C_{1-7}$alkyl, $C_{5-12}$aryl, $C_{3-12}$heterocyclyl, or $C_{1-7}$alkyl;
(e.g., —C(=O)OH, —C(=O)OMe, —C(=O)OEt)
—OR² and —SR², wherein $R^2$ is —H, $C_{5-12}$aryl-$C_{1-7}$alkyl, $C_{5-12}$aryl, $C_{3-12}$heterocyclyl, or $C_{1-7}$alkyl;
(e.g., —OH, —OMe, —OEt; —SH, —SMe, SEt)
—C(=O)NR$^3$R$^4$,
    wherein each of $R^3$ and $R^4$ is independently —H; or $C_{5-12}$aryl-$C_{1-7}$alkyl, $C_{5-12}$aryl, $C_{3-12}$heterocyclyl, or $C_{1-7}$alkyl; or $R^3$ and $R^4$ taken together with the nitrogen atom to which they are attached form a ring having from 3 to 7 ring atoms;
    (e.g., —C(=O)NH$_2$, —C(=O)NHMe, —C(=O)NHEt, —C(=O)NMe$_2$,
    —C(=O)morpholino, —C(=O)piperidino, —C(=O)piperizino) —NR$^5$R$^6$,
    wherein each of $R^5$ and $R^6$ is independently —H; or $C_{5-12}$aryl-$C_{1-7}$alkyl, $C_{5-12}$aryl, $C_{3-12}$heterocyclyl, or $C_{1-7}$alkyl; or $R^5$ and $R^6$ taken together with the nitrogen atom to which they are attached form a ring having from 3 to 7 ring atoms;
    (e.g., —NH$_2$, —NHMe, —NMe$_2$, —NHEt, —NEt$_2$, morpholino, piperidino, piperazino)
—NR$^7$C(=O)R$^8$,
    wherein:
        $R^7$ is —H or $C_{1-3}$alkyl;
        $R^8$ is $C_{5-12}$aryl-$C_{1-7}$alkyl, $C_{5-12}$aryl, $C_{3-12}$heterocyclyl, or $C_{1-7}$alkyl;
    (e.g., —NHC(=O)Me, —NMeC(=O)Me, —NHC(=O)Et, —NMeC(=O)Et) —S(=O)R$^9$ or —S(=O)$_2$R$^9$,
    wherein $R^9$ is $C_{1-7}$alkyl, $C_{5-12}$aryl, or $C_{5-12}$aryl-$C_{1-7}$alkyl;
    (e.g., —S(=O)Me, —S(=O)$_2$Me, —S(=O)$_2$Et, —S(=O)$_2$Et)
—F, —Cl, —Br, or —I;
—CN;
    wherein each $C_{1-5}$alkyl, $C_{2-5}$alkenyl, $C_{2-5}$alkynyl, $C_{3-6}$cycloalkyl, $C_{3-6}$cycloalkenyl, $C_{5-12}$aryl-$C_{1-7}$alkyl, $C_{5-12}$aryl, $C_{3-12}$heterocyclyl, and $C_{1-7}$alkyl is independently unsubstituted or substituted;
and additionally $R^{P1}$ and $R^{P2}$ taken together may be —CH=CH—CH=CH—.

In one embodiment, each of $R^{P1}$, $R^{P2}$, and $R^{P4}$ is independently —H or a group selected from:
aliphatic saturated $C_{1-5}$alkyl;
    (e.g., -Me, -Et, -nPr, -iPr, -nBu, -iBu, -sBu, -tBu)
aliphatic $C_{2-5}$alkenyl;
    (e.g., —CH=CH$_2$, —CH$_2$—CH=CH$_2$)
aliphatic $C_{2-5}$alkynyl;
    (e.g., —C≡CH, —CH$_2$—C≡CH)
saturated $C_{3-6}$cycloalkyl;
    (e.g., cyclopropyl, cyclobutyl, cyclopentyl, cyclohexyl)
$C_{3-6}$cycloalkenyl;
    (e.g., cyclopropenyl, cyclobutenyl, cyclopentenyl, cyclohexenyl)
aliphatic saturated $C_{1-5}$haloalkyl;
    (e.g., —CF$_3$, —CH$_2$CF$_3$, —CF$_2$CF$_3$)
—C(=O)OR$^1$,
    wherein $R^1$ is —H, $C_{5-12}$aryl-$C_{1-7}$alkyl, $C_{5-12}$aryl, $C_{3-12}$heterocyclyl, or $C_{1-7}$alkyl;
    (e.g., —C(=O)OH, —C(=O)OMe, —C(=O)OEt)
—OR$^2$,
    wherein $R^2$ is —H, $C_{5-12}$aryl-$C_{1-7}$alkyl, $C_{5-12}$aryl, $C_{3-12}$heterocyclyl, or $C_{1-7}$alkyl;
    (e.g., —OH, —OMe, —OEt)
—SR$^2$,
    wherein $R^2$ is $C_{5-12}$aryl-$C_{1-7}$alkyl, $C_{5-12}$aryl, $C_{3-12}$heterocyclyl, or $C_{1-7}$alkyl;
    (e.g., —SMe, —SEt)
—C(=O)NR$^3$R$^4$,
    wherein each of $R^3$ and $R^4$ is independently —H; or $C_{5-12}$aryl-$C_{1-7}$alkyl, $C_{5-12}$aryl, $C_{3-12}$heterocyclyl, or $C_{1-7}$alkyl; or $R^3$ and $R^4$ taken together with the nitrogen atom to which they are attached form a ring having from 3 to 7 ring atoms;
    (e.g., —C(=O)NH$_2$, —C(=O)NHMe, —C(=O)NHEt, —C(=O) NMe$_2$,
    —C(=O)morpholino, —C(=O)piperidino, —C(=O)piperizino)
—NR$^1$R$^6$,
    wherein each of $R^5$ and $R^6$ is independently —H; or $C_{5-12}$aryl-$C_{1-7}$alkyl, $C_{5-12}$aryl, $C_{3-12}$heterocyclyl, or $C_{1-7}$alkyl; or $R^5$ and $R^6$ taken together with the nitrogen atom to which they are attached form a ring having from 3 to 7 ring atoms;
    (e.g., —NH$_2$, —NHMe, —NMe$_2$, —NHEt, —NEt$_2$, morpholino, piperidino, piperazino)
—NR$^7$C(=O)R$^8$,
    wherein:
        $R^7$ is —H or $C_{1-3}$alkyl;
        $R^8$ is $C_{5-12}$aryl-$C_{1-7}$alkyl, $C_{5-12}$aryl, $C_{3-12}$heterocyclyl, or $C_{1-7}$alkyl;
    (e.g., —NHC(=O)Me, —NMeC(=O)Me, —NHC(=O)Et, —NMeC(=O)Et)
—F, —Cl, —Br, or —I;
—CN;
    wherein each $C_{1-5}$alkyl, $C_{2-5}$alkenyl, $C_{2-5}$alkynyl, $C_{3-6}$cycloalkyl, $C_{3-6}$cycloalkenyl, $C_{5-12}$aryl-$C_{1-7}$alkyl, $C_{5-12}$aryl, $C_{3-12}$heterocyclyl, and $C_{1-7}$alkyl is independently unsubstituted or substituted;
and additionally $R^{P1}$ and $R^{P2}$ taken together may be —CH=CH—CH=CH—.

In one embodiment, each of $R^{P1}$, $R^{P2}$, and $R^{P4}$ is independently —H or a group selected from:
aliphatic saturated $C_{1-5}$alkyl;
    (e.g., -Me, -Et, -nPr, -iPr, -nBu, -iBu, -sBu, -tBu)
aliphatic $C_{2-5}$alkenyl;
    (e.g., —CH=CH$_2$, —CH$_2$—CH=CH$_2$)
aliphatic $C_{2-5}$alkynyl;
    (e.g., —C≡CH, —CH$_2$—C≡CH)
saturated $C_{3-6}$cycloalkyl;
    (e.g., cyclopropyl, cyclobutyl, cyclopentyl, cyclohexyl)
$C_{3-6}$cycloalkenyl;
    (e.g., cyclopropenyl, cyclobutenyl, cyclopentenyl, cyclohexenyl)
aliphatic saturated $C_{1-5}$haloalkyl;
    (e.g., —CF$_3$, —CH$_2$CF$_3$, —CF$_2$CF$_3$)
—C(=O)OR$^1$,
    wherein $R^1$ is —H, $C_{5-12}$aryl-$C_{1-7}$alkyl, $C_{5-12}$aryl, $C_{3-12}$heterocyclyl, or $C_{1-7}$alkyl;
    (e.g., —C(=O)OH, —C(=O)OMe, —C(=O)OEt)
—OR$^2$,
    wherein $R^2$ is —H, $C_{5-12}$aryl-$C_{1-7}$alkyl, $C_{5-12}$aryl, $C_{3-12}$heterocyclyl, or $C_{1-7}$alkyl;
    (e.g., —OH, —OMe, —OEt)
—C(=O)NR$^3$R$^4$,
    wherein each of $R^3$ and $R^4$ is independently —H; or $C_{5-12}$aryl-$C_{1-7}$alkyl, $C_{5-12}$aryl, $C_{3-12}$heterocyclyl, or $C_{1-7}$alkyl; or $R^3$ and $R^4$ taken together with the nitrogen atom to which they are attached form a ring having from 3 to 7 ring atoms;

(e.g., —C(=O)NH$_2$, —C(=O)NHMe, —C(=O)NHEt, —C(=O)NMe$_2$, —C(=O)morpholino, —C(=O)piperidino, —C(=O)piperizino)

—NR$^5$R$^6$,
  wherein each of R$^5$ and R$^6$ is independently —H; or C$_{5-12}$aryl-C$_{1-7}$alkyl, C$_{5-12}$aryl, C$_{3-12}$heterocyclyl, or C$_{1-7}$alkyl; or R$^5$ and R$^6$ taken together with the nitrogen atom to which they are attached form a ring having from 3 to 7 ring atoms;
  (e.g., —NH$_2$, —NHMe, —NMe$_2$, —NHEt, —NEt$_2$, morpholino, piperidino, piperazino)

—NR$^7$C(=O)R$^8$,
  wherein:
    R$^7$ is —H or C$_{1-3}$alkyl;
    R$^8$ is C$_{5-12}$aryl-C$_{1-7}$alkyl, C$_{5-12}$aryl, C$_{3-12}$heterocyclyl, or C$_{1-7}$alkyl;
  (e.g., —NHC(=O)Me, —NMeC(=O)Me, —NHC(=O)Et, —NMeC(=O)Et)

—F, —Cl, —Br, or —I;
—CN;
  wherein each C$_{1-5}$alkyl, C$_{2-5}$alkenyl, C$_{2-5}$alkynyl, C$_{3-6}$cycloalkyl, C$_{3-6}$cycloalkenyl, C$_{5-12}$aryl-C$_{1-7}$alkyl, C$_{5-12}$aryl, C$_{3-12}$heterocyclyl, and C$_{1-7}$alkyl is independently unsubstituted or substituted;

and additionally R$^{P1}$ and R$^{P2}$ taken together may be —CH=CH—CH=CH—.

Examples of optional substituents on R$^{P1}$, R$^{P2}$, and R$^{P4}$ include those described under the heading "Substituents on the Group R$^{N1}$" above, and/or under the heading "Substituents on the Group A" below.

When R$^{P1}$ and R$^{P2}$ together are —CH=CH—CH=CH—, then, together with the atoms they are attached to, they form a benzene ring fused to the central phenylene ring; together they form a naphthyl group. Thus, in one embodiment, the compounds are selected from compounds of the following formula, and pharmaceutically acceptable salts, solvates, amides, esters, ethers, N-oxides, chemically protected forms, and prodrugs thereof:

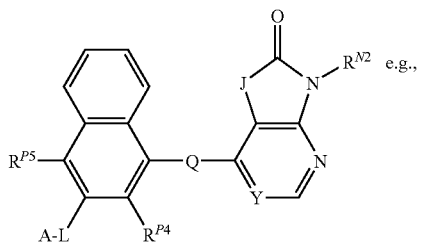 e.g.,

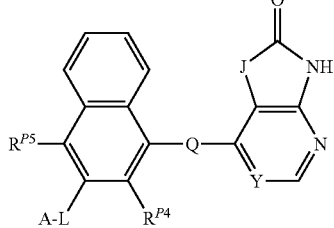

In one embodiment, R$^{P1}$ and R$^{P2}$ taken together are —CH=CH—CH=CH—; and each of R$^{P5}$ and R$^{P4}$ is independently as defined herein.

In one embodiment, R$^{P1}$ and R$^{P2}$ taken together are —CH=CH—CH=CH—; and each of R$^{P5}$ and R$^{P4}$ is independently —H.

In one embodiment, the alternative that R$^{P1}$ and R$^{P2}$ taken together are —CH=CH—CH=CH— is excluded.

The Group R$^{P5}$

In one embodiment, R$^{P5}$ is independently —H or a group selected from:
  R$^{P5}$ is independently —H or a group selected from:
    aliphatic saturated C$_{1-5}$alkyl;
    aliphatic C$_{2-5}$alkenyl;
    aliphatic C$_{2-5}$alkynyl;
    saturated C$_{3-6}$cycloalkyl;
    C$_{3-6}$cycloalkenyl;
    aliphatic saturated C$_{1-5}$haloalkyl;
    —C(=O)OR$^1$,
      wherein R$^1$ is —H, C$_{5-12}$aryl-C$_{1-7}$alkyl, C$_{5-12}$aryl, C$_{3-12}$heterocyclyl, or C$_{1-7}$alkyl;
    —OR$^2$ and —SR$^2$,
      wherein R$^2$ is —H, C$_{5-12}$aryl-C$_{1-7}$alkyl, C$_{5-12}$aryl, C$_{3-12}$heterocyclyl, or C$_{1-7}$alkyl;
    —C(=O)NH$_2$, —C(=O)NHMe, —C(=O)NHEt, —C(=O)NMe$_2$,
    —C(=O)morpholino, —C(=O)piperidino, —C(=O)piperizino;
    —NH$_2$, —NHMe, —NMe$_2$, —NHEt, —NEt$_2$, morpholino, piperidino, piperazino;
    —NHC(=O)Me, —NMeC(=O)Me, —NHC(=O)Et, —NMeC(=O)Et;
    —S(=O)R$^9$ or —S(=O)$_2$R$^9$,
      wherein R$^9$ is C$_{1-7}$alkyl, C$_{5-12}$aryl, or C$_{5-12}$aryl-C$_{1-7}$alkyl;
    —F, —Cl, —Br, or —I;
    —CN;
    wherein each C$_{1-5}$alkyl, C$_{2-5}$alkenyl, C$_{2-5}$alkynyl, C$_{3-6}$cycloalkyl, C$_{3-6}$cycloalkenyl, C$_{5-12}$aryl-C$_{1-7}$alkyl, C$_{5-12}$aryl, C$_{3-12}$heterocyclyl, and C$_{1-7}$alkyl is independently unsubstituted or substituted;
    and additionally R$^{P1}$ and R$^{P5}$ taken together may be —CH=CH—CH=CH—.

In one embodiment, R$^{P5}$ is independently —H or a group selected from:
  aliphatic saturated C$_{1-5}$alkyl;
    (e.g., -Me, -Et, -nPr, -iPr, -nBu, -iBu, -sBu, -tBu)
  aliphatic C$_{2-5}$alkenyl;
    (e.g., —CH=CH$_2$, —CH$_2$—CH=CH$_2$)
  aliphatic C$_{2-5}$alkynyl;
    (e.g., —C≡CH, —CH$_2$—C≡CH)
  saturated C$_{3-6}$cycloalkyl;
    (e.g., cyclopropyl, cyclobutyl, cyclopentyl, cyclohexyl)
  C$_{3-6}$cycloalkenyl;
    (e.g., cyclopropenyl, cyclobutenyl, cyclopentenyl, cyclohexenyl)
  aliphatic saturated C$_{1-5}$haloalkyl;
    (e.g., —CF$_3$, —CH$_2$CF$_3$, —CF$_2$CF$_3$)
  —C(=O)OR$^1$,
    wherein R$^1$ is —H, C$_{5-12}$aryl-C$_{1-7}$alkyl, C$_{5-12}$aryl, C$_{3-12}$heterocyclyl, or C$_{1-7}$alkyl;
    (e.g., —C(=O)OH, —C(=O)OMe, —C(=O)OEt)
  —OR$^2$,
    wherein R$^2$ is —H, C$_{5-12}$aryl-C$_{1-7}$alkyl, C$_{5-12}$aryl, C$_{3-12}$heterocyclyl, or C$_{1-7}$alkyl;
    (e.g., —OH, —OMe, —OEt)
  —C(=O)NH$_2$, —C(=O)NHMe, —C(=O)NHEt, —C(=O)NMe$_2$,
  —C(=O)morpholino, —C(=O)piperidino, —C(=O)piperizino;
  —NH$_2$, —NHMe, —NMe$_2$, —NHEt, —NEt$_2$, morpholino, piperidino, piperazino;

—NHC(=O)Me, —NMeC(=O)Me, —NHC(=O)Et, —NMeC(=O)Et;
—F, —Cl, —Br, or —I;
—CN;
wherein each $C_{1-5}$alkyl, $C_{2-5}$alkenyl, $C_{2-5}$alkynyl, $C_{3-6}$cycloalkyl, $C_{3-6}$cycloalkenyl, $C_{5-12}$aryl-$C_{1-7}$alkyl, $C_{5-12}$aryl, $C_{3-12}$heterocyclyl, and $C_{1-7}$alkyl is independently unsubstituted or substituted;
and additionally $R^{P1}$ and $R^{P2}$ taken together may be —CH=CH—CH=CH—.

Examples of optional substituents on $R^{P5}$ include those described under the heading "Substituents on the Group $R^{N1}$" above, and/or under the heading "Substituents on the Group A" below.

When $R^{P1}$ and $R^{P5}$ together are —CH=CH—CH=CH—, then, together with the atoms they are attached to, they form a benzene ring fused to the central phenylene ring; together they form a naphthyl group. Thus, in one embodiment, the compounds are selected from compounds of the following formula, and pharmaceutically acceptable salts, solvates, amides, esters, ethers, N-oxides, chemically protected forms, and prodrugs thereof:

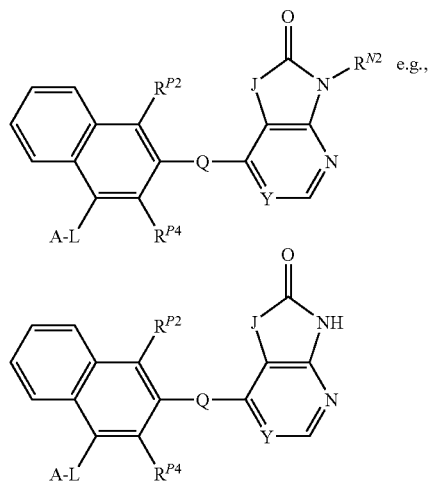

In one embodiment, $R^{P1}$ and $R^{P5}$ taken together are —CH=CH—CH=CH—; and each of $R^{P2}$ and $R^{P4}$ is independently as defined herein.

In one embodiment, $R^{P1}$ and $R^{P5}$ taken together are —CH=CH—CH=CH—; and each of $R^{P2}$ and $R^{P4}$ is independently —H.

In one embodiment, the alternative that $R^{P1}$ and $R^{P5}$ taken together are —CH=CH—CH=CH— is excluded.

The Groups $R^{P1}$, $R^{P2}$, $R^{P5}$, and $R^{P4}$

In one embodiment, each of $R^{P1}$, $R^{P2}$, $R^{P5}$, and $R^{P4}$ is independently —H or a group selected from:
-Me, -Et, -nPr, -iPr, -nBu, -iBu, -sBu, -tBu;
—CH=CH$_2$, —CH$_2$—CH=CH$_2$;
—C≡CH, —CH$_2$—C≡CH;
cyclopropyl, cyclobutyl;
cyclopropenyl, cyclobutenyl;
—CF$_3$, —CH$_2$CF$_3$, —CF$_2$CF$_3$;
—S(=O)Me, —S(=O)$_2$Me, —S(=O)$_2$Et, —S(=O)$_2$Et;
—F, —Cl, —Br, or —I;
—CN; and
—SR$^2$, wherein R$^2$ is aliphatic saturated $C_{1-3}$alkyl.

In one embodiment, each of $R^{P1}$, $R^{P2}$, $R^{P5}$, and $R^{P4}$ is independently —H or a group selected from:
-Me, -Et, -nPr, -iPr, -nBu, -iBu, -sBu, -tBu;
—CH=CH$_2$, —CH$_2$—CH=CH$_2$;
—C≡CH, —CH$_2$—C≡CH;
cyclopropyl, cyclobutyl;
cyclopropenyl, cyclobutenyl;
—CF$_3$, —CH$_2$CF$_3$, —CF$_2$CF$_3$;
—F, —Cl, —Br, or —I; and
—CN.

In one embodiment, each of $R^{P1}$, $R^{P2}$, $R^{P5}$, and $R^{P4}$ is independently —H or a group selected from:
aliphatic saturated $C_{1-3}$alkyl,
aliphatic $C_{2-3}$alkenyl,
aliphatic saturated $C_{1-5}$haloalkyl,
—S(=O)R$^9$ and —S(=O)$_2$R$^9$, wherein R$^9$ is aliphatic saturated $C_{1-3}$alkyl;
—F, —Cl, and
—SR$^2$, wherein R$^2$ is aliphatic saturated $C_{1-3}$alkyl.

In one embodiment, each of $R^{P1}$, $R^{P2}$, $R^{P5}$, and $R^{P4}$ is independently —H or a group selected from:
aliphatic saturated $C_{1-3}$alkyl,
aliphatic $C_{2-3}$alkenyl,
aliphatic saturated $C_{1-5}$haloalkyl, and
—F, —Cl.

In one embodiment, each of $R^{P1}$, $R^{P2}$, $R^{P5}$, and $R^{P4}$ is independently —H or a group selected from:
-Me, -Et, -nPr, -iPr;
—CH=CH$_2$, —CH$_2$—CH=CH$_2$;
—CF$_3$;
—S(=O)Me, —S(=O)$_2$Me;
—F, —Cl; and
—SMe, —SEt.

In one embodiment, each of $R^{P1}$, $R^{P2}$, $R^{P5}$, and $R^{P4}$ is independently —H or a group selected from:
-Me, -Et, -nPr, -iPr;
—CH=CH$_2$, —CH$_2$—CH=CH$_2$;
—CF$_3$; and
—F, —Cl.

In one embodiment, each of $R^{P1}$, $R^{P2}$, $R^{P5}$, and $R^{P4}$ is independently —H, -Me, —CF$_3$, —S(=O)Me, —S(=O)$_2$Me, —F, —Cl, or —SMe.

In one embodiment, each of $R^{P1}$, $R^{P2}$, $R^{P5}$, and $R^{P4}$ is independently —H, -Me, —CF$_3$, —F, or —Cl.

In one embodiment, each of $R^{P1}$ and $R^{P2}$ is independently as defined above, and each of $R^{P5}$ and $R^{P4}$ is independently —H.

In one embodiment, each of $R^{P1}$ and $R^{P2}$ is independently as defined above, but is other than —H, and each of $R^{P5}$ and $R^{P4}$ is independently —H.

In one embodiment, each of $R^{P1}$ and $R^{P5}$ is independently as defined above, and each of $R^{P2}$ and $R^{P4}$ is independently —H.

In one embodiment, each of $R^{P1}$ and $R^{P5}$ is independently as defined above, but is other than —H, and each of $R^{P2}$ and $R^{P4}$ is independently —H.

In one embodiment, each of $R^{P2}$ and $R^{P5}$ is independently as defined above, and each of $R^{P1}$ and $R^{P4}$ is independently —H.

In one embodiment, each of $R^{P2}$ and $R^{P5}$ is independently as defined above, but is other than —H, and each of $R^{P1}$ and $R^{P4}$ is independently —H.

In one embodiment, exactly three of $R^{P1}$, $R^{P2}$, $R^{P5}$, and $R^{P4}$ is independently as defined above, but is other than —H, and the remaining one is independently —H.

In one embodiment, exactly one of $R^{P1}$, $R^{P2}$, $R^{P5}$, and $R^{P4}$ is independently as defined above, but is other than —H, and each of the remainder is independently —H.

In one embodiment, each of $R^{P1}$, $R^{P2}$, $R^{P5}$, and $R^{P4}$ is independently —H.

In one embodiment, $R^{P1}$ and $R^{P2}$ taken together are —CH=CH—CH=CH—; and each of $R^{P5}$ and $R^{P4}$ is independently as defined herein.

In one embodiment, $R^{P1}$ and $R^{P2}$ taken together are —CH=CH—CH=CH—; and each of $R^{P5}$ and $R^{P4}$ is independently —H.

In one embodiment, $R^{P1}$ and $R^{P5}$ taken together are —CH=CH—CH=CH—; and each of $R^{P2}$ and $R^{P4}$ is independently as defined herein.

In one embodiment, $R^{P1}$ and $R^{P5}$ taken together are —CH=CH—CH=CH—; and each of $R^{P2}$ and $R^{P4}$ is independently —H.

The Right-Hand Motif

In one embodiment, the right-hand motif is:

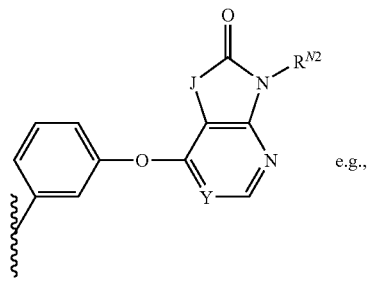

e.g.,

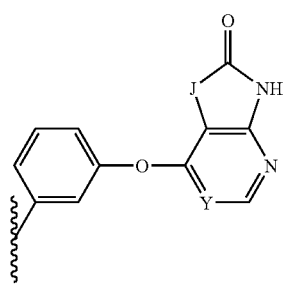

In one embodiment, the right-hand motif is:

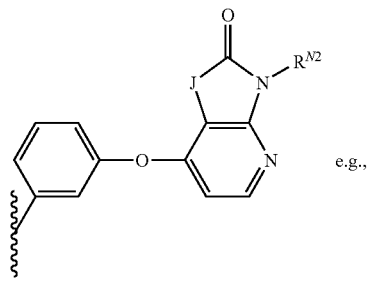

e.g.,

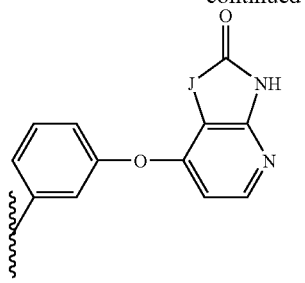

In one embodiment, the right-hand motif is:

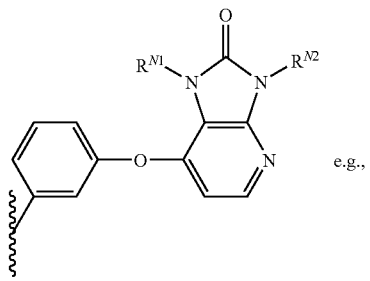

e.g.,

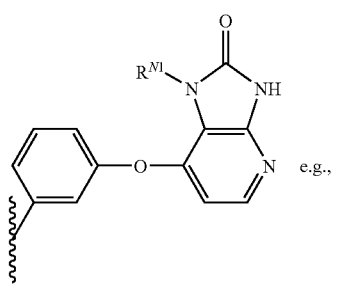

e.g.,

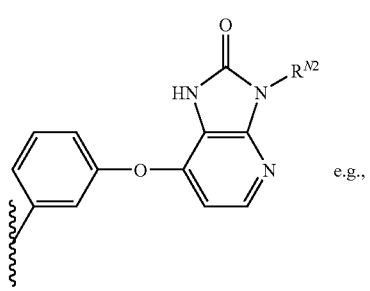

e.g.,

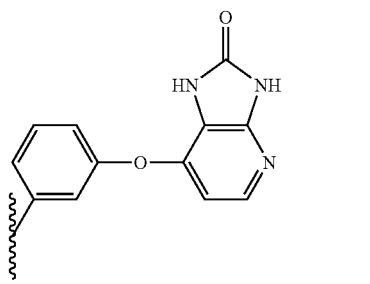

In one embodiment, the right-hand motif is:

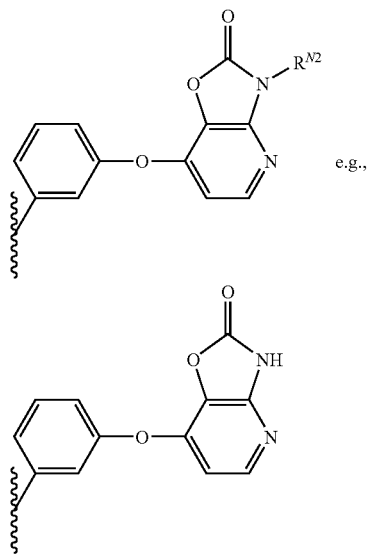

e.g.,

The Linker Group L

The linker group, L, is independently:
a linker group formed by a chain of 2, 3, or 4 linker moieties; wherein:
each linker moiety is independently —$CH_2$—, —$NR^N$—, —C(=X)—, or —S(=O)$_2$—;
either: exactly one linker moiety is —$NR^N$—,
or: exactly two linker moieties are —$NR^N$—;
either: exactly one linker moiety is —C(=X)—, and no linker moiety is —S(=O)$_2$—,
or: exactly one linker moiety is —S(=O)$_2$—, and no linker moiety is —C(=X)—;
no two adjacent linker moieties are —$NR^N$—.

In one embodiment, L, is independently:
a linker group formed by a chain of 2, 3, or 4 linker moieties; wherein:
each linker moiety is independently —$CH_2$—, —$NR^N$—, or —C(=X)—;
either: exactly one linker moiety is —$NR^N$—,
or: exactly two linker moieties are —$NR^N$—;
exactly one linker moiety is —C(=X)—;
no two adjacent linker moieties are —$NR^N$—;
or:
a linker group formed by a chain of 2, 3, or 4 linker moieties; wherein:
each linker moiety is independently —$CH_2$—, —$NR^N$—, or —S(=O)$_2$—;
either: exactly one linker moiety is —$NR^N$—,
or: exactly two linker moieties are —$NR^N$—;
exactly one linker moiety is —S(=O)$_2$—;
no two adjacent linker moieties are —$NR^N$—.

The Linker Group L: Amides, Ureas, etc.

In one embodiment, L is independently:
a linker group formed by a chain of 2, 3, or 4 linker moieties; wherein:
each linker moiety is independently —$CH_2$—, —$NR^N$—, or —C(=X)—;
either: exactly one linker moiety is —$NR^N$—,
or: exactly two linker moieties are —$NR^N$—;
exactly one linker moiety is —C(=X)—;
no two adjacent linker moieties are —$NR^N$—.

The phrase "no two adjacent linker moieties are —$NR^N$—" is intended to exclude possibilities such as —$NR^N$—$NR^N$—C(=X)—.

In one embodiment, exactly one linker moiety is —$NR^N$—.
In one embodiment, exactly two linker moieties are —$NR^N$—.
In one embodiment, no linker moiety is —$CH_2$—.
In one embodiment, exactly one linker moiety is —$CH_2$—.
In one embodiment, exactly two linker moieties are —$CH_2$—.

In one embodiment, the linker group, L, includes a group —$NR^N$—C(=X)— or —C(=X)—$NR^N$— (as in, for example, —$NR^N$—C(=X), —$NR^N$—C(=X)—$NR^N$—, —$NR^N$—$CH_2$—C(=X)—$NR^N$—, etc.).

In one embodiment, the linker group, L, includes a group —$NR^N$—C(=X)—$NR^N$— (as in, for example, —$NR^N$—C(=X)—$NR^N$—, —$NR^N$—C(=X)—$NR^N$—$CH_2$—, etc.).

In one embodiment, the linker group, L, is formed by a chain of 2 or 3 linker moieties.
In one embodiment, the linker group, L, is formed by a chain of 3 or 4 linker moieties.
In one embodiment, the linker group, L, is formed by a chain of 2 linker moieties.
In one embodiment, the linker group, L, is formed by a chain of 3 linker moieties.
In one embodiment, the linker group, L, is formed by a chain of 4 linker moieties.

In one embodiment, the group A-L- is independently selected from:
A-$NR^N$—C(=X)—$NR^N$— ("ureas/thioureas")
A-$CH_2$—$NR^N$—C(=X)—$NR^N$—
A-$NR^N$—C(=X)—$NR^N$—$CH_2$—

In one embodiment, the group A-L- is independently selected from:
A-$NR^N$—C(=X)— ("forward amides/thioamides")
A-$CH_2$—$NR^N$—C(=X)—
A-$NR^N$—C(=X)—$CH_2$—
A-$CH_2$—$NR^N$—C(=X)—$CH_2$—
A-$CH_2$—$CH_2$—$NR^N$—C(=X)—
A-$NR^N$—C(=X)—$CH_2$—$CH_2$—
A-$NR^N$—C(=X)—$CH_2$—$NR^N$— ("forward amides/thioamide amines")
A-$NR^N$—$CH_2$—$NR^N$—C(=X)—
A-C(=X)—$NR^N$— ("reverse amides/thioamides")
A-$CH_2$—C(=X)—$NR^N$—
A-C(=X)—$NR^N$—$CH_2$—
A-$CH_2$—C(=X)—$NR^N$—$CH_2$—
A-$CH_2$—$CH_2$—C(=X)—$NR^N$—
A-C(=X)—$NR^N$—$CH_2$—$CH_2$—
A-$NR^N$—$CH_2$—C(=X)—$NR^N$— ("reverse amides/thioamide amines")
A-C(=X)—$NR^N$—$CH_2$—$NR^N$—

In one embodiment, the group A-L- is independently selected from:
A-C(=X)—$CH_2$—$NR^N$—
A-C(=X)—$CH_2$—$NR^N$—$CH_2$—
A-C(=X)—$CH_2$—$CH_2$—$NR^N$—
A-$CH_2$—C(=X)—$CH_2$—$NR^N$—
A-$NR^N$—$CH_2$—C(=X)—
A-$NR^N$—$CH_2$—C(=X)—$CH_2$—
A-$NR^N$—$CH_2$—$CH_2$—C(=X)—
A-$CH_2$—$NR^N$—$CH_2$—C(=X)—

In one embodiment, the group A-L- is independently selected from:
A-$NR^N$—C(=X)—$NR^N$—
A-$CH_2$—$NR^N$—C(=X)—$NR^N$—
A-$NR^N$—C(=X)—

A-C(=X)—NR$^N$—
A-NR$^N$—CH$_2$—C(=X)—NR$^N$—
A-CH$_2$—NR$^N$—C(=X)—

In one embodiment, the group A-L- is independently selected from:
A-NR$^N$—C(=X)—NR$^N$ ("ureas/thioureas")
A-CH$_2$—NR$^N$—C(=X)—NR$^N$—
A-NR$^N$—C(=X)—NR$^N$CH$_2$—

In one embodiment, the group A-L- is independently A-NR$^N$—C(=X)—NR$^N$—.

In one embodiment, the group A-L- is independently selected from:
A-NR$^N$—C(=X)—
A-C(=X)—NR$^N$—

In one embodiment, the group A-L- is independently: A-C(=X)—NR$^N$—.

In one embodiment, X is =O ("ureas", "amides", etc.).

In one embodiment, X is =S ("thioureas", "thioamides", etc.).

In one embodiment, the group A-L- is independently A-NR$^N$—C(=O)—NR$^N$—.

In one embodiment, the group A-L- is independently A-NH—C(=O)—NH—.

In one embodiment, the group A-L- is independently: A-C(=O)—NR$^N$—.

In one embodiment, the group A-L- is independently: A-C(=O)—NH—.

In one embodiment, the group A-L- is independently A-NR$^N$—C(=O)—.

In one embodiment, the group A-L- is independently A-NH—C(=O)—.

The Linker Group L: Sulfonamides Etc.

In one embodiment, L is independently:
a linker group formed by a chain of 2, 3, or 4 linker moieties; wherein:
each linker moiety is independently —CH$_2$—, —NR$^N$—, or —S(=O)$_2$—;
either: exactly one linker moiety is —NR$^N$—,
or: exactly two linker moieties are —NR$^N$—;
exactly one linker moiety is —S(=O)$_2$—;
no two adjacent linker moieties are —NR$^N$—.

The phrase "no two adjacent linker moieties are —NR$^N$—" is intended to exclude possibilities such as —NR$^N$—NR$^N$—S(=O)$_2$—.

In one embodiment, exactly one linker moiety is —NR$^N$—.

In one embodiment, exactly two linker moieties are —NR$^N$—.

In one embodiment, no linker moiety is —CH$_2$—.

In one embodiment, exactly one linker moiety is —CH$_2$—.

In one embodiment, exactly two linker moieties are —CH$_2$—.

In one embodiment, the linker group, L, includes a group —NR$^N$—S(=O)$_2$— or —S(=O)$_2$—NR$^N$— (as in, for example, —NR$^N$—S(=O)$_2$—, —NR$^N$—S(=O)$_2$—NR$^N$—, —NR$^N$—CH$_2$—S(=O)$_2$—NR$^N$—, etc.).

In one embodiment, the linker group, L, includes a group —NR$^N$—S(=O)$_2$—NR$^N$— (as in, for example, —NR$^N$—S(=O)$_2$—NR$^N$—, —NR$^N$—S(=O)$_2$—NR$^N$—CH$_2$—, etc.).

In one embodiment, the linker group, L, is formed by a chain of 2 or 3 linker moieties.

In one embodiment, the linker group, L, is formed by a chain of 3 or 4 linker moieties.

In one embodiment, the linker group, L, is formed by a chain of 2 linker moieties.

In one embodiment, the linker group, L, is formed by a chain of 3 linker moieties.

In one embodiment, the linker group, L, is formed by a chain of 4 linker moieties.

In one embodiment, the group A-L- is independently selected from:
A-NR$^N$—S(=O)$_2$—NR$^N$— ("sulfamides")
A-NR$^N$—S(=O)$_2$—NR$^N$—CH$_2$—
A-CH$_2$—NR$^N$—S(=O)$_2$—NR$^N$—

In one embodiment, the group A-L- is independently selected from:
A-NR$^N$—S(=O)$_2$— ("forward sulfonamides")
A-NR$^N$—S(=O)$_2$—CH$_2$—
A-CH$_2$—NR$^N$—S(=O)$_2$—
A-CH$_2$—NR$^N$—S(=O)$_2$—CH$_2$—
A-CH$_2$—CH$_2$—NR$^N$—S(=O)$_2$—
A-NR$^N$—S(=O)$_2$—CH$_2$—CH$_2$—
A-NR$^N$—S(=O)$_2$—CH$_2$—NR$^N$— ("forward sulfonamides amine")
A-NR$^N$—CH$_2$—NR$^N$—S(=O)$_2$—
A-S(=O)$_2$—NR$^N$— ("reverse sulfonamides")
A-S(=O)$_2$—NR$^N$—CH$_2$—
A-CH$_2$—S(=O)$_2$—NR$^N$—
A-CH$_2$—S(=O)$_2$—NR$^N$—CH$_2$—
A-CH$_2$—CH$_2$—S(=O)$_2$—NR$^N$—
A-S(=O)$_2$—NR$^N$—CH$_2$—CH$_2$—
A-S(=O)$_2$—NR$^N$—CH$_2$—NR$^N$— ("reverse sulfonamides amine")
A-NR$^N$—CH$_2$—S(=O)$_2$—NR$^N$—

In one embodiment, the group A-L- is independently selected from:
A-NR$^N$—S(=O)$_2$—NR$^N$—
A-NR$^N$—S(=O)$_2$—
A-S(=O)$_2$—NR$^N$—
A-CH$_2$—NR$^N$—S(=O)$_2$—NR$^N$—
A-CH$_2$—NR$^N$—S(=O)$_2$—

In one embodiment, the group A-L- is independently selected from:
A-NR$^N$—S(=O)$_2$—
A-S(=O)$_2$—NR$^N$—

In one embodiment, the group A-L- is independently: A-S(=O)$_2$—NR$^N$—.

In one embodiment, the group A-L- is independently: A-S(=O)$_2$—NH—.

The Groups R$^N$

Each of the groups R$^N$ is independently —H, saturated C$_{1-3}$alkyl, or C$_{2-3}$alkenyl.

In one embodiment, each of the groups R$^N$ is independently —H or saturated C$_{1-3}$alkyl.

In one embodiment, each of the groups R$^N$ is independently —H or -Me.

In one embodiment, each of the groups R$^N$ is independently —H.

For example:

In one embodiment, the group A-L- is independently A-NH—C(=X)—NH—.

In one embodiment, the group A-L- is independently A-NH—C(=O)—NH—.

Some Preferred Classes of Compounds: Ureas
One particularly preferred class of compounds has the following motif:
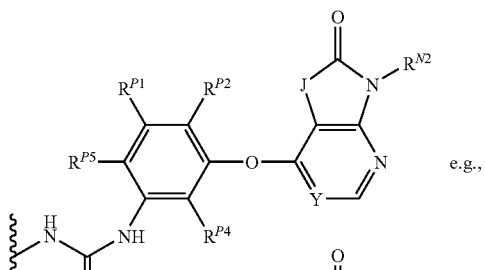
e.g.,
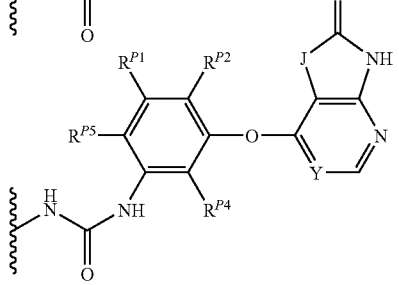
One particularly preferred class of compounds has the following motif:
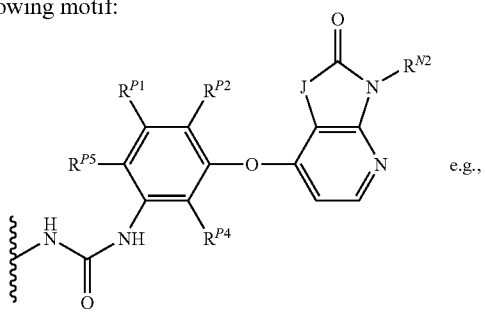
e.g.,
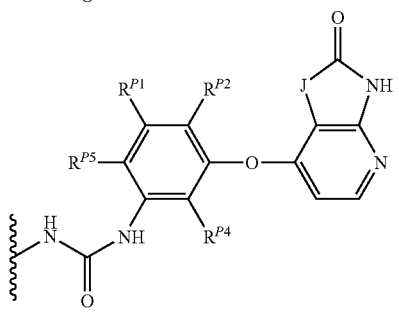
One particularly preferred class of compounds has the following motif:
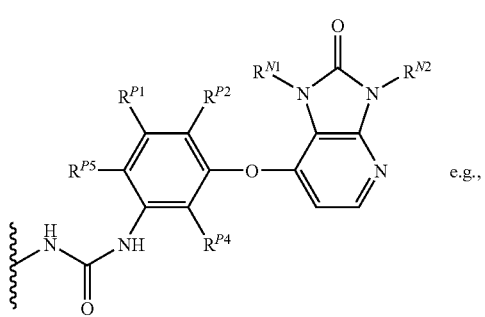
e.g.,
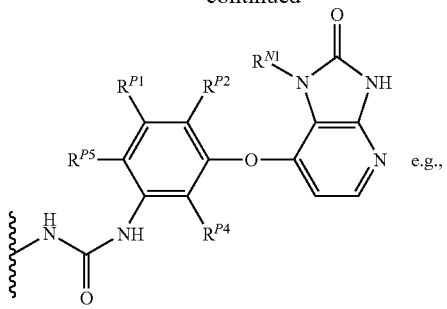
e.g.,
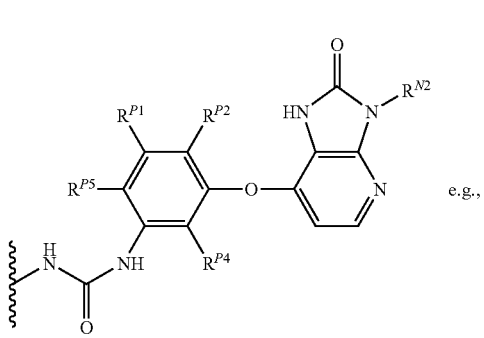
e.g.,
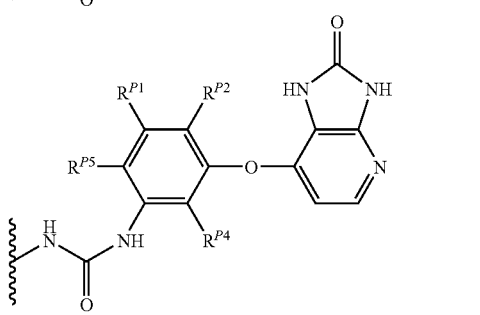
One particularly preferred class of compounds has the following motif:
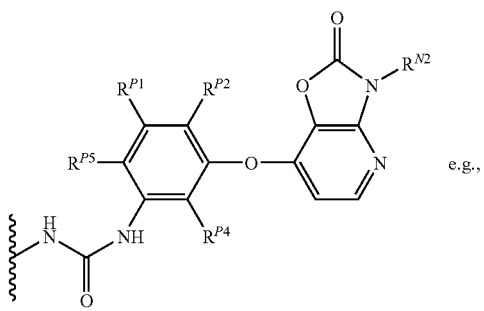
e.g.,
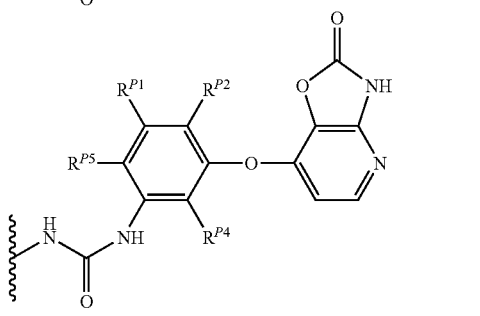

One particularly preferred class of compounds has the following motif:
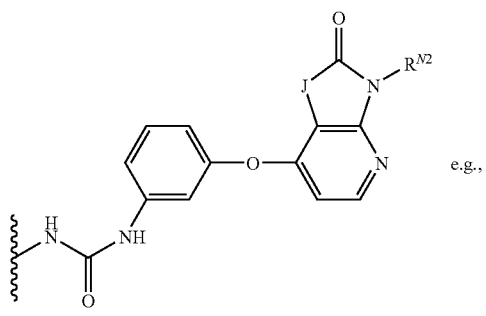 e.g.,
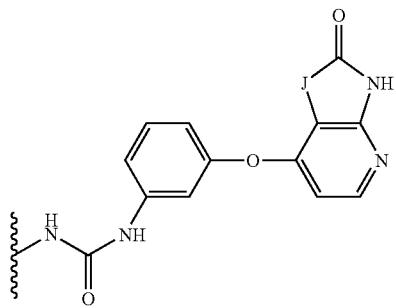
One particularly preferred class of compounds has the following motif:
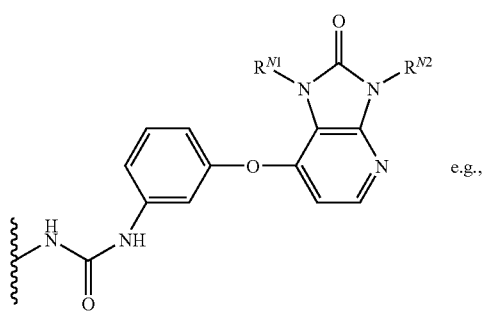 e.g.,
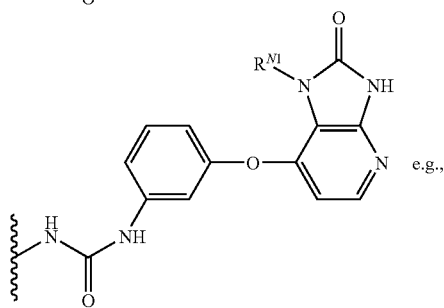 e.g.,
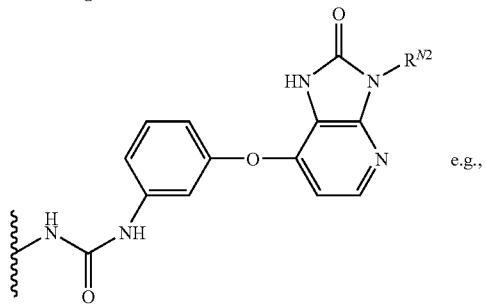 e.g.,
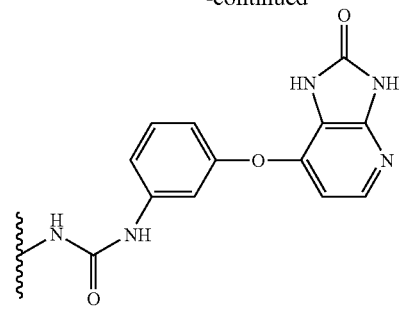
One particularly preferred class of compounds has the following motif:
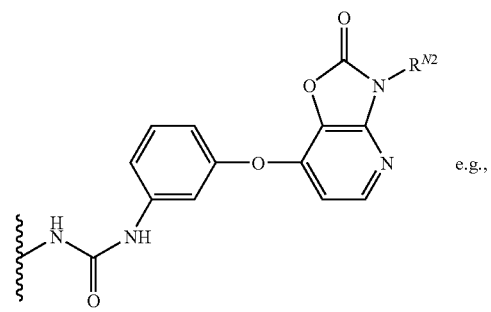 e.g.,
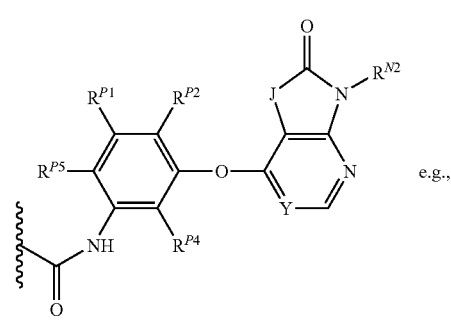
Some Preferred Classes of Compounds: Amides
One particularly preferred class of compounds has the following motif:
 e.g.,

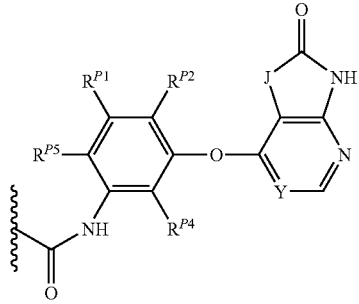
One particularly preferred class of compounds has the following motif:
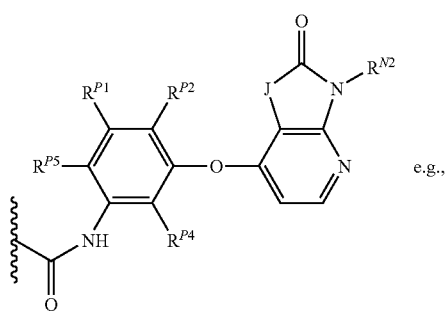
e.g.,
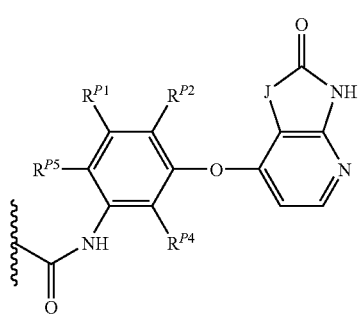
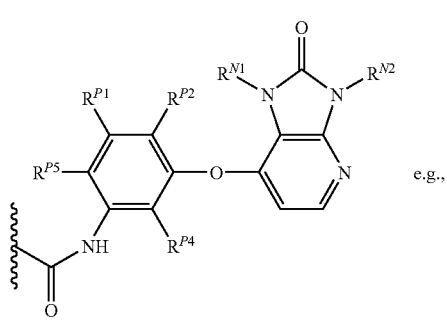
e.g.,
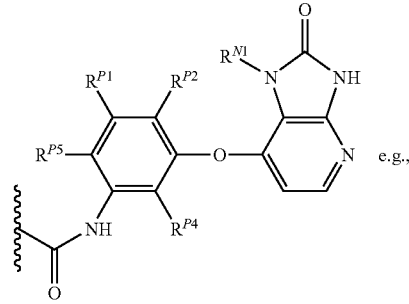
e.g.,
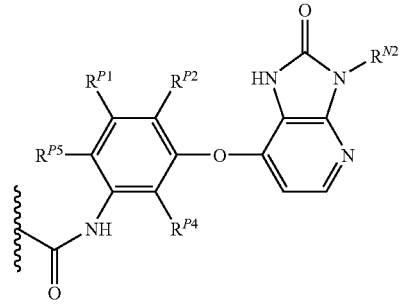
e.g.,
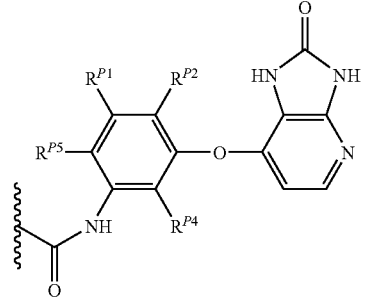
One particularly preferred class of compounds has the following motif:
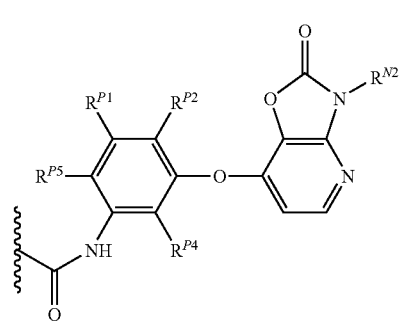
e.g.,
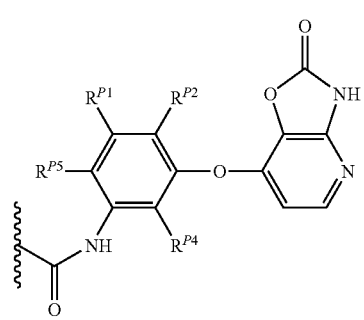

One particularly preferred class of compounds has the following motif:
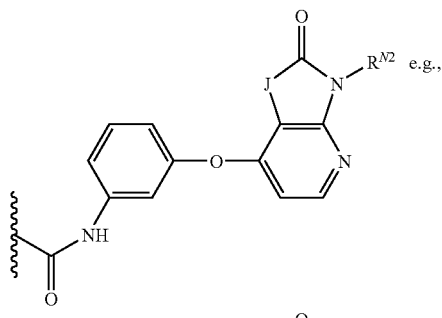
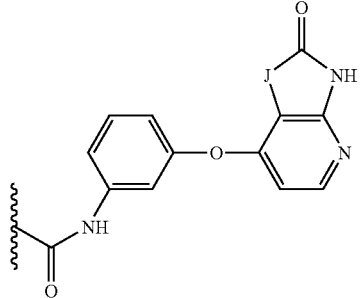
One particularly preferred class of compounds has the following motif:
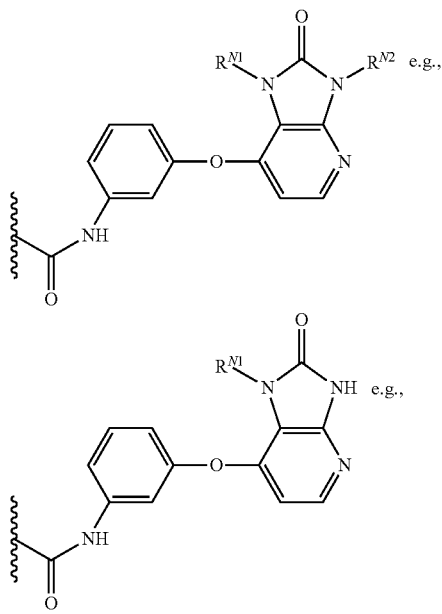
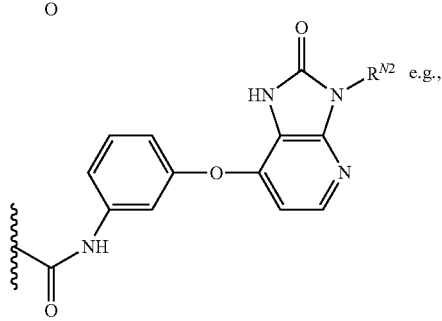
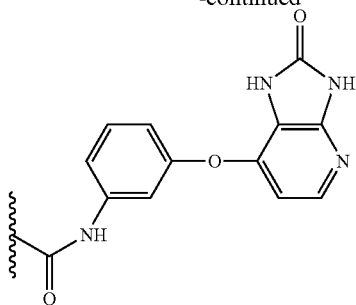
One particularly preferred class of compounds has the following motif:
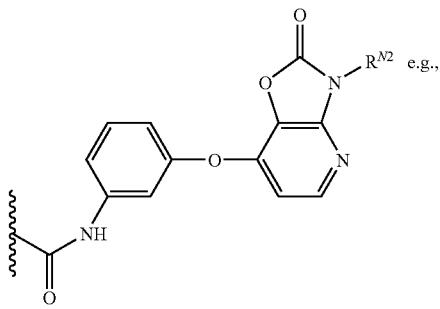
Some Preferred Classes of Compounds: Reverse Amides
One particularly preferred class of compounds has the following motif:
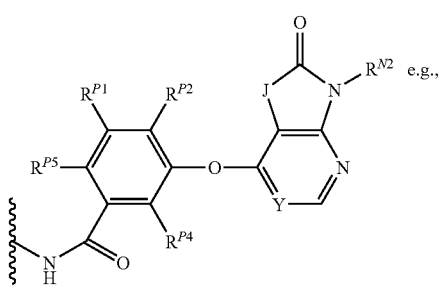

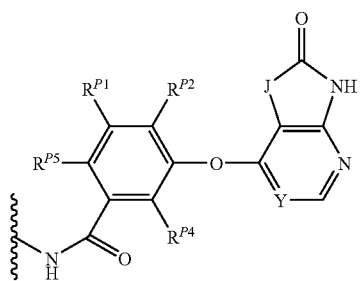
One particularly preferred class of compounds has the following motif:
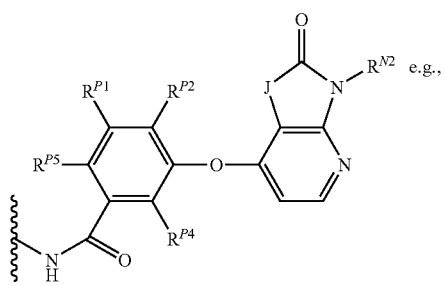
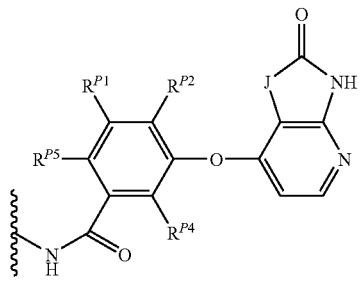
One particularly preferred class of compounds has the following motif:
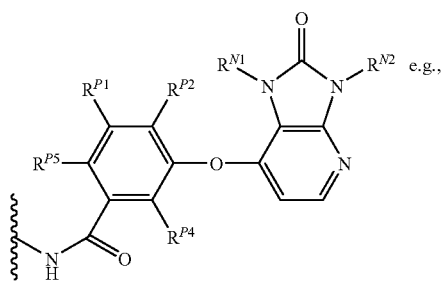
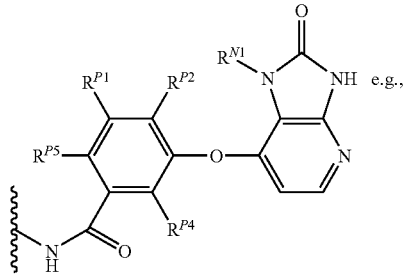
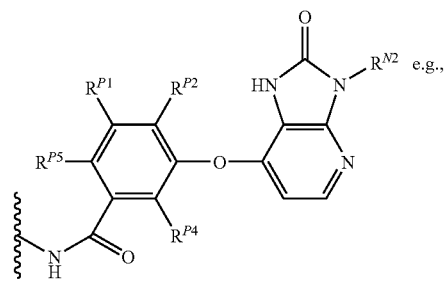
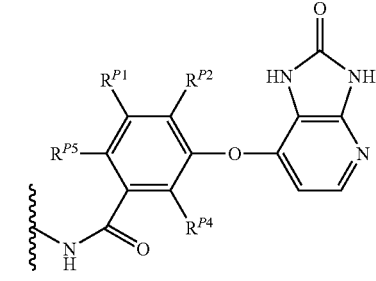
One particularly preferred class of compounds has the following motif:
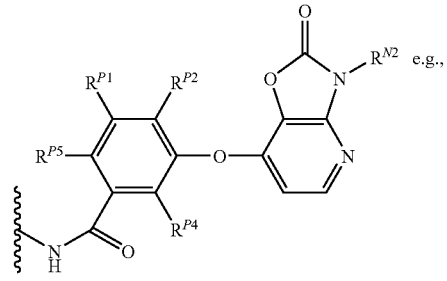
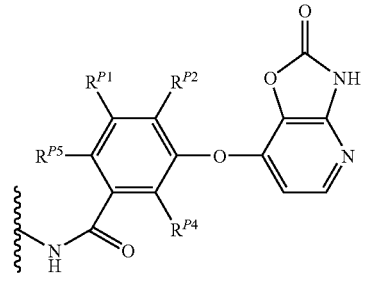
One particularly preferred class of compounds has the following motif:
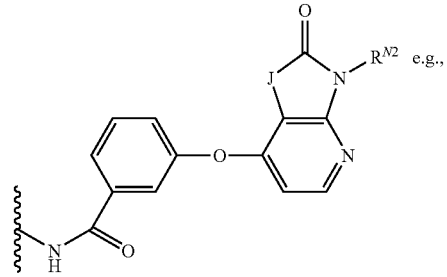

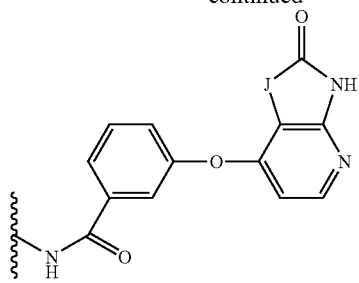

One particularly preferred class of compounds has the following motif:

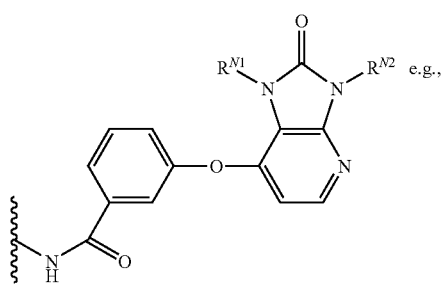 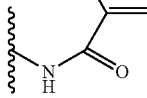

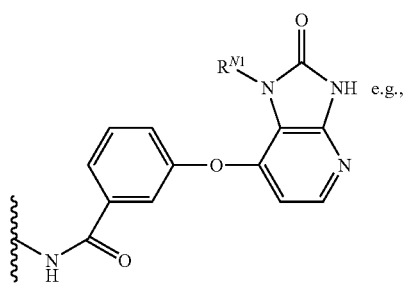

One particularly preferred class of compounds has the following motif:

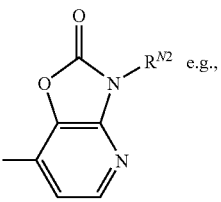

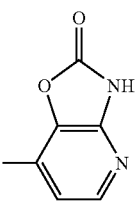

Some Preferred Classes of Compounds: Sulfonamides

In one embodiment, the —NH—C(=O)—NH— group in the structures shown above under the heading "Some Preferred Classes of Compounds: Ureas" is replaced with —S(=O)$_2$NH—, as in for example:

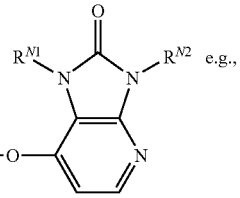

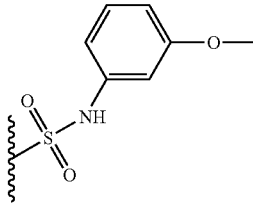

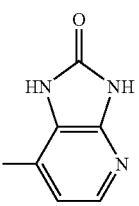

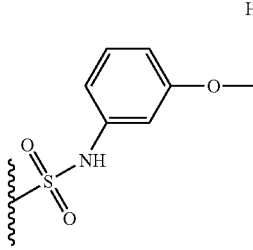

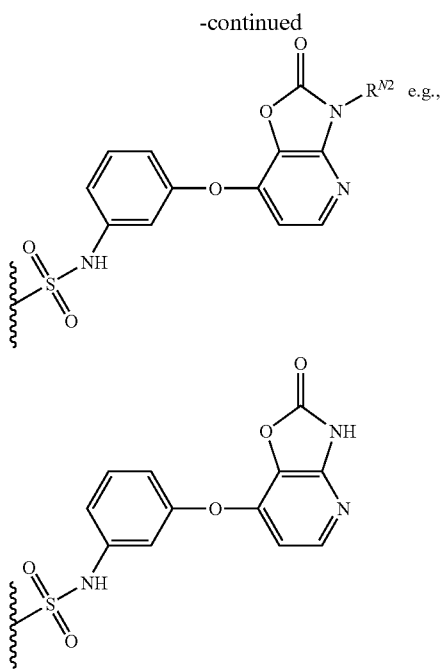

The Group A

The group A is independently:
$C_{6-14}$carboaryl,
$C_{5-14}$heteroaryl,
$C_{3-12}$carbocyclic,
$C_{3-12}$heterocyclic;
and is independently unsubstituted or substituted.

In one embodiment, A is independently $C_{6-14}$carboaryl or $C_{5-14}$heteroaryl, and is independently unsubstituted or substituted.

In one embodiment, A is independently $C_{6-12}$carboaryl or $C_{5-12}$heteroaryl, and is independently unsubstituted or substituted.

In one embodiment, A is independently $C_{6-10}$carboaryl or $C_{5-10}$heteroaryl, and is independently unsubstituted or substituted.

In one embodiment, A is independently monocyclic or bicyclic (e.g., "5-6" fused rings, "6-6" fused rings) $C_{6-10}$carboaryl or monocyclic or bicyclic $C_{5-10}$heteroaryl (e.g., having 1, 2, 3, 4, or 5 aromatic ring heteroatoms, e.g., selected from nitrogen and oxygen), and is independently unsubstituted or substituted.

In one embodiment, A is independently monocyclic $C_6$carboaryl or monocyclic $C_{5-6}$heteroaryl (e.g., having 1, 2, or 3 aromatic ring heteroatoms, e.g., selected from nitrogen and oxygen), and is independently unsubstituted or substituted.

In one embodiment, A is independently derived from: benzene (i.e., phenyl), naphthalene (i.e., naphthyl), fluorene, pyrrole, pyridine, furan, thiophene, oxazole, isoxazole, oxadiazole, thiazole, isothiazole, thiadiazole, imidazole, pyrazole, pyridazine, pyrimidine, pyrazine, tetrazole, benzofuran, chroman, indole, isoindole, 2,3-dihydro-1H-indole, benzimidazole, 1,3-dihydrobenzimidazole, benzoxazole, benzothiofuran, benzothiazole, benzothiadiazole, quinoline, isoquinoline, pyridopyridine, quinoxaline, 1,2,3,4-tetrahydroquinoxaline, 3,4-dihydro-2H-benzo[1,4]oxazine, benzodiazepine, carbazole, acridine; and is independently unsubstituted or substituted (including, e.g., 1,3-dihydrobenzimidazol-2-one; 1,3-dihydro-indol-2-one, etc.).

The phrase "derived from," as used in this context, pertains to groups that have the same ring atoms, in the same orientation/configuration, as the parent compound, and so include carbonyl-substituted, and other substituted derivatives. For example, 1-methyl-1H-pyrrolyl is derived from "pyrrole". In the simplest case, the phrase "is independently derived from . . ." may be replaced with "is independently a monovalent, monodentate moiety obtained by removing a hydrogen atom from a ring atom of . . . ."

In one embodiment, A is independently derived from: benzene, naphthalene, pyrrole, pyridine, furan, thiophene, benzothiophene, oxazole, isoxazole, thiadiazole, benzothiadiazole, oxadiazole, thiazole, isothiazole, imidazole, pyrazole, pyridazine, pyrimidine, pyrazine, tetrazole, quinoline, isoquinoline; and is independently unsubstituted or substituted.

In one embodiment, A is independently: phenyl, naphthyl, pyrrolyl, pyridinyl, furanyl, thienyl, benzothienyl, oxazolyl, isoxazolyl, thiadiazolyl, benzothiadiazolyl, oxadiazolyl, thiazolyl, isothiazolyl, imidazolyl, pyrazolyl, pyridazinyl, pyrimidinyl, pyrazinyl, tetrazolyl, quinolinyl, isoquinolinyl; and is independently unsubstituted or substituted.

In one embodiment, A is independently: phenyl, naphthyl, pyrazolyl, pyridinyl, furanyl, benzothienyl, benzothiadiazolyl, quinolinyl, isoquinolinyl; and is independently unsubstituted or substituted.

In one embodiment, A is independently: phenyl, naphthyl, pyrazolyl, pyridinyl, furanyl, benzothienyl, benzothiadiazolyl; and is independently unsubstituted or substituted.

In one embodiment, A is independently: phenyl, naphthyl, pyrazolyl, and pyridinyl; and is independently unsubstituted or substituted.

In one embodiment, A is independently phenyl, and is independently unsubstituted or substituted.

In one embodiment, A is independently pyrazolyl, and is independently unsubstituted or substituted.

In one embodiment, A is independently pyridinyl, and is independently unsubstituted or substituted.

In one embodiment, A is independently naphthyl, and is independently unsubstituted or substituted.

In one embodiment, A is independently $C_{3-12}$carbocyclic (e.g., saturated $C_{3-12}$cycloalkyl, $C_{3-12}$cycloalkenyl) or $C_{3-12}$heterocyclic, and is independently unsubstituted or substituted.

In one embodiment, A is independently $C_{5-10}$carbocyclic (e.g., saturated $C_{3-10}$cycloalkyl, $C_{3-10}$cycloalkenyl) or $C_{5-10}$heterocyclic, and is independently unsubstituted or substituted.

In one embodiment, A is independently monocyclic or bicyclic $C_{3-12}$carbocyclic (e.g., saturated $C_{3-12}$cycloalkyl, $C_{3-12}$cycloalkenyl) or monocyclic or bicyclic $C_{3-12}$heterocyclic, and is independently unsubstituted or substituted.

In one embodiment, A is independently $C_{5-8}$carbocyclic (e.g., saturated $C_{5-8}$cycloalkyl, $C_{5-8}$cycloalkenyl) or $C_{5-8}$heterocyclic, and is independently unsubstituted or substituted.

In one embodiment, A is independently monocyclic $C_{5-8}$carbocyclic (e.g., saturated $C_{5-8}$cycloalkyl, $C_{6-8}$cycloalkenyl) or monocyclic $C_{5-8}$heterocyclic (e.g., having 1, 2, or 3 ring heteroatoms, e.g., selected from nitrogen and oxygen), and is independently unsubstituted or substituted.

In one embodiment, A is independently derived from: cyclopentane, cyclohexane, tetrahydrofuran, tetrahydropyran, dioxane, pyrrolidine, piperidine, piperzine; and is independently unsubstituted or substituted (including, e.g., piperidinone, dimethyltetrahydropyran, etc.).

In one embodiment, A is independently: cyclopentyl, cyclohexyl, tetrahydrofuranyl, tetrahydropyranyl, dioxanyl, pyrrolidinyl, piperidinyl, piperzinyl; and is independently unsubstituted or substituted (including, e.g., piperidinonyl, dimethyltetrahydropyranyl, etc.).

In one embodiment, A is independently selected from those (core groups) exemplified under the heading "Some Preferred Embodiments" and is independently unsubstituted or substituted, for example, with one or more substituents independently selected from those substituents exemplified under the heading "Some Preferred Embodiments."

Substituents on the Group A

The group A is independently unsubstituted or substituted.

In one embodiment, A is independently unsubstituted.

In one embodiment, A is independently substituted.

In one embodiment, A is independently unsubstituted or substituted with one or more (e.g., 1 to 5; 1 to 4; 1 to 3; 1 or 2; 2 to 5; 2 to 4; 2 or 3; 1; 2; 3; 4; 5) substituents.

In one embodiment, the substituents are independently selected from the following:

(1) carboxylic acid; (2) ester; (3) amido or thioamido; (4) acyl; (5) halo; (6) cyano; (7) nitro; (8) hydroxy; (9) ether; (10) thiol; (11) thioether; (12) acyloxy; (13) carbamate; (14) amino; (15) acylamino or thioacylamino; (16) aminoacylamino or aminothioacylamino; (17) sulfonamino; (18) sulfonyl; (19) sulfonate; (20) sulfonamido; (21) $C_{5-20}$aryl-$C_{1-7}$alkyl; (22) $C_{5-20}$aryl; (23) $C_{3-20}$heterocyclyl; (24) $C_{1-7}$alkyl; (25) oxo; (26) imino; (27) hydroxyimino; (28) phosphate.

In one embodiment, additionally, two adjacent substituents, if present, taken together, may form —OCH$_2$O—, —OCH$_2$CH$_2$O—, or —OCH$_2$CH$_2$CH$_2$O—.

In one embodiment, the substituents are independently selected from the following:

(1) —C(=O)OH;
(2) —C(=O)OR$^1$, wherein R$^1$ is independently as defined in (21), (22), (23) or (24);
(3) —C(=O)NR$^2$R$^3$ or —C(=S)NR$^2$R$^3$, wherein each of R$^2$ and R$^3$ is independently —H; or as defined in (21), (22), (23) or (24); or R$^2$ and R$^3$ taken together with the nitrogen atom to which they are attached form a ring having from 3 to 7 ring atoms;
(4) —C(=O)R$^4$, wherein R$^4$ is independently —H, or as defined in (21), (22), (23) or (24);
(5) —F, —Cl, —Br, —I;
(6) —CN;
(7) —NO$_2$;
(8) —OH;
(9) —OR$^5$, wherein R$^5$ is independently as defined in (21), (22), (23) or (24);
(10) —SH;
(11) —SR$^6$, wherein R$^6$ is independently as defined in (21), (22), (23) or (24);
(12) —OC(=O)R$^7$, wherein R$^7$ is independently as defined in (21), (22), (23) or (24);
(13) —OC(=O)NR$^8$R$^9$, wherein each of R$^8$ and R$^9$ is independently —H; or as defined in (21), (22), (23) or (24); or R$^8$ and R$^9$ taken together with the nitrogen atom to which they are attached form a ring having from 3 to 7 ring atoms;
(14) —NR$^{10}$R$^{11}$, wherein each of R$^{10}$ and R$^{11}$ is independently —H; or as defined in (21), (22), (23) or (24); or R$^{10}$ and R$^{11}$ taken together with the nitrogen atom to which they are attached form a ring having from 3 to 7 ring atoms;
(15) —NR$^{12}$C(=O)R$^{13}$ or —NR$^{12}$C(=S)R$^{13}$, wherein R$^{12}$ is independently —H; or as defined in (21), (22), (23) or (24); and R$^{13}$ is independently —H, or as defined in (21), (22), (23) or (24);
(16) —NR$^{14}$C(=O)NR$^{15}$R$^{16}$ or —NR$^{14}$C(=S)NR$^{15}$R$^{16}$, wherein R$^{14}$ is independently —H; or as defined in (21), (22), (23) or (24); and each of R$^{15}$ and R$^{16}$ is independently —H; or as defined in (21), (22), (23) or (24); or R$^{15}$ and R$^{16}$ taken together with the nitrogen atom to which they are attached form a ring having from 3 to 7 ring atoms;
(17) —NR$^{17}$SO$_2$R$^{18}$, wherein R$^{17}$ is independently —H; or as defined in (21), (22), (23) or (24); and R$^{18}$ is independently —H, or as defined in (21), (22), (23) or (24);
(18) —SO$_2$R$^{19}$, wherein R$^{19}$ is independently as defined in (21), (22), (23) or (24);
(19) —OSO$_2$R$^{20}$ and wherein R$^{20}$ is independently as defined in (21), (22), (23) or (24);
(20) —SO$_2$NR$^{21}$R$^{22}$, wherein each of R$^{21}$ and R$^{22}$ is independently —H; or as defined in (21), (22), (23) or (24); or R$^{21}$ and R$^{22}$ taken together with the nitrogen atom to which they are attached form a ring having from 3 to 7 ring atoms;
(21) $C_{5-20}$aryl-$C_{1-7}$alkyl, for example, wherein $C_{5-20}$aryl is as defined in (22); unsubstituted or substituted, e.g., with one or more groups as defined in (1) to (28);
(22) $C_{5-20}$aryl, including $C_{6-20}$carboaryl and $C_{5-20}$heteroaryl; unsubstituted or substituted, e.g., with one or more groups as defined in (1) to (28);
(23) $C_{3-20}$heterocyclyl; unsubstituted or substituted, e.g., with one or more groups as defined in (1) to (28);
(24) $C_{1-7}$alkyl, including:
saturated $C_{1-7}$alkyl;
unsaturated $C_{1-7}$alkyl, e.g., $C_{2-7}$alkenyl and $C_{2-7}$alkynyl;
cyclic $C_{1-7}$alkyl, e.g., $C_{3-7}$cycloalkyl $C_{3-7}$cycloalkenyl, $C_{3-7}$cycloalkynyl;
aliphatic (linear or branched) $C_{1-7}$alkyl;
unsubstituted $C_{1-7}$alkyl;
substituted $C_{1-7}$alkyl, e.g., substituted with one or more groups as defined in (1) to (23) and (25) to (28),
e.g., halo-$C_{1-7}$alkyl;
e.g., amino-$C_{1-7}$alkyl (e.g., —(CH$_2$)$_w$-amino, w is 1, 2, 3, or 4);
e.g., carboxy-$C_{1-7}$alkyl (e.g., —(CH$_2$)$_w$—COOH, w is 1, 2, 3, or 4);
e.g., acyl-$C_{1-7}$alkyl (e.g., —(CH$_2$)$_w$—C(=O)R$^4$, w is 1, 2, 3, or 4);
e.g., hydroxy-$C_{1-7}$alkyl (e.g., —(CH$_2$)$_w$—OH, w is 1, 2, 3, or 4);
e.g., $C_{1-7}$alkoxy-$C_{1-7}$alkyl (e.g., —(CH$_2$)$_w$—O—$C_{1-7}$alkyl, w is 1, 2, 3, or 4);
(25) =O;
(26) =NR$^{23}$, wherein R$^{23}$ is independently —H; or as defined in (21), (22), (23) or (24);
(27) =NOH;
(28) —P(=O)(OR$^{24}$)$_2$ and —OP(=O)(OR$^{24}$)$_2$, wherein each R$^{24}$ is independently —H; or as defined in (21), (22), (23) or (24).

In one embodiment, additionally, two adjacent substituents, if present, taken together, may form —OCH$_2$O—, —OCH$_2$CH$_2$O—, or —OCH$_2$CH$_2$CH$_2$O—.

In one embodiment, the substituents are independently selected from the following:

(1) —C(=O)OH;
(2) —C(=O)OMe, —C(=O)OEt, —C(=O)O(iPr), —C(=O)O(tBu); —C(=O)O(cPr); —C(=O)OCH$_2$CH$_2$OH, —C(=O)OCH$_2$CH$_2$OMe, —C(=O)OCH$_2$CH$_2$OEt; —C(=O)OPh, —C(=O)OCH$_2$Ph;
(3) —(C=O)NH$_2$, —(C=O)NMe$_2$, —(C=O)NEt$_2$, —(C=O)N(iPr)$_2$, —(C=O)N(CH$_2$CH$_2$OH)$_2$; —(C=O)-morpholino, —(C=O)NHPh, —(C=O)NHCH$_2$Ph;
(4) —C(=O)H, —(C=O)Me, —(C=O)Et, —(C=O)(tBu), —(C=O)-cHex, —(C=O)Ph; —(C=O)CH$_2$Ph;
(5) —F, —Cl, —Br, —I;
(6) —CN;
(7) —NO$_2$;

(8) —OH;
(9) —OMe, —OEt, —O(iPr), —O(tBu), —OPh, —OCH$_2$Ph; —OCF$_3$, —OCH$_2$CF$_3$, —OCF$_2$CF$_2$H;
—OCH$_2$CH$_2$OH, —OCH$_2$CH$_2$OMe, —OCH$_2$CH$_2$OEt;
—OCH$_2$CH$_2$NH$_2$, —OCH$_2$CH$_2$NMe$_2$, —OCH$_2$CH$_2$N(iPr)$_2$;
—OCH$_2$CH$_2$-morpholino, —OCH$_2$CH$_2$-piperazino, —OCH$_2$CH$_2$-pyrrolidino;
—OPh-Me, —OPh-OH, —OPh-OMe, —OPh-F, —OPh-Cl, —OPh-Br, —OPh-I;
(10) —SH;
(11) —SMe, —SEt, —SPh, —SCH$_2$Ph;
(12) —OC(=O)Me, —OC(=O)Et, —OC(=O)(iPr), —OC(=O)(tBu); —OC(=O)(cPr);
—OC(=O)CH$_2$CH$_2$OH, —OC(=O)CH$_2$CH$_2$OMe, —OC(=O)CH$_2$CH$_2$OEt;
—OC(=O)Ph, —OC(=O)CH$_2$Ph;
(13) —OC(=O)NH$_2$, —OC(=O)NHMe, —OC(=O)NMe$_2$, —OC(=O)NHEt, —OC(=O)NEt$_2$, —OC(=O)NHPh, —OC(=O)NCH$_2$Ph;
(14) —NH$_2$, —NHMe, —NHEt, —NH(iPr), —NMe$_2$, —NEt$_2$, —N(iPr)$_2$, —N(CH$_2$CH$_2$OH)$_2$; —NHPh, —NHCH$_2$Ph; piperidino, piperazino, morpholino;
(15) —NH(C=O)Me, —NH(C=O)Et, —NH(C=O)nPr, —NH(C=O)Ph, —NHC(=O)CH$_2$Ph; —NMe(C=O)Me, —NMe(C=O)Et, —NMe(C=O)Ph, —NMeC(=O)CH$_2$Ph;
(16) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;
(17) —NHSO$_2$Me, —NHSO$_2$Et, —NHSO$_2$Ph, —NHSO$_2$PhMe, —NHSO$_2$CH$_2$Ph; —NMeSO$_2$Me, —NMeSO$_2$Et, —NMeSO$_2$Ph, —NMeSO$_2$PhMe, —NMeSO$_2$CH$_2$Ph;
(18) —SO$_2$Me, —SO$_2$CF$_3$, —SO$_2$Et, —SO$_2$Ph, —SO$_2$PhMe, —SO$_2$CH$_2$Ph;
(19) —OSO$_2$Me, —OSO$_2$CF$_3$, —OSO$_2$Et, —OSO$_2$Ph, —OSO$_2$PhMe, —OSO$_2$CH$_2$Ph;
(20) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;
(21) —CH$_2$Ph, —CH$_2$Ph-Me, —CH$_2$Ph-OH, —CH$_2$Ph-F, —CH$_2$Ph-Cl;
(22) -Ph, -Ph-Me, -Ph-OH, -Ph-OMe, -Ph-NH$_2$, -Ph-F, -Ph-Cl, -Ph-Br, -Ph-I;
pyridyl, pyrazinyl, pyrimidinyl, pyridazinyl; furanyl, thiophenyl, pyrrolyl, imidazolyl, pyrazolyl, oxazolyl, thiazolyl, thiadiazolyl;
(23) pyrrolidinyl, imidazolidinyl, pyrazolidinyl, piperidinyl, piperazinyl, azepinyl, tetrahydrofuranyl, tetrahydropyranyl, morpholinyl, azetidinyl;
(24) -Me, -Et, -nPr, -iPr, -nBu, -iBu, -sBu, -tBu, -nPe, -iPe, ter-Pe, neo-Pe;
-cPr, -cHex; —CH=CH$_2$, —CH$_2$—CH=CH$_2$;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$;
—CH$_2$CH$_2$-morpholino, —CH$_2$CH$_2$-piperazino, —CH$_2$CH$_2$-pyrrolidino;
(25) =O;
(26) =NH, =NMe; =NEt;
(27) =NOH;
(28) —OP(=O)(OH)$_2$, —P(=O)(OH)$_2$, —OP(=O)(OMe)$_2$, —P(=O)(OMe)$_2$.

In one embodiment, additionally, two adjacent substituents, if present, taken together, may form —OCH$_2$O—, —OCH$_2$CH$_2$O—, or —OCH$_2$CH$_2$CH$_2$O—.

In one embodiment, the substituents are independently selected from those defined above in groups (3), (5), (6), (8), (9), (14), (15), (18), (20), (21), (22), (23), (24), and (25).

In one embodiment, additionally, two adjacent substituents, if present, taken together, may form —OCH$_2$O—, —OCH$_2$CH$_2$O—, or —OCH$_2$CH$_2$CH$_2$O—.

In one embodiment, the substituents are independently selected from -G$^1$ and -G$^2$, and additionally, two adjacent substituents, if present, taken together, may form —OCH$_2$CH$_2$O— or —OCH$_2$CH$_2$CH$_2$O—, wherein:

each -G$^1$ is independently: —F, —Cl, —Br, —I, —R$^Z$, —CF$_3$, —OH, —OR$^Z$, —SR$^Z$, —OCF$_3$, —OCF$_2$CF$_2$H, —SCF$_3$, —SCF$_2$CF$_2$H, —NH$_2$, —NHR$^Z$, —NR$^Z_2$, pyrrolidino, piperidino, piperazino, N-methyl-piperazino, morpholino, or thiomorpholino;

wherein each R$^Z$ is saturated aliphatic C$_{1-6}$alkyl or saturated C$_{3-6}$cycloalkyl; and each -G$^2$ is independently: phenyl, pyridyl, pyrimidinyl, pyrazinyl, pyridazinyl, pyrrolyl, imidazolyl, or —CH$_2$-phenyl;

wherein each phenyl, pyridyl, pyrimidinyl, pyrazinyl, pyridazinyl, pyrrolyl, and imidazolyl is optionally substituted with one or more groups -G$^1$.

In one embodiment, the substituents are independently selected from the following:
—F, —Cl, —Br, —I;
—OH;
—OMe, —OEt, —OCF$_3$;
—NH$_2$, —NHMe, —NHEt, piperidino, piperazino, morpholino;
-Me, -Et, —CF$_3$.

In one embodiment, additionally, two adjacent substituents, if present, taken together, may form —OCH$_2$CH$_2$O— or —OCH$_2$CH$_2$CH$_2$O—.

In one embodiment, the substituents are independently selected from those defined under the heading "Substituents on the Group R$^{N1}$" above.

In one embodiment, the substituents are independently selected from those substituents exemplified under the heading "Some Preferred Embodiments."

In one embodiment, A is optionally substituted phenyl, and the substituents on the phenyl group are independently selected from:
(2) —C(=O)OMe, —C(=O)OEt, —C(=O)O(iPr), —C(=O)O(tBu); —C(=O)O(cPr); —C(=O)OCH$_2$CH$_2$OH, —C(=O)OCH$_2$CH$_2$OMe, —C(=O)OCH$_2$CH$_2$OEt; —C(=O)OCH$_2$Ph;
(3) —(C=O)NH$_2$, —(C=O)NMe$_2$, —(C=O)NEt$_2$, —(C=O)N(iPr)$_2$, —(C=O)N(CH$_2$CH$_2$OH)$_2$; —(C=O)-morpholino, —(C=O)NHPh, —(C=O)NHCH$_2$Ph;
(5) —F, —Cl, —Br, —I;
(6) —CN;
(8) —OH;
(9) —OMe, —OEt, —O(iPr), —O(tBu), —OPh, —OCH$_2$Ph; —OCF$_3$, —OCH$_2$CF$_3$, —OCF$_2$CF$_2$H;
—OCH$_2$CH$_2$OH, —OCH$_2$CH$_2$OMe, —OCH$_2$CH$_2$OEt; —OCH$_2$CH$_2$NH$_2$, —OCH$_2$CH$_2$NMe$_2$, —OCH$_2$CH$_2$N(iPr)$_2$;
—OCH$_2$CH$_2$-morpholino, —OCH$_2$CH$_2$-piperazino, —OCH$_2$CH$_2$-pyrrolidino;

—OPh-Me, —OPh-OMe, —OPh-F, —OPh-Cl, —OPh-Br, —OPh-I;
(11) —SMe, —SEt, —SPh, —SCH$_2$Ph;
(13) —OC(=O)NH$_2$, —OC(=O)NHMe, —OC(=O)NMe$_2$, —OC(=O)NHEt, —OC(=O)NEt$_2$, —OC(=O)NHPh, —OC(=O)NCH$_2$Ph;
(14) —NH$_2$, —NHMe, —NHEt, —NH(iPr), —NMe$_2$, —NEt$_2$, —N(iPr)$_2$, —N(CH$_2$CH$_2$OH)$_2$; —NHPh, —NHCH$_2$Ph; piperidino, piperazino, morpholino;
(15) —NH(C=O)Me, —NH(C=O)Et, —NH(C=O)nPr, —NH(C=O)Ph, —NHC(=O)CH$_2$Ph; —NMe(C=O)Me, —NMe(C=O)Et, —NMe(C=O)Ph, —NMeC(=O)CH$_2$Ph;
(17) —NHSO$_2$Me, —NHSO$_2$Et, —NHSO$_2$Ph, —NHSO$_2$PhMe, —NHSO$_2$CH$_2$Ph;
(18) —SO$_2$Me, —SO$_2$CF$_3$, —SO$_2$Et, —SO$_2$Ph, —SO$_2$PhMe, —SO$_2$CH$_2$Ph;
(20) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;
(21) —CH$_2$Ph, —CH$_2$Ph-Me, —CH$_2$Ph-OH, —CH$_2$Ph-F, —CH$_2$Ph-Cl;
(22) -Ph, -Ph-Me, -Ph-OH, -Ph-OMe, -Ph-NH$_2$, -Ph-F, -Ph-Cl, -Ph-Br, -Ph-I;
pyridyl, pyrazinyl, pyrimidinyl, pyridazinyl; furanyl, thiophenyl, pyrrolyl, imidazolyl, pyrazolyl, oxazolyl, thiazolyl, thiadiazolyl;
(23) pyrrolidinyl, imidazolidinyl, pyrazolidinyl, piperidinyl, piperazinyl, azepinyl, tetrahydrofuranyl, tetrahydropyranyl, morpholinyl, azetidinyl;
(24) -Me, -Et, -nPr, -iPr, -nBu, -iBu, -sBu, -tBu, -nPe, -iPe, ter-Pe, neo-Pe;
-cPr, -cHex; —CH=CH$_2$, —CH$_2$—CH=CH$_2$;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$;
—CH$_2$CH$_2$-morpholino, —CH$_2$CH$_2$-piperazino, —CH$_2$CH$_2$-pyrrolidino.

In one embodiment, additionally, two adjacent substituents, if present, taken together, may form —OCH$_2$O—, —OCH$_2$CH$_2$O—, or —OCH$_2$CH$_2$CH$_2$O—.

In one embodiment, A is optionally substituted phenyl, and the substituents on the phenyl group are independently selected from:
(5) —F, —Cl, —Br, —I;
(8) —OH;
(9) —OMe, —OEt, —O(iPr), —O(tBu), —OPh, —OCH$_2$Ph; —OCF$_3$, —OCH$_2$CF$_3$;
—OCH$_2$CH$_2$OH, —OCH$_2$CH$_2$OMe, —OCH$_2$CH$_2$OEt;
—OCH$_2$CH$_2$NH$_2$, —OCH$_2$CH$_2$NMe$_2$,
(14) —NH$_2$, —NHMe, —NHEt, —NH(iPr), —NMe$_2$, —NEt$_2$, —N(iPr)$_2$, —N(CH$_2$CH$_2$OH)$_2$;
—NHPh, —NHCH$_2$Ph; piperidino, piperazino, morpholino;
(22) -Ph, -Ph-Me, -Ph-OMe, -Ph-F, -Ph-Cl;
pyridyl, pyrazinyl, pyrimidinyl, pyridazinyl; furanyl, thiophenyl, pyrrolyl, imidazolyl, pyrazolyl, oxazolyl, thiazolyl, thiadiazolyl;
(23) pyrrolidinyl, piperidinyl, piperazinyl, azepinyl, tetrahydrofuranyl, tetrahydropyranyl, morpholinyl, azetidinyl;
(24) -Me, -Et, -nPr, -iPr, -nBu, -iBu, -sBu, -tBu, -nPe;
-cPr, -cHex; —CH=CH$_2$, —CH$_2$—CH=CH$_2$;
—CF$_3$, —CHF$_2$, —CH$_2$F, —CH$_2$CH$_2$F, —CH$_2$CHF$_2$, and —CH$_2$CF$_3$;

—CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$.

In one embodiment, additionally, two adjacent substituents, if present, taken together, may form —OCH$_2$O—, —OCH$_2$CH$_2$O—, or —OCH$_2$CH$_2$CH$_2$O—.

In one embodiment, A is optionally substituted pyrazolyl, and has the following formula:

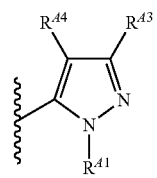

wherein:
$R^{44}$ is H;
$R^{43}$ is independently selected from:
(5) —F, —Cl, —Br, —I;
(22) -Ph;
(24) -Me, -Et, -nPr, -iPr, -nBu, -iBu, -sBu, -tBu, -nPe;
-cPr, -cHex;
—CF$_3$, —CHF$_2$, —CH$_2$F, —CH$_2$CH$_2$F, —CH$_2$CHF$_2$, and —CH$_2$CF$_3$;
$R^{41}$ is independently selected from:
(22) -Ph, -Ph-Me, -Ph-OH, -Ph-OMe, -Ph-NH$_2$, -Ph-F, -Ph-Cl, -Ph-Br, -Ph-I;
pyridyl, pyrazinyl, pyrimidinyl, pyridazinyl; furanyl, thiophenyl, pyrrolyl, imidazolyl, pyrazolyl, oxazolyl, thiazolyl, thiadiazolyl;
(23) pyrrolidinyl, piperidinyl, piperazinyl, azepinyl, tetrahydrofuranyl, tetrahydropyranyl, morpholinyl, azetidinyl;
(24) -Me, -Et, -nPr, -iPr, -nBu, -iBu, -sBu, -tBu, -nPe;
-cPr, -cHex; —CH=CH$_2$, —CH$_2$—CH=CH$_2$;
—CF$_3$, —CHF$_2$, —CH$_2$F, —CH$_2$CH$_2$F, —CH$_2$CHF$_2$, and —CH$_2$CF$_3$;
—CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$.

Some Preferred Classes of Compounds (A) One particularly preferred class of compounds are compounds selected from compounds of the following formula, and pharmaceutically acceptable salts, solvates, amides, esters, ethers, N-oxides, chemically protected forms, and prodrugs thereof:

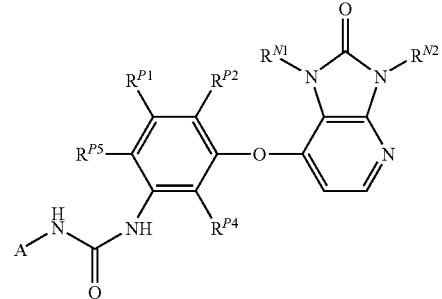

wherein:
$R^{N1}$ is independently as defined herein;
$R^{N2}$ is independently as defined herein;

each of $R^{P1}$, $R^{P2}$, $R^{P5}$, and $R^{P4}$ is independently as defined herein;
A is independently as defined herein.

(B) One particularly preferred class of compounds are compounds selected from compounds of the following formula, and pharmaceutically acceptable salts, solvates, amides, esters, ethers, N-oxides, chemically protected forms, and prodrugs thereof:

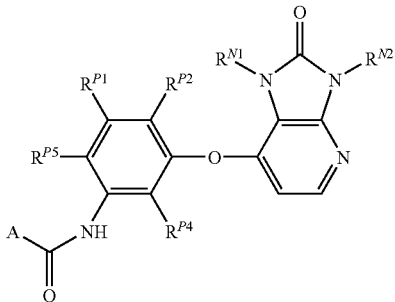

wherein:
$R^{N1}$ is independently as defined herein;
$R^{N2}$ is independently as defined herein;
each of $R^{P1}$, $R^{P2}$, $R^{P5}$, and $R^{P4}$ is independently as defined herein;
A is independently as defined herein (C) One particularly preferred class of compounds are compounds selected from compounds of the following formula, and pharmaceutically acceptable salts, solvates, amides, esters, ethers, N-oxides, chemically protected forms, and prodrugs thereof:

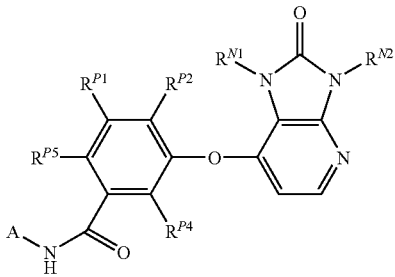

wherein:
$R^{N1}$ is independently as defined herein;
$R^{N2}$ is independently as defined herein;
each of $R^{P1}$, $R^{P2}$, $R^{P5}$, and $R^{P4}$ is independently as defined herein;
A is independently as defined herein.

For each of classes (A) through (C), the following embodiments are also preferred embodiments:

In one embodiment, each of $R^{P1}$, $R^{P2}$, $R^{P5}$, and $R^{P4}$ is independently —H, -Me, —$CF_3$, —F, —Cl, or —SMe.

In one embodiment, each of $R^{P1}$, $R^{P2}$, $R^{P5}$, and $R^{P4}$ is independently —H, -Me, —$CF_3$, —F, or —Cl.

In one embodiment, $R^{P1}$ and $R^{P2}$ taken together are —CH=CH—CH=CH—; and each of $R^{P5}$ and $R^{P4}$ is independently —H.

In one embodiment, $R^{P1}$ and $R^{P5}$ taken together are —CH=CH—CH=CH—; and each of $R^{P2}$ and $R^{P4}$ is independently —H.

(D) One particularly preferred class of compounds are compounds selected from compounds of the following formula, and pharmaceutically acceptable salts, solvates, amides, esters, ethers, N-oxides, chemically protected forms, and prodrugs thereof:

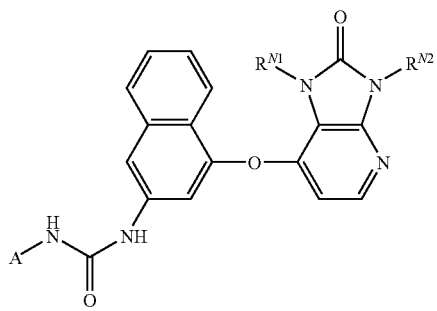

wherein:
$R^{N1}$ is independently as defined herein;
$R^{N2}$ is independently as defined herein;
A is independently as defined herein.

(E) One particularly preferred class of compounds are compounds selected from compounds of the following formula, and pharmaceutically acceptable salts, solvates, amides, esters, ethers, N-oxides, chemically protected forms, and prodrugs thereof:

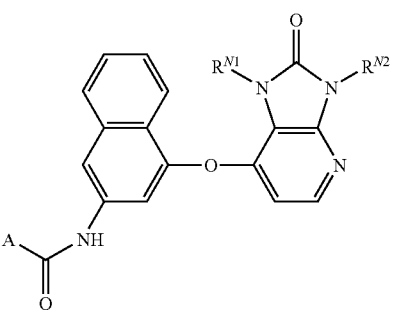

wherein:
$R^{N1}$ is independently as defined herein;
$R^{N2}$ is independently as defined herein;
A is independently as defined herein (F) One particularly preferred class of compounds are compounds selected from compounds of the following formula, and pharmaceutically acceptable salts, solvates, amides, esters, ethers, N-oxides, chemically protected forms, and prodrugs thereof:

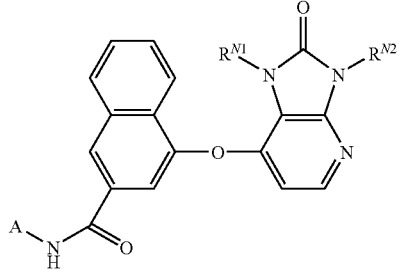

51 wherein:

R^{N1} is independently as defined herein;

R^{N2} is independently as defined herein;

A is independently as defined herein.

(G) One particularly preferred class of compounds are compounds selected from compounds of the following formula, and pharmaceutically acceptable salts, solvates, amides, esters, ethers, N-oxides, chemically protected forms, and prodrugs thereof:

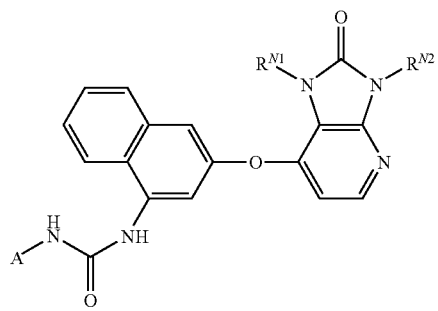

wherein:

R^{N1} is independently as defined herein;

R^{N2} is independently as defined herein;

A is independently as defined herein.

(H) One particularly preferred class of compounds are compounds selected from compounds of the following formula, and pharmaceutically acceptable salts, solvates, amides, esters, ethers, N-oxides, chemically protected forms, and prodrugs thereof:

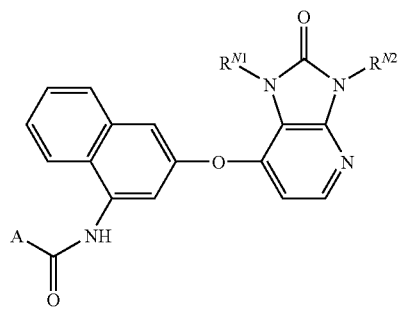

wherein:

R^{N1} is independently as defined herein;

R^{N2} is independently as defined herein;

A is independently as defined herein (I) One particularly preferred class of compounds are compounds selected from compounds of the following formula, and pharmaceutically acceptable salts, solvates, amides, esters, ethers, N-oxides, chemically protected forms, and prodrugs thereof:

52

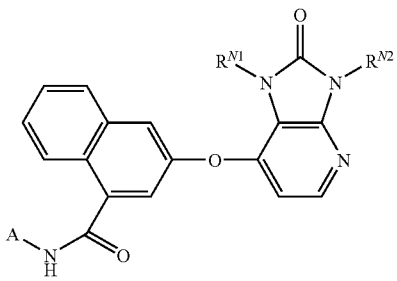

wherein:

$R^{N1}$ is independently as defined herein;

$R^{N2}$ is independently as defined herein;

A is independently as defined herein.

For each of classes (A) through (I), the following embodiments are especially preferred:

In one embodiment, $R^{N1}$ is independently —H or -Me.

In one embodiment, $R^{N1}$ is independently —H.

In one embodiment, $R^{N2}$ is independently —H or -Me.

In one embodiment, $R^{N2}$ is independently —H.

In one embodiment, A is independently: phenyl, naphthyl, pyrazolyl, pyridinyl, furanyl, benzothienyl, benzothiadiazolyl, quinolinyl, isoquinolinyl; and is independently unsubstituted or substituted.

In one embodiment, A is independently: phenyl, naphthyl, pyrazolyl, pyridinyl, furanyl, benzothienyl, benzothiadiazolyl; and is independently unsubstituted or substituted.

In one embodiment, A is independently phenyl, and is independently unsubstituted or substituted.

In one embodiment, A is a phenyl group of the following formula:

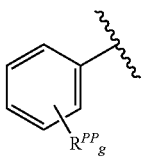

wherein:

g is independently 0, 1, 2, 3, 4, or 5;

each $R^{PP}$ is independently a substituent as defined under the heading "Substituents on the Group A".

In one embodiment, g is independently 0, 1, or 2.

In one embodiment, g is independently 0.

In one embodiment, g is independently 1.

In one embodiment, g is independently 2.

In one embodiment, each $R^{PP}$ is independently (5) halo, (9) ether (e.g., $C_{1-7}$alkoxy), or (24) $C_{1-7}$alkyl, including, e.g., halo-$C_{1-7}$alkyl, etc., e.g., —F, —Cl, —Br, —I, —OMe, —OCF$_3$, -Me, —CF$_3$.

In one embodiment, A is independently pyrazolyl, and is independently unsubstituted or substituted.

In one embodiment, A is a pyrazolyl group of the following formula:

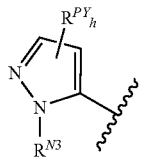

wherein:

h is independently 0, 1 or 2;

each $R^{PY}$ is independently a substituent as defined under the heading "Substituents on the Group A"; and $R^{N3}$ is independently as defined for $R^{N1}$ or $R^{A1}$.

In one embodiment, A is a pyrazolyl group of selected from groups of the following formulae:

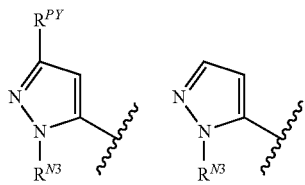

In one embodiment, h is independently 0 or 1.

In one embodiment, h is independently 0.

In one embodiment, h is independently 1.

In one embodiment, h is independently 1 and $R^{PY}$ is independently (24) $C_{1-7}$alkyl.

In one embodiment, h is independently 1 and $R^{PY}$ is independently saturated $C_{1-7}$alkyl.

In one embodiment, $R^{N3}$ is independently as defined for $R^{N1}$.

In one embodiment, $R^{N3}$ is independently as defined for $R^{A1}$.

In one embodiment, $R^{N3}$ is independently (21) $C_{5-20}$aryl-$C_{1-7}$alkyl or (22) $C_{5-20}$aryl, and is independently unsubstituted or substituted, for example, with one or more (e.g., 1, 2, 3, 4, etc.) substituents, e.g., selected from substituents as defined under the heading "Substituents on the Group A", e.g., (5) halo, (9) ether (e.g., $C_{1-7}$alkoxy), (24) $C_{1-7}$alkyl, etc.

In one embodiment, $R^{N3}$ is independently phenyl, and is independently unsubstituted or substituted, for example, with one or more (e.g., 1, 2, 3, 4, etc.) substituents, e.g., selected from substituents as defined under the heading "Substituents on the Group A", e.g., (5) halo, (9) ether (e.g., $C_{1-7}$alkoxy), (24) $C_{1-7}$alkyl, including, e.g., halo-$C_{1-7}$alkyl, etc., e.g., —F, —Cl, —Br, —I, —OMe, —OCF$_3$, -Me, —CF$_3$.

For example:

(J) One particularly preferred class of compounds are compounds selected from compounds of the following formula, and pharmaceutically acceptable salts, solvates, amides, esters, ethers. N-oxides, chemically protected forms, and prodrugs thereof:

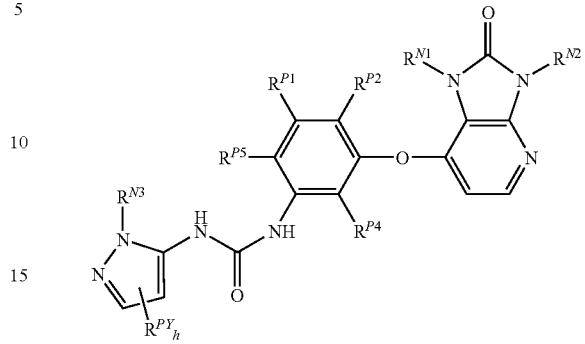

wherein:

$R^{N1}$ is independently as defined herein;

$R^{N2}$ is independently as defined herein;

each of $R^{P1}$, $R^{P2}$, $R^{P5}$, and $R^{P4}$ is independently as defined herein;

h is independently 0, 1 or 2;

each $R^{PY}$ is independently a substituent as defined under the heading "Substituents on the Group A";

$R^{N3}$ is independently as defined for $R^{N1}$ or $R^{A1}$.

(K) One particularly preferred class of compounds are compounds selected from compounds of the following formula, and pharmaceutically acceptable salts, solvates, amides, esters, ethers, N-oxides, chemically protected forms, and prodrugs thereof:

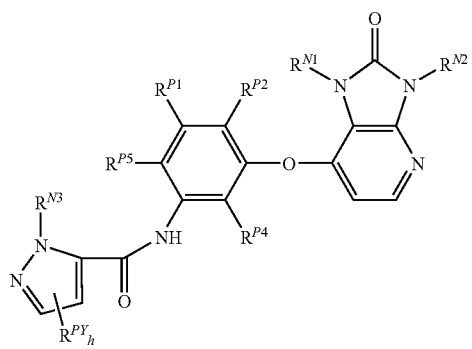

wherein:

$R^{N1}$ is independently as defined herein;

$R^{N2}$ is independently as defined herein;

each of $R^{P1}$, $R^{P2}$, $R^{P5}$, and $R^{P4}$ is independently as defined herein;

h is independently 0, 1 or 2;

each $R^{PY}$ is independently a substituent as defined under the heading "Substituents on the Group A";

$R^{N3}$ is independently as defined for $R^{N1}$ or $R^{A1}$.

(L) One particularly preferred class of compounds are compounds selected from compounds of the following formula, and pharmaceutically acceptable salts, solvates, amides, esters, ethers, N-oxides, chemically protected forms, and prodrugs thereof:

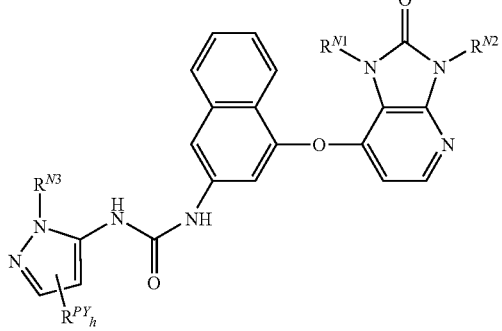

wherein:
$R^{N1}$ is independently as defined herein;
$R^{N2}$ is independently as defined herein;
h is independently 0, 1 or 2;
each $R^{PY}$ is independently a substituent as defined under the heading "Substituents on the Group A";
$R^{N3}$ is independently as defined for $R^{N1}$.

(M) One particularly preferred class of compounds are compounds selected from compounds of the following formula, and pharmaceutically acceptable salts, solvates, amides, esters, ethers, N-oxides, chemically protected forms, and prodrugs thereof:

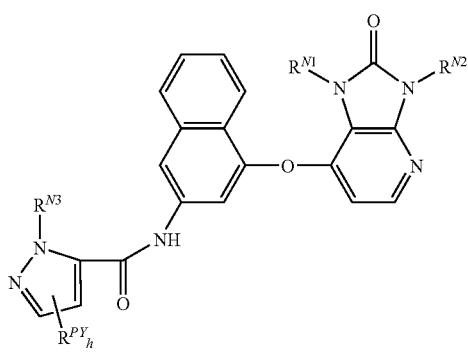

wherein:
$R^{N1}$ is independently as defined herein;
$R^{N2}$ is independently as defined herein;
h is independently 0, 1 or 2;
each $R^{PY}$ is independently a substituent as defined under the heading "Substituents on the Group A";
$R^{N3}$ is independently as defined for $R^{N1}$.

(N) One particularly preferred class of compounds are compounds selected from compounds of the following formula, and pharmaceutically acceptable salts, amides, esters, ethers, N-oxides, chemically protected forms, and prodrugs thereof:

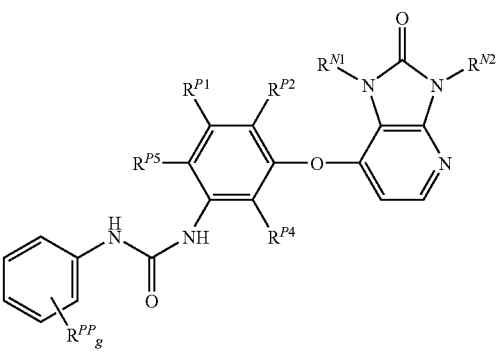

wherein:
$R^{N1}$ is independently as defined herein;
$R^{N2}$ is independently as defined herein;
each of $R^{P1}$, $R^{P2}$, $R^{P5}$, and $R^{P4}$ is independently as defined herein;
g is independently 0, 1, 2, 3, 4, or 5;
each $R^{PP}$ is independently a substituent as defined under the heading "Substituents on the Group A".

(O) One particularly preferred class of compounds are compounds selected from compounds of the following formula, and pharmaceutically acceptable salts, solvates, amides, esters, ethers, N-oxides, chemically protected forms, and prodrugs thereof:

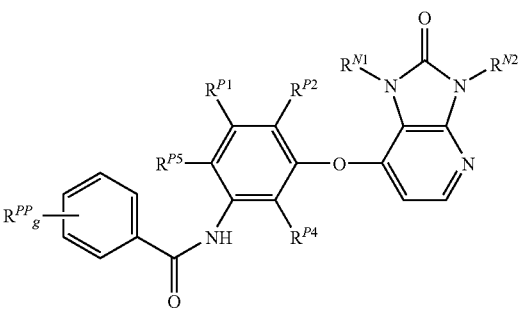

wherein:
$R^{N1}$ is independently as defined herein;
$R^{N2}$ is independently as defined herein;
each of $R^{P1}$, $R^{P2}$, $R^{P5}$, and $R^{P4}$ is independently as defined herein;
g is independently 0, 1, 2, 3, 4, or 5;
each $R^{PP}$ is independently a substituent as defined under the heading "Substituents on the Group A".

(P) One particularly preferred class of compounds are compounds selected from compounds of the following formula, and pharmaceutically acceptable salts, solvates, amides, esters, ethers, N-oxides, chemically protected forms, and prodrugs thereof:

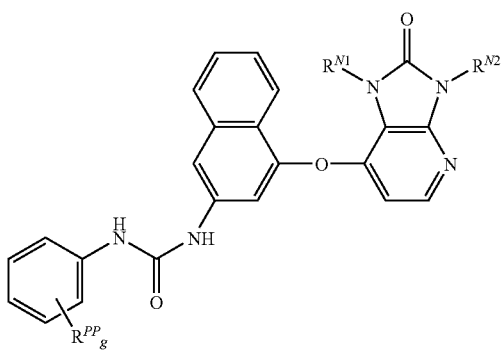

wherein:
$R^{N1}$ is independently as defined herein;
$R^{N2}$ is independently as defined herein;
g is independently 0, 1, 2, 3, 4, or 5;
each $R^{PP}$ is independently a substituent as defined under the heading "Substituents on the Group A".

(Q) One particularly preferred class of compounds are compounds selected from compounds of the following formula, and pharmaceutically acceptable salts, solvates, amides, esters, ethers, N-oxides, chemically protected forms, and prodrugs thereof:

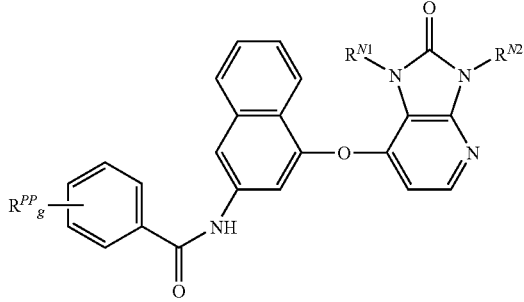

wherein:

$R^{N1}$ is independently as defined herein;
$R^{N2}$ is independently as defined herein;
g is independently 0, 1, 2, 3, 4, or 5;
each $R^{PP}$ is independently a substituent as defined under the heading "Substituents on the Group A".

An Especially Preferred Class of Compounds

One particularly preferred class of compounds are compounds selected from compounds of the following formulae, and pharmaceutically acceptable salts, solvates, amides, esters, ethers, N-oxides, chemically protected forms, and prodrugs thereof:

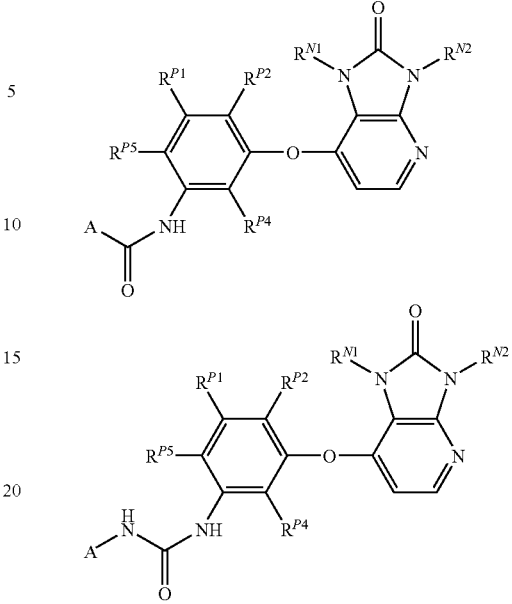

wherein:
$R^{N1}$ is independently —H or -Me;
$R^{N2}$ is independently —H or -Me;
each of $R^{P1}$, $R^{P2}$, $R^{P4}$ and $R^{P5}$ is independently —H or —F; and
A is independently phenyl or pyrazolyl; and is independently unsubstituted or substituted, for example, with one or more groups selected from: —F, —Cl, —Br, —I, —$R^{ZZ}$, —$CF_3$, —OH, —$OR^{ZZ}$, —$OCF_3$, —$OCF_2CF_2H$, —$SCF_3$, pyrrolyl, pyrrolidinyl, piperidinyl, and -Ph; wherein each —$R^{ZZ}$ is independently saturated aliphatic $C_{1-4}$alkyl; and wherein -Ph is phenyl and is independently unsubstituted or substituted, for example, with one or more groups selected from: —F, —Cl, —Br, —I, —$R^{ZZ}$, —$CF_3$, —OH, —$OR^{ZZ}$, and —$OCF_3$.

Molecular Weight

In one embodiment, the compound has a molecular weight of 300 to 1000.

In one embodiment, the bottom of range is 325; 350; 375; 400; 425; 450.

In one embodiment, the top of range is 900; 800; 700; 600; 500.

In one embodiment, the range is 300 to 900.
In one embodiment, the range is 300 to 800.
In one embodiment, the range is 300 to 700.
In one embodiment, the range is 300 to 600.
In one embodiment, the range is 300 to 500.

Some Preferred Embodiments

All plausible and compatible combinations of the embodiments described above are explicitly disclosed herein as if each and every combination was individually recited.

Examples of some preferred compounds (where A-L- is A-NH—C(=O)—NH—, Q is —O—, and Y is —CH=) (here each R is independently —H or -Me) are shown below.

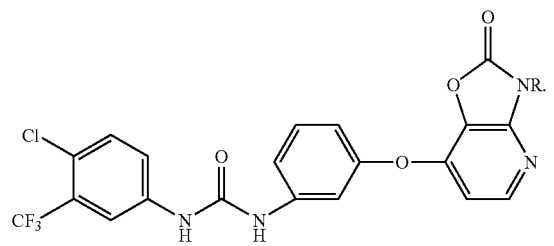
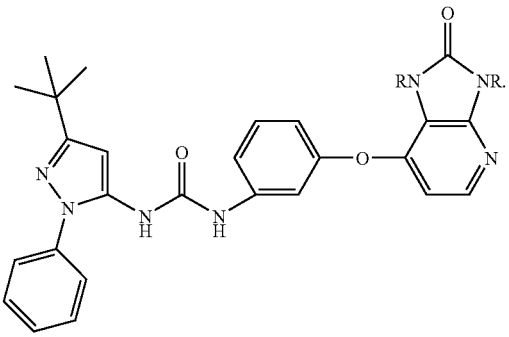
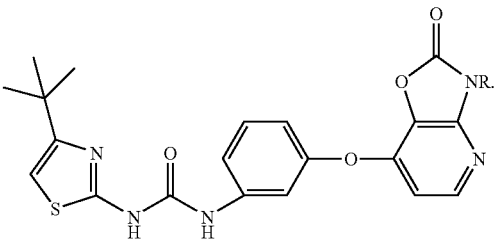
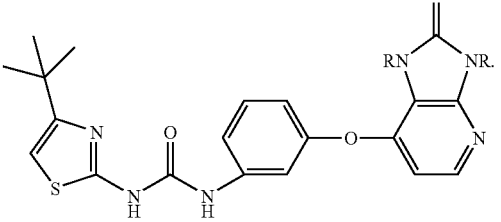
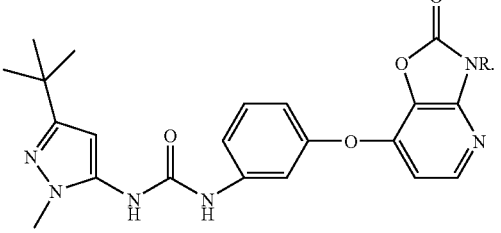
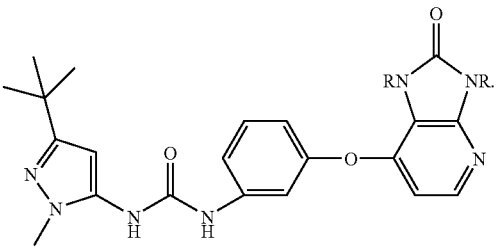
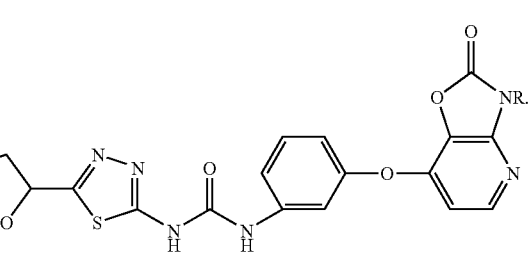

| 12 | 17 |
|---|---|
| 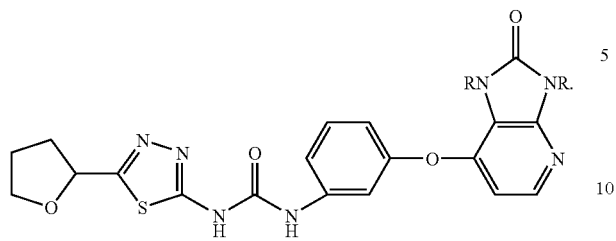 | 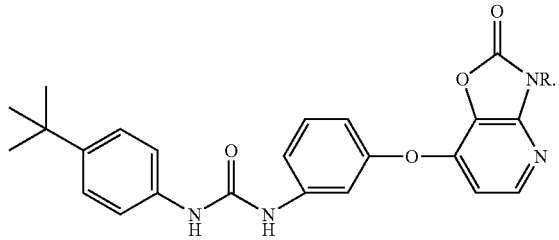 |
| 13 | 18 |
| 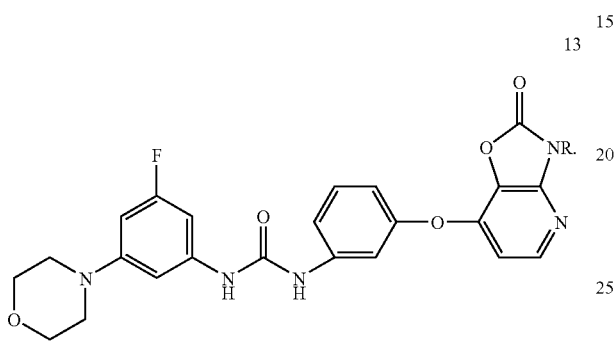 | 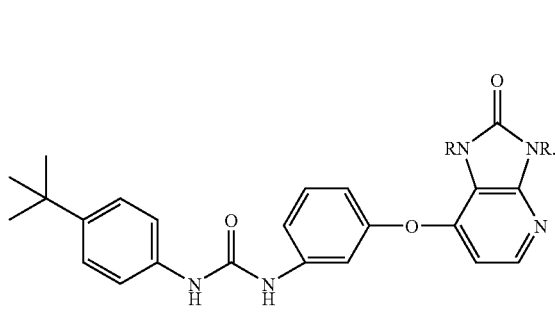 |
| 14 | 19 |
| 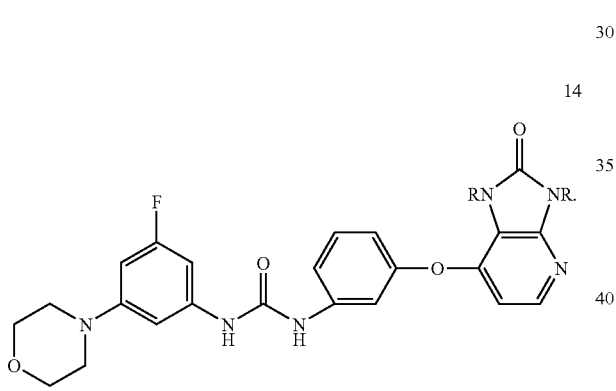 | 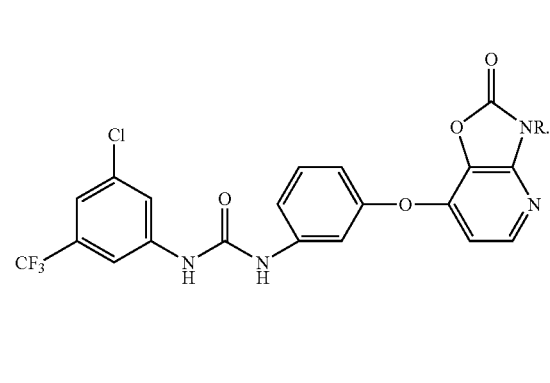 |
| 15 | 20 |
| 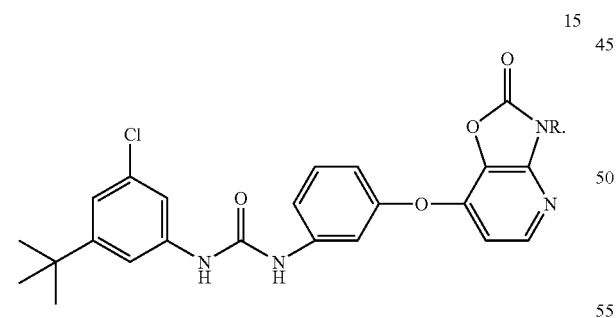 | 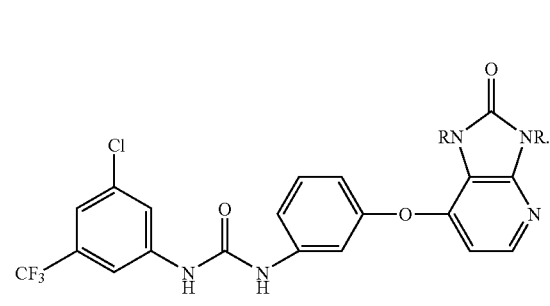 |
| 16 | 21 |
| 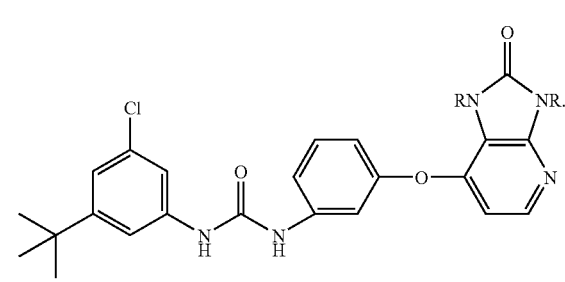 | 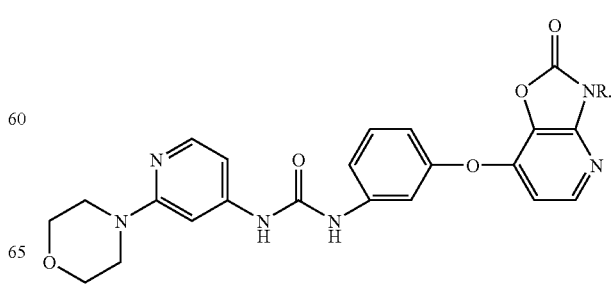 |

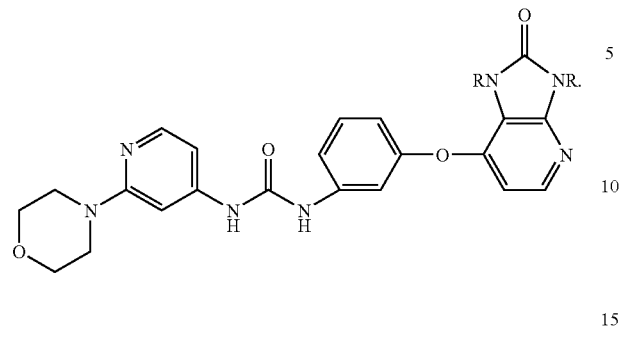
22
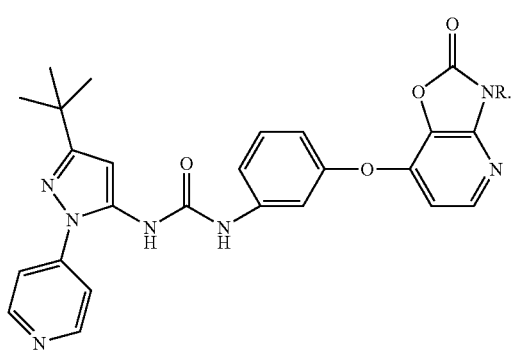
23
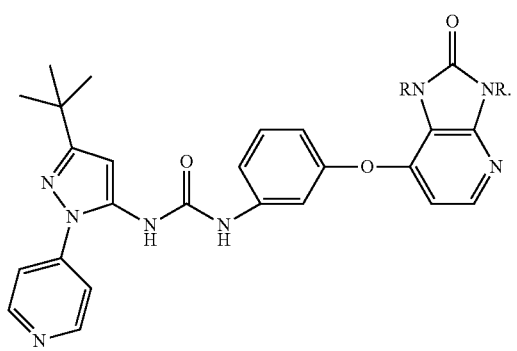
24
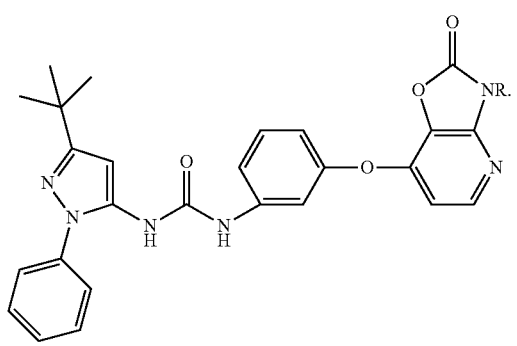
25
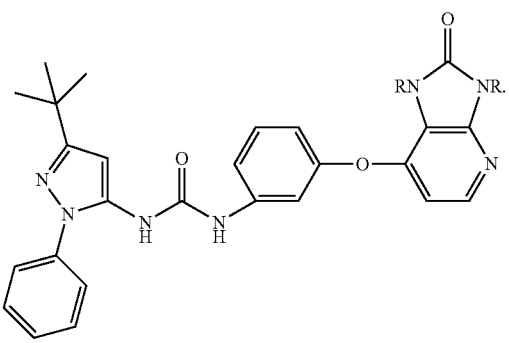
26
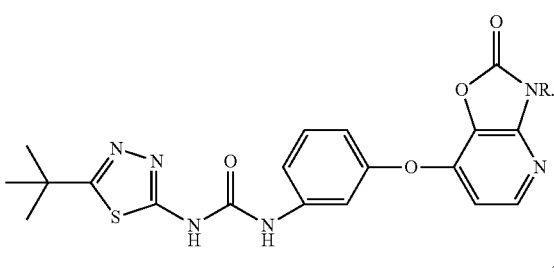
27
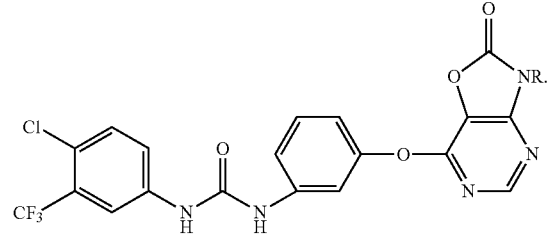
28
29
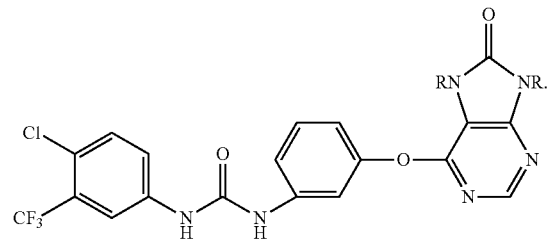
30
Examples of some preferred compounds (where A-L- is A-NH—C(=O)—NH—, Q is —O—, and Y is —N=) (here each R is independently —H or -Me) are shown below.

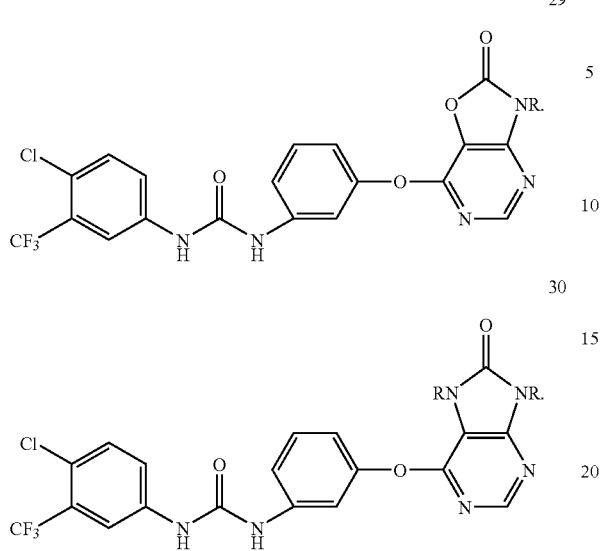
Examples of some preferred compounds (where A-L- is A-C(=O)—NH—, Q is —O—, and Y is —CH=) (here each R is independently —H or -Me) are shown below.
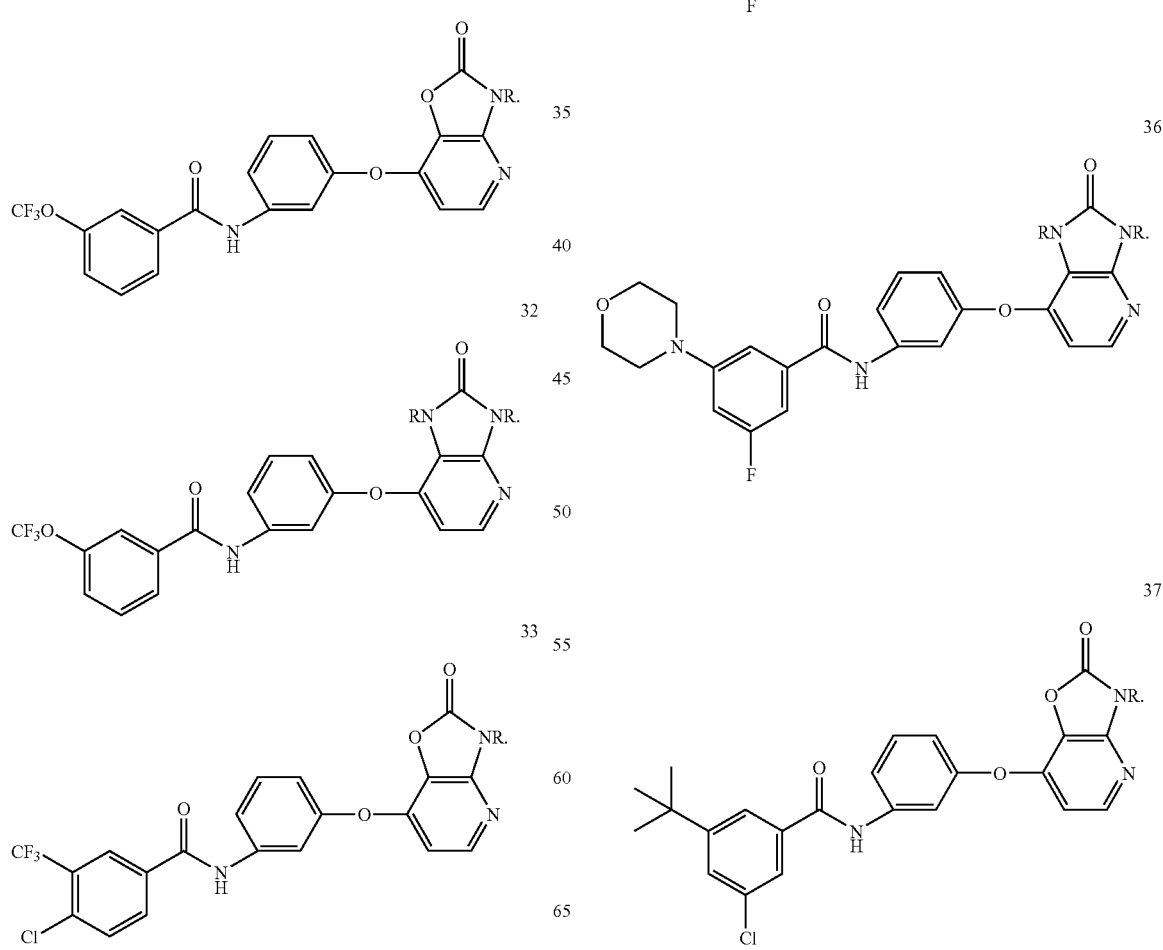
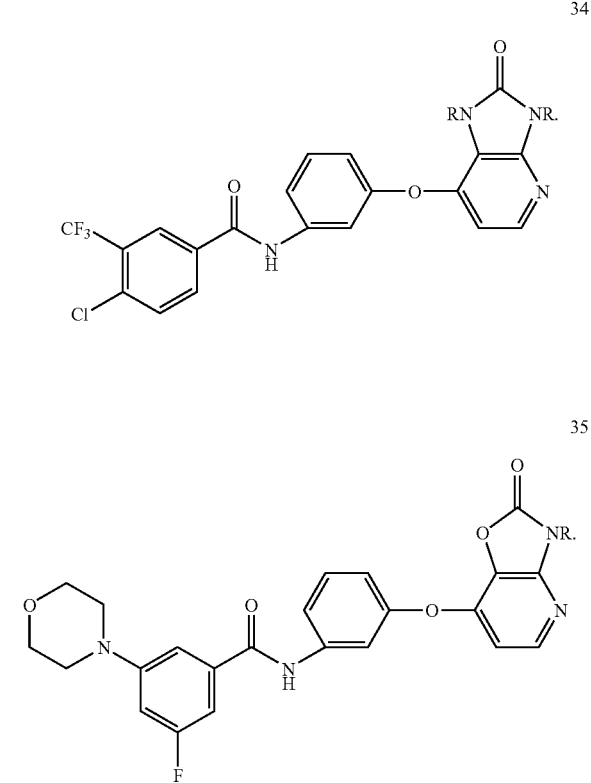

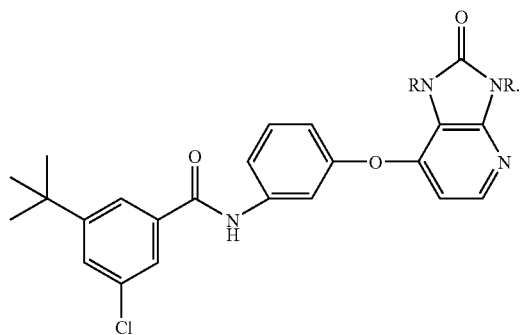
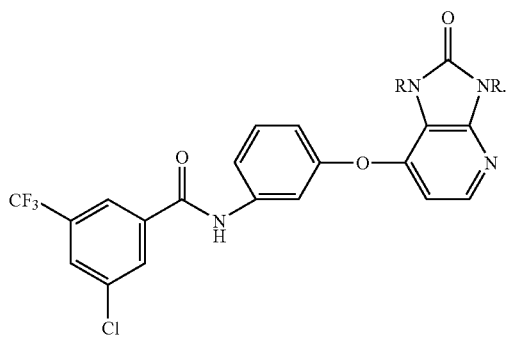

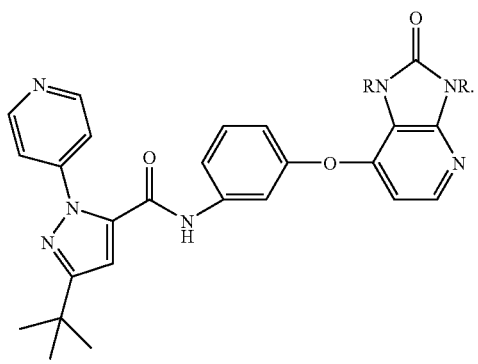
46
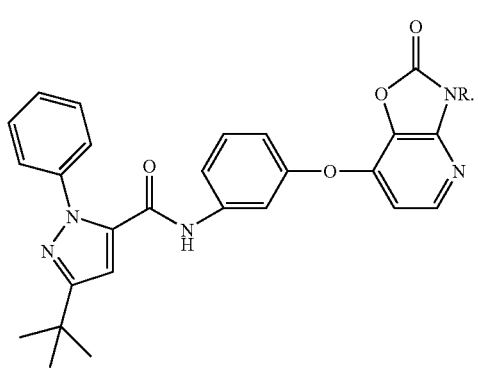
47
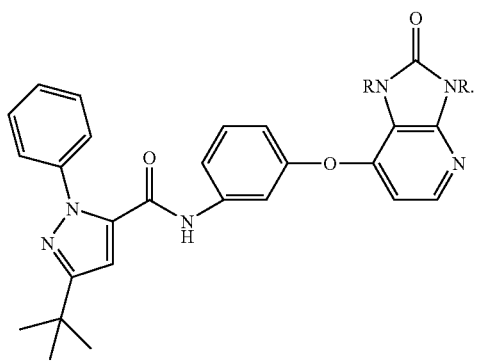
48
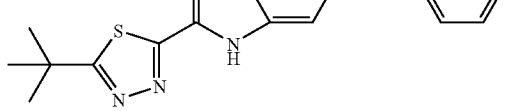
49
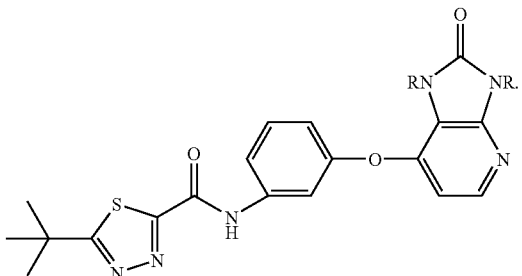
50
Examples of some preferred compounds (where A-L- is A-S(=O)$_2$—NH—, Q is —O—, and Y is —CH=) (here each R is independently —H or -Me) are shown below.
51
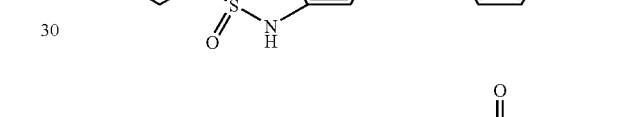
52
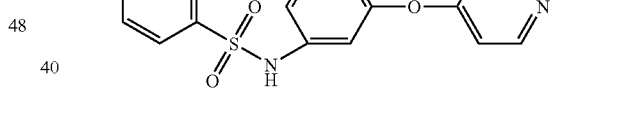
53
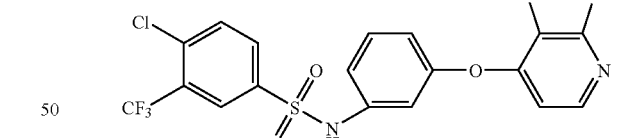
54
Examples of some preferred compounds (where A-L- is A-NH—S(=O)$_2$—NH—, Q is —O—, and Y is —CH=) (here each R is independently —H or -Me) are shown below.

55. 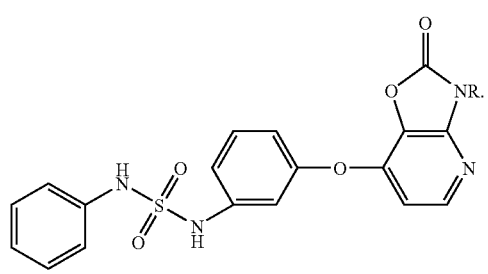
56. 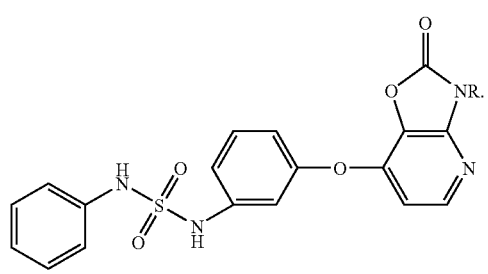
57. 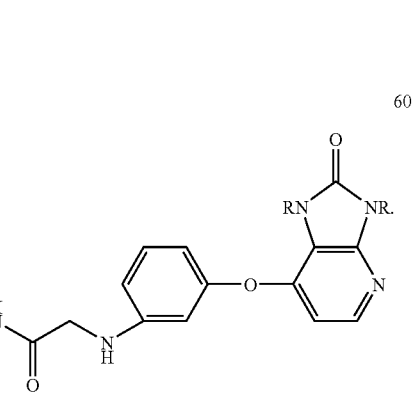
58. 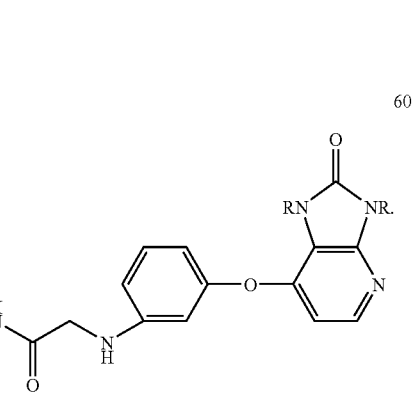
59. 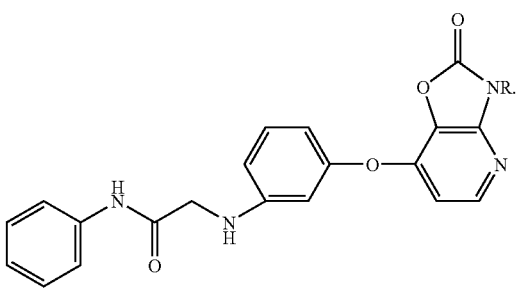
60. 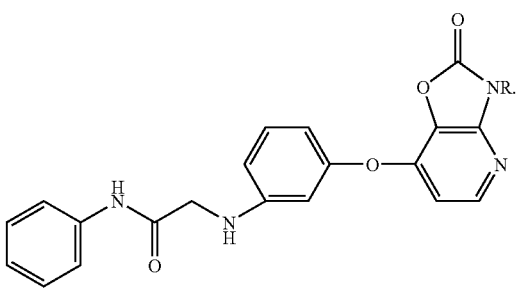
61. 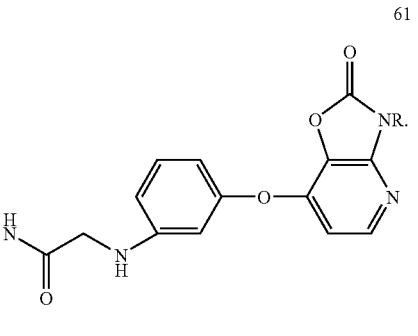
62. 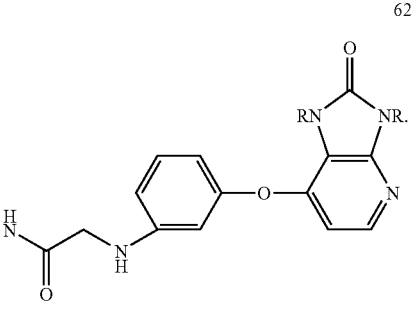
Examples of some preferred compounds (where A-L- is A-NH—C(=O)—CH₂—NH—, Q is —O—, and Y is —CH=) (here each R is independently —H or -Me) are shown below.

Additional examples of compounds include the following:
1 CJS 3256
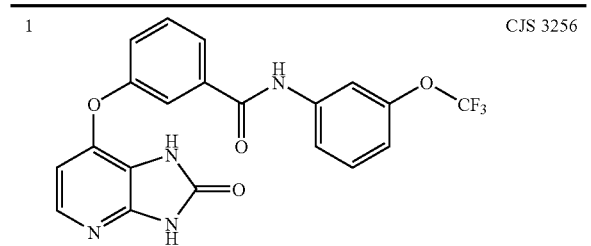
2 CJS 3440
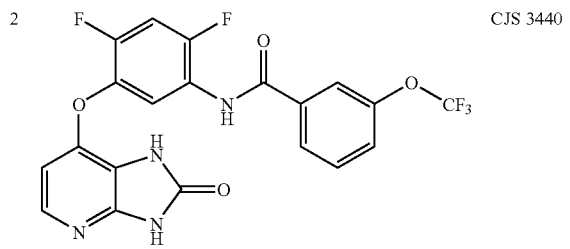
3 CJS 3441
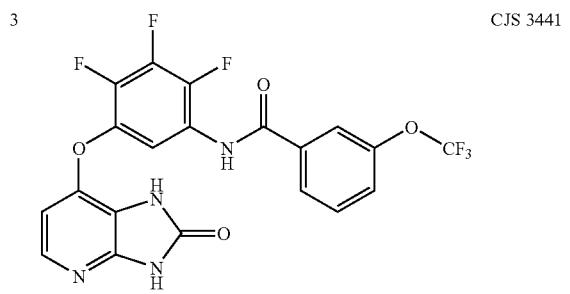
4 CJS 3513
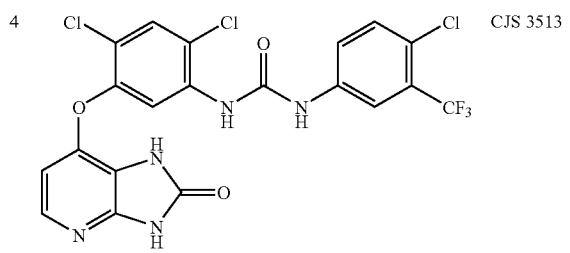
5 CJS 3517
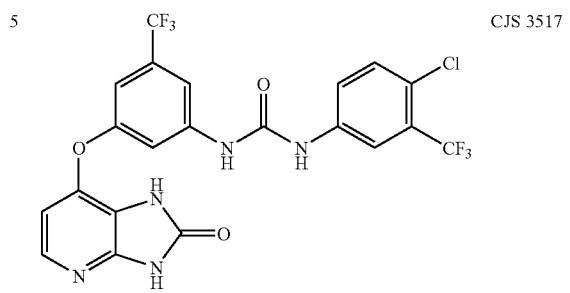
6 CJS 3518
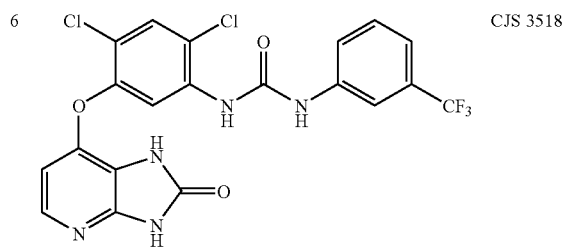
7 CJS 3678
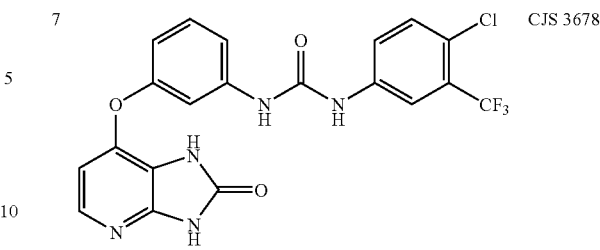
8 CJS 3683
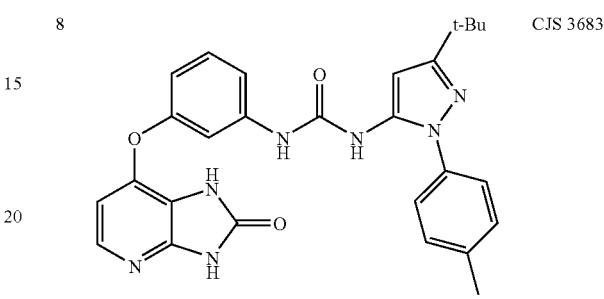
9 CJS 3684
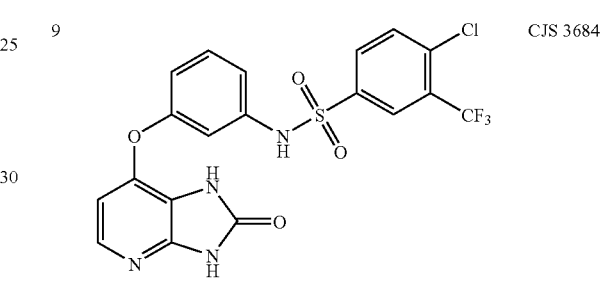
10 CJS 3685
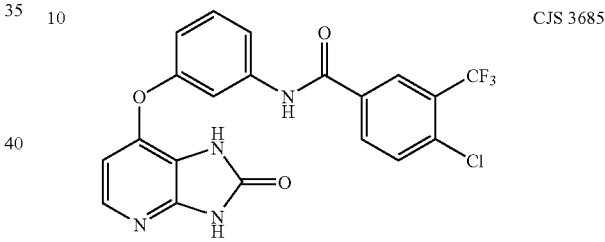
11 CJS 3686
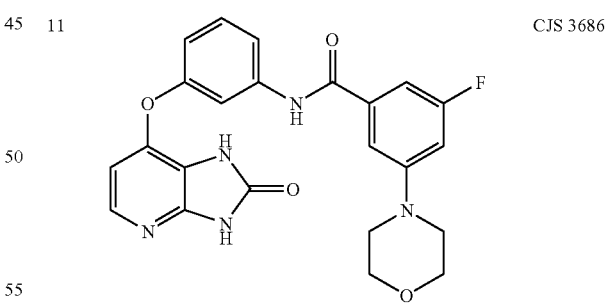
12 CJS 3687
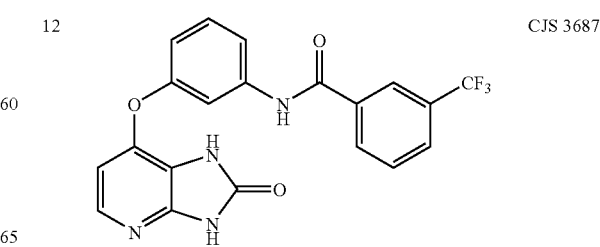

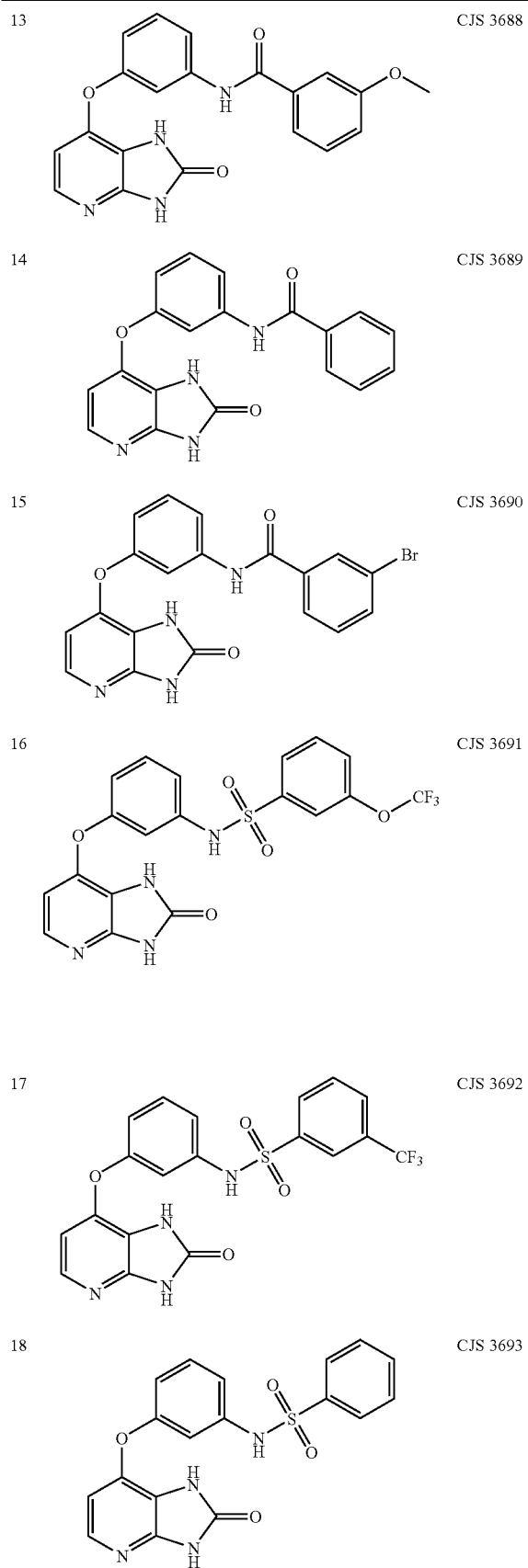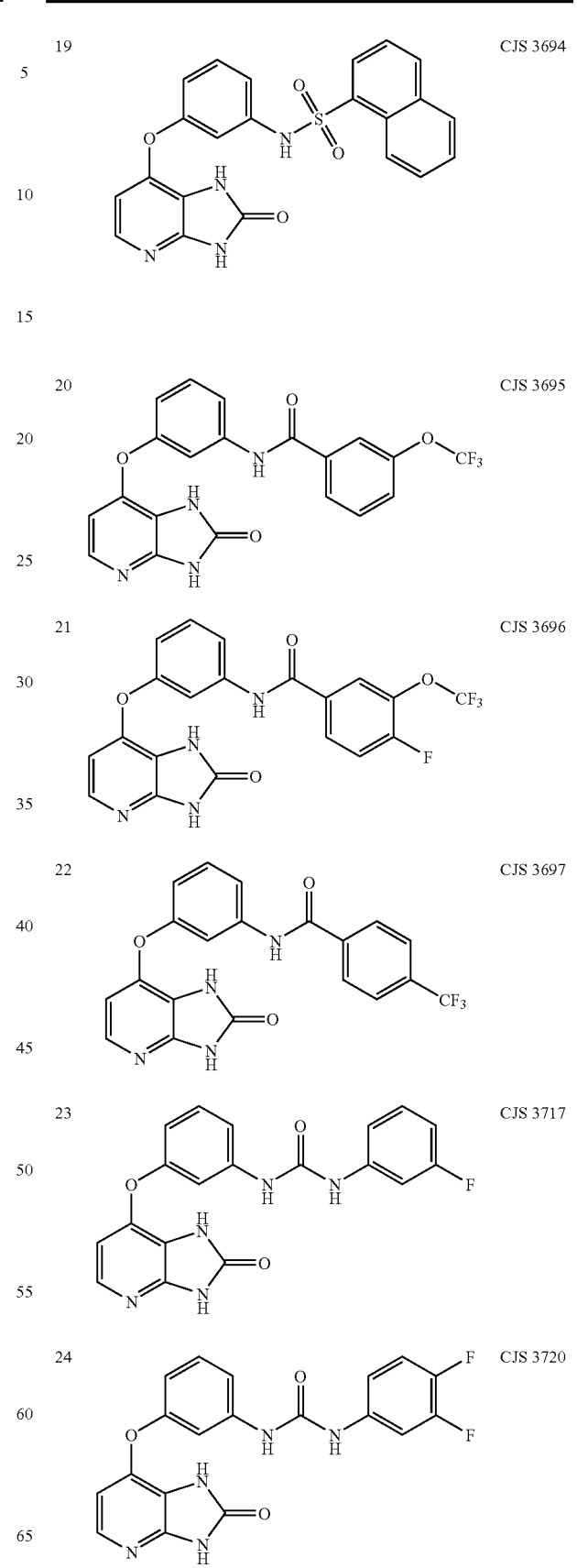

| | | |
|---|---|---|
| 25 | 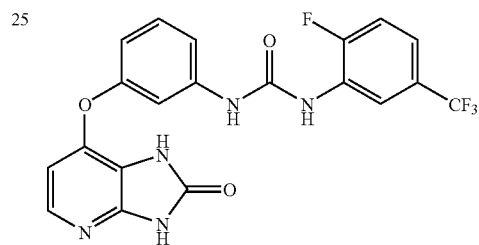 | CJS 3721 |
| 26 | 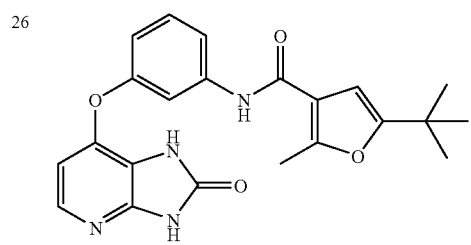 | CJS 3722 |
| 27 | 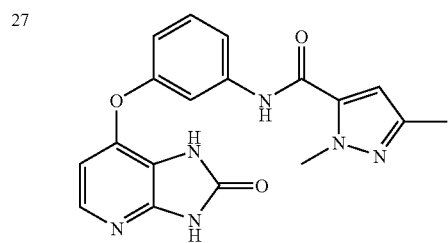 | CJS 3724 |
| 28 | 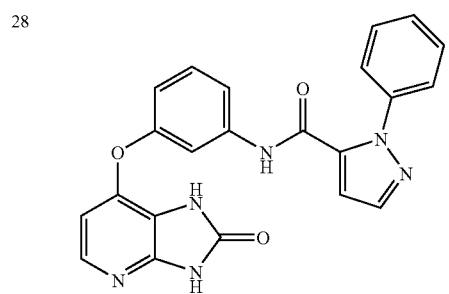 | CJS 3725 |
| 29 | 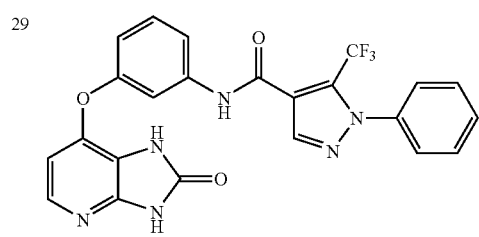 | CJS 3726 |
| 30 | 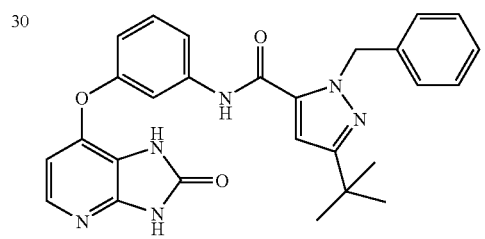 | CJS 3727 |
| 31 | 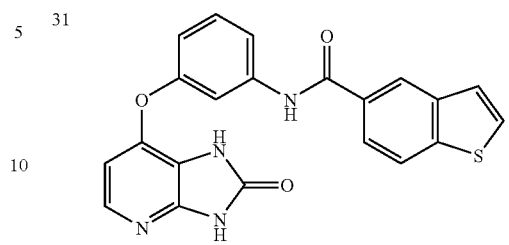 | CJS 3728 |
| 32 | 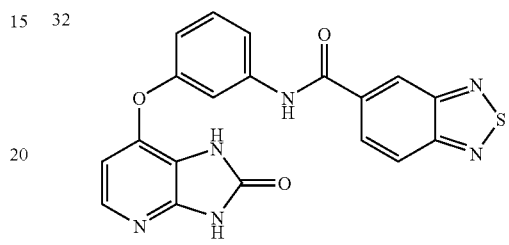 | CJS 3729 |
| 33 | 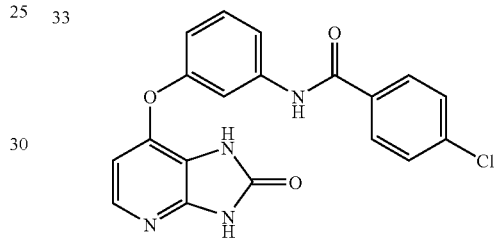 | CJS 3730 |
| 34 | 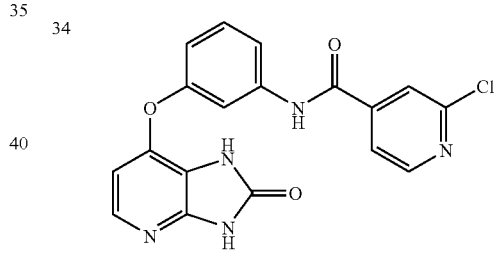 | CJS 3731 |
| 35 | 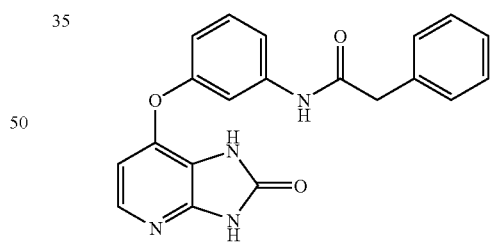 | CJS 3732 |
| 36 | 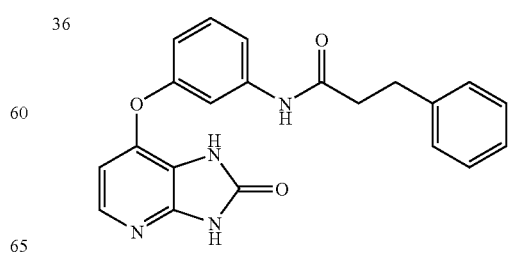 | CJS 3733 |

Additional examples of compounds include the following:
| | | |
|---|---|---|
| 37 | 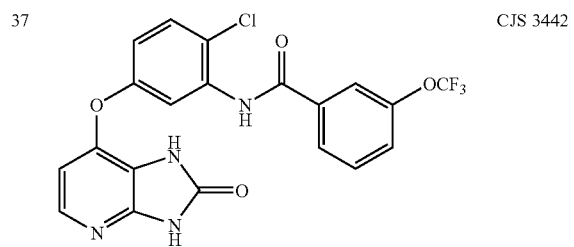 | CJS 3442 |
| 38 | 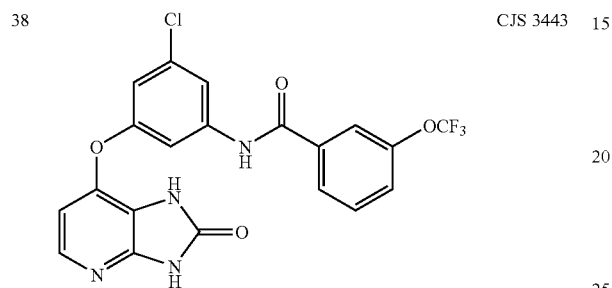 | CJS 3443 |
| 39 | 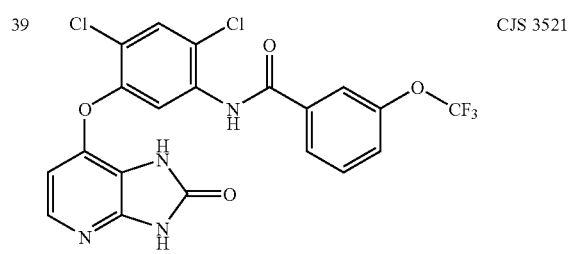 | CJS 3521 |
| 40 | 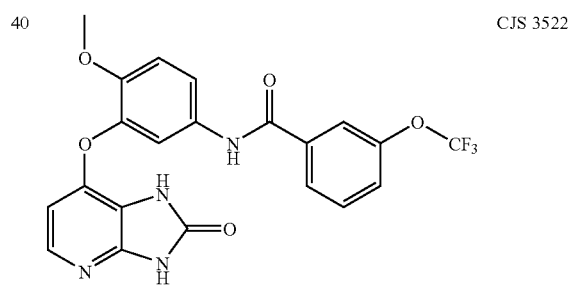 | CJS 3522 |
| 41 | 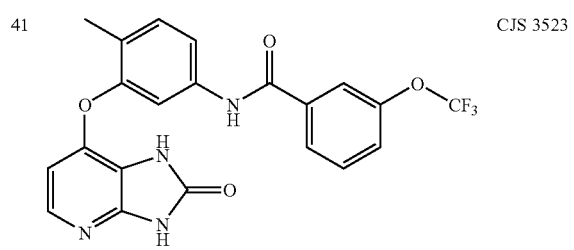 | CJS 3523 |
| 42 | 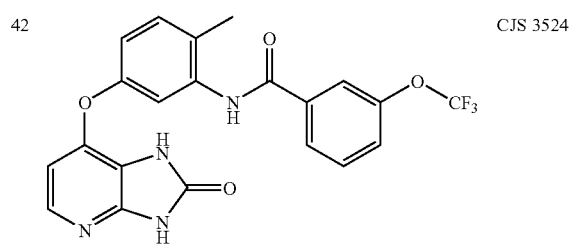 | CJS 3524 |
-continued
| | | |
|---|---|---|
| 43 | 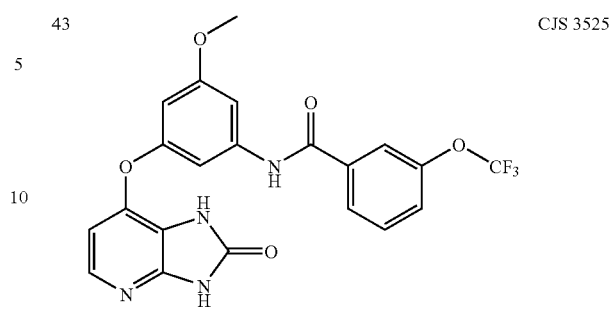 | CJS 3525 |
| 44 | 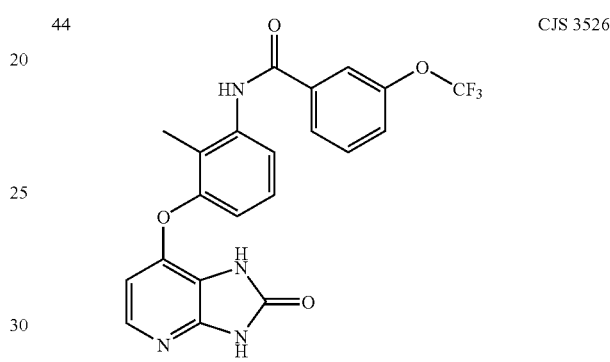 | CJS 3526 |
| 45 | 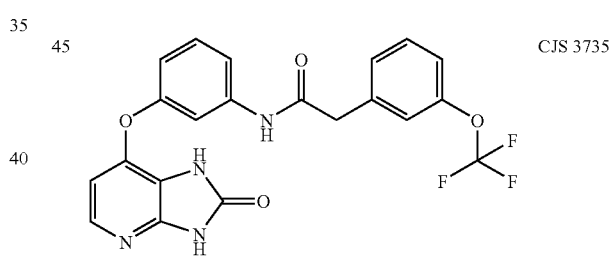 | CJS 3735 |
| 46 | 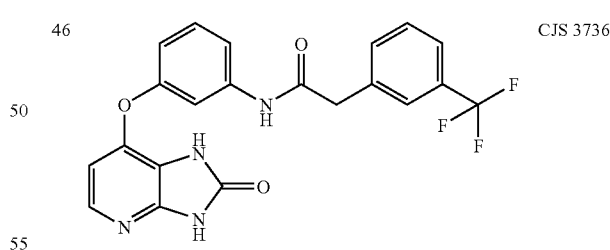 | CJS 3736 |
| 47 | 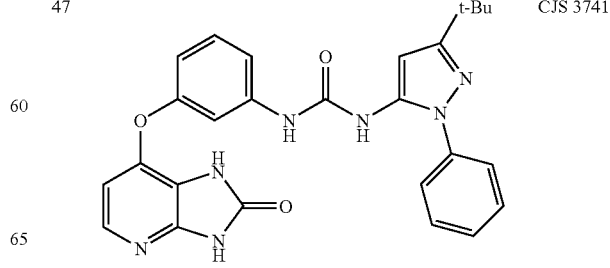 | CJS 3741 |

| | | |
|---|---|---|
| 48 | 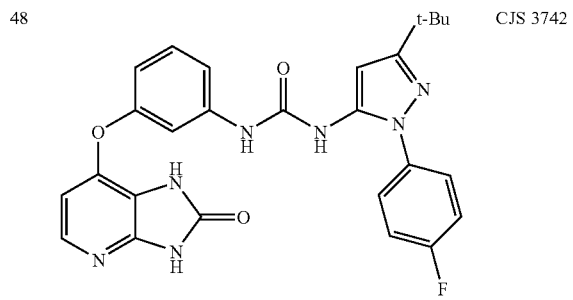 | CJS 3742 |
| 49 | 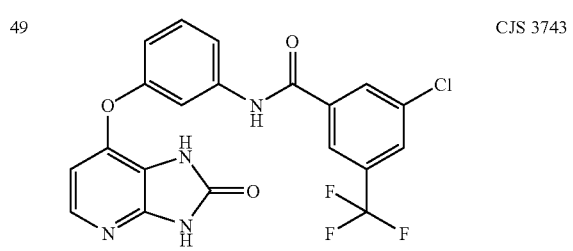 | CJS 3743 |
| 50 | 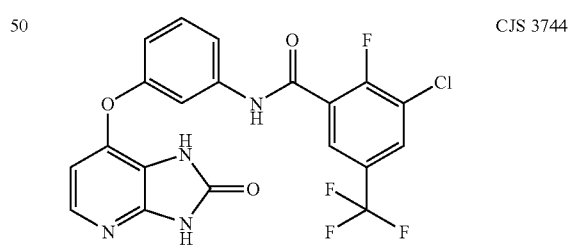 | CJS 3744 |
| 51 | 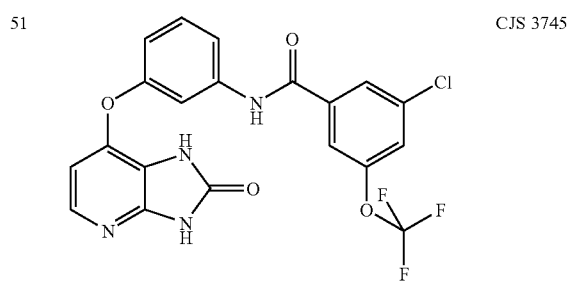 | CJS 3745 |
| 52 | 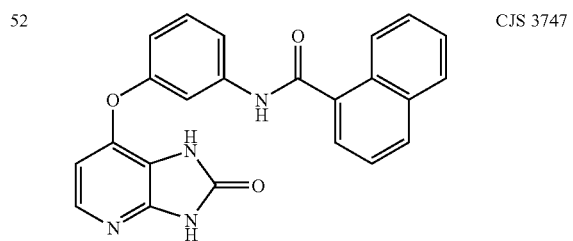 | CJS 3747 |
| 53 | 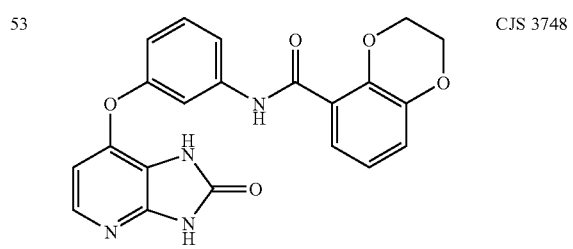 | CJS 3748 |
| | | |
|---|---|---|
| 54 | 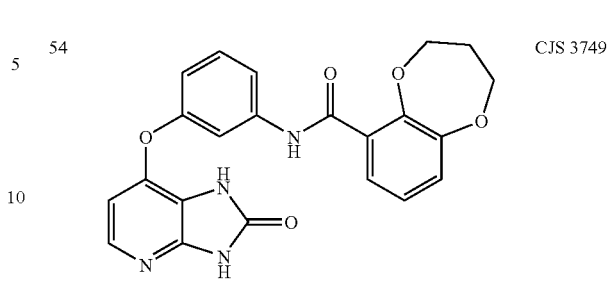 | CJS 3749 |
| 55 | 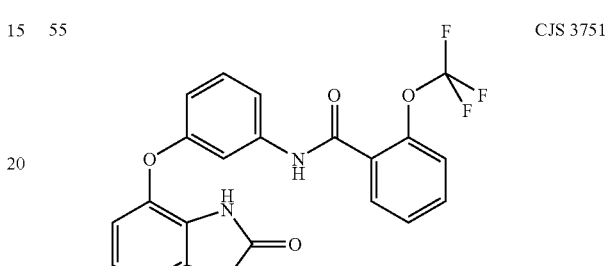 | CJS 3751 |
| 56 | 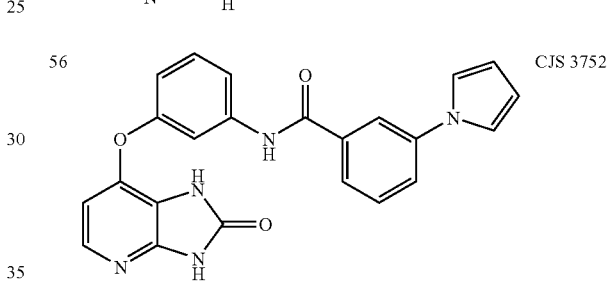 | CJS 3752 |
| 57 | 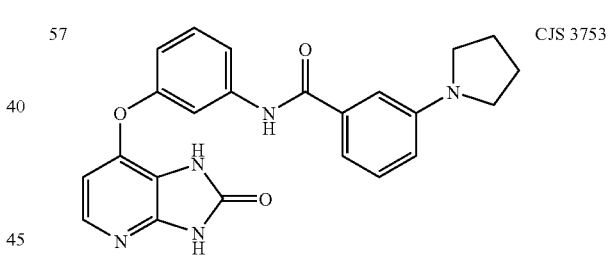 | CJS 3753 |
| 58 | 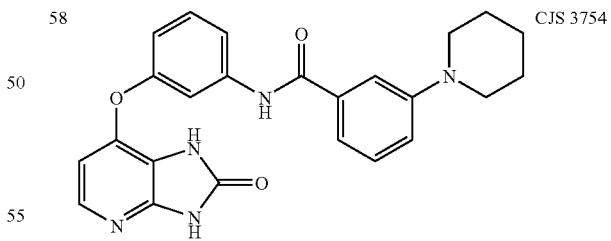 | CJS 3754 |
| 59 | 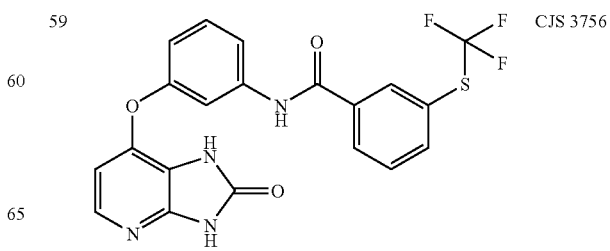 | CJS 3756 |

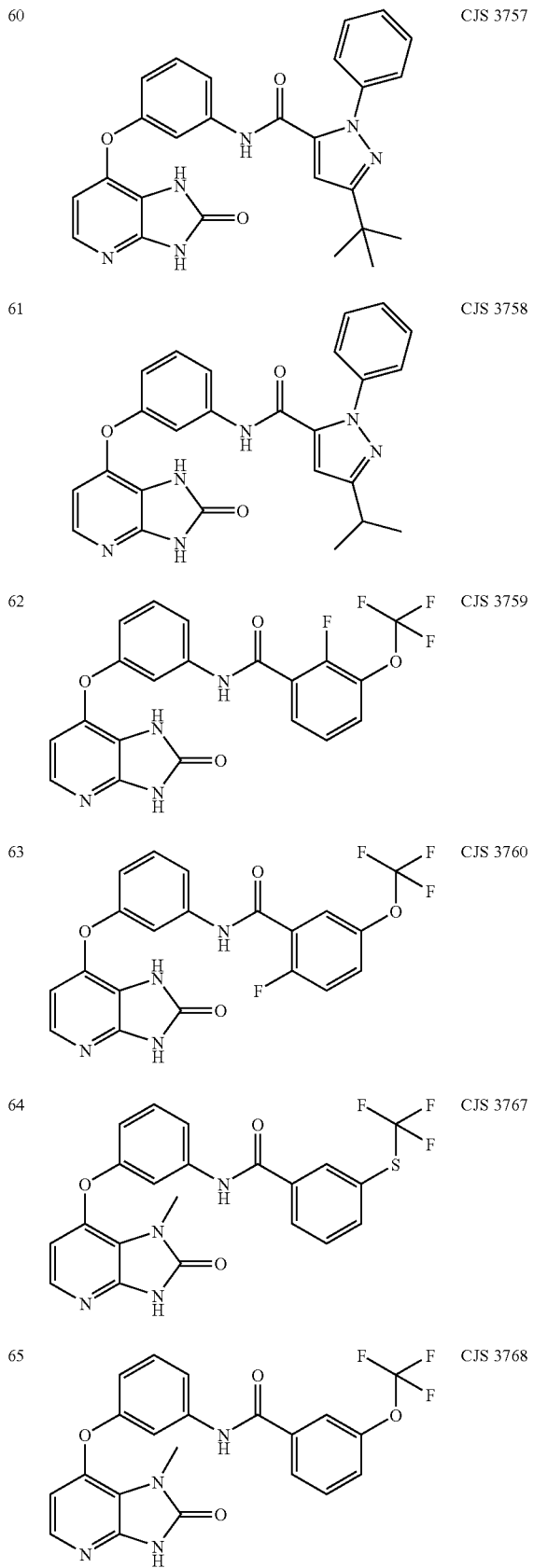
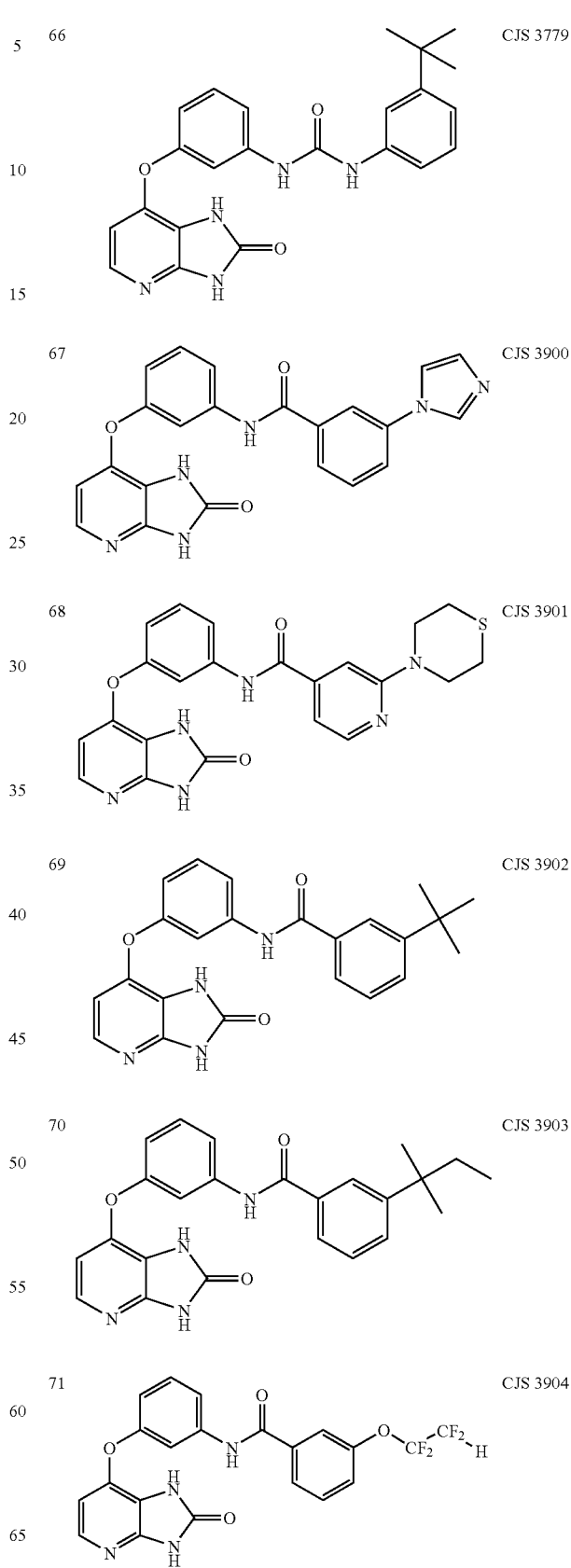

-continued

72 CJS 3906

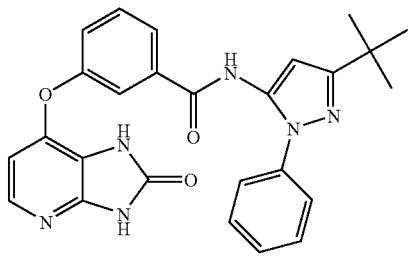

Chemical Terms

The term "carbo," "carbyl," "hydrocarbo," and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond. Compounds and/or groups may be partially unsaturated or fully unsaturated.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked ring atoms, more preferably 3 to 8 covalently linked ring atoms, yet more preferably 5 to 6 covalently linked ring atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 ring heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene, decalin, etc.), bridged (e.g., as in norbornane, adamantane, etc.), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl. Note that the first prefix may vary according to other limitations; for example, for unsaturated alkyl groups, the first prefix must be at least 2; for cyclic and branched alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl ($C_4$), pentenyl ($C_5$), and hexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl," as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of cycloalkyl groups include $C_{3-20}$cycloalkyl, $C_{3-15}$cycloalkyl, $C_{3-10}$cycloalkyl, $C_{3-7}$cycloalkyl.

Examples of cycloalkyl groups include, but are not limited to, those derived from saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds:
camphene ($C_{10}$), limonene ($C_{10}$), pinene ($C_{10}$);

polycyclic hydrocarbon compounds having an aromatic ring:
indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Carbocyclyl: The term "carbocyclyl," as used herein, pertains to a monovalent moiety obtained by removing a hydrogen atom from a non-aromatic ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{5-20}$heterocyclyl, $C_{3-15}$heterocyclyl, $C_{5-15}$heterocyclyl, $C_{3-12}$heterocyclyl, $C_{5-12}$heterocyclyl, $C_{3-10}$heterocyclyl, $C_{5-10}$heterocyclyl, $C_{3-7}$heterocyclyl, $C_{5-7}$heterocyclyl, and $C_{5-6}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{5-20}$aryl, $C_{5-15}$aryl, $C_{5-12}$aryl, $C_{5-10}$aryl, $C_{5-7}$aryl, $C_{5-6}$aryl, $C_5$aryl, and $C_6$aryl.

The ring atoms may be all carbon atoms, as in "carboaryl groups." Examples of carboaryl groups include $C_{3-20}$carboaryl, $C_{5-20}$carboaryl, $C_{5-15}$carboaryl, $C_{5-12}$carboaryl, $C_{5-10}$carboaryl, $C_{5-7}$carboaryl, $C_{5-6}$carboaryl, $C_5$carboaryl, and $C_6$carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H- indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups." Examples of heteroaryl groups include $C_{3-20}$heteroaryl, $C_{5-20}$heteroaryl, $C_{5-15}$heteroaryl, $C_{5-12}$heteroaryl, $C_{5-10}$heteroaryl, $C_{5-7}$heteroaryl, $C_{5-6}$heteroaryl, $C_5$heteroaryl, and $C_6$heteroaryl.

Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:
$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
$C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);
$C_{11}$heterocylic groups (with 2 fused rings) derived from benzodiazepine ($N_2$);
$C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and,
$C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) that have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N⁺(→O⁻)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms.

Monocyclic examples of such groups include, but are not limited to, those derived from:
$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$C_{10}$: tetralone, decalone;
$C_{14}$: anthrone, phenanthrone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$); benzodiazepinone ($C_{11}$); benzodiazepinedione ($C_{11}$);
$N_4$: purinone ($C_9$) (e.g., guanine).

Still more examples of cyclic groups which bear one or more oxo (=O) groups on ring carbon atoms include, but are not limited to, those derived from:
cyclic anhydrides (—C(=O)—O—C(=O)— in a ring), including but not limited to maleic anhydride ($C_5$), succinic anhydride ($C_5$), and glutaric anhydride ($C_6$);
cyclic carbonates (—O—C(=O)—O— in a ring), such as ethylene carbonate ($C_5$) and 1,2-propylene carbonate ($C_5$);
imides (—C(=O)—NR—C(=O)— in a ring), including but not limited to, succinimide ($C_5$), maleimide ($C_5$), phthalimide, and glutarimide ($C_6$);
lactones (cyclic esters, —O—C(=O)— in a ring), including, but not limited to, β-propiolactone, γ-butyrolactone, δ-valerolactone (2-piperidone), and ε-caprolactone;
lactams (cyclic amides, —NR—C(=O)— in a ring), including, but not limited to, ε-propiolactam ($C_4$), γ-butyrolactam (2-pyrrolidone) ($C_5$), δ-valerolactam ($C_6$), and ε-caprolactam ($C_7$);
cyclic carbamates (—O—C(=O)—NR— in a ring), such as 2-oxazolidone ($C_5$);
cyclic ureas (—NR—C(=O)—NR— in a ring), such as 2-imidazolidone ($C_5$) and pyrimidine-2,4-dione (e.g., thymine, uracil) ($C_6$).

Includes Other Forms

Unless otherwise specified, a reference to a particular group also includes the well known ionic, salt, solvate, and protected forms thereof. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exoforms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

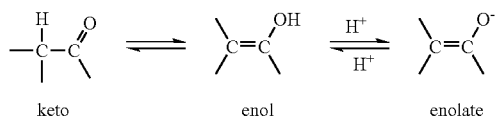

keto          enol          enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate forms thereof.

Chemically Protected Forms

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihalo alkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

Unless otherwise specified, a reference to a particular compound also includes prodrugs thereof.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of compounds of the present invention are described herein. These and/or other well known methods may be modified and/or adapted in known ways in order to facilitate the synthesis of additional compounds within the scope of the present invention.

Descriptions of general laboratory methods and procedures, useful for the preparation of the compounds described herein, are provided in *Vogel's Textbook of Practical Organic Chemistry, 5th Edition,* 1989, (Editors: Furniss, B. S., Hannaford, A. J., Smith, P. W. G., Tatchell, A. R.) (published by Longmann, UK).

Methods for the synthesis of pyridine compounds in particular are described in *Heterocyclic Chemistry, 3rd Edition,* 1998, Joule, J. A, Mills, R. and Smith, G. F. (published by Chapman & Hall, UK).

Many of the compounds described herein can be prepared via a key intermediate: 4-(3-amino-phenoxy)-3-nitro-pyridin-2-amine, (2), conveniently substituted on the phenyl ring. This intermediate can be prepared from commercially available starting material, 4-chloro-3-nitro-pyridin-2-amine, (1), and substituted 3-amino-phenols. Compounds 2 are then protected selectively at the 3-amino group, for example as a Boc carbamate or trifluoroacetamide, to afford intermediates, (3). The intermediates, (3), can also be obtained directly from 4-chloro-3-nitro-pyridin-2-amine, (1), and N-Boc-protected 3-amino-phenols. An example of such a method is illustrated in the following scheme.

Scheme 1

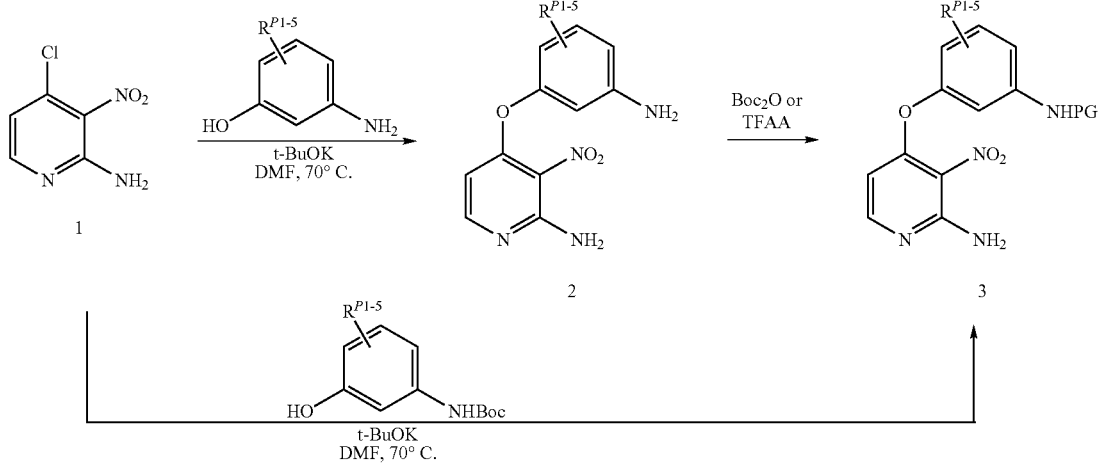

PG = Boc or COCF$_3$

Note that compounds with substituted or unsubstituted phenyl groups have been synthesised and are described herein. The following Schemes are illustrated using unsubstituted phenyl or specifically substituted phenyl, but it should be understood that these methods are also suitable for the preparation of compounds with substituted (or differently substituted) phenyl rings.

In one approach, the protected intermediate (3) is converted to another key intermediate: 7-(3-amino-phenoxy)-1,3-dihydro-imidazo[4,5-b]pyridin-2-one, (6).

For example, the nitro group of the protected intermediate, (3), may be reduced to an amino group with Pd/C and ammonium formate or hydrogen, and then the imidazolone, (5), formed. Deprotection of the Boc group with TFA or trifluoroacetamide with ammonia affords the common intermediate, (6). An example of such a method is illustrated in the following scheme:

This key intermediate (6) may then be used to prepare a range of compounds with different linker groups, L, and different terminal groups, A.

For example, the key intermediate (6) can be reacted with activated carboxylic acids or acid chloride to afford amides (NHCO); with activated thioacetic acids to afford thioamides (NHCS); with isocyanates or with activated carbamates to afford ureas (NHCONH); with isothiocyanates to afford thioureas (NHCSNH); with sulfonyl chlorides to afford sulfonamides ($SO_2NH$); with activated sulfamoyl derivatives to afford sulfamides ($NHSO_2NH$); with haloacetic amide to afford glycinamides ($NHCH_2CONH$). Examples of such methods are illustrated in the following scheme.

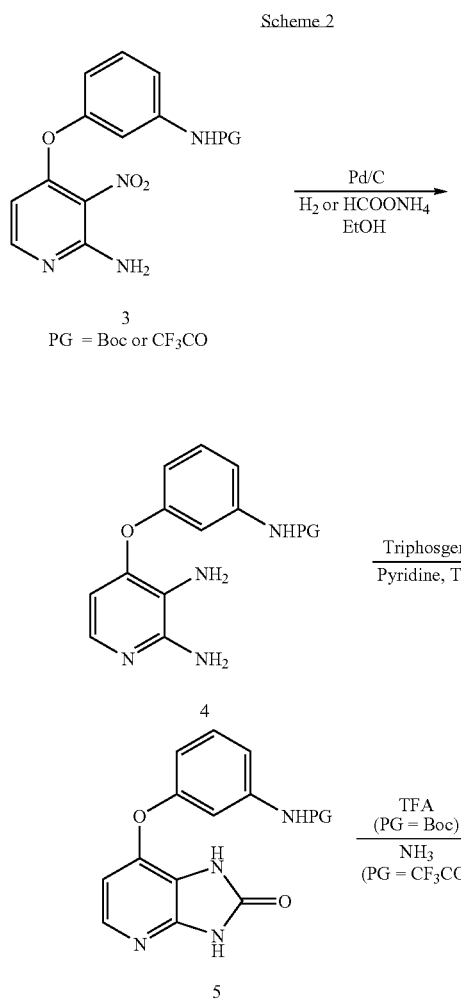

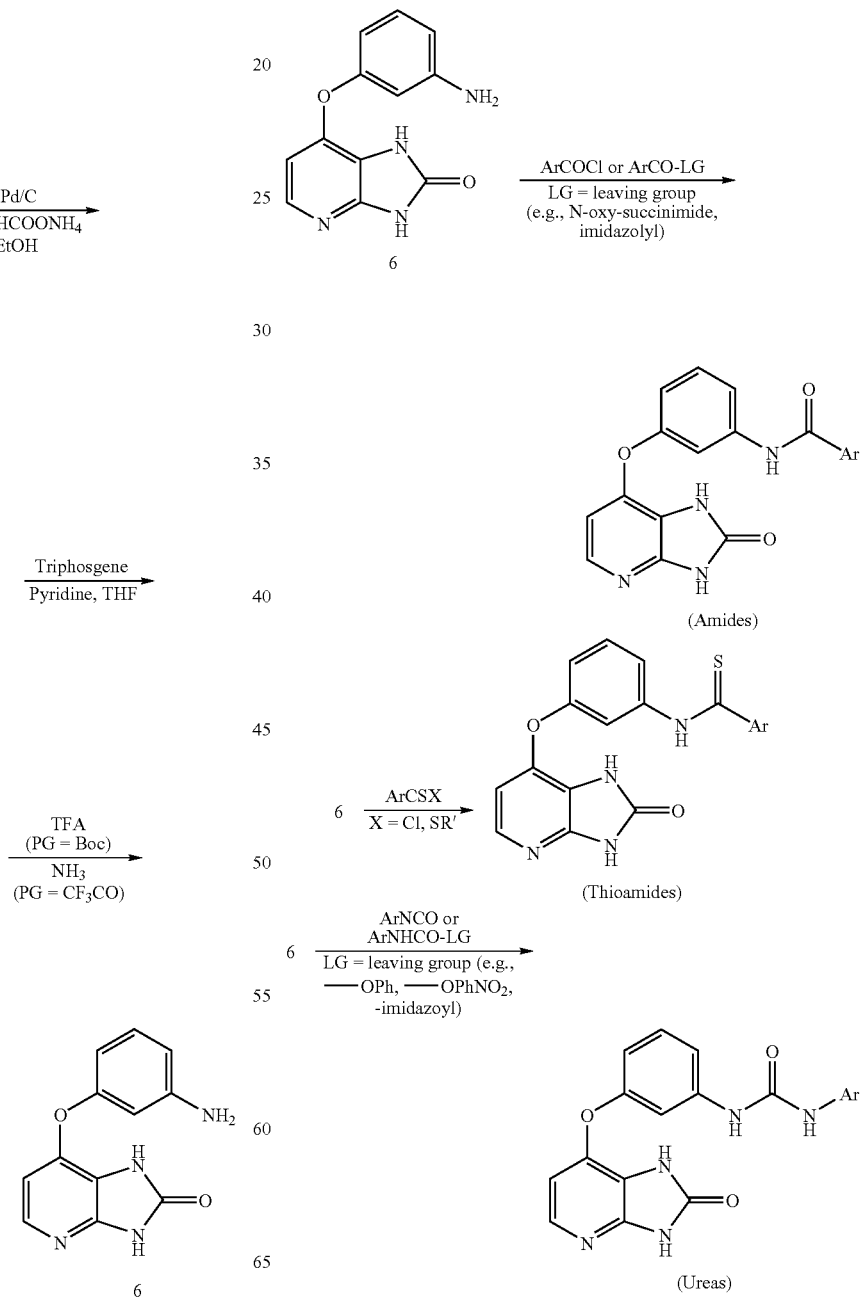

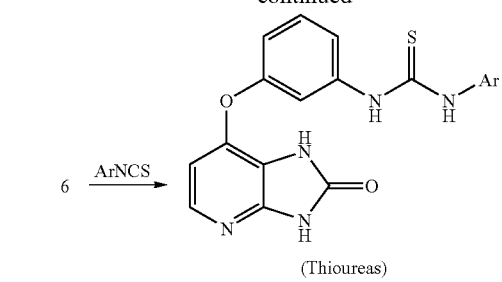

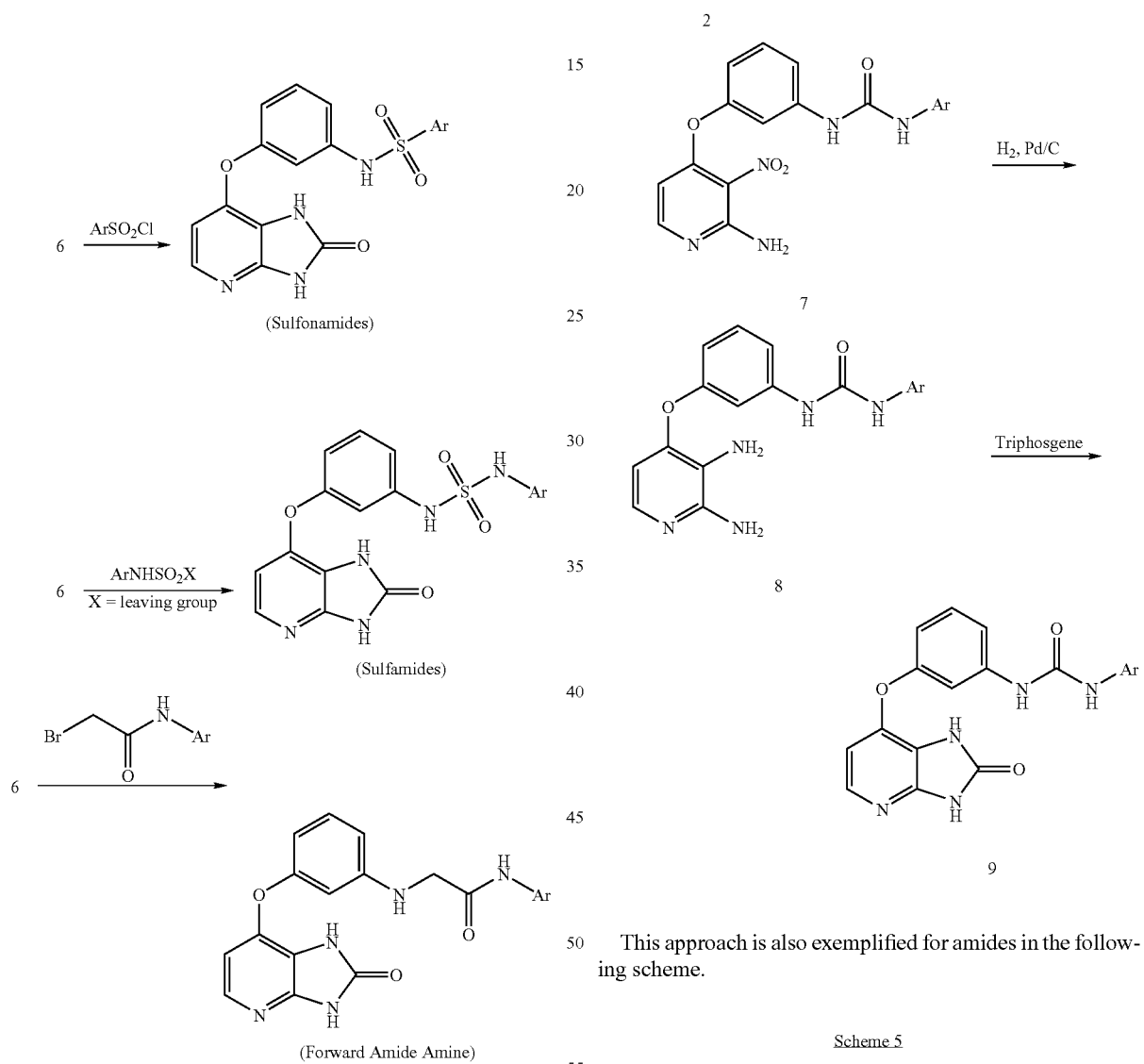

In another approach, the key intermediate (2) is first converted to a urea, thiourea, amide, thioamide, sulfonamide, or sulfamide, using a method as described in the scheme above, and then converted to an imidazo[4,5-b]pyridine-2-one.

This approach is exemplified for ureas in the following scheme. For example, the reaction of key intermediate (2) with isocyanates produces ureas, (7). Reduction of nitro group, to give (8), followed by cyclisation to an imidazolone, affords the final product, (9). An example of such a method is illustrated in the following scheme.

This approach is also exemplified for amides in the following scheme.

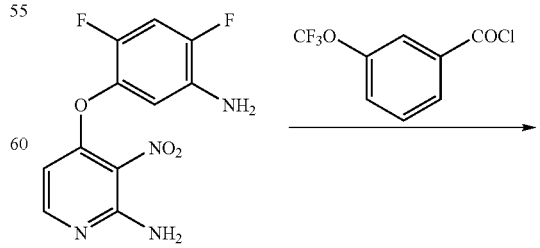

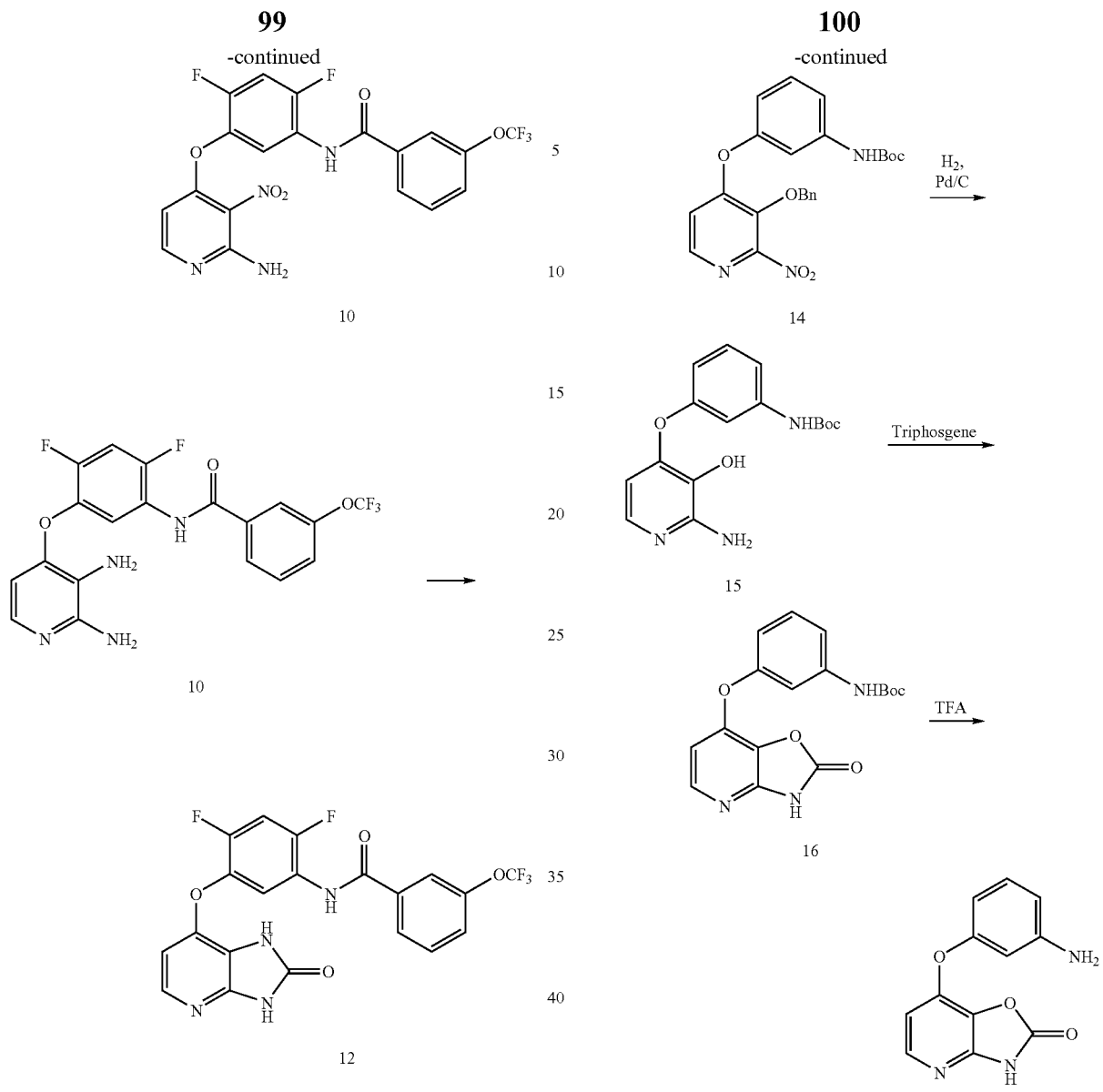

In another approach, another key intermediate is prepared from 4-chloro-3-benzyloxy-2-nitropyridine, (13), by replacing the chloro group with a meta Boc-amino-phenoxy group to afford (14). Then the benzyl group is removed concomitant with the reduction of the nitro to afford the intermediate, (15). The oxazolone ring is closed using triphosgene, phosgene or carbonyldiimidazole to generate (16), and the initial amino group is deprotected to give the desired intermediate: 7-(3-amino-phenoxy)-3H-oxazolo[4,5-b]pyridin-2-one, (17). An example of such method is illustrated in the following scheme.

Scheme 6

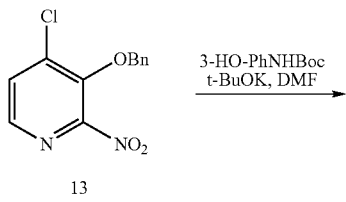

Again, this key intermediate (17) may then be used to prepare a range of compounds with different linker groups, L, and different terminal groups, A.

In another approach, the key intermediate (21) is prepared starting from intermediate (4). The more nucleophilic 3-amino group on the pyridine is selectively converted to a carbamate, the Boc group is deprotected, and the carbamate is alkylated. Ring closure under basic conditions affords imidazo[4,5-b]pyridine-2-one.

For example, intermediate (4) is converted to ethyl carbamate (18) and the Boc group is removed with TFA to afford (19). Deprotonation of the acidic carbamate proton with NaH creates an anion on N-3 of pyridine that is alkylated to afford the intermediate (20). Intermediate (20) is cyclised to the common intermediate (21) in the presence of base. An example of such a method is illustrated in the following scheme.

Scheme 7

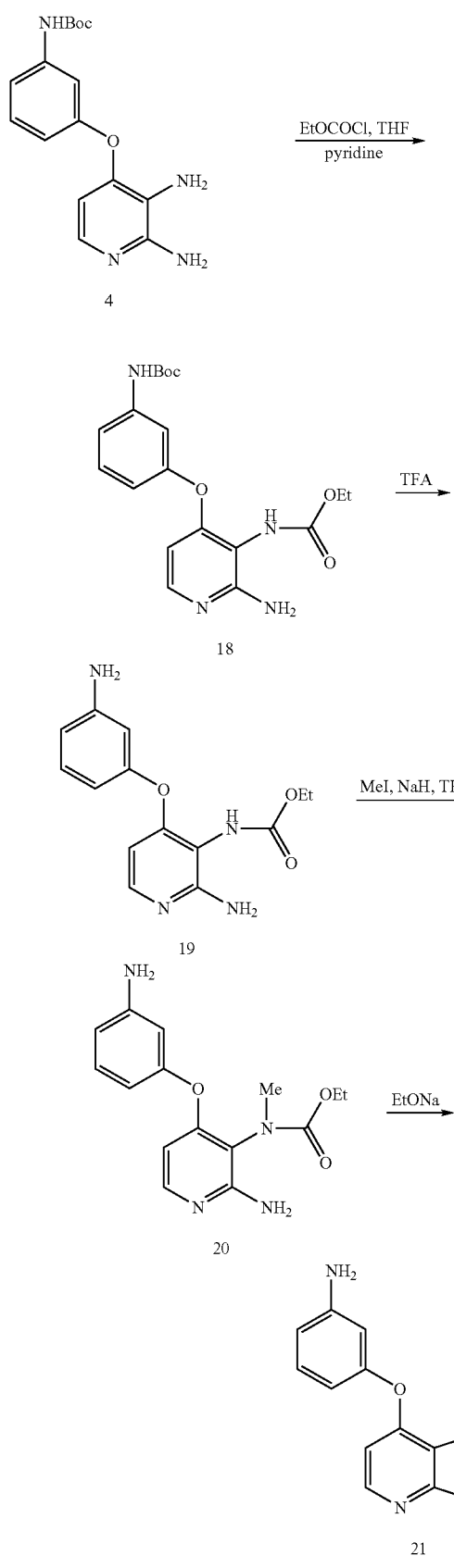

Again, this key intermediate (21) may then be used to prepare a range of compounds with different linker groups, L, and different terminal groups, A.

In another approach, the key intermediate (26) is prepared starting with intermediate (22). Replacement of the chloro group with N-Boc protected 3-aminophenolate yields (23) directly. Reduction of the nitro group, formation of cyclic imidazolone, and removal of the Boc group affords the intermediate (26). An example of such a method is illustrated in the following scheme.

Scheme 8

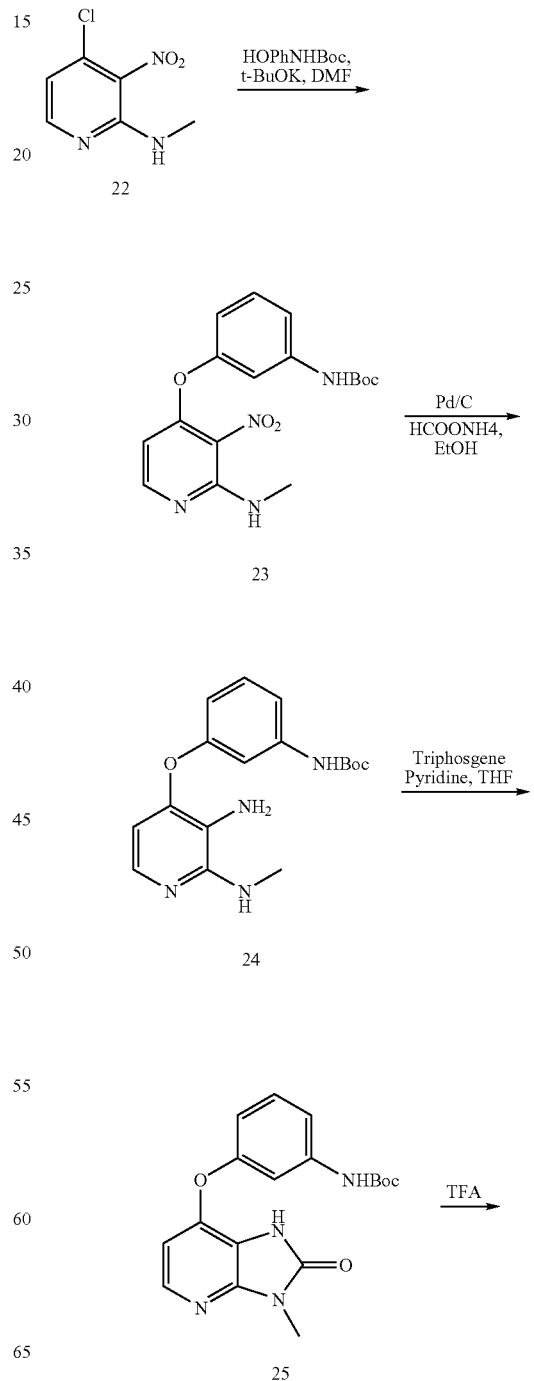

103
-continued

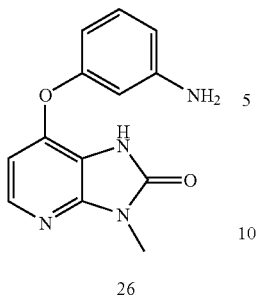

26

104
-continued

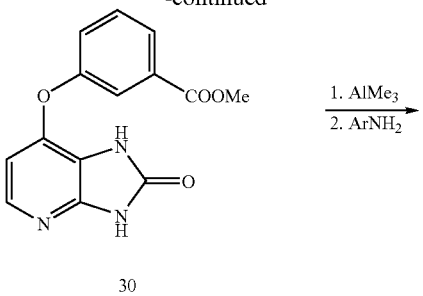

30

Again, this key intermediate, (26), may be used to prepare a range of compounds with different linker groups, L, and different terminal groups, A.

Compounds containing the reverse amide linker can be prepared from the starting material 1 and 3-hydroxybenzoic ester (for example methyl 3-hydroxybenzoate, (27); other esters can equally be used). The intermediate (28) thus obtained can be reduced to the diamino compound (29), and cyclised to the pyridoimidazolone (30). The ester group is hydrolysed and the carboxylic acid formed activated with oxalyl chloride or carbonyldiimidazole (CDI). This activated acid can then be coupled with amines in order to afford final compounds (31) with various A groups, where the linker L is C(=O)NH. An alternative method is to react the ester intermediate, (30), directly with the amine, in the presence of a strong base or AlMe$_3$, to obtain the final compounds, (31). An example of such a method is illustrated in the following scheme.

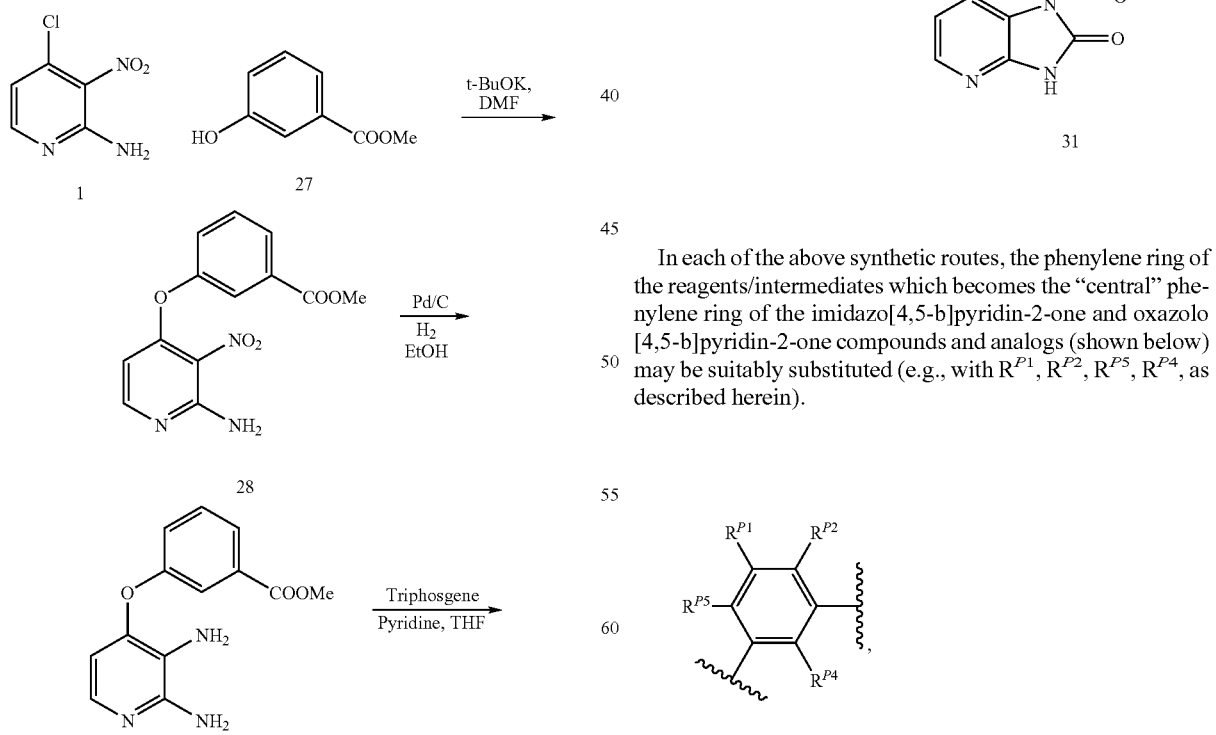

In each of the above synthetic routes, the phenylene ring of the reagents/intermediates which becomes the "central" phenylene ring of the imidazo[4,5-b]pyridin-2-one and oxazolo[4,5-b]pyridin-2-one compounds and analogs (shown below) may be suitably substituted (e.g., with $R^{P1}$, $R^{P2}$, $R^{P5}$, $R^{P4}$, as described herein).

Additional synthetic routes (to vary the group Q) are described in, or may readily be derived from the synthetic routes described in, the following documents:

| -Q- | Literature Reference(s) |
| --- | --- |
| —(CH$_2$)$_0$—X—(CH$_2$)$_1$— | Tetrahedron, 1987, 43(11), 2557-2564. |
| —(CH$_2$)$_0$—X—(CH$_2$)$_2$— | Tetrahedron Letters, 1994, 35(40), 7343-7346. |
| —(CH$_2$)$_1$—X—(CH$_2$)$_0$— | U.S. Pat. No. 6,492,529, 10 Dec. 2002 |
| —(CH$_2$)$_2$—X—(CH$_2$)$_0$— | Tetrahedron, 1988, 44(21), 6677-6680. |
| —(CH$_2$)$_1$—X—(CH$_2$)$_1$— | U.S. Pat. No. 6,492,529, 10 Dec. 2002 |

Additional synthetic routes (to vary the group L) are described in, or may readily be derived from the synthetic routes described in, the following documents:

| A-L- | Literature Reference(s) |
| --- | --- |
| A-NHC(=X)— | Tetrahedron Letters, 1995, 36(37), 6745-6756. |
| A-C(=X)NH— | Tetrahedron Letters, 1995, 36(37), 6745-6746. |
| A-NHC(=X)NH— | Eur. J. of Medicinal Chemistry, 1981, 16 (4), 321-326; Tetrahedron, 2000, 56(4), 629-637; Synthetic Communications, 1997, 27(13), 2255-2260. |
| A-NHSO$_2$— | J. Med. Chem., 1991, 34(4), 1356-1362; Japanese Patent No 57-038777; J. Het. Chem., 1980, 17(1), 11-16. |
| A-NHSO$_2$NH— | Polish Journal of Chemistry, 1991, 65(11), 2053-2055; International (PCT) Patent Publication No WO 2001/036383. |
| A-CH$_2$NHC(=X)— | Tetrahedron Letters, 1995, 36(37), 6745-6746. |
| A-CH$_2$NHC(=X)NH— | Eur. J. of Medicinal Chemistry, 1981, 16 (4), 321-326; Tetrahedron, 2000, 56(4), 629-637; Synthetic Communications, 1997, 27(13), 2255-2260. |
| A-NHCH$_2$C(=X)NH— | J. Organic Chemistry, 1978, 43(17), 3394-3396; Journal of the Chemical Society, Perkin Transactions 1: Organic and Bio-Organic Chemistry, 1987, (8), 1841-1843; Indian Journal of Chemistry, Section B: Organic Chemistry Including Medicinal Chemistry, 1992, 31B(6), 349-350; Tetrahedron Letters, 1995, 36(37), 6745-6746. |
| A-NHCH$_2$C(=X)— | Journal of the Chemical Society, Perkin Transactions 1: Organic and Bio-Organic Chemistry (8), 1987, 1841-1843; Journal of Organic Chemistry, 1978, 43(17), 3394-3396; Bulletin of the Chem. Soc. of Japan, 1997, 70(3), 509-523. |

Additional synthetic routes (to vary the group L) are described in, or may readily be derived from the synthetic routes described in, the following documents:

| A-L- | Literature Reference(s) |
| --- | --- |
| A-NR$^N$—CO—CH$_2$— | Biorganic & Medicinal Chem Lett., 2003, 13(12), 1989-1992. |
| A-CH$_2$—CO—NR$^N$— | Biorganic & Medicinal Chemistry, 2001, 9(8), 2061-71. |
| A-CH$_2$—NR$^N$—CO— | Il Farmaco, 1999, 54(6), 364-374. |
| A-NR$^N$—CH$_2$—CO— | Journal of Organic Chemistry, 1978, 43(17), 3394-3396. |
| A-CO—CH$_2$—NR$^N$— | Journal of Medicinal Chemistry, 1989, 32(10), 2363-2367. |
| A-CH$_2$—CO—NR$^N$—CH$_2$— | Journal of Medicinal Chemistry, 2003, 46(20), 4297-4312. |
| A-CH$_2$—NR$^N$—CO—CH$_2$— | Journal of Organic Chemistry, 2003, 68(3), 1165-1167. |
| A-CH$_2$—CH$_2$—CO—NR$^N$— | Polish J. of Pharmacology & Pharmacy, 1990, 42(1), 69-77. |
| A-CH$_2$—CH$_2$—NR$^N$—CO— | J. American Chemical Society, 2002, 124(11), 2560-2567. |
| A-CH$_2$—CO—CH$_2$—NR$^N$— | Journal of Heterocyclic Chemistry, 1981, 18(3), 561-563. |
| A-CH$_2$—NR$^N$—CH$_2$—CO— | Tetrahedron, 2002, 58(49), 9865-9870. |
| A-NR$^N$—CO—CH$_2$—CH$_2$— | Tetrahedron Letters, 2003, 44(9), 1951-1955. |
| A-CO—CH$_2$—CH$_2$—NR$^N$— | Chemical & Pharmaceutical Bulletin, 1985, 3(9), 3775-3786. |
| A-CO—CH$_2$—CH$_2$—NR$^N$— | Indian Journal of Chemistry, Section B: 1988, 27B(2), 156-157. |
| A-NR$^N$—CH$_2$—CH$_2$—CO— | Indian Journal of Chemistry, Section B: 1988, 27B(2), 156-157. |
| A-NR$^N$—CH$_2$—CO—CH$_2$— | Tetrahedron Letters, 1981, 22(20), 2799-2802. |
| A-CO—CH$_2$—NR$^N$—CH$_2$— | Tetrahedron, 2002, 58(49), 9865-9870. |
| A-NR$^N$—CH$_2$—CO—NR$^N$— | Indian Journal of Chemistry, Section B: 1988, 27B(2), 156-157. |
| A-NR$^N$—CH$_2$—NR$^N$—CO— | J. of the Institute of Chemists (India), 1980. 52(3), 113-114. |
| A-CO—NR$^N$—CH$_2$—NR$^N$— | Journal of heterocyclic Chemistry, 1985, 22(1), 137-140. |
| A-NR$^N$—SO$_2$—CH$_2$— | Journal of Organic Chemistry, 1979, 44(13), 2055-2061. |
| A-CH$_2$—SO$_2$—NR$^N$— | International (PCT) Patent Publication No WO 2004/014300. |
| A-CH$_2$—NR$^N$—SO$_2$— | Organic Letters, 2003, 5(2), 105-107. |
| A-NR$^N$—CH$_2$—SO$_2$— | Archive Der Pharmazie, 1974, 307(8), 653-655. |
| A-SO$_2$—CH$_2$—NR$^N$— | Archive Der Pharmazie, 1974, 307(8), 653-655. |
| A-CH$_2$—SO$_2$—NR$^N$—CH$_2$— | Journal of medicinal Chemistry, 2003, 46(20), 4297-4312. |
| A-CH$_2$—NR$^N$—SO$_2$—CH$_2$— | Journal of medicinal Chemistry, 2001, 44(13), 2253-2258. |
| A-CH$_2$—CH$_2$—SO$_2$—NR$^N$— | Bioorganic & Medicinal Chemistry, 2002, 10(8), 2597-2610. |
| A-CH$_2$—CH$_2$—NR$^N$—SO$_2$— | Organic Letters, 2003, 5(2), 105-107. |
| A-CH$_2$—SO$_2$—CH$_2$—NR$^N$— | Chemistry of heterocyclic Compounds, 2002, 38(9), 1077-1088. |

-continued

| A-L- | Literature Reference(s) |
|---|---|
| A-NR$^N$—CH$_2$—SO$_2$—CH$_2$— | Chemistry of heterocyclic Compounds, 2002, 38(9), 1077-1088. |
| A-SO$_2$—CH$_2$—NR$^N$—CH$_2$— | Chemical & Pharmaceutical Bulletin, 1977, 25(11), 2964-2968. |
| A-CH$_2$—NR$^N$—CH$_2$—SO$_2$— | Synlett, 2003, 8, 1129-1132. |
| A-NR$^N$—SO$_2$—CH$_2$—CH$_2$— | Bioorganic & Medicinal Chemistry, 2002, 10(8), 2597-2610. |
| A-SO$_2$—NR$^N$—CH$_2$—CH$_2$— | Chemical & Pharmaceutical Bulletin, 1985, 33(9), 3775-3786. |
| A-SO$_2$—CH$_2$—CH$_2$—NR$^N$— | Tetrahedron, 1988, 44(19), 6095-6106. |
| A-NR$^N$—CH$_2$—CH$_2$—SO$_2$— | Tetrahedron, 1988, 44(19), 6095-6106. |
| A-CH$_2$—NR$^N$—SO$_2$—NR$^N$— | Journal of Organic Chemistry, 1980, 45(26), 5373, 5375. |
| A-NR$^N$—CH$_2$—SO$_2$—NR$^N$— | Japanese Patent No 56-65863, 3 Jun. 1981. |
| A-NR$^N$—CH$_2$—NR$^N$—SO$_2$— | Current science, 1981, 50(7), 305-307. |
| A-NR$^N$—SO$_2$—CH$_2$—NR$^N$— | Japanese Patent No 56-65863, 3 Jun. 1981. |
| A-SO$_2$—NR$^N$—CH$_2$—NR$^N$— | Journal of Heterocyclic Chemistry, 2003, 40(4), 569-573. |

Uses

The imidazo[4,5-b]pyridin-2-one and oxazolo[4,5-b]pyridin-2-one compounds and analogs thereof, described herein, are useful, for example, in the treatment of diseases and conditions that are ameliorated by the inhibition of RAF (e.g., B-RAF), such as, for example, proliferative conditions, cancer, etc.

Use in Methods of Inhibiting RAF (e.g., B-RAF)

One aspect of the present invention pertains to a method of inhibiting RAF (e.g., B-RAF) activity in a cell, in vitro or in vivo, comprising contacting the cell with an effective amount of a compound, as described herein.

Suitable assays for determining RAF (e.g., B-RAF) inhibition are described below, as well as in the Examples below.

B-RAF Assays:

B-raf kinase activity is measured using a 4-tiered cascade enzyme assay similar to that described by Marais R., et al., 1997, *J. Biol. Chem.*, Vol. 272, pp. 4378-4383. B-Raf containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:100 into an assay mixture containing GST-MEK-H6 (6.5 µg/ml) and GST-ERK-H6 (100 µg/ml) in a buffer containing 800 µM ATP and appropriate concentrations of inhibitor or diluent as control. The mixture is incubated for up to 10 minutes at 30° C. to activate the ERK in a B-Raf dependent manner within the cascade. The reaction is then stopped by addition of 20 mM EDTA. The extent of activation of the GST-ERK is then determined by adding a portion of this quenched reaction mixture to a further reaction mixture containing MBP and 100 µM ATP/gamma [$^{32}$P]ATP. After 12 minutes' incubation at 30° C., the incorporation of [$^{32}$P] into the MBP substrate, as a measure of B-raf activity, is determined by precipitation with phosphoric acid and isolation by filtration on p81 phosphocellulose paper. The % inhibition of the B-raf kinase activity is calculated and plotted in order to determine the concentration of test compound required to inhibit 50% of the B-raf kinase activity (IC$_{50}$).

Alternatively, B-raf kinase activity is measured using a different 4-tiered cascade enzyme assay. B-Raf containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:250 into an assay mixture containing GST-MEK-H6 (25 µg/ml), GST-ERK-H6 (281.25 µg/ml) and MBP in a buffer containing appropriate concentrations of inhibitor or diluent as control. 0.03 µL (100 µM) ATP is added and the mixture is incubated for up to 10 minutes at 30° C. to activate the ERK in a B-Raf dependent manner within the cascade. The extent of activation of the GST-ERK is then determined by adding 0.033 µL (100 µM) HOT $^{32}$Pα. After 10 minutes' incubation at 30° C., the reaction is stopped by isolation of a portion of the reaction mixture on p81 phosphocellulose paper and submersion of this paper in 0.4% orthophosphoric acid. Incorporation of [$^{32}$P] into the MBP substrate, as a measure of B-raf activity, is determined using a Packard Cernekov counter. The % inhibition of the B-raf kinase activity is calculated and plotted in order to determine the concentration of test compound required to inhibit 50% of the B-raf kinase activity (IC$_{50}$).

C-RAF Assay:

C-raf (human) is diluted to a 10× working stock in 50 mM Tris pH 7.5, 0.1 mM EGTA, 0.1 mM sodium vanadate, 0.1% β-mercaptoethanol, 1 mg/ml BSA. One unit equals the incorporation of 1 nmol of phosphate per minute into myelin basic protein per minute. In a final reaction volume of 25 µl, c-raf (5-10 mU) is incubated with 25 mM Tris pH 7.5, 0.02 mM EGTA, 0.66 mg/ml myelin basic protein, 10 mM Mg Acetate, [γ-$^{33}$P-ATP] (specific activity approx 500 cpm/pmol, concentration as required) and appropriate concentrations of inhibitor or diluent as control. The reaction is initiated by the addition of Mg$^2+$+[γ-$^{33}$P-ATP]. After incubation for 40 minutes at room temperature, the reaction is stopped by the addition of 5 µl of a 3% phosphoric acid solution. 10 µl of the reaction is spotted onto a P30 filtermat and washed 3 times for 5 minutes in 75 mM phosphoric acid and once in methanol prior to drying and counting to determine the C-raf activity. The % inhibition of the C-raf kinase activity is calculated and plotted in order to determine the concentration of test compound required to inhibit 50% of the C-raf kinase activity (IC$_{50}$).

Selectivity:

In one embodiment, the compound selectively inhibits one RAF (e.g., B-RAF), over at least one other RAF (e.g., A-RAF and/or C-RAF).

For example, in one embodiment, the ratio of the IC$_{50}$ value for B-RAF to the IC$_{50}$ value for the other RAF (e.g., A-RAF and/or C-RAF) is at least 10, more preferably at least 100, most preferably at least 1000.

Use in Methods of Inhibiting Cell Proliferation Etc.

The compounds (i.e., imidazo[4,5-b]pyridin-2-one and oxazolo[4,5-b]pyridin-2-one compounds and analogs thereof) described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting cells (or the cell) with an effective amount of a compound, as described herein.

In one embodiment, the method is a method of regulating (e.g., inhibiting) cell proliferation (e.g., proliferation of a cell), in vitro or in vivo, comprising contacting cells (or the cell) with an effective amount of a compound, as described herein.

In one embodiment, the method is performed in vitro.

In one embodiment, the method is performed in vivo.

In one embodiment, the compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described in the examples below.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a compound as described herein for use in a method of treatment of the human or animal body by therapy.

Use in the Manufacture of Medicaments

Another aspect of the present invention pertains to use of a compound, as described herein, in the manufacture of a medicament for use in treatment.

In one embodiment, the medicament comprises the compound.

Methods of Treatment

Another aspect of the present invention pertains to a method of treatment comprising administering to a patient in need of treatment a therapeutically effective amount of a compound as described herein, preferably in the form of a pharmaceutical composition.

Conditions Treated—Conditions Ameliorated by the Inhibition of RAF

In one embodiment (e.g., of use in methods of therapy, of use in the manufacture of medicaments, of methods of treatment), the treatment is treatment of a disease or condition that is characterised by the up-regulation and/or activation of RAF (e.g., B-RAF), and/or is ameliorated by the inhibition of RAF (e.g., B-RAF).

In one embodiment, the treatment is treatment of cancer that is characterised by the up-regulation and/or activation of RAF (e.g., B-RAF), and/or is ameliorated by the inhibition of RAF (e.g., B-RAF).

Conditions Treated—Conditions Ameliorated by the Inhibition of RTKs

In one embodiment (e.g., of use in methods of therapy, of use in the manufacture of medicaments, of methods of treatment), the treatment is treatment of a disease or condition that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of cancer that is characterised by the up-regulation and/or activation of a receptor tyrosine kinase (RTK), and/or is ameliorated by the inhibition of a receptor tyrosine kinase (RTK).

Conditions Treated—Conditions Characterised by Angiogenesis

In one embodiment (e.g., of use in methods of therapy, of use in the manufacture of medicaments, of methods of treatment), the treatment is treatment of a disease or condition that is characterised by inappropriate, excessive, and/or undesirable angiogenesis (as "anti-angiogenesis agents"). Examples of such conditions are discussed above.

Conditions Treated—Prolifative Conditions and Cancer

The compounds of the present invention are useful in the treatment of proliferative conditions (as "anti-proliferative agents"), cancer (as "anti-cancer agents"), etc. The term "antiproliferative agent" as used herein, pertain to a compound which treats a proliferative condition (i.e., a compound which is useful in the treatment of a proliferative condition). The terms "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth.

The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

One of ordinary skill in the art is readily able to determine whether or not a candidate compound treats a proliferative condition, or treats cancer, for any particular cell type. For example, assays which may conveniently be used to assess the activity offered by a particular compound are described in the examples below.

Note that active compounds includes both compounds with intrinsic activity (drugs) as well as prodrugs of such compounds, which prodrugs may themselves exhibit little or no intrinsic activity.

In one embodiment (e.g., of use in methods of therapy, of use in the manufacture of medicaments, of methods of treatment), the treatment is treatment of a proliferative condition.

In one embodiment, the treatment is treatment of a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, skin cancer, squamous cancer, Kaposi's sarcoma, melanoma, malignant melanoma, lymphoma, or leukemia.

In one embodiment, the treatment is treatment of:
a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
a hematopoietic tumor of myeloid lineage, for example acute and chronic myelogenous leukemias, myelodysplastic syndrome, or promyelocytic leukemia;
a tumour of mesenchymal origin, for example fibrosarcoma or habdomyosarcoma;
a tumor of the central or peripheral nervous system, for example astrocytoma, neuroblastoma, glioma or schwannoma;
melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of melanoma or malignant melanoma.

In one embodiment, the treatment is treatment of colorectal cancer.

The compounds of the present invention may be used in the treatment of the cancers described herein, independent of the mechanisms discussed herein.

Conditions Treated—Prolifative Conditions and Cancer Associated with RAF

Cancers with, for example, activating mutations of ras, raf and EGFR or over expression of ras, raf and EGFR including any of the isoforms thereof, may be particularly sensitive to inhibitors of RAF (e.g., B-RAF) activity. Patients with activating mutants of RAF (e.g., B-RAF) may also find treatment with inhibitors of RAF (e.g., B-RAF) activity particularly beneficial. Cancers with other abnormalities leading to an upregulated raf-MEK-ERK pathway signal may also be particularly sensitive to treatment with inhibitors of RAF (e.g., B-RAF) activity. Examples of such abnormalities include constitutive activation of a growth factor receptor; overexpression of one or more growth factor receptors; and overexpression of one or more growth factors.

In one embodiment (e.g., of use in methods of therapy, of use in the manufacture of medicaments, of methods of treatment), the treatment is treatment of a proliferative condition as described above, for example, cancer, that is characterised by:
(a) activating mutants of ras or raf;
(b) upregulation of ras or raf;
(c) upregulated raf-MEK-ERK pathway signals;
(d) upregulation of growth factor receptors, such as ERBB2 and EGFR.

In one embodiment, the proliferative condition is characterised by cells which overexpress RAF (e.g., B-RAF) or express or overexpress mutant raf (e.g., B-RAF). In one embodiment, the proliferative condition is characterised by cells which overexpress raf (e.g., B-RAF). In one embodiment, the proliferative condition is characterised by cells which express or overexpress mutant RAF (e.g., B-RAF). In one embodiment, the proliferative condition is characterised by cells which overexpress RAF (e.g., B-RAF), or overexpress mutant RAF (e.g., B-RAF), as compared to corresponding normal cells. In one embodiment, the overexpression is by a factor of 1.5, 2, 3, 5, 10, or 20.

In one embodiment (e.g., of use in methods of therapy, of use in the manufacture of medicaments, of methods of treatment), the treatment is treatment of a condition associated with a mutated form of RAF (e.g., B-RAF), such as, for example, the mutations described in Wan, P., et al., 2004, Cell, Vol. 116, pp. 855-867 and Stratton et al., 2003, published international patent application publication number WO 03/056036.

Conditions Treated—Inflammation Etc.

The compounds of the present invention are useful in the treatment of conditions associated with inflammation (as "anti-inflammation agents"), etc.

The function of inflammatory cells is controlled by many factors the effects of which are mediated by different signal transduction pathways. Although some key pro-inflammatory functions are mediated by p38 Map kinase (e.g., TNF release), others are mediated by other pathways. The raf-MEK-ERK pathway, in particular, is an important activating and proliferative signal in many inflammatory cells. B and T lymphocytes, in particular, require activation of the raf-MEK-ERK pathway for clonal expansion and generation of effector populations (see, e.g., Cantrell, D. A., 2003, Immunol Rev., Vol. 192, pp. 122-130; Genot, E. and Cantrell, D. A., 2000, Curr. Opin. Immunol., Vol. 12(3), pp. 289-294).

In one embodiment, the treatment is treatment of: inflammatory diseases, such as rheumatoid arthritis, osteoarthritis, rheumatoid spondylitis, gouty arthritis, traumatic arthritis, rubella arthritis, psoriatic arthritis, and other arthritic conditions; Alzheimer's disease; toxic shock syndrome, the inflammatory reaction induced by endotoxin or inflammatory bowel disease; tuberculosis; atherosclerosis; muscle degeneration; Reiter's syndrome; gout; acute synovitis; sepsis; septic shock; endotoxic shock; gram negative sepsis; adult respiratory distress syndrome; cerebral malaria; chronic pulmonary inflammatory disease; silicosis; pulmonary sarcoisosis; bone resorption diseases; reperfusion injury; graft versus host reaction; allograft rejections; fever and myalgias due to infection, such as influenza, cachexia, in particular cachexia secondary to infection or malignancy, cachexia secondary to acquired immune deficiency syndrome (AIDS); AIDS; ARC (AIDS related complex); keloid formation; scar tissue formation; Crohn's disease; ulcerative colitis; pyresis; chronic obstructive pulmonary disease (COPD); acute respiratory distress syndrome (ARDS); asthma; pulmonary fibrosis; bacterial pneumonia.

In one preferred embodiment, the treatment is treatment of: arthritic conditions, including rheumatoid arthritis and rheumatoid spondylitis; inflammatory bowel disease, including Crohn's disease and ulcerative colitis; and chronic obstructive pulmonary disease (COPD).

In one preferred embodiment, the treatment is treatment of: an inflammatory disorder characterized by T-cell proliferation (T-cell activation and growth), for example, tissue graft rejection, endotoxin shock, and glomerular nephritis.

Screening

Prior to treatment, a patient may be screened to determine whether a disease or condition from which the patient is or may be suffering is one which would be susceptible to treatment with a compound that inhibits RAF (e.g., B-RAF) activity or has activity against an RTK (e.g., FGFR-1, FGFR-2, FGFR-3, VEGFR-2, Tie2, EphB2).

For example, a biological sample taken from a patient may be analysed to determine whether a condition or disease, such as cancer, that the patient is or may be suffering from is one which is characterised by elevated expression or activation of RAF (e.g., B-RAF), or an RTK (e.g., FGFR-1, FGFR-2, FGFR-3, VEGFR-2, Tie2, EphB2), or is the result of an activating mutation. Thus, the patient may be subjected to a diagnostic test to detect a marker characteristic of over-expression or activation of RAF (e.g., B-RAF) or an RTK (e.g., FGFR-1, FGFR-2, FGFR-3, VEGFR-2, Tie2, EphB2), or a mutation thereof.

As used herein, the term "marker" includes genetic markers (including, e.g., the measurement of DNA composition to identify mutations of raf, ras, MEK, ERK or a growth factor such as ERBB2 or EGFR) and markers which are characteristic of upregulation of raf, ras, MEK, ERK, growth factors receptors such as ERBB2 or EGFR including enzyme activity, enzyme levels, enzyme state (e.g. phosphorylated or not) and mRNA levels of the aforementioned proteins. Methods for identification and analysis of mutations are well known. See, for example, *Anticancer Research*, 1999, Vol. 19(4A), pp. 2481-2483; *Clin. Chem.*, 2002, Vol. 48, p. 428; *Cancer Research*, 2003, Vol. 63(14), pp. 3955-3957.

The term "marker" further includes genetic markers including, for example, the measurement of DNA composition to identify mutations of RTKs, e.g., FGFR-1, FGFR-2, FGFR-3, VEGFR-2, Tie2, and EphB2. The term "marker" also includes markers that are characteristic of up-regulation of RTKs, including enzyme activity, enzyme levels, enzyme state (e.g., phosphorylated or not) and mRNA levels of the aforementioned proteins.

Upregulation includes elevated expression or over expression, including gene amplification (i.e., multiple gene copies), increased expression by a transcriptional effect, hyperactivity, and activation, including activation by mutations.

Other tumours that have an upregulated raf-MEK-ERK pathway signal may also be particularly sensitive to inhibitors of RAF (e.g., B-RAF) activity. A number of assays exist which can identify tumours that exhibit upregulation in the raf-MEK-ERK pathway, including the commercially available MEK1/2 (MAPK Kinase) assay from Chemicon International. Upregulation can result from over expression or activation of growth factor receptors such as ERBB2 and EGFR, or mutant ras or raf proteins.

Typical methods for screening for over expression, upregulation or mutants include, but are not limited to, standard methods such as reverse-transcriptase polymerase chain reaction (RT-PCR) or in-situ hybridisation.

In screening by RT-PCR, the level of mRNA for the aforementioned proteins in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described, for example, in Ausubel, F. M. et al., eds., *Current Protocols in Molecular Biology*, 2004 (John Wiley & Sons Inc.); Innis, M. A. et-al., eds., *PCR Protocols: A Guide to Methods and Applications*, 1990 (Academic Press). Reactions and manipulations involving nucleic acid techniques are also described in Sambrook et al., *Molecular Cloning: A Laboratory Manual*, 3rd edition, 2001 (Cold Spring Harbor Laboratory Press). Alternatively, a commercially available kit for RT-PCR (e.g., Roche Molecular Biochemicals) may be used, or methodology as set forth in U.S. Pat. Nos. 4,666,828; 4,683,202; 4,801,531; 5,192,659, 5,272,057, 5,882,864, and 6,218,529.

An example of an in-situ hybridisation technique would be fluorescence in situ hybridisation (FISH) (see, e.g., Angerer, 1987, *Meth. Enzymol.*, Vol. 152, p. 649). Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, in order to enable specific hybridization with the target nucleic acid(s) under stringent conditions. Standard methods for carrying out FISH are described, for example, in Ausubel, F. M. et al., eds., *Current Protocols in Molecular Biology*, 2004 (John Wiley & Sons Inc.); Bartlett, John M. S., "Fluorescence In Situ Hybridization Technical Overview," in: *Molecular Diagnosis of Cancer, Methods and Protocols, 2nd ed.* (*Series: Methods in Molecular Medicine*), March 2004, pp. 77-88 (ISBN: 1-59259-760-2).

Alternatively, the protein products expressed from the mRNAs may be assayed by immunohistochemistry of tumour sections, solid phase immunoassay with microtiter plates, Western blotting, 2-dimensional SDS-polyacrylamide gel electrophoresis, ELISA, and other methods known in the art for detection of specific proteins. Detection methods would include the use of site specific antibodies, such as, phospho raf, phospho ERK, phospho MEK, or phosphotyrosine. In addition to tumour biopsies, other samples which could be utilised include pleural fluid, peritoneal fluid, urine, stool biopsies, sputum, blood (isolation and enrichment of shed tumour cells).

In addition, mutant forms of raf, EGFR or ras can be identified by direct sequencing of, for example, tumour biopsies using PCR and methods to sequence PCR products directly, for example, using methods as described herein. These and other well-known techniques for detection of the over expression, activation, or mutations may be used.

Also, abnormal levels of proteins such as raf, ras and EGFR can be measured using standard enzyme assays, for example for raf those assays described herein.

Alternative methods for the measurement of the over expression or activation of FGFR, Tie, VEGFR or Eph kinases, in particular VEGFR including the isoforms thereof, include the measurement of microvessel density. This can be measured, for example, using methods described by Orre and Rogers, 1999, *Int. J. Cancer*, Vol. 84(2), pp. 101-108. Assay methods also include the use of markers; for example, in the case of VEGFR, markers include CD31, CD34 and CD105 (Mineo et al., 2004, *J. Clin. Pathol.*, Vol. 57(6), pp. 591-597).

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development. Examples of such combinations are set out below.

In one embodiment, the compounds (i.e., imidazo[4,5-b]pyridin-2-one and oxazolo[4,5-b]pyridin-2-one compounds and analogs thereof described herein are combined with one or more (e.g., 1, 2, 3, 4) additional therapeutic agents, as described below.

One aspect of the present invention pertains to a compound as described herein, in combination with one or more additional therapeutic agents, as described below.

Examples of additional therapeutic agents that may be administered together (whether concurrently or at different time intervals) with the compounds described herein include:
- (a) topoisomerase I inhibitors;
- (b) antimetabolites;
- (c) tubulin targeting agents;
- (d) DNA binder and topoisomerase II inhibitors;
- (e) alkylating agents;
- (f) monoclonal antibodies;
- (g) anti-hormones;
- (h) signal transduction inhibitors;
- (i) proteasome inhibitors;
- (j) DNA methyl transferases;
- (k) cytokines and retinoids.

The particular combination would be at the discretion of the physician who would select dosages using his common general knowledge and dosing regimens known to a skilled practitioner.

The agents (i.e., the compound described here, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use, as described below.

Other Uses

The compounds described herein may also be used as cell culture additives to inhibit cell proliferation, etc.

The compounds described herein may also be used as part of an in vitro assay, for example, in order to determine whether a candidate host is likely to benefit from treatment with the compound in question.

The compounds described herein may also be used as a standard, for example, in an assay, in order to identify other active compounds, other anti-proliferative agents, other anti-cancer agents, etc.

Kits

One aspect of the invention pertains to a kit comprising (a) an active compound as described herein, or a composition (e.g., a pharmaceutical composition) comprising an active compound as described herein, e.g., preferably provided in a suitable container and/or with suitable packaging; and (b) instructions for use, e.g., written instructions on how to administer the active compound or composition.

The written instructions may also include a list of indications for which the active ingredient is a suitable treatment.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus.

In one preferred embodiment, the subject/patient is a human.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 µg to about 250 mg (more typically about 100 µg to about 25 mg) per kilogram body weight of the subject per day. Where the active compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

All starting materials, reagents and solvents for reactions were reagent grade and used as purchased. Chromatography solvents were HPLC grade and were used without further purification. Reactions were monitored by thin layer chromatography (TLC) analysis using Merck silica gel 60 F-254 thin layer plates. Flash column chromatography was carried out on Merck silica gel 60 (0.015-0.040 mm) or in disposable Isolute Flash Si and Si II silica gel columns. Preparative TLC was performed on either Macherey-Nagel [809 023] pre-coated TLC plates SIL G-25 $UV_{254}$ or Analtech [2015] pre-coated preparative TLC plates, 2000 μm with $UV_{254}$. LCMS analyses were performed on a Micromass LCT/Water's Alliance 2795 HPLC system with a Discovery 5 μm, C18, 50 mm×4.6 mm i.d. column from Supelco at a temperature of 22° C. using the following solvent systems: Solvent A: Methanol; Solvent B: 0.1% formic acid in water at a flow rate of 1 mL/min. Gradient starting with 10% A/90% B from 0-0.5 minutes then 10% A/90% B to 90% A/10% B from 0.5 minutes to 6.5 minutes and continuing at 90% A/10% B up to 10 minutes. From 10-10.5 minutes the gradient reverted back to 10% A/90% where the concentrations remained until 12 minutes. UV detection was at 254 nm and ionisation was positive or negative ion electrospray. Molecular weight scan range is 50-1000. Samples were supplied as 1 mg/mL in DMSO or methanol with 3 μL injected on a partial loop fill. NMR spectra were recorded in DMSO-$d_6$ on a Bruker DPX 250 MHz or a Bruker Advance 500 MHz spectrometer.

(I) Coupling of 2-Amino-3-nitro-4-chloronyridine with Phenolates

Synthesis 1

4-(3-aminophenoxy)-3-nitropyridin-2-amine

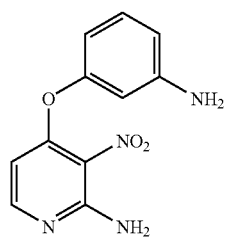

Method A. 3-Hydroxyaniline (2.07 g, 19.0 mmol) was dissolved in dry DMF (65 mL) and the solution was degassed by argon bubbling for 10 minutes. Potassium tert-butoxide (2.13 g, 19.0 mmol) was added and the stirring was continued for 1 hour at room temperature. 4-Chloro-3-nitropyridin-2-amine (3.0 g, 17.3 mmol) was added as a solid in one portion and the reaction mixture was subsequently heated at 80° C. for 20 hours. The solvent was evaporated in vacuo and the brown oily residue was taken up in 1M HCl (aq) (50 mL). This layer was washed with EtOAc (3×50 mL) and subsequently basified to pH ~10 with 1M NaOH (aq). The brown precipitate was collected, washed with $H_2O$ (3×25 mL) and dried in vacuo, to afford 4-(3-aminophenoxy)-3-nitropyridin-2-amine (3.50 g, 80%). $^1$H-NMR (δ, ppm, DMSO-$d_6$): 5.39 (s, 2H, $NH_2$), 6.02 (d, 1H, $H_{Py,5}$, J=5.7 Hz), 6.23-6.30 (m, 2H, $H_{arom,Ph}$), 6.47 (d, 1H, $H_{arom,Ph'}$, J=8.0 Hz), 7.04-7.24 (m, 3H, $NH_2+H_{arom,Ph'}$), 7.48 (m, 2H, $H_{arom}$), 7.98 (d, 1H, $H_{Py,5}$); LC-MS (m/z): 247 (M+H, 100).

Synthesis 2

4-(3-N-(tert-Butoxycarbonyl)aminophenoxy)-3-nitro-2-amino-pyridine

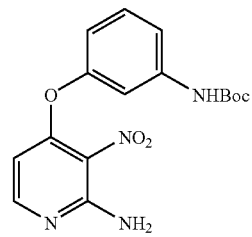

Method A was used with 3-N-BOC-amino-phenol to afford the title compound as a glassy yellow solid (1.9 g, 96%). $^1$H-NMR (DMSO), δ (ppm), J (Hz): 1.46 (s, 9H, $(CH_3)_3$ C), 5.36 (s, 2H, $NH_2$), 6.00 (d, 1H, $H_{Pyr}$, J=5.7), 6.77 (d, 1H, $H_{arom4\ or\ 6}$, J=6.9), 7.32-7.36 (m, 2H, $H_{arom}$), 8.01 (d, 1H, $H_{Pyr}$), 9.56 (s, 1H, NH); MS-LC, $R_f$=7.10 min, $(C_{16}H_{18}N_4O_5)$, m/z: 346.1 [$M^+$+1], 100.

Synthesis 3

4-(5-Amino-2,4-dichlorophenoxy)-3-nitropyridin-2-amine

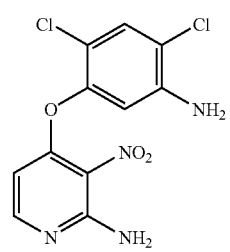

Method A was used with 2,4-dichloro-5-hydroxyaniline to afford the title compound as a yellow powder (1.186 g, 67%). $^1$H-NMR (δ, ppm, DMSO-$d_6$): 5.81 (s, 2H, $NH_{2,Ph}$), 5.95 (d, 1H, $H_{Py,5}$, J=5.6 Hz), 6.67 (s, 1H, $H_{Ph,11}$), 7.22 (s, 2H, $NH_{2,Py}$), 7.49 (s, 1H, $NH_{Ph,8}$), 7.99 (d, 1H, $H_{2,Py,6}$, J=2.5 Hz).

$^{13}$C-NMR (δ, ppm, DMSO-d$_6$): 99.8 (C-4); 107.7 (C-11); 110.5 (C-2); 114.6 (C-7); 121.1 (C-9); 129.9 (C-8); 145.5 (C-10); 147.8 (C-6); 153.3 (C-5); 153.7 (C-1); 157.7 (C-3). LC-MS (m/z): 314 (M+H, 100).

Synthesis 4

4-(3-Amino-5-(trifluoromethyl)phenoxy)-3-nitropyridin-2-amine

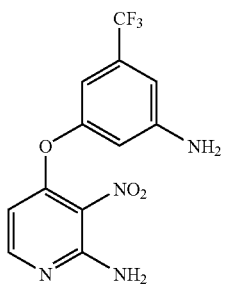

Method A was used with 3-amino-5-(trifluoromethyl)phenol to afford the title compound as a yellow solid solid (544 mg, 56%). $^1$H-NMR (δ, ppm, DMSO-d$_6$): 5.93 (s, 2H, NH$_{2,Ph}$), 6.11 (d, 1H, H$_{Py,5}$, J=5.6 Hz), 6.53 (s, 1H, H$_{arom}$), 6.56 (s, 1H, H$_{arom}$), 6.77 (s, 1H, H$_{arom}$), 7.23 (s, 2H, NH$_{2,Py}$), 8.05 (d, 1H, H$_{Py,6}$, J=5.6 Hz). $^{13}$C-NMR (δ, ppm, DMSO-d$_6$): 101.3 (C-4); 102.7 (C-11); 106.9 (C-9); 107.5 (C-7); 122.1 (C-2); 122.6 (C-10); 131.2 (C-12); 151.4 (C-8); 153.2 (C-5); 153.7 (C-1); 154.8 (C-6); 157.9 (C-3). LC-MS (m/z): 314 (M+H, 100).

Synthesis 5

4-(5-Amino-2-methoxyphenoxy)-2-amino-3-nitropyridine

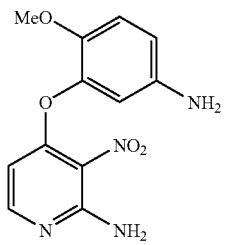

Method A was used with 5-amino-2-methoxyphenol to afford the title compound as a orange solid (1.8 g, 90%). $^1$H-NMR (δ, ppm, DMSO-d$_6$): 3.60 (s, 3H, CH$_3$); 4.95 (bs, 2H, NH$_{2,Ph}$), 5.85 (d, 1H, H$_{Py,4}$, J=5.7 Hz), 6.38 (d, 1H, H$_{Ph,8}$, J=2.6 Hz), 6.48 (dd, 1H, H$_{Ph,9}$, J=8.7 Hz and J=2.6 Hz), 6.91 (d, 1H, H$_{Ph,11}$, J=8.7 Hz), 7.10 (bs, 2H, NH$_{2,Py}$), 7.94 (d, 1H, H$_{Py,5}$, J=5.7 Hz). $^{13}$C-NMR (δ, ppm, DMSO-d$_6$): 56.5 (CH$_3$); 99.5 (C-4); 107.7 (C-11); 112.0 (C-9); 115.6 (C-8); 121.2 (C-2); 141.3 (C-10); 141.7 (C-6); 143.7 (C-7); 152.7 (C-5); 159.0 (C-1); 162.2 (C-3). LC-MS (m/z): 277 (M+H, 100).

Synthesis 6

4-(3-Amino-5-(trifluoromethyl)phenoxy)-3-nitropyridin-2-amine

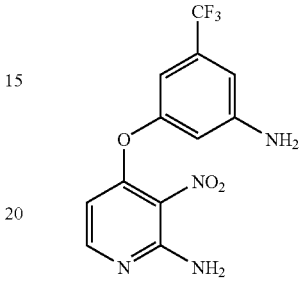

Method A was used with 3-amino-5-(trifluoromethyl)phenol to afford the title compound as a yellow solid solid (544 mg, 56%). $^1$H-NMR (δ, ppm, DMSO-d$_6$): 5.93 (s, 2H, NH$_{2,Ph}$), 6.11 (d, 1H, H$_{Py,5}$, J=5.6 Hz), 6.53 (s, 1H, H$_{arom}$), 6.56 (s, 1H, H$_{arom}$), 6.77 (s, 1H, H$_{arom}$), 7.23 (s, 2H, NH$_{2,Py}$), 8.05 (d, 1H, H$_{Py,6}$, J=5.6 Hz). $^{13}$C-NMR (δ, ppm, DMSO-d$_6$): 101.3, 102.7, 106.9, 107.5, 122.1, 122.6, 131.2, 151.4, 153.2, 153.7, 154.8, 157.9. LC-MS (m/z): 314 (M+H, 100).

Synthesis 7

4-(3-amino-4-methylphenoxy)-3-nitropyridin-2-amine

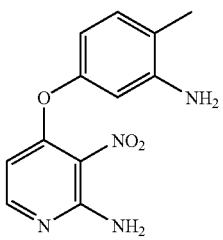

Method A was used with 3-amino-4-methylphenol (1.9 g, 15.7 mmol), to afford the title compound as a brown solid (767 mg, 19%). $^1$H-NMR (δ, ppm, DMSO-d$_6$): 2.04 (s, 3H, CH$_3$); 5.68 (d, 1H, H$_{Py,5}$, J=5.9 Hz), 6.64 (d, 1H, H$_{arom8}$, J=2.4 Hz), 6.70 (dd, 1H, H$_{arom12}$, J=2.5 Hz and J=8.2 Hz), 7.14 (d, 1H, H$_{arom11}$, J=8.3 Hz), 7.66 (d, 1H, H$_{Py,6}$, J=5.9 Hz), 7.88 (bs, 2H, NH$_2$), 9.45 (bs, 1H, NH$_2$), 10.02 (bs, 1H, NH$_2$).

$^{13}$C-NMR (δ, ppm, DMSO-d$_6$): 16.3, 97.7, 113.7, 114.5, 116.0, 124.2, 131.5, 136.7, 150.3, 152.4, 155.9, 156.1. LC-MS (m/z): 261 (M+H, 100).

Synthesis 8

4-(5-Amino-2-methylphenoxy)-2-amino-3-nitropyridine

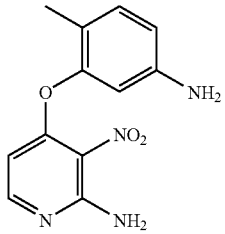

Method A was used with 5-amino-o-cresol (3 g, 24.4 mmol), to afford the title compound as an orange solid (3.38 g, 90%). $^1$H-NMR (δ, ppm, DMSO-d$_6$): 1.91 (s, 3H, CH$_3$), 5.19 (bs, 2H, NH$_{2,arom}$), 5.84 (d, 1H, H$_{Py,5}$, J=5.7 Hz), 6.27 (d, 1H, H$_{arom}$), 6.44 (d, 1H, H$_{arom}$, J=8.2 Hz), 6.97 (s, 1H, H$_{arom}$, J=7.9 Hz), 7.12 (bs, 2H, NH$_{2,Py}$), 7.96 (d, 1H, H$_{Py,6}$, J=5.7 Hz). $^{13}$C-NMR (δ, ppm, DMSO-d$_6$): 14.4, 99.6, 105.9, 112.2, 115.2, 121.4, 131.8, 148.7, 151.5, 153.0, 153.7, 158.7. LC-MS (m/z): 261 (M+H, 100).

Synthesis 9

4-(3-amino-2-methylphenoxy)-3-nitropyridin-2-amine

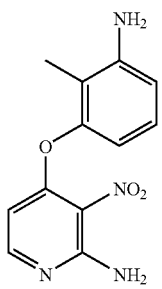

Method A was used with 3-amino-2-methylphenol (1.5 g, 11.9 mmol), to afford the title compound (860 mg, 28%) as an orange solid after purification on silica gel (Eluant: DCM/EtOAc: 1/1). $^1$H-NMR (δ, ppm, DMSO-d$_6$): 1.84 (s, 3H, CH$_3$), 5.18 (bs, 2H, NH$_2$), 5.79 (d, 1H, H$_{Py,5}$, J=5.7 Hz), 6.28 (d, 1H, H$_{arom10}$, J=7.9 Hz), 6.58 (d, 1H, H$_{arom12}$, J=8.0 Hz), 6.96 (t, 1H, H$_{arom11}$, J=8.0 Hz), 7.07 (bs, 2H, NH$_2$), 7.93 (d, 1H, H$_{Py,6}$, J=5.7 Hz). $^{13}$C-NMR (δ, ppm, DMSO-d$_6$): 9.4, 99.4, 108.0, 111.8, 112.7, 121.1, 126.9, 148.8, 151.3, 152.8, 153.2, 158.9. LC-MS (m/z): 261 (M+H, 100).

Synthesis 10

4-(3-amino-5-methoxyphenoxy)-3-nitropyridin-2-amine

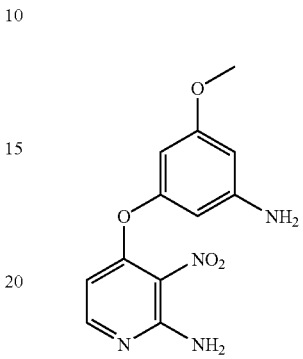

Method A was used with 3-amino-5-methoxyphenol (336 mg, 2.4 mmol), to afford the title compound (328 mg, 49%) as yellow solid after purification on silica gel (Eluant: DCM/EtOAc: 1/1, Rf 0.53). $^1$H-NMR (δ, ppm, DMSO-d$_6$): 3.66 (s, 3H, CH$_3$); 5.39 (bs, 2H, NH$_{2,Ph}$), 5.88 (t, 1H, H$_{Ph}$, J=2.1 Hz), 5.91 (t, 1H, H$_{Ph}$, J=1.9 Hz), 6.05 (t, 1H, H$_{Ph}$, J=2.0 Hz), 6.08 (d, 1H, H$_{Py,5}$, J=5.7 Hz), 7.08 (bs, 2H, NH$_{2,Py}$), 7.99 (d, 1H, H$_{Py,6}$, J=5.7 Hz). $^{13}$C-NMR (δ, ppm, DMSO-d$_6$): 54.8, 93.7, 96.5, 97.9, 100.8, 121.9, 151.1, 152.8, 153.5, 154.8, 158.6, 161.2. LC-MS (m/z): 277 (M+H, 100).

Synthesis 11

4-(5-Amino-2,4-difluorophenoxy)-3-nitropyridin-2-amine

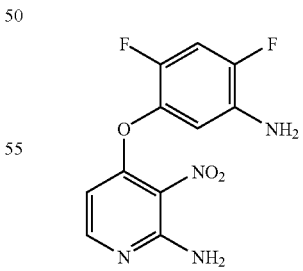

Method A was used with 5-amino-2,4-difluorophenol to afford the title compound as a yellow solid (0.487 g, 43%). $^1$H NMR δ(DMSO) 5.28 (bs, 2H, NH$_2$), 6.02 (d, 1H, H$_{Py,5}$, J=5.5 Hz), 6.67 (t, 1H, H$_{arom,6}$, J=8.5 Hz), 7.17 (bs, 2H, NH$_{2,Py}$), 7.31 (t, 1H, H$_{arom,3}$, J=11 Hz), 8.01 (d, 1H, H$_{Py,6}$, J=5.5 Hz). $^{19}$F NMR δ(DMSO) −133.44, −144.63. MS m/z 283 (M$^+$+1).

Synthesis 12

4-(5-Amino-2,3,4-trifluorophenoxy)-3-nitropyridin-2-amine

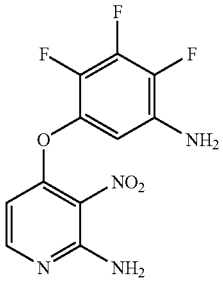

Method A was used with 5-amino-2,3,4-trifluorophenol to afford the title compound as a yellow solid (178 mg, 40%). $^1$H NMR δ(DMSO) 5.63 (s, 2H, 2-NH$_2$), 6.17 (d, 1H, H$_{Py,5}$ J=5.5 Hz), 6.49 (d, 1H, H$_{arom,6'}$, J=8.0 Hz), 7.23 (s, 2H, 5'-NH$_2$), 8.04 (d, 1H, H$_{Py,5}$ J=5.5 Hz). $^{19}$F NMR δ(DMSO) −159.32 (t, 1F, F3, J=21.0 Hz), −159.55 (ddd, 1F, aromF, J=5.5, 8.0+21.0 Hz), −168.95 (dt, aromF, J=6.5+21.5 Hz).

Synthesis 13

4-(3-Amino-4-chlorophenoxy)-3-nitropyridin-2-amine

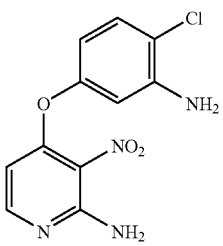

Method A was used with 3-amino-4-chlorophenol to afford the title compound as a yellow solid (0.64 g, 57%). $^1$H NMR δ(DMSO) 5.61 (bs, 2H, NH$_2$), 6.07 (d, 1H, H$_{Py,5}$, J=5.5 Hz), 6.34 (dd, 1H, H$_{arom,5}$, J=3+8.5 Hz), 6.55 (d, 1H, H$_{arom,2}$, J=3 Hz), 7.12 (bs, 2H, NH$_{2,Py}$), 7.25 (t, 1H, H$_{arom,5}$, J=8.5 Hz), 8.01 (d, 1H, H$_{Py,6}$, J=5.5 Hz).

Synthesis 14

4-(3-Amino-5-chlorophenoxy)-3-nitropyridin-2-amine

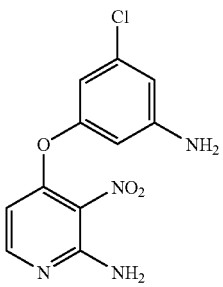

Method A was used with 3-amino-5-chlorophenol to afford the title compound as a yellow solid (0.136 g, 40%). $^1$H NMR δ(DMSO) 5.71 (bs, 2H, NH$_2$), 6.12 (d, 1H, H$_{Py,5}$, J=5.5 Hz), 6.25 (t, 1H, H$_{arom}$, J=2 Hz), 6.32 (t, 1H, H$_{arom}$, J=2 Hz), 6.50 (t, 1H, H$_{arom}$, J=2 Hz), 7.14 (bs, 2H, NH$_{2,Py}$), 8.04 (d, 1H, H$_{Py,6}$, J=5.5 Hz). MS m/z 281/3 (M$^+$+1).

(II) Boc Protection of Amine

Synthesis 15

4-(3-N-(tert-butoxycarbonyl)aminophenoxy)-2-amino-3-nitropyridine

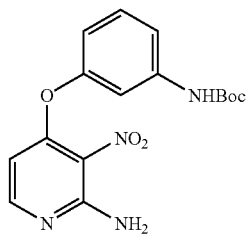

Method B. 4-(3-Aminophenoxy)-3-nitropyridin-2-amine (3.50 g, 13.8 mmol) was dissolved in THF (60 mL) and di-tert-butyl dicarbonate (9.0 g, 41.4 mmol) was added and the solution stirred for 16 hrs at room temperature. The solvent was evaporated and the residue purified by column chromatography (eluent gradient CH$_2$Cl$_2$ to CH$_2$Cl$_2$:EtOAc 1:1), to afford 4-(3-N-(tert-butoxycarbonyl)-aminophenoxy)-3-nitropyridin-2-amine (3.61 g, 75%).

Synthesis 16

4-(5-N-(tert-butoxycarbonyl)amino-2-methoxyphenoxy)-2-amino-3-nitropyridine

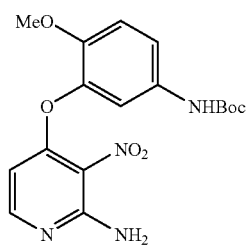

Method B was used with 4-(5-amino-2-methoxyphenoxy)-3-nitropyridin-2-amine to afford the title compound as an orange solid (935 mg, 69%). $^1$H-NMR (δ, ppm, DMSO-d$_6$): 1.45 (s, 3H, tBu); 3.69 (s, 3H, CH$_3$); 5.82 (d, 1H, H$_{Py,4}$, J=5.7 Hz), 7.11-7.13 (m, 3H, 1H$_{Ph}$+NH$_{2,Py}$), 7.30-7.35 (m, 2H, J=8.8 Hz, J=2.0 Hz, H$_{arom}$), 7.94 (d, 1H, H$_{Py,5}$, J=5.7 Hz), 9.35 (bs, 1H, NH$_{carbamate}$). $^{13}$C-NMR (δ, ppm, DMSO-d$_6$): 27.9 (tBu); 55.9 (CH$_3$); 79.0 (C-tBu); 99.3 (C-4); 112.2 (C-11); 113.9 (C-8); 116.6 (C-9); 121.1 (C-2); 133.4 (C-10);

140.4 (C-6); 145.7 (C-7); 152.6 (C-13); 152.8 (C-5); 153.6 (C-1); 158.8 (C-3). LC-MS (m/z): 376 (M+H, 100).

Synthesis 17 tert-butyl 3-(2-amino-3-nitropyridin-4-yloxy)-4-methylphenylcarbamate

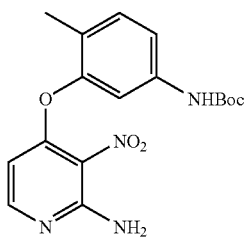

Method B was used with 4-(5-Amino-2-methylphenoxy)-2-amino-3-nitropyridine (2.73 g, 11.4 mmol), to afford the title compound as a yellow solid (3.26 g, 79%). $^1$H-NMR ($\delta$, ppm, DMSO-$d_6$): 1.45 (s, 9H, t-Bu); 2.03 (s, 3H, $CH_3$); 5.81 (d, 1H, $H_{Py,5}$, J=5.6 Hz), 7.17-7.31 (m, 3H, $H_{arom}$), 7.96 (d, 1H, $H_{Py,6}$, J=5.6 Hz), 9.51 (bs, 1H, $NH_{carbamate}$). $^{13}$C-NMR ($\delta$, ppm, DMSO-$d_6$): 15.0, 27.1, 83.3, 97.9, 116.5, 119.0, 123.1, 127.7, 131.5, 136.7, 149.4, 149.7, 150.6, 152.9, 156.0. LC-MS (m/z): 361 (M+H, 100).

(III) Trifluoroacetamide Protection

Synthesis 18

N-(5-(2-Amino-3-nitropyridin-4-yloxy)-2,4-dichlorophenyl)-2,2,2-trifluoroacetamide

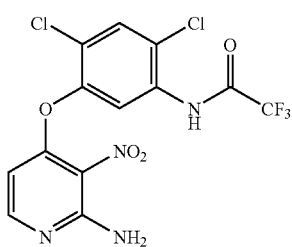

Method C. 4-(5-Amino-2,4-dichlorophenoxy)-3-nitropyridin-2-amine (450 mg, 1.4 mmol) was suspended in dry DCM (4.5 mL). Pyridine (3.4 equiv., 4.76 mmol, 395 μL) and trifluoroacetic anhydride (1.1 equiv., 1.54 mmol, 240 μL) were added, and the reaction mixture was stirred at RT for 2 hours. The solvent was evaporated and the residue was taken in water, and the insoluble residue was recovered by filtration. Purification on silica gel (eluent: EtOAc/DCM: 1/1) afforded the title compound (520 mg, 89%) as a yellow powder. $^1$H-NMR ($\delta$, ppm, DMSO-$d_6$): 6.01 (d, 1H, $H_{Py,5}$, J=5.6 Hz), 7.31 (s, 2H, $NH_{2,Py}$), 7.67 (s, 1H, $H_{Ph,11}$), 8.03 (s, 1H, $NH_{Ph,8}$), 8.07 (d, 1H, $H_{Py,6}$, J=5.3 Hz), 11.60 (bs, 1H, $NHCOCF_3$). LC-MS (m/z): 410 (M+H, 100).

(IV) Reduction of Nitro Group

1. Reduction En-Route to Common Intermediates (According to Scheme 2)

Synthesis 19

4-(3-N-(tert-Butoxycarbonyl)aminophenoxy)-2,3-diamino-pyridine

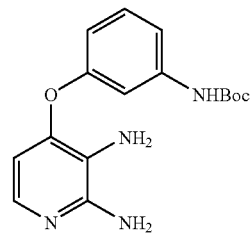

Method D. 4-(3-N-(tert-butoxycarbonyl)aminophenyloxy)-2,3-diamino-pyridine (2.5 g, 7.2 mmol) in 450 mL AcOEt:EtOH 1:1 were stirred for 7 h at room temperature under hydrogen atmosphere in the presence of 500 mg Pd/C 10%. After catalyst filtration and evaporation to dryness, the title compound was obtained as a brown glassy solid (2.17 g, 95%). $^1$H-NMR (DMSO), $\delta$ (ppm), J (Hz): 1.45 (s, 9H, $(CH_3)_3$ C), 4.39 (s, 2H, 5-$NH_2$), 5.36 (s, 2H, 6-$NH_2$), 6.02 (d, 1H, $H_{Pyr}$, J=5.6), 6.58 (d, 1H, $H_{arom4\ or\ 6}$, J=7.9), 7.19-7.21 (m, 2H, $H_{arom}$), 7.25 (d, 1H, $H_{Pyr}$), 9.41 (s, 1H, NH); MS-LC, $R_f$=4.03 min, ($C_{16}H_{20}N_4O_3$), m/z: 316.1 [$M^+$+1], 100.

Synthesis 20

N-(5-(2,3-Diamino-pyridin-4-yloxy)-2,4-dichlorophenyl)-2,2,2-trifluoroacetamide

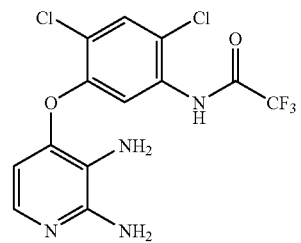

Method D was used with N-(5-(2-amino-3-nitropyridin-4-yloxy)-2,4-dichlorophenyl)-2,2,2-trifluoroacetamide to afford the title compound as a brown solid (498 mg, 92%). $^1$H-NMR ($\delta$, ppm, DMSO-$d_6$): 5.02 (s, 2H, $NH_{2,Py}$), 6.12 (d, 1H, $H_{Py,5}$, J=6.4 Hz), 6.64 (s, 2H, $NH_{2,Py}$), 7.23 (s, 1H, H$_{Ph,11}$), 7.28 (d, 1H, H$_{Py,6}$, J=6.4 Hz), 7.96 (s, 1H, NH$_{Ph,8}$). LC-MS (m/z): 380 (M+H, 100).

Synthesis 21

4-(5-N-(tert-Butoxycarbonyl)amino-2-methoxyphenoxy)-2,3-diamino-pyridine

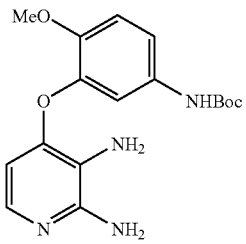

Method D was used with 4-(5-N-(tert-butoxycarbonyl)amino-2-methoxyphenoxy)-2-amino-3-nitropyridine to afford the title compound as a pale brown solid (727 mg, 78%). $^1$H-NMR (δ, ppm, DMSO-d$_6$): 1.43 (s, 9H, tBu); 3.70 (s, 3H, CH$_3$); 4.34 (bs, 2H, NH$_2$); 5.46 (bs, 2H, NH$_2$); 5.77 (d, 1H, H$_{Py,4}$, J=5.6 Hz), 7.03 (d, 1H, H$_{arom}$, J=8.9 Hz), 7.17 (m, 2H, H$_{arom}$, +H$_{Py,5}$, J=5.6 Hz), 7.21 (d, 1H, H$_{arom}$, J=7.9 Hz), 9.22 (bs, 1H, NH$_{carbamate}$). $^{13}$C-NMR (δ, ppm, DMSO-d$_6$): 28.0 (tBu); 55.9 (CH$_3$); 78.8 (C-tBu); 101.6 (C-4); 111.7 (C-11); 113.5 (C-8); 114.6 (C-9); 118.0 (C-2); 133.1 (C-10); 135.6 (C-5); 143.0 (C-6); 146.1 (C-1); 148.5 (C-3); 149.81 (C-7); 152.6 (C-13). LC-MS (m/z): 348 (M+H, 100).

Synthesis 22

4-(5-N-(tert-Butoxycarbonyl)amino-2-methylphenoxy)-2,3-diamino-pyridine

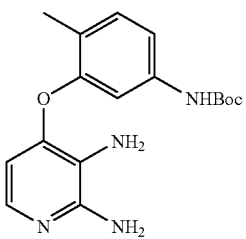

Method D was used with 4-(5-N-(tert-butoxycarbonyl)amino-2-methylphenoxy)-2-amino-3-nitropyridine to afford the title compound as a brown solid (1.46 g, 53%). $^1$H-NMR (δ, ppm, DMSO-d$_6$): 1.42 (s, 3H, tBu); 2.08 (s, 3H, CH$_3$); 4.39 (bs, 2H, NH$_2$); 5.50 (bs, 2H, NH$_2$); 5.81 (d, 1H, H$_{Py,4}$, J=5.6 Hz), 7.02-7.09 (m, 3H, H$_{Ph}$), 7.20 (d, 1H, H$_{Py,5}$, J=5.6 Hz), 9.29 (bs, 1H, NH$_{carbamate}$). $^{13}$C-NMR (δ, ppm, DMSO-d$_6$): 15.1 (CH$_3$); 27.9 (tBu); 78.9 (C-tBu); 102.3 (C-4); 108.9 (C-11); 113.7 (C-9); 118.6 (C-2); 122.0 (C-7); 130.9 (C-8); 135.6 (C-5); 138.6 (C-10); 147.6 (C-1); 149.9 (C-6); 152.5 (C-3); 153.2 (C-13). LC-MS (m/z): 330 (M+H, 100).

(V) Reduction of Nitro Group

2. Reduction of Coupled Intermediates (According to Scheme 4 and Scheme 5)

Synthesis 23

1-(5-(2,3-diamino-pyridin-4-yloxy)-2,4-dichlorophenyl)-3-(4-chloro-3-(trifluoromethyl)phenyl)urea

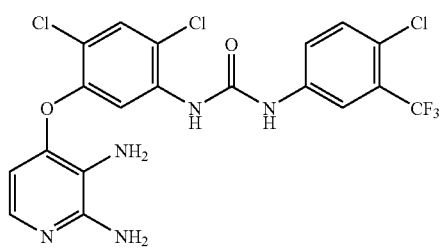

Method D was used with 1-(5-(2-amino-3-nitropyridin-4-yloxy)-2,4-dichlorophenyl)-3-(4-chloro-3-(trifluoromethyl)phenyl)urea to afford the title compound as a pale brown powder (80 mg, 17%). $^1$H-NMR (δ, ppm, DMSO-d$_6$): 5.53 (s, 2H, NH$_2$), 6.05 (d, 1H, H$_{Py,5}$, J=5.7 Hz), 7.62 (m, 3H, H$_{arom}$+H$_{Py,6}$, J=5.7 Hz), 7.79 (s, 1H, H$_{arom}$), 7.94 (m, 2H, H$_{arom}$), 8.53 (s, 1H, NH$_{urea}$), 9.93 (s, 1H, NH$_{urea}$). $^{13}$C-NMR (δ, ppm, DMSO-d$_6$): 102.1 (C-4); 112.1 (C-11); 116.7 (C-); 116.8 (C-); 117.2 (C-); 117.7 (C-); 120.3 (C-); 123.0 (C-); 126.6 (C-); 126.8 (C-); 129.8 (C-); 132.0 (C-); 135.6 (C-10 or 13); 138.5 (C-10 or 13); 143.2 (C-6); 149.4 (C-12); 149.5 (C-5); 151.6 (C-1); 153.0 (C-3). LC-MS (m/z): 505 (M+H, 100).

Synthesis 24

1-(5-(2,3-diamino-pyridin-4-yloxy)-2,4-dichlorophenyl)-3-(3-(trifluoromethyl)phenyl)urea

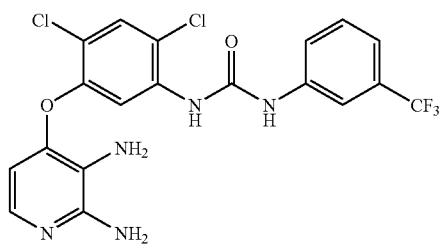

Method D was used with 1-(5-(2-amino-3-nitropyridin-4-yloxy)-2,4-dichlorophenyl)-3-(3-(trifluoromethyl)phenyl)urea to afford the title compound as a brown solid (64 mg, 77%). $^1$H-NMR (δ, ppm, DMSO-d$_6$): 4.55 (s, 1H, NH$_2$), 4.69 (s, 1H, NH$_2$), 5.98 (d, 1H, H$_{Py,5}$, J=5.6 Hz), 7.35 (m, 2H, H$_{arom}$+H$_{Py,6}$, J=5.5 Hz), 7.54 (m, 3H, H$_{arom}$), 7.89 (d, 1H, H$_{arom}$, J=1.5 Hz), 7.99 (d, 1H, H$_{arom}$, J=6.8 Hz), 8.50 (s, 1H, NH$_{urea}$), 9.82 (s, 1H, NH$_{urea}$) $^{13}$C-NMR (δ, ppm, DMSO-d$_6$): 102.7 (C-4); 103.3 (C-11); 111.8 (C-2); 114.0 (C-14); 116.9 (C-16); 117.6 (C-7); 118.6 (C-18); 119.2 (C-9); 121.8 (C-17); 124.8 (C-15); 129.8 (C-19); 129.9 (C-8); 135.1 (C-10); 135.8

(C-5); 139.7 (C-13); 146.3 (C-6); 147.7 (C-1); 150.1 (C-3); 151.7 (C-12). LC-MS (m/z): 471 (M+H, 100).

Synthesis 25

1-(3-(2,3-Diaminopyridin-4-yloxy)-5-(trifluoromethyl)phenyl)-3-(4-chloro-3-(trifluoromethyl)phenyl)urea

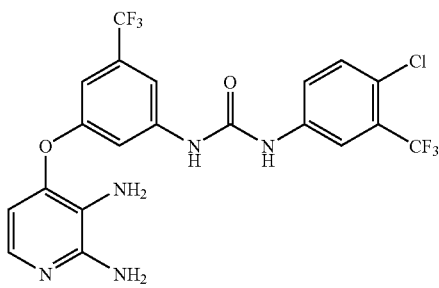

Method D was used with 1-(3-(2-amino-3-nitropyridin-4-yloxy)-5-(trifluoromethyl)phenyl)-3-(4-chloro-3-(trifluoromethyl)phenyl)urea to afford the title compound as a pale pink solid (88 mg, 40%). $^1$H-NMR (δ, ppm, DMSO-d$_6$): 4.62 (bs, 2H, NH$_2$), 5.71 (bs, 2H, NH$_2$), 6.20 (d, 1H, H$_{Py,4}$, J=5.6 Hz), 6.90 (m, 1H, H$_{arom}$), 7.23 (m, 1H, H$_{arom}$), 7.31 (d, 1H, H$_{Py,5}$, J=5.6 Hz), 7.61 (s, 1H, H$_{arom}$), 7.65 (d, 1H, H$_{arom}$, J=2.5 Hz), 7.68 (m, 1H, H$_{arom}$), 8.04 (d, 1H, H$_{arom}$, J=2.5 Hz), 9.23 (s, 1H, NH$_{urea}$), 9.35 (s, 1H, NH$_{urea}$). $^{13}$C-NMR (δ, ppm, DMSO-d$_6$): 105.3 (C-4); 107.3 (C-11); 108.8 (C-9); 109.9 (C-7); 117.0 (C-15); 117.1 (C-2); 121.1 (C-17); 122.5 (C-16); 122.7 (C-10); 123.4 (C-19); 126.6 (C-20); 130.5 (C-12); 131.9 (C-18); 135.0 (C-5); 138.8 (C-14); 141.6 (C-8); 144.7 (C-1); 150.4 (C-3); 152.1 (C-13); 157.1 (C-6). LC-MS (m/z): 505 (M+H, 100).

Synthesis 26

N-(3-(2,3-diaminopyridin-4-yloxy)-4-methoxyphenyl)-3-(trifluoromethoxy)benzamide

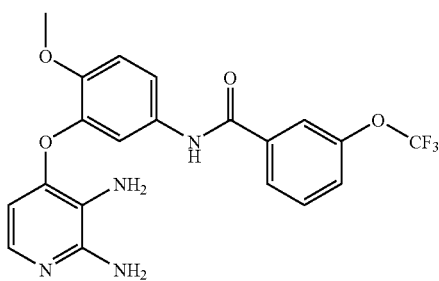

Method D was used with N-(3-(2-amino-3-nitropyridin-4-yloxy)-4-methoxyphenyl)-3-(trifluoromethoxy)benzamide (340 mg, 0.73 mmol), to afford the title compound after purification by column chromatography (eluent gradient: EtOAc/DCM: 1/1 then EtOAc/MeOH: 95/5) as a solid (197 mg, 62%). $^1$H-NMR (δ, ppm, DMSO-d$_6$): 3.77 (s, 3H, CH$_3$), 4.39 (bs, 2H, NH$_2$), 5.52 (bs, 2H, NH$_2$), 5.88 (d, 1H, H$_{Py,5}$, J=5.6 Hz), 7.15 (d, 1H, H$_{arom}$, J=8.9 Hz), 7.21 (d, 1H, H$_{Py,6}$, J=5.6 Hz), 7.46 (d, 1H, H$_{arom}$, J=2.5 Hz), 7.57 (dt, 1H, H$_{arom}$, J=8.2 Hz, J=2.1 Hz, J=1.1 Hz), 7.60 (dd, 1H, H$_{arom}$, J=8.9 Hz, J=2.5 Hz), 7.65 (t, 1H, H$_{arom}$, J=8.0 Hz), 7.87 (bs, 1H, H$_{arom}$), 7.97 (d, 1H, H$_{arom}$, J=7.8 Hz), 10.29 (bs, 1H, NH$_{amide}$). $^{13}$C-NMR (δ, ppm, DMSO-d$_6$): 55.8, 102.2, 113.2, 113.3, 116.8, 118.6, 119.9, 120.9, 123.8, 126.6, 130.4, 132.2, 135.6, 136.8, 143.3, 147.3, 148.1, 148.2, 149.9, 163.3. LC-MS (m/z): 435 (M+H, 100).

Synthesis 27

N-(3-(2,3-diaminopyridin-4-yloxy)-4-methylphenyl)-3-(trifluoromethoxy)benzamide

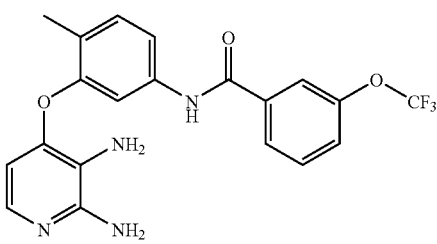

Method D was used with N-(3-(2-amino-3-nitropyridin-4-yloxy)-4-methylphenyl)-3-(trifluoromethoxy)benzamide (980 mg, 2.2 mmol), to afford the title compound after purification by column chromatography (eluent gradient: EtOAc/DCM: 1/1 then EtOAc/MeOH: 95/5) as a green solid (185 mg, 20%). $^1$H-NMR (δ, ppm, DMSO-d$_6$): 2.07 (s, 3H, CH$_3$), 4.50 (bs, 2H, NH$_2$), 5.63 (bs, 2H, NH$_2$), 6.43 (d, 1H, H$_{Py,5}$, J=5.8 Hz), 6.89 (d, 1H, H$_{arom}$, J=2.2 Hz), 6.92 (dd, 1H, H$_{arom}$, J=8.2 Hz, J=2.2 Hz), 7.19 (d, 1H, H$_{arom}$, J=8.3 Hz), 7.24 (d, 1H, H$_{Py,6}$, J=5.8 Hz), 7.77 (m, 2H, H$_{arom}$), 7.88 (s, 1H, NH$_{amide}$), 8.00 (s, 1H, H$_{arom}$), 8.18 (m, 1H, H$_{arom}$). $^{13}$C-NMR (δ, ppm, DMSO-d$_6$): 14.9, 103.5, 111.4, 116.0, 117.9, 118.9, 120.8, 121.7, 126.5, 128.7, 130.9, 131.1, 131.3, 134.1, 134.7, 141.9, 148.4, 148.6, 149.2, 162.8. LC-MS (m/z): 419 (M+H, 100).

Synthesis 28

N-(2,4-dichloro-5-(2,3-diaminopyridin-4-yloxy)phenyl)-3-(trifluoromethoxy)benzamide

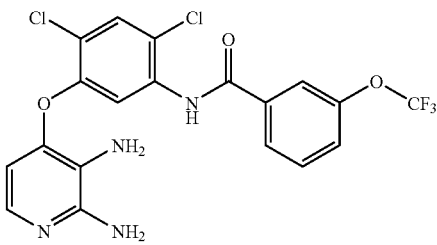

Method D was used with N-(5-(2-amino-3-nitropyridin-4-yloxy)-2,4-dichlorophenyl)-3-(trifluoromethoxy)benzamide (150 mg, 0.29 mmol), to afford the title compound as a yellow solid (136 mg, 96%). $^1$H-NMR (δ, ppm, DMSO-d$_6$): 6.33 (d, 1H, H$_{Py,5}$, J=7.0 Hz), 7.35 (d, 1H, H$_{Py,6}$, J=7.0 Hz), 7.59 (m, 2H, H$_{arom}$), 7.63 (m, 1H, H$_{arom}$), 7.69 (m, 1H, H$_{arom}$), 7.89 (bs, 1H, H$_{arom}$), 7.98 (s, 1H, H$_{arom}$), 8.00 (d, 1H, H$_{arom}$, J=7.8

Hz), 10.39 (s, 1H, NH$_2$), 13.19 (bs, 1H, H$_{amide}$). $^{13}$C-NMR (δ, ppm, DMSO-d$_6$): 103.5, 118.9, 120.2, 120.6, 120.9, 121.9, 122.9, 124.3, 124.5, 126.3, 126.8, 130.7, 135.1, 135.6, 145.8, 147.4, 148.3, 163.9, 170.2. LC-MS (m/z): 474 (M, 100).

Synthesis 29

N-(3-(2,3-diaminopyridin-4-yloxy)-2-methylphenyl)-3-(trifluoromethoxy)benzamide

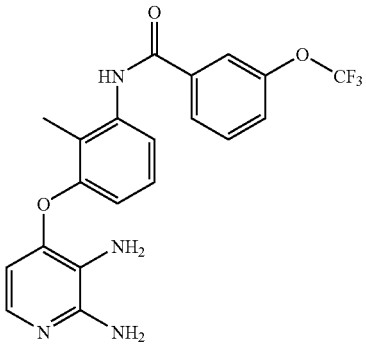

Method D was used with N-(3-(2-amino-3-nitropyridin-4-yloxy)-2-methylphenyl)-3-(trifluoromethoxy)benzamide (427 mg, 0.95 mmol), to afford the title compound as a brown solid (229 mg, 57%). $^1$H-NMR (δ, ppm, DMSO-d$_6$): 2.08 (s, 3H, CH$_3$), 4.46 (s, 2H, NH$_2$), 5.53 (s, 2H, NH$_2$), 5.83 (d, 1H, H$_{Py,5}$, J=5.6 Hz), 6.85 (m, 1H, H$_{arom}$), 7.19-7.26 (m, 3H, 2H$_{arom}$+H$_{Py,6}$) 7.61 (m, 1H, H$_{arom}$), 7.69 (t, 1H, H$_{arom}$, J=7.9 Hz), 7.93 (s, 1H, H$_{arom}$), 8.05 (d, 1H, H$_{arom}$, J=7.7 Hz), 10.18 (s, 1H, NH$_{amide}$). $^{13}$C-NMR (δ, ppm, DMSO-d$_6$): 11.0, 102.2, 117.0, 118.6, 120.0, 120.9, 122.6, 124.0, 125.9, 126.2, 126.6, 130.5, 135.7, 136.4, 137.5, 147.7, 148.3, 149.9, 153.6, 163.7. LC-MS (m/z): 419 (M+H, 100).

Synthesis 30

N-(3-(2,3-diaminopyridin-4-yloxy)-5-methoxyphenyl)-3-(trifluoromethoxy)benzamide

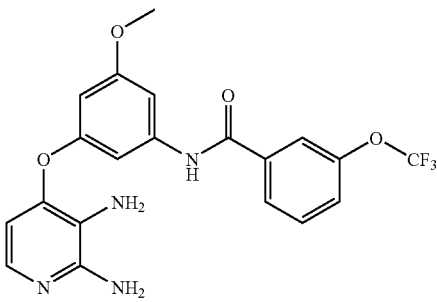

Method D was used with N-(3-(2-amino-3-nitropyridin-4-yloxy)-5-methoxyphenyl)-3-(trifluoromethoxy)benzamide (300 mg, 0.65 mmol), to afford the title compound as a dark solid (206 mg, 73%). $^1$H-NMR (δ, ppm, DMSO-d$_6$): 3.76 (s, 3H, CH$_3$), 4.55 (bs, 2H, NH$_2$), 5.67 (bs, 2H, NH$_2$), 6.15 (d, 1H, H$_{Py,5}$, J=5.6 Hz), 6.41 (t, 1H, H$_{arom}$, J=2.2 Hz), 7.05 (t, 1H, H$_{arom}$, J=1.9 Hz), 7.28-7.29 (m, 2H, H$_{arom}$+H$_{Py,6}$), 7.58-7.60 (m, 1H, H$_{arom}$), 7.66 (t, 1H, H$_{arom}$, J=7.9 Hz), 7.87 (m, 1H, H$_{arom}$), 7.97-7.98 (m, 1H, H$_{arom}$), 10.36 (bs, 1H, NH$_{amide}$). $^{13}$C-NMR (δ, ppm, DMSO-d$_6$): 55.2, 99.8, 100.9, 101.8, 104.8, 118.9, 120.1, 120.4, 123.9, 126.6, 130.4, 135.3, 136.8, 140.6, 146.1, 148.2, 150.3, 157.1, 160.3, 163.8. LC-MS (m/z): 435 (M+H, 100).

Synthesis 31

N-(5-(2,3-diaminopyridin-4-yloxy)-2-methylphenyl)-3-(trifluoromethoxy)benzamide

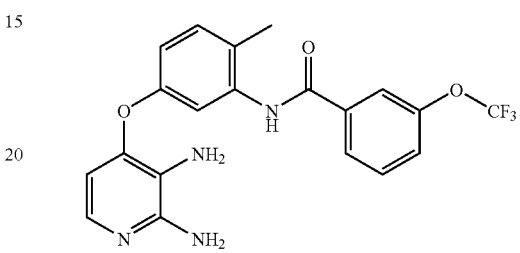

Method D was used with N-(5-(2-amino-3-nitropyridin-4-yloxy)-2-methylphenyl)-3-(trifluoromethoxy)benzamide (900 mg, 2.0 mmol), to afford the title compound as a dark purple solid (757 mg, 90%). $^1$H-NMR (δ, ppm, DMSO-d$_6$): 2.21 (s, 3H, CH$_3$), 4.96 (bs, 2H, NH$_2$), 5.92 (bs, 2H, NH$_2$), 6.08 (d, 1H, H$_{Py,5}$, J=5.7 Hz), 6.88 (dd, 1H, H$_{arom}$, J=2.6 Hz and J=8.3 Hz), 7.06 (d, 1H, H$_{arom}$, J=2.4 Hz), 7.27 (m, 1H, H$_{arom}$+H$_{Py,6}$, J=5.7 Hz), 7.80 (m, 1H, H$_{arom}$), 7.90 (m, 1H, H$_{arom}$), 7.95 (m, 1H, H$_{arom}$), 8.02 (d, 1H, H$_{arom}$, J=7.8 Hz), 10.08 (s, 1H, NH$_{amide}$). $^{13}$C-NMR (δ, ppm, DMSO-d$_6$): 17.1, 116.0, 116.2, 120.0, 120.1, 123.9, 124.4, 126.6, 128.0, 128.5, 130.5, 131.1, 134.2, 136.4, 136.9, 147.0, 148.1, 149.8, 153.6, 163.6. LC-MS (m/z): 419 (M+H, 100).

Synthesis 32

N-(5-(2,3-Diaminopyridin-4-yloxy)-2,4-difluorophenyl)-3-(trifluoromethoxy)benzamide

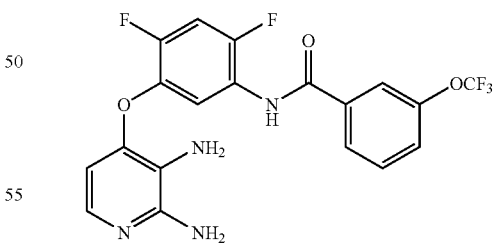

Method D was used with N-(5-(2-amino-3-nitropyridin-4-yloxy)-2,4-difluorophenyl)-3-(trifluoromethoxy)benzamide to afford the title compound (170 mg, 86%). $^1$H NMR δ (DMSO) 4.55 (s, 2H, NH$_2$), 5.61 (s, 2H, NH$_2$), 6.01 (d, 1H, H$_{py,5}$, J=5.5 Hz), 7.25 (d, 1H, H$_{py,6}$, J=5.5 Hz), 7.34 (t, 1H, H$_{arom,6'}$, J=8 Hz), 7.59 (t, 1H, H$_{arom,3'}$, J=10.5 Hz), 7.62 (d, 1H, H$_{arom}$), 7.67 (t, 1H, H$_{arom,5'}$, J=8 Hz), 7.88 (s, 1H, H$_{arom,2'}$), 7.99 (d, 1H, H$_{arom}$, J=8 Hz), 10.3 (s, 1H, CONH).

$^{19}$F NMR δ (DMSO) −56.76 (s, 1F, CF$_3$), −121.73 (s, 1F, aromF), −130.76 (s, 1F, aromF). MS m/z 400 (M$^+$).

Synthesis 33

N-(5-(2,3-Diaminopyridin-4-yloxy)-2,3,4-trifluorophenyl)-3-(trifluoromethoxy)benzamide

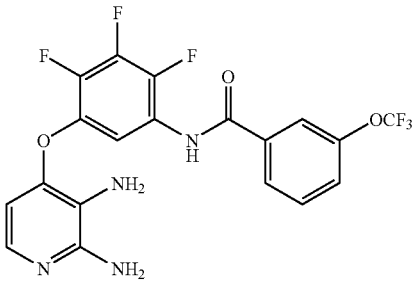

Method D was used with N-(5-(2-amino-3-nitropyridin-4-yloxy)-2,3,4-trifluorophenyl)-3-(trifluoromethoxy)benzamide to afford the title compound (92 mg 80%). $^1$H NMR δ(DMSO) 4.72 (s, 2H, NH$_2$), 5.81 (s, 2H, NH$_2$), 6.19 (d, 1H, H$_{py,5}$, J=5.5 Hz), 7.07 (t, 1H, H$_{arom,6''}$, J=6.5 Hz), 7.29 (d, 1H, H$_{py,6}$, J=5.5 Hz), 7.64 (d, 1H, H$_{arom}$, J=7.5 Hz), 7.68 (t, 1H, H$_{arom,5''}$, J=8.0 Hz), 7.88 (s, 1H, H$_{arom,2''}$), 7.99 (d, 1H, H$_{arom}$, J=7.5 Hz), 10.49 (s, 1H, NH$_{amide}$). $^{19}$F NMR δ(DMSO) −56.78 (s, 3F, CF$_3$), −145.32 (m, 1F, aromF), −155.31 (m, 1F, aromF), −158.41 (m, 1F, F3).

Synthesis 34

N-(2-Chloro-5-(2,3-Diaminopyridin-4-yloxy)phenyl)-3-(trifluoromethoxy)benzamide

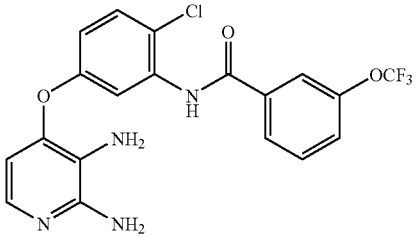

Method D was used with N-(5-(2-Amino-3-nitropyridin-4-yloxy)-2-chlorophenyl)-3-(trifluoromethoxy)benzamide to afford the title compound (62 mg, 50%). $^1$H NMR δ (DMSO) 4.51 (s, 2H, NH$_2$), 5.63 (s, 2H, NH$_2$), 6.13 (d, 1H, H$_{py,5}$, J=5.5 Hz), 6.95 (dd, 1H, H$_{arom,5}$, J=3+9 Hz), 7.23 (d, 1H, H$_{arom,2}$, J=3 Hz), 7.29 (d, 1H, H$_{py,6}$, J=5.5 Hz), 7.54 (d, 1H, H$_{arom,6}$, J=9 Hz), 7.62 (dt, 1H, H$_{arom}$, J=1+8 Hz), 7.69 (t, 1H, H$_{arom,5'}$, J=8 Hz), 7.90 (s, 1H, H$_{arom,2'}$), 8.01 (dt, 1H, H$_{arom}$, J=1+8 Hz), 10.22 (s, 1H, CONH). $^{19}$F NMR δ (DMSO) −56.36 (s, 3F, CF$_3$). MS m/z 439 (M$^+$+1).

Synthesis 35

N-(3-Chloro-5-(2,3-Diaminopyridin-4-yloxy)phenyl)-3-(trifluoromethoxy)benzamide

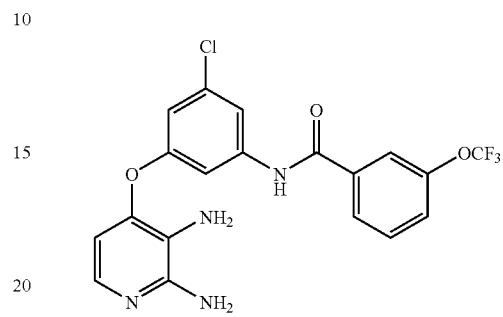

Method D was used with N-(3-(2-Amino-3-nitropyridin-4-yloxy)-5-chlorophenyl)-3-(trifluoromethoxy)benzamide and with 5% sulphided platinum on carbon as catalyst to afford the title compound (92 mg, 98%). $^1$H NMR δ (DMSO) 4.53 (s, 2H, NH$_2$), 5.66 (s, 2H, NH$_2$), 6.19 (d, 1H, H$_{py,5}$, J=5.5 Hz), 6.82 (t, 1H, H$_{arom}$, J=2 Hz), 7.31 (d, 1H, H$_{py,6}$, J=5.5 Hz), 7.34 (t, 1H, H$_{arom}$, J=2 Hz), 7.61 (d, 1H, H$_{arom}$, J=8 Hz), 7.68 (t, 1H, H$_{arom}$, J=8 Hz), 7.73 (t, 1H, H$_{arom}$, J=2 Hz), 7.87 (s, 1H, H$_{arom,2'}$), 7.97 (d, 1H, H$_{arom}$, J=8 Hz), 10.51 (s, 1H, CONH). $^{19}$F NMR δ (DMSO)-56.37 (s, 3F, CF$_3$). MS m/z 439/441 (M$^+$+1).

(VI) Formation of Pyridoimidazolones from 2,3-Diaminopyridyl Intermediates

1. Cyclisation En-Route to Common Intermediates (According to Scheme 2)

Synthesis 36 tert-Butyl 3-(2-oxo-2,3-dihydro-1H-imidazo[4,5-b]pyridin-7-yloxy)-phenyl carbamate

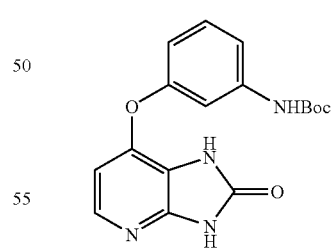

Method E. To 4-(3-N-(tert-butoxycarbonyl)aminophenoxy)-2,3-diamino-pyridine (1.6 g, 5.06 mmol) dissolved in 40 mL THF dry and 2.4 ml pyridine, stirred under Ar at 0° C., a solution containing triphosgene (1.51 g, 5.1 mmol) in 10 mL THF was added dropwise during 1.0-1.5 h. The reaction mixture was stirred 2 h further at 0° C. then allowed to reach room temperature and stirred for an additional 18 h. The solvent was evaporated to dryness, the residue retaken in 10 mL acetone and precipitated with 50 mL water. After filtration 674 g (39%) the title compound was obtained as a solid (674 g, 39%). $^{1}$H-NMR (δ, ppm, DMSO-$d_6$): 1.46 (s, 9H, tBu), 6.43 (d, 1H, $H_{Py,5}$, J=5.9 Hz), 6.72-6.76 (m, 1H, $H_{arom,Ph}$), 7.30-7.32 (m, 3H, $H_{arom,Ph}$), 7.79 (d, 1H, $H_{Py,6}$), 9.47 (s, 1H, NHBoc), 11.14 and 11.36 (s, NH, $NH_{Py}$). LC-MS (m/z): 287 (M, 100).

Synthesis 37 tert-Butyl 3-(2,3-dihydro-2-oxo-1H-imidazo[4,5-b]pyridin-7-yloxy)-4-methoxyphenyl carbamate

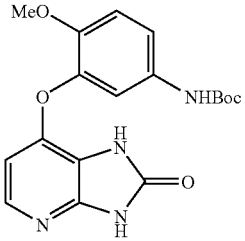

Method E was used with 4-(5-N-(tert-butoxycarbonyl)amino-2-methoxyphenoxy)-2,3-diamino-pyridine to afford the title compound as a white solid (264 mg, 34%). $^{1}$H-NMR (δ, ppm, DMSO-$d_6$): 1.44 (s, 9H, tBu); 3.69 (s, 3H, $CH_3$); 6.13 (d, 1H, $H_{Py,4}$, J=5.9 Hz), 7.13 (d, 1H, $H_{arom,10}$, J=9.0 Hz), 7.31-7.32 (m, 2H, $H_{arom,8,11}$), 7.70 (d, 1H, $H_{Py,5}$, J=5.9 Hz), 9.35 (bs, 1H, $NH_{carbamate}$), 11.20 (s, 1H, $NH_{urea}$), 11.34 (s, 1H, $NH_{urea}$). $^{13}$C-NMR (δ, ppm, DMSO-$d_6$): 28.1 (tBu); 56.0 ($CH_3$); 79.0 (C-tBu); 103.9 (C-4); 111.9 (C-2); 112.3 (C-12); 113.9 (C-9); 115.9 (C-10); 133.4 (C-11); 141.2 (C-5); 141.3 (C-7); 146.0 (C-1); 146.2 (C-3); 146.7 (C-8); 152.7 (C-14); 154.2 ($C_{urea}$). LC-MS (m/z): 372 (M+H, 100).

Synthesis 38 tert-butyl 3-(2,3-dihydro-2-oxo-1H-imidazo[4,5-b]pyridin-7-yloxy)-4-methylphenylcarbamate

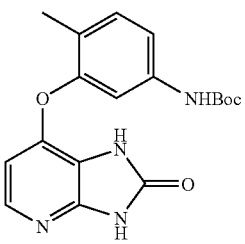

Method E was used with tert-butyl 3-(2,3-diaminopyridin-4-yloxy)-4-methylphenylcarbamate (1 g, 3.0 mmol), to afford the title compound as a yellow solid (132 mg, 14%). $^{1}$H-NMR (δ, ppm, DMSO-$d_6$): 1.43 (s, 9H, t-Bu); 2.06 (s, 3H, $CH_3$); 6.20 (d, 1H, $H_{Py,5}$, J=5.9 Hz), 7.22 (m, 3H, $H_{Ph}$), 7.73 (d, 1H, $H_{Py,6}$. J=6.0 Hz), 9.38 (bs, 1H, $NH_{carbamate}$), 11.18 (bs, 1H, $NH_{urea3}$), 11.35 (bs, 1H, $NH_{urea3}$). $^{13}$C-NMR (δ, ppm, DMSO-$d_6$): 14.8, 27.9, 79.0, 104.7, 109.6, 112.5, 114.8, 122.3, 131.4, 138.9, 141.3, 145.2, 146.7, 151.8, 152.5, 154.1. LC-MS (m/z): 357 (M+H, 100).

(VII) Formation of Pyridoimidazolones from 2,3-Diaminopyridyl Intermediates

2. Cyclisation of Coupled Intermediates (According to Scheme 4 and Scheme 5)

Synthesis 39

1-(5-(2,3-Dihydro-2-oxo-1H-imidazo[4,5-b]pyridin-7-yloxy)-2,4-dichlorophenyl)-3-(4-chloro-3-(trifluoromethyl)phenyl)urea (CJS 3513)

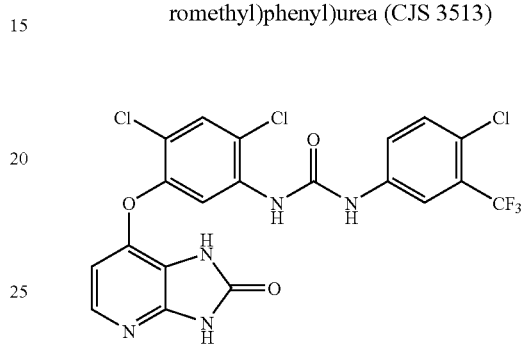

Method E was used with 1-(5-(2,3-diamino-pyridin-4-yloxy)-2,4-dichlorophenyl)-3-(4-chloro-3-(trifluoro-methyl)phenyl)urea to afford the title compound as a pale brown powder (33 mg, 39%). $^{1}$H-NMR (δ, ppm, DMSO-$d_6$): 6.38 (d, 1H, $H_{Py,5}$, J=5.4 Hz), 7.60 (m, 2H, $H_{arom}$), 7.78 (d, 1H, $H_{Py,4}$, J=5.3 Hz), 7.89 (s, 1H, $H_{arom}$), 8.00 (s, 1H, $H_{arom}$), 8.13 (s, 1H, $H_{arom}$), 8.67 (s, 1H, $NH_{urea}$), 10.12 (s, 1H, $NH_{urea}$), 11.32 (s, 1H, $NH_{Py}$), 11.48 (bs, 1H, $NH_{Py}$). $^{13}$C-NMR (δ, ppm, DMSO-$d_6$): 104.9 (C-4); 112.6 (C-); 113.2 (C-); 116.6 (C-); 118.4 (C-); 118.6 (C-); 122.8 (C-); 123.0 (C-); 123.6 (C-); 126.8 (C-); 130.3 (C-); 132.0 (C-); 136.0 (C-); 138.5 (C-); 141.2 (C-); 144.1 (C-); 146.9 (C-); 148.3 (C-); 151.6 (C-); 154.0 (C-). LC-MS (m/z): 531 (M+H, 100).

Synthesis 40

1-(3-(2,3-Dihydro-2-oxo-1H-imidazo[4,5-b]pyridin-7-yloxy)-5-(trifluoromethyl)phenyl)-3-(4-chloro-3-(trifluoromethyl)phenyl)urea (CJS 3517)

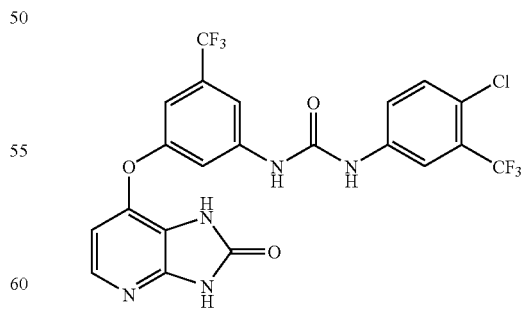

Method E was used with 1-(3-(2,3-diaminopyridin-4-yloxy)-5-(trifluoromethyl)phenyl)-3-(4-chloro-3-(trifluoromethyl)phenyl)urea to afford the title compound as a white powder (42 mg, 54%). $^{1}$H-NMR (δ, ppm, DMSO-$d_6$): 6.66 (d, 1H, $H_{Py,4}$, J=6.0 Hz), 7.12 (m, 1H, $H_{arom}$), 7.46 (m, 1H, H$_{arom}$), 7.61-7.66 (m, 2H, H$_{arom}$), 7.73 (m, 1H, H$_{arom}$), 7.87 (d, 1H, H$_{Py,5}$ J=6.0 Hz), 8.05 (d, 1H, H$_{arom}$, J=2.1 Hz), 9.86 (s, 1H, NH$_{urea}$), 9.93 (s, 1H, NH$_{urea}$), 11.40 (s, 1H, NH$_{Py}$), 11.72 (bs, 1H, NH$_{Py}$). $^{13}$C-NMR (δ, ppm, DMSO-d$_6$): 107.2 (C-4); 108.8 (C-12); 110.3 (C-10); 111.5 (C-8); 114.6 (C-2); 116.6 (C-16); 121.5 (C-18); 122.6 (C-17); 123.0 (C-20); 124.5 (C-11); 126.5 (C-21); 131.1 (C-13); 131.9 (C-19); 138.8 (C-15); 139.4 (C-5); 142.1 (C-9); 144.0 (C-1); 146.2 (C-3); 152.3 (C-14); 153.9 (C-6); 155.3 (C-7). LC-MS (m/z): 532 (M+H, 100).

Synthesis 41

1-(5-(2,3-Dihydro-2-oxo-1H-imidazo[4,5-b]pyridin-7-yloxy)-2,4-dichlorophenyl)-3-(3-(trifluoromethyl)phenyl)urea (CJS 3518)

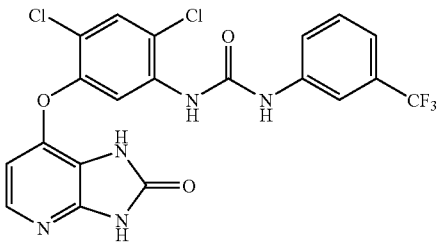

Method E was used with 1-(5-(2,3-diamino-pyridin-4-yloxy)-2,4-dichlorophenyl)-3-(3-(trifluoro methyl)phenyl)urea to afford the title compound as a grey powder (49 mg, 84%). $^1$H-NMR (δ, ppm, DMSO-d$_6$): 6.41 (d, 1H, H$_{Py,5}$, J=6.0 Hz), 7.34 (m, 1H, H$_{arom}$), 7.50-7.55 (m, 3H, H$_{arom}$), 7.80 (d, 1H, H$_{Py,4}$, J=6.0 Hz), 7.94 (s, 1H, H$_{arom}$), 8.18 (s, 1H, H$_{arom}$), 8.63 (s, 1H, NH$_{urea}$), 9.92 (s, 1H, NH$_{urea}$), 11.39 (s, 1H, NH$_{Py}$), 11.61 (bs, 1H, NH$_{Py}$). $^{13}$C-NMR (δ, ppm, DMSO-d$_6$): 104.9 (C-4); 112.8 (C-2); 113.3 (C-12); 114.1 (C-15); 118.3 (C-16); 118.7 (C-17); 121.9 (C-19); 122.9 (C-8); 125.0 (C-10); 129.4 (C-20); 129.9 (C-18); 130.3 (C-9); 136.2 (C-11); 139.7 (C-14); 140.3 (C-5); 144.5 (C-7); 146.5 (C-1); 148.2 (C-3); 151.8 (C-13); 154.0 (C-6). LC-MS (m/z): 498 (M+H, 100).

Synthesis 42

N-(2-methyl-3-(2-oxo-2,3-dihydro-1H-imidazo[4,5-b]pyridin-7-yloxy)phenyl)-3-(trifluoromethoxy)benzamide (CJS3526)

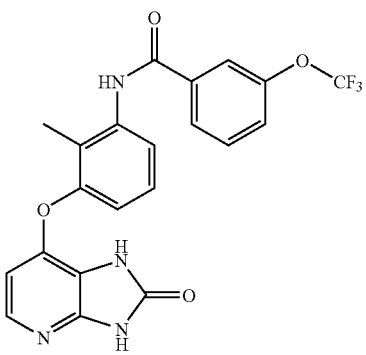

Method E was used with N-(3-(2,3-diaminopyridin-4-yloxy)-2-methylphenyl)-3-(trifluoromethoxy)benzamide (229 mg, 0.55 mmol), to afford the title compound as a pale brown solid (208 mg, 24%). $^1$H-NMR (δ, ppm, DMSO-d$_6$): 2.07 (s, 3H, CH$_3$), 6.21 (d, 1H, H$_{Py,5}$, J=5.9 Hz), 7.07 (dd, 1H, H$_{arom}$, J=5.7 Hz, J=3.4 Hz), 7.33 (m, 2H, H$_{arom}$), 7.62 (m, 1H, H$_{arom}$), 7.69 (t, 1H, H$_{arom}$, J=7.9 Hz), 7.77 (d, 1H, H$_{Py,6}$, J=5.9 Hz), 7.93 (s, 1H, H$_{arom}$), 8.05 (d, 1H, H$_{arom}$, J=7.6 Hz), 10.27 (s, 1H, NH$_{amide}$), 11.29 (s, 1H, NH$_{urea}$), 11.43 (bs, 1H, NH$_{urea}$). $^{13}$C-NMR (δ, ppm, DMSO-d$_6$): 11.0, 104.4, 112.6, 118.2, 118.9, 120.0, 120.9, 123.8, 124.0, 126.5, 126.7, 130.6, 136.3, 137.9, 140.9, 145.5, 146.6, 148.2, 152.1, 154.0, 163.7. LC-MS (m/z): 445 (M+H, 100).

Synthesis 43

N-(2-methyl-5-(2-oxo-2,3-dihydro-1H-imidazo[4,5-b]pyridin-7-yloxy)phenyl)-3-(trifluoromethoxy)benzamide (CJS3524)

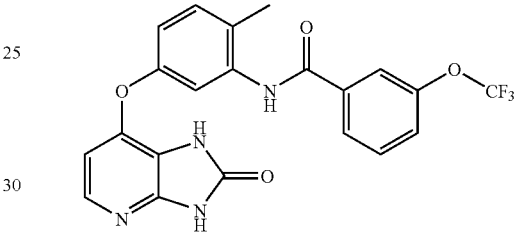

Method E was used with N-(5-(2,3-diaminopyridin-4-yloxy)-2-methylphenyl)-3-(trifluoromethoxy)benzamide (321 mg, 0.76 mmol), to afford the title compound as a pale yellow solid (87 mg, 26%). $^1$H-NMR (δ, ppm, DMSO-d$_6$): 2.27 (s, 3H, CH$_3$), 6.48 (d, 1H, H$_{Py,5}$, J=5.8 Hz), 6.98 (dd, 1H, H$_{arom}$, J=8.2 Hz, J=2.3 Hz), 7.17 (d, 1H, H$_{arom}$, J=2.2 Hz), 7.35 (d, 1H, H$_{arom}$, J=8.3 Hz), 7.43 (s, 1H), 7.64 (d, 1H, H$_{Py,6}$, J=5.8 Hz), 7.75 (m, 2H, H$_{arom}$), 7.97 (s, 1H, H$_{arom}$), 8.14 (m, 1H, H$_{arom}$), 10.27 (bs, 1H, NH$_{urea3}$), 11.09 (bs, 1H, NH$_{urea3}$). $^{13}$C-NMR (δ, ppm, DMSO-d$_6$): 17.1, 103.4, 110.6, 114.6, 116.5, 120.9, 121.7, 126.4, 128.1, 128.8, 131.1, 131.2, 131.4, 132.7, 139.3, 141.0, 145.2, 148.3, 148.8, 153.5, 163.2. LC-MS (m/z): 445 (M+H, 100).

Synthesis 44

N-(4-methoxy-3-(2-oxo-2,3-dihydro-1H-imidazo[4,5-b]pyridin-7-yloxy)phenyl)-3-(trifluoromethoxy)benzamide (CJS 3522)

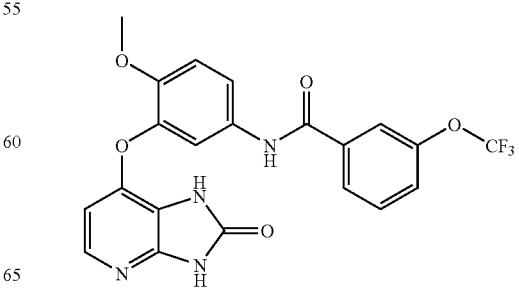

Method E was used with N-(3-(2,3-diaminopyridin-4-yloxy)-4-methoxyphenyl)-3-(trifluoromethoxy)benzamide (176 mg, 0.4 mmol), to afford the title compound as a pale green solid (132 mg, 72%). $^1$H-NMR (δ, ppm, DMSO-d$_6$): 3.76 (s, 3H, CH$_3$), 6.37 (d, 1H, H$_{Py,5}$, J=6.4 Hz), 7.27 (d, 1H, H$_{arom10}$, J=9.0 Hz), 7.59-7.65 (m, 3H, H$_{arom11,17,20}$), 7.73 (d, 1H, H$_{arom13}$, J=2.4 Hz), 7.81 (d, 1H, H$_{Py,6}$, J=6.4 Hz), 7.88 (s, 1H, H$_{arom19}$), 7.99 (d, 1H, H$_{arom21}$, J=7.7 Hz), 10.41 (bs, 1H, NH$_{urea3}$), 11.63 (bs, 1H, NH$_{urea3}$),12.01 (bs, 1H, NH$_{amide}$). $^{13}$C-NMR (δ, ppm, DMSO-d$_6$): 55.9, 104.5, 113.1, 113.8, 114.5, 118.9, 120.0, 121.0, 123.9, 126.6, 130.6, 132.5, 136.8, 137.6, 140.6, 144.6, 147.2, 147.3, 148.2, 153.7, 163.5. LC-MS (m/z): 461 (M+H, 100).

Synthesis 45

N-(2,4-dichloro-5-(2-oxo-2,3-dihydro-1H-imidazo[4,5-b]pyridin-7-yloxy)phenyl)-3-(trifluoromethoxy)benzamide (CJS3521)

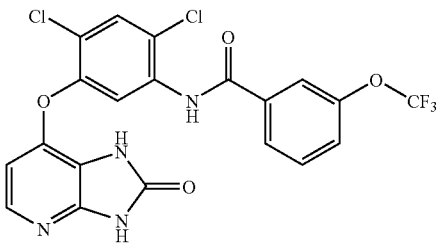

Method E was used with N-(2,4-dichloro-5-(2,3-diaminopyridin-4-yloxy)phenyl)-3-(trifluoromethoxy)benzamide (110 mg, 0.23 mmol), to afford the title compound as a pale brown solid (20 mg, 17%). $^1$H-NMR (δ, ppm, DMSO-d$_6$): 6.43 (d, 1H, H$_{Py,5}$, J=5.4 Hz), 7.54 (s, 1H, H$_{arom}$), 7.62 (d, 1H, H$_{arom}$, J=6.9 Hz), 7.68 (t, 1H, H$_{arom}$, J=7.6 Hz), 7.82 (d, 1H, H$_{Py,6}$, J=5.6 Hz), 7.88 (s, 1H, H$_{arom}$), 7.96 (s, 1H, H$_{arom}$), 7.99 (d, 1H, H$_{arom}$, J=7.3 Hz), 10.35 (s, 1H, H$_{amide}$), 11.30 (bs, 1H, NH$_{urea}$), 11.45 (bs, 1H, NH$_{urea3}$). $^{13}$C-NMR (δ, ppm, DMSO-d$_6$): 105.6, 113.2, 118.9, 119.9, 120.1, 120.9, 122.7, 124.4, 125.8, 126.8, 130.6, 135.0, 135.6, 141.3, 143.5, 147.1, 148.2, 148.7, 154.0, 163.8. $^{19}$F-NMR (δ, ppm, DMSO-d$_6$): −56.76. LC-MS (m/z): 499 (M, 100).

Synthesis 46

N-(4-methyl-3-(2-oxo-2,3-dihydro-1H-imidazo[4,5-b]pyridin-7-yloxy)phenyl)-3-(trifluoromethoxy)benzamide (CJS3523)

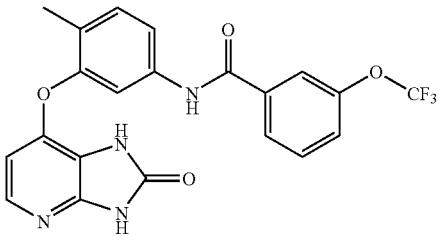

Method E was used with 7-(5-amino-2-methylphenoxy)-1H-imidazo[4,5-b]pyridin-2(3H)-one (60 mg, 0.23 mmol), to afford the title compound as a yellow solid (35 mg, 34%). $^1$H-NMR (δ, ppm, DMSO-d$_6$): 2.24 (s, 3H, CH$_3$), 5.79 (bs, 2H), 6.42 (d, 1H, H$_{Py,5}$, J=5.5 Hz), 7.41 (dd, 1H, H$_{arom}$, J=7.9 Hz, J=1.0 Hz), 7.49 (s, 1H, H$_{arom}$), 7.52 (d, 1H, H$_{arom}$, J=8.2 Hz), 7.66 (d, 1H, H$_{Py,6}$, J=5.5 Hz), 7.79 (m, 2H), 8.05 (s, 1H, H$_{arom}$), 8.21 (m, 1H, H$_{arom}$), 10.67 (bs, 1H, NH$_{urea3}$), 11.09 (bs, 1H, NH$_{urea3}$). $^{13}$C-NMR (δ, ppm, DMSO-d$_6$): 15.7, 95.7, 109.2, 119.4, 120.9, 121.8, 123.3, 126.6, 128.9, 129.2, 130.8, 131.3, 131.5, 132.8, 135.1, 140.5, 143.9, 148.4, 148.9, 152.1, 162.7. LC-MS (m/z): 445 (M+H, 100).

Synthesis 47

N-(3-methoxy-5-(2-oxo-2,3-dihydro-1H-imidazo[4,5-b]pyridin-7-yloxy)phenyl)-3-(trifluoromethoxy)benzamide (CJS3525)

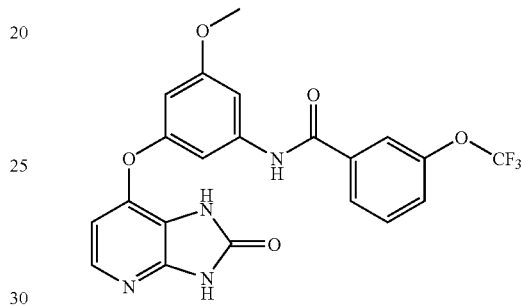

Method E was used with N-(3-(2,3-diaminopyridin-4-yloxy)-5-methoxyphenyl)-3-(trifluoromethoxy)benzamide (185 mg, 0.42 mmol), to afford the title compound as a pale yellow solid (54 mg, 27%). $^1$H-NMR (δ, ppm, DMSO-d$_6$): 3.77 (s, 3H, CH$_3$), 6.53-6.56 (m, 2H, H$_{arom}$+H$_{Py,5}$), 7.17 (m, 1H, H$_{arom}$), 7.35 (m, 1H, H$_{arom}$), 7.60 (m, 1H, H$_{arom}$), 7.67 (m, 1H, H$_{arom}$), 7.82 (d, 1H, H$_{Py,6}$, J=5.9 Hz), 7.87 (s, 1H, H$_{arom}$), 7.97 (d, 1H, H$_{arom}$, J=7.8 Hz), 10.39 (s, 1H, NH$_{amide}$), 11.18 (s, 1H, NH$_{urea}$), 11.39 (bs, 1H, NH$_{urea}$). $^{13}$C-NMR (δ, ppm, DMSO-d$_6$): 55.4, 100.9, 102.1, 102.9, 106.7, 113.7, 118.9, 120.0, 124.0, 126.6, 130.5, 136.6, 140.8, 141.2, 144.3, 147.0, 148.1, 154.1, 155.6, 160.5, 163.9. LC-MS (m/z): 461 (M+H, 100).

Synthesis 48

N-(2,4-Difluoro-5-(2-oxo-2,3-dihydro-1H-imidazo[4,5-b]pyridin-7-yloxy)phenyl)-3-(trifluoromethoxy)benzamide (CJS 3440)

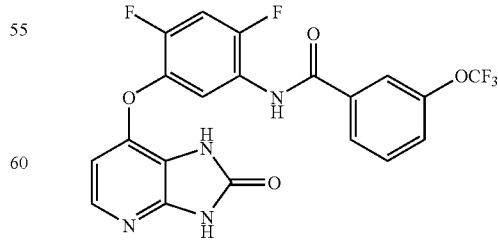

Method E was used with N-(5-(2,3-diaminopyridin-4-yloxy)-2,4-difluorophenyl)-3-(trifluoromethoxy)benzamide to afford the title compound as a white solid (44 mg, 35%). $^1$H NMR δ(DMSO) 6.45 (d, 1H, H$_{Py,5}$, J=6 Hz), 7.61 (m, 2H, H$_{arom}$), 7.68 (m, 2H, H$_{arom}$), 7.81 (d, 1H, H$_{py,6}$, J=6 Hz), 7.89 (1H, s, H$_{arom,2'}$), 7.99 (1H, d, H$_{arom}$, J=7.0 Hz), 10.45 (bs, 1H, NH$_{amide}$), 11.30 (bs, 1H, NH$_{Py3}$), 11.45 (bs, 1H, NH$_{Py2}$). $^{19}$F NMR δ (DMSO) −56.77 (s, 1F, CF$_3$), −119.87 (s, 1F, aromF), −129.83 (s, 1F, aromF).

Synthesis 49

N-(2,3,4-Trifluoro-5-(2-oxo-2,3-dihydro-1H-imidazo[4,5-b]pyridin-7-yloxy)phenyl)-3-(trifluoromethoxy)benzamide (CJS 3441)

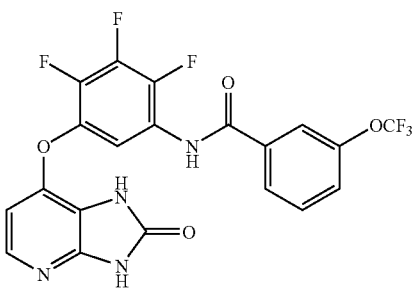

Method E was used with N-(5-(2,3-diaminopyridin-4-yloxy)-2,3,4-trifluorophenyl)-3-(trifluoromethoxy)benzamide to afford the title compound (39 mg, 40%). $^1$H NMR δ(DMSO) 6.65 (d, 1H, H$_{py,5}$, J=6.0 Hz), 7.32 (t, 1H, H$_{arom,6'}$, J=6.5 Hz), 7.63 (d, 1H, H$_{arom}$, J=8.0 Hz), 7.68 (t, 1H, H$_{arom,5''}$, J=8.0 Hz), 7.84 (d, 1H, H$_{py,6}$, J=6 Hz), 7.88 (s, 1H, H$_{arom,2''}$), 7.98 (d, 1H, H$_{arom}$, J=8.0 Hz), 10.52 (s, 1H, NH$_{amide}$), 11.26 (s, 1H, pyrNH), 11.47 (s, 1H, pyrNH). $^{19}$F NMR δ(DMSO) −56.78 (s, 1F, CF$_3$), −143.71 (m, 1F, aromF), −154.05 (m, 1F, aromF), −157.47 (m, 1F, F3). (MS m/z) 485 (M+H, 100).

Synthesis 50

N-(2-chloro-5-(2-oxo-2,3-dihydro-1H-imidazo[4,5-b]pyridin-7-yloxy)phenyl)-3-(trifluoromethoxy)benzamide (CJS 3442)

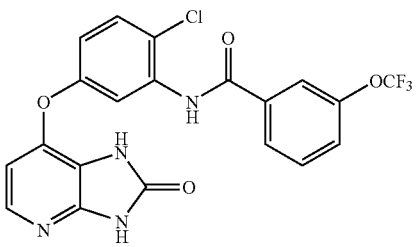

Method E was used with N-(3-Chloro-5-(2,3-Diaminopyridin-4-yloxy)phenyl)-3-(trifluoromethoxy)benzamide to afford the title compound as a white solid (47 mg, 51%). $^1$H NMR δ(DMSO) 6.64 (d, 1H, H$_{py,5}$, J=6 Hz), 7.03 (t, 1H, H$_{arom}$, J=2 Hz), 7.45 (t, 1H, H$_{arom}$, J=2 Hz), 7.62 (dt, 1H, H$_{arom}$, J=1+8 Hz), 7.69 (t, 1H, H$_{arom,5'}$, J=8 Hz), 7.83 (d, 1H, H$_{py,6}$, J=6 Hz), 7.90 (1H, s, H$_{arom,2'}$), 8.01 (1H, dt, H$_{arom}$, J=1+8 Hz), 10.27 (s, 1H, NH$_{amide}$), 11.23 (s, 1H, NH$_{Py3}$), 11.41 (bs, 1H, NH$_{Py2}$). $^{19}$F NMR δ (DMSO) −56.37 (s, 3F, CF$_3$). MS m/z 465 (M$^+$+1).

Synthesis 51

N-(3-chloro-5-(2-oxo-2,3-dihydro-1H-imidazo[4,5-b]pyridin-7-yloxy)phenyl)-3-(trifluoromethoxy)benzamide (CJS 3443)

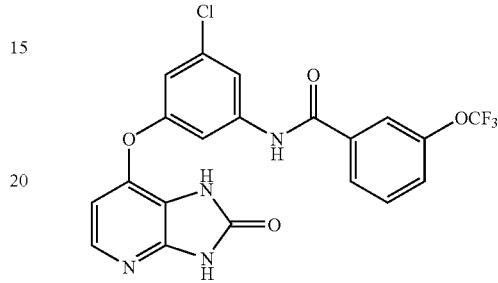

Method E was used with N-(2-Chloro-5-(2,3-Diaminopyridin-4-yloxy)phenyl)-3-(trifluoromethoxy)benzamide to afford the title compound as a white solid (35 mg, 54%). $^1$H NMR δ(DMSO) 6.64 (d, 1H, H$_{py,5}$, J=6 Hz), 7.03 (t, 1H, H$_{arom}$, J=2 Hz), 7.45 (t, 1H, H$_{arom}$, J=2 Hz), 7.62 (dt, 1H, H$_{arom}$, J=1+8 Hz), 7.69 (t, 1H, H$_{arom,5'}$, J=8 Hz), 7.82 (t, 1H, H$_{arom}$, J=2 Hz), 7.86 (d, 1H, H$_{py,6}$, J=6 Hz), 7.9 (1H, s, H$_{arom,2'}$), 7.97 (1H, dt, H$_{arom}$, J=1+8 Hz), 10.53 (s, 1H, NH$_{amide}$), 11.2 (s, 1H, NH$_{Py3}$), 11.45 (s, 1H, NH$_{Py2}$). $^{19}$F NMR δ (DMSO) −56.37 (s, 3F, CF$_3$). MS m/z 465/7 (M$^+$+1).

(VIII) Deprotection of Boc Carbamate

Synthesis 52

7-(3-Aminophenoxy)-1H-imidazo[4,5-b]pyridin-2(3H)-one

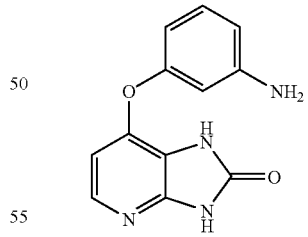

Method F: tert-Butyl 3-(2-oxo-2,3-dihydro-1H-imidazo[4,5-b]pyridin-7-yl-oxy)phenyl carbamate (412 mg, 1.44 mmol) was dissolved in trifluoroacetic acid (TFA) (8 mL) and the solution was stirred at room temperature for 3 hours. Excess TFA was evaporated in vacuo and the resulting viscous oil was taken up in water (3 mL). Saturated NaHCO$_3$ (aq) was added until pH 7. The resulting precipitate was collected by filtration, washed with water and dried to afford the title compound as an off-white solid (252 mg, 72%). $^1$H-NMR (δ, ppm, DMSO-d$_6$): 5.29 (bs, 2H, NH$_2$), 6.24-6.44 (m, 4H, $H_{Py,5+Ph}$), 7.06 (t, 1H, $H_{arom,Ph}$, J=7.9 Hz, 7.76 (d, 1H, $H_{Py,6}$, J=5.9 Hz), 11.19 (bs, 2H, $NH_{Py}$); LC-MS (m/z): 243 (M+H, 100).

Synthesis 53

7-(5-Amino-2-methoxyphenoxy)-1H-imidazo[4,5-b]pyridin-2(3H)-one

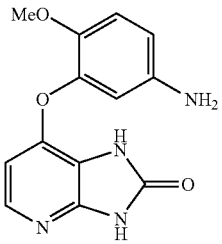

Method F was used with tert-butyl 3-(2,3-dihydro-2-oxo-1H-imidazo[4,5-b]pyridin-7-yloxy)-4-methoxyphenyl carbamate to afford the title compound (34 mg, 18%). $^1$H-NMR (δ, ppm, DMSO-$d_6$): 3.59 (s, 3H, $CH_3$), 4.89 (bs, 2H, $NH_2$), 6.16 (d, 1H, $H_{Py,4}$, J=5.9 Hz), 6.37 (d, 1H, $H_{11}$, J=2.5 Hz), 6.46 (dd, 1H, $H_{10}$, J=8.6 Hz, J=2.5 Hz), 6.91 (d, 1H, $H_8$, J=8.7 Hz), 7.70 (d, 1H, $H_{Py,5}$, J=5.9 Hz), 11.17 (bs, 1H, $NH_{urea3}$), 11.31 (bs, 1H, $NH_{urea3}$). $^{13}$C-NMR (δ, ppm, DMSO-$d_6$): 56.4 ($CH_3$); 104.1 (C-4); 107.8 (C-12); 111.3 (C-10); 111.8 (C-2); 115.5 (C-9); 141.0 (C-5); 141.8 (C-11); 142.4 (C-7); 143.6 (C-8); 146.3 (C-1); 146.5 (C-3); 154.0 (C-6). LC-MS (m/z): 273 (M+H, 100).

Synthesis 54

7-(5-amino-2-methylphenoxy)-1H-imidazo[4,5-b]pyridin-2(3H)-one

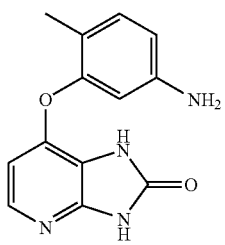

The compound was obtained after purification of the triphosgene's reaction with -butyl 3-(2,3-diaminopyridin-4-yloxy)-4-methylphenylcarbamate. $^1$H-NMR (δ, ppm, DMSO-$d_6$): 2.17 (s, 3H, $CH_3$), 5.81 (bs, 2H, $NH_2$); 6.36 (s, 1H, $H_{arom}$), 6.80 (d, 1H, $H_{Py,5}$, J=5.2 Hz), 6.90 (s, 1H, $H_{arom}$), 7.20 (d, 1H, $H_{Py,6}$, J=5.8 Hz), 7.63 (s, 1H, $H_{arom}$), 9.66 (bs, 1H, $NH_{Py}$), 10.54 (bs, 1H, $NH_{Py}$). $^{13}$C-NMR (δ, ppm, DMSO-$d_6$): 15.5, 96.0, 111.9, 115.8, 123.7, 130.8, 130.9, 132.2, 135.8, 139.0, 143.2, 152.2, 155.7. LC-MS (m/z): 257 (M+H, 100).

(X) Synthesis of Ureas from Isocyanates and Amines

1. Ureas from Pyridoimidazolone Intermediates (According to Scheme 3)

Synthesis 55

1-(4-Chloro-3-(trifluoromethyl)phenyl)-3-(3-(2-oxo-2,3-dihydro-1H-imidazo[4,5-b]pyridin-7-yloxy)phenyl)urea (CJS 3678)

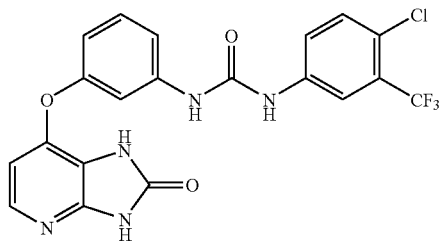

Method G: A mixture of 4-chloro-3-(trifluoromethyl)phenyl isocyanate (33 mg, 0.16 mmol) and 7-(3-aminophenoxy)-1H-imidazo[4,5-b]pyridin-2(3H)-one (30 mg, 0.13 mmol) in anhydrous THF (1.5 mL) was stirred at room temperature for 14 h. Next, the solvent was evaporated and the solid residue was washed with $Et_2O$ to afford the title compound as an off-white solid (33 mg, 55%). $^1$H-NMR (δ, ppm, DMSO-$d_6$): 6.45 (d, 1H, $H_{Py,5}$, J=5.85 Hz), 6.78 (d, 1H, $H_{arom,Ph}$, J=8.2 Hz), 7.25 (d, 1H, $H_{arom,Ph'}$, J=7.9 Hz), 7.34-7.39 (m, 2H, $H_{arom,Ph}$), 7.55-7.67 (m, 2H, $H_{arom,Ph+Ph'}$), 7.79 (d, 1H, $H_{Py,6}$, J=5.85 Hz), 8.06 (s, 1H, $H_{arom,Ph'}$), 9.14 (s, 1H, $NH_{urea}$), 9.29 (s, 1H, $NH_{urea}$), 11.23 (s, 1H, $NH_{Py3}$), 11.42 (s, 1H, $NH_{Py2}$). $^{13}$C-NMR (δ, ppm, DMSO-$d_6$): 106.30, 109.24, 112.95, 114.68, 116.87, 117.15, 122.45, 123.18, 123.46, 123.82, 123.86, 126.70, 130.29, 141.05, 141.29, 144.75, 147.16, 152.32, 154.27, 154.83. HRMS (EI): m/z [M+H] calcd for $C_{20}H_{14}ClF_3N_5O_3$: 464.0737; found: 464.0727.

Synthesis 56

1-(3-Fluorophenyl)-3-(3-(2-oxo-2,3-dihydro-1H-imidazo[4,5-b]pyridin-7-yloxy)phenyl)urea (CJS 3717)

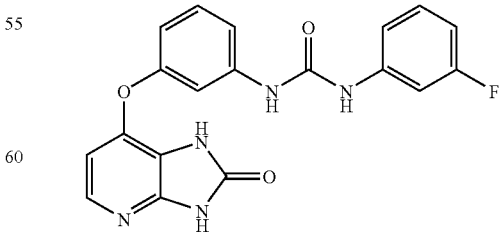

Method G was used with 7-(3-aminophenoxy)-1H-imidazo[4,5-b]pyridin-2(3H)-one and 3-fluoro-phenylisocyanate to afford the title compound (10 mg, 16%). $^1$H-NMR (DMSO), δ (ppm), J (Hz): 6.40 (d, 1H, H$_{Pyr}$, J=5.9 Hz), 6.74-6.79 (m, 1H, H$_{arom2'}$), 7.21 (d, 1H, H$_{arom4\ or\ 6}$, J=8.05 Hz), 7.27 (d, 1H, H$_{arom6\ or\ 4}$), 7.30-7.46 (m, 5H, H$_{arom4'}$, H$_{arom5'}$, H$_{arom6'}$, H$_{arom2}$, H$_{arom\ 5}$), 7.79 (d, 1H, H$_{Pyr}$), 9.04 (s, 2H, NH$_{urea}$), 11.17 (s, 1H, NH$_{im}$), 11.37 (s, 1H, NH$_{im}$); MS-LC, R$_f$=6.84 min, (C$_{19}$H$_{14}$FN$_5$O$_3$), m/z: 380.1 [M$^+$+H], 100.

Synthesis 57

1-(3,4-Difluorophenyl)-3-(3-(2-oxo-2,3-dihydro-1H-imidazo[4,5-b]pyridin-7-yloxy)phenyl)urea (CJS 3720)

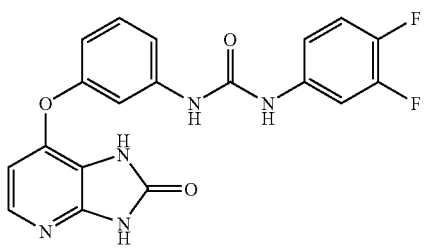

Method G was used with 7-(3-aminophenoxy)-1H-imidazo[4,5-b]pyridin-2(3H)-one and 3,4-difluoro-phenylisocyanate to afford the title compound (16 mg, 23%). $^1$H-NMR (DMSO), δ (ppm), J (Hz): 6.45 (d, 1H, H$_{Pyr}$, J=5.9), 6.76 (s, 1H, H$_{arom2'}$, J=2.2, J=11.05), 7.26-7.40 (m, 5H, H$_{arom\ 6'}$, H$_{arom\ 2}$, H$_{arom\ 4}$, H$_{arom\ 5}$, H$_{arom\ 6}$), 7.56-7.68 (m, 1H, H$_{arom\ 5'}$), 7.78 (d, 1H, H$_{Pyr}$), 8.55 (d, 1H, H$_{arom\ 4'}$, J=7.2), 9.00 (s, 1H, NH$_{urea}$), 9.01 (s, 1H, NH$_{urea}$), 11.17 (s, 1H, NH$_{im}$), 11.36 (s, 1H, NH$_{im}$); MS-LC, R$_f$=7.07 min, (C$_{19}$H$_{13}$F$_2$N$_5$O$_3$), m/z: 398.1 [M$^+$+1], 100.

Synthesis 58

1-(6-fluoro-3-(trifluoromethyl)phenyl)-3-(3-(2-oxo-2,3-dihydro-1H-imidazo[4,5-b]pyridin-7-yloxy)phenyl)urea (CJS 3721)

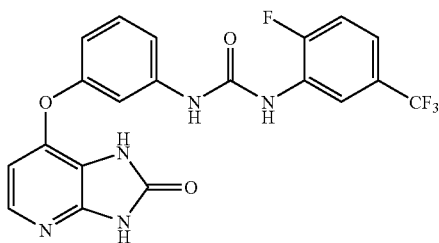

Method G was used with 7-(3-aminophenoxy)-1H-imidazo[4,5-b]pyridin-2(3H)-one and 2-fluoro-5-trifluoromethyl-phenylisocyanate to afford the title compound (15 mg, 20%). $^1$H-NMR (DMSO), δ (ppm), J (Hz): 6.45 (d, 1H, H$_{Pyr}$, J=5.9), 6.79 (s, 1H, H$_{arom5'}$, J=2.1, J=8.0), 7.20 (d, 1H, H$_{arom\ 4\ or\ 6}$, J=7.9), 7.21-7.41 (m, 3H, H$_{arom\ 3'}$, H$_{arom\ 2}$, H$_{arom\ 6\ or\ 4}$), 7.50 (t, 1H, H$_{arom\ 5}$, J=10.7), 7.79 (d, 1H, H$_{Pyr}$), 8.55 (d, 1H, H$_{arom\ 4'}$, J=7.2), 8.93 (s, 1H, NH$_{urea}$), 9.38 (s, 1H, NH$_{urea}$), 11.23 (s, 1H, NH$_{im}$), 11.42 (s, 1H, NH$_{im}$); MS-LC, R$_f$=7.64 min, (C$_{20}$H$_{13}$F$_4$N$_5$O$_3$), m/z: 448.1 [M$^+$+1], 100.

Synthesis 59

1-(3-tert-Butyl-phenyl)-3-(3-(2-oxo-2,3-dihydro-1H-imidazo[4,5-b]pyridin-7-yloxy)phenyl)urea (CJS 3779)

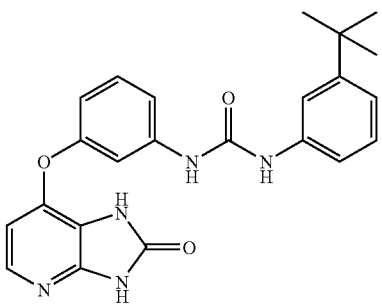

Using method Method G was used with phenyl 3-tert-butyl-isocyanate (0.25 mmol) and 7-(4-aminophenoxy)-1H-imidazo[4,5-b]-pyridin-2(3H)-one (40 mg, 0.16 mmol), heated at 42° C. for 18 hours, a solid was obtained (65 mg, 96.8%). $^1$H-NMR (δ, ppm, DMSO-d$_6$): 1.26 (s, 9H, t-Bu), 6.45 (d, 1H, H$_{Py,5}$, J=5.9 Hz), 7.18-7.42 (m, 8H, H$_{arom}$), 7.14 (d, 1H, H$_{arom}$, J=8.1 Hz), 7.30-7.38 (m, 3H, H$_{arom}$), 7.51-7.56 (m, 2H, H$_{arom}$), 7.79 (d, 1H, H$_{Py,\ 6}$, J=5.9 Hz), 8.61 (s, 1H, NH$_{urea}$), 8.78 (s, 1H, NH$_{urea}$), 11.21 (s, 1H, NH$_{Py7}$), 11.41 (s, 1H, NH$_{Py9}$). LC-MS, t$_R$=5.04 minutes, m/z: 418.2 (M+H)$^+$, calculated for C$_{23}$H$_{24}$N$_5$O$_3$. HRMS (EI): m/z [M+H] calculated for C$_{23}$H$_{24}$N$_5$O$_3$: 418.1843; found: 418.1870.

(XI) Synthesis of Ureas from Isocyanates and Amines

2. Ureas from 2-Amino-3-nitropyridine Intermediates (According to Scheme 4)

Synthesis 60

1-(5-(2-Amino-3-nitropyridin-4-yloxy)-2,4-dichlorophenyl)-3-(4-chloro-3-(trifluoro methyl)phenyl) urea

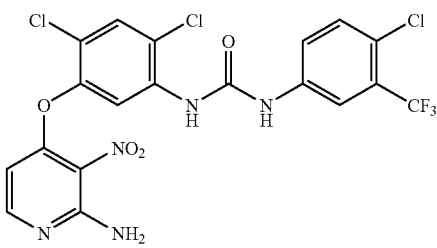

Method G was used with 4-(5-amino-2,4-dichlorophenoxy)-2-amino-3-nitropyridine and 4-chloro-3-trifluoromethylphenyl isocyanate to afford the title compound as a yellow powder (740 mg, 73%). $^1$H-NMR (δ, ppm, DMSO-d$_6$): 6.01 (d, 1H, H$_{Py,5}$, J=5.6 Hz), 7.26 (s, 2H, NH$_{2,Py}$), 7.62 (m, 2H, H$_{arom}$), 7.90 (s, 1H, H$_{arom}$), 8.03 (m, 2H, H$_{arom}$+H$_{Py6}$), 8.21 (s, 1H, H$_{arom}$), 8.63 (s, 1H, NH$_{urea}$), 9.95 (s, 1H, NH$_{urea}$).

$^{13}$C-NMR (δ, ppm, DMSO-d$_6$): 99.7 (C-4); 114.1 (C-11); 116.8 (C-); 116.9 (C-); 118.7 (C-); 119.7 (C-); 121.1 (C-); 123.1 (C-); 123.2 (C-); 123.8 (C-); 130.5 (C-); 132.2 (C-); 136.2 (C-10 or 13); 138.5 (C-10 or 13); 147.4 (C-6); 151.7 (C-12); 153.4 (C-5); 153.9 (C-1); 157.6 (C-3). LC-MS (m/z): 535 (M+H, 100).

Synthesis 61

1-(5-(2-Amino-3-nitropyridin-4-yloxy)-2,4-dichlorophenyl)-3-(3-(trifluoromethyl)phenyl)urea

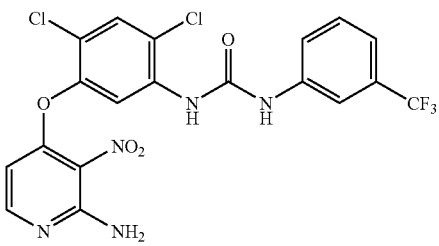

Method G was used with 4-(5-amino-2,4-dichlorophenoxy)-2-amino-3-nitropyridine and 3-trifluoromethylphenyl isocyanate to afford the title compound as a yellow solid (92 mg, 58%). $^1$H-NMR (δ, ppm, DMSO-d$_6$): 6.01 (d, 1H, H$_{Py,5}$, J=5.6 Hz), 7.26 (s, 2H, NH$_{2,Py}$), 7.35-7.37 (m, 1H, H$_{arom}$), 7.53-7.55 (m, 2H, H$_{arom}$), 7.90 (s, 1H, H$_{arom}$), 7.98 (s, 1H, H$_{arom}$), 8.03 (d, 1H, H$_{Py,6}$, J=5.6 Hz), 8.24 (s, 1H, H$_{arom}$), 8.62 (s, 1H, NH$_{urea}$), 9.86 (s, 1H, NH$_{urea}$). $^{13}$C-NMR (δ, ppm, DMSO-d$_6$): 99.6 (C-4); 113.9 (C-11); 114.1 (C-14); 118.4 (C-2); 118.7 (C-16); 119.4 (C-7); 121.0 (C-18); 121.9 (C-9); 125.1 (C-15); 129.5 (C-19); 130.0 (C-17); 130.4 (C-8); 136.3 (C-10); 139.7 (C-13); 147.3 (C-6); 151.7 (C-12); 153.4 (C-5); 153.8 (C-1); 157.6 (C-3). LC-MS (m/z): 501 (M+H, 100).

Synthesis 62

1-(3-(2-amino-3-nitropyridin-4-yloxy)-5-(trifluoromethyl)phenyl)-3-(4-chloro-3-(trifluoromethyl)phenyl)urea

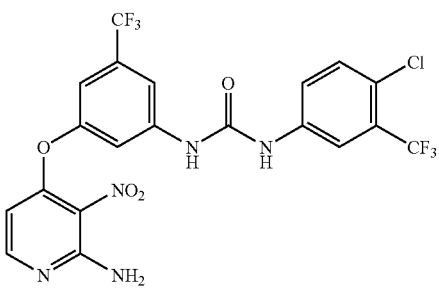

Method G was used with 4-(3-amino-5-(trifluoromethyl)phenoxy)-3-nitropyridin-2-amine and 4-chloro-3-trifluoromethylphenyl isocyanate to afford the title compound as a yellow powder (262 mg, 98%). $^1$H-NMR (δ, ppm, DMSO-d$_6$): 6.17 (d, 1H, H$_{Py,4}$, J=5.6 Hz), 7.19 (m, 1H, H$_{arom}$), 7.28 (bs, 2H, NH$_{Py}$), 7.56 (s, 1H, H$_{arom}$), 7.61 (d, 1H, H$_{arom}$, J=8.7 Hz), 7.68 (dd, 1H, H$_{arom}$, J=8.7 Hz, J=2.1 Hz), 7.80 (s, 1H, H$_{arom}$), 8.07 (d, 1H, H$_{arom}$, J=2.3 Hz), 8.08 (d, 1H, H$_{Py,5}$, J=5.6 Hz), 9.43 (bs, 2H, NH$_{urea}$). $^{13}$C-NMR (δ, ppm, DMSO-d$_6$): 101.5 (C-4); 109.9 (C-11); 111.6 (C-9); 113.0 (C-7); 117.1 (C-15); 117.2 (C-2); 122.2 (C-17); 122.8 (C-16); 123.5 (C-19); 124.4 (C-10); 126.6 (C-20); 131.0 (C-12); 131.9 (C-18); 138.7 (C-14); 142.1 (C-8); 152.2 (C-13); 153.5 (C-5); 153.9 (C-1); 154.4 (C-6); 157.8 (C-3). LC-MS (m/z): 536 (M+H, 100).

(XII) Synthesis of Ureas from Activated Carbamates and Amines

According to Scheme 3

Synthesis 63

1-(3-tert-Butyl-1-p-tolyl-1H-pyrazol-5-yl)-3-(3-(2-oxo-2,3-dihydro-1H-imidazo[4,5-b]pyridin-7-yloxy)phenyl)urea (CJS 3683)

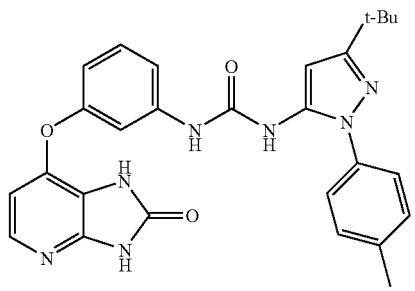

Method J: A solution of phenyl 3-tert-butyl-1-p-tolyl-1H-pyrazol-5-ylcarbamate (67 mg, 0.20 mmol) and 7-(4-aminophenoxy)-1H-imidazo[4,5-b]pyridin-2(3H)-one (30 mg, 0.13 mmol) in anhydrous DMSO (1 mL) was heated at 85° C. for 2 hours. After cooling to room temperature, the solution was diluted with EtOAc (10 mL) and this layer was washed twice with H$_2$O and once with brine. The organic layer was dried over MgSO$_4$ and the solvent was evaporated under reduced pressure. The solid residue was washed with Et$_2$O, to afford the title compound as an off-white solid (33 mg, 51%). $^1$H-NMR (δ, ppm, DMSO-d$_6$): 1.25 (s, 9H, t-Bu), 2.35 (s, 3H, CH$_3$), 6.32 (s, 1H, H$_{Pyz,4}$), 6.42 (d, 1H, H$_{Py,5}$, J=6.0 Hz), 6.74 (d, 1H, H$_{arom}$, J=8.0 Hz), 7.14 (d, 2H, H$_{arom}$, J=8.0 Hz), 7.27-7.39 (m, 6H, H$_{arom}$), 7.77 (d, 1H, H$_{Py,6}$, J=6.0 Hz), 8.52 (bs, 1H, NH$_{urea}$), 9.33 (bs, 1H, NH$_{urea}$), 11.26 (bs, 2H, NH$_{Py3}$). $^{13}$C-NMR (δ, ppm, DMSO-d$_6$): 20.58, 30.20, 31.99, 95.32, 106.30, 108.70, 112.71, 113.74, 114.14, 124.28, 129.63, 130.27, 136.07, 136.72, 136.94, 141.21, 144.69, 147.29, 151.52, 154.33, 154.41, 154.90, 160.49. HRMS (EI): m/z [M+H] calcd for C$_{27}$H$_{28}$N$_7$O$_3$: 498.2254; found: 498.2247.

Synthesis 64

1-(3-tert-Butyl-1-phenyl-1H-pyrazol-5-yl)-3-(3-(2-oxo-2,3-dihydro-1H-imidazo[4,5-b]pyridin-7-yloxy)phenyl)urea (CJS 3741)

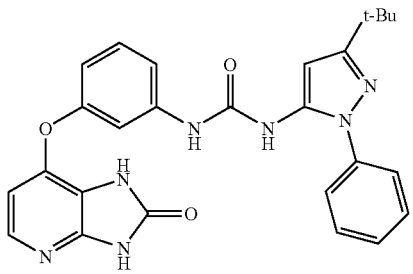

Method J was used with phenyl 3-tert-butyl-1-phenyl-1H-pyrazol-5-ylcarbamate (84 mg, 0.30 mmol) and 7-(4-aminophenoxy)-1H-imidazo[4,5-b]-pyridin-2(3H)-one (50 mg, 0.21 mmol), heated at 42° C. for 18 hours, a solid was obtained (39 mg, 41.3%). $^1$H-NMR ($\delta$, ppm, DMSO-d$_6$): 1.27 (s, 9H, t-Bu), 6.35 (s, 1H, H$_{Pyz,4}$), 6.44 (d, 1H, H$_{Py,5}$, J=5.9 Hz), 6.75 (dd, 1H, H$_{arom}$, J=2.4 Hz, J=8.0 Hz), 7.15 (dd, 1H, H$_{arom}$, J=1.1 Hz, J=8.0 Hz), 7.30-7.33 (m, 2H, H$_{arom}$), 7.38-7.42 (m, 1H, H$_{arom}$), 7.51-7.53 (m, 2H, H$_{arom}$), 7.78 (d, 1H, H$_{Py,6}$, J=5.9 Hz), 8.39 (s, 1H, NH$_{urea}$), 9.17 (s, 1H, NH$_{urea}$), 11.15 (s, 1H, NH$_{Py7}$), 11.15 (s, 1H, NH$_{Py9}$). LC-MS, t$_R$=4.80 minutes, m/z: 484.20 (M+H)$^+$, calculated for C$_{26}$H$_{26}$N$_7$O$_3$. HRMS (EI): m/z [M+H] calculated for C$_{26}$H$_{26}$N$_7$O$_3$: 448.2097; found: 480.2094.

Synthesis 65

1-(3-tert-Butyl-1-(4-fluorophenyl)-1H-pyrazol-5-yl)-3-(3-(2-oxo-2,3-dihydro-1H-imidazo[4,5-b]pyridin-7-yloxy)phenyl)urea (CJS 3742)

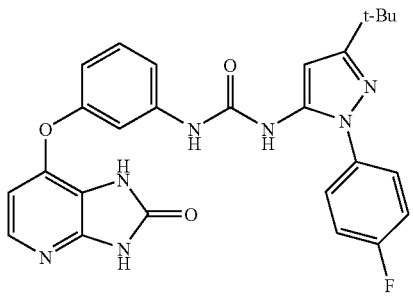

Method J was used with phenyl 3-tert-butyl-1-(4-fluorophenyl)-1H-pyrazol-5-ylcarbamate (106 mg, 0.30 mmol) and 7-(4-aminophenoxy)-1H-imidazo[4,5-b]-pyridin-2(3H)-one (50 mg, 0.21 mmol), heated at 42° C. for 18 hours, a solid was obtained (55 mg, 52.1%). $^1$H-NMR ($\delta$, ppm, DMSO-d$_6$): 1.26 (s, 9H, t-Bu), 6.33 (s, 1H, H$_{Pyz,4}$), 6.43 (d, 1H, H$_{Py,5}$, J=5.9 Hz), 6.75 (dd, 1H, H$_{arom}$, J=1.8 Hz, J=8.1 Hz), 7.14 (d, 1H, H$_{arom}$, J=8.1 Hz), 7.30-7.38 (m, 3H, H$_{arom}$), 7.51-7.56 (m, 2H, H$_{arom}$), 7.78 (d, 1H, H$_{Py,6}$, J=5.9 Hz), 8.43 (s, 1H, NH$_{urea}$), 9.20 (s, 1H, NH$_{urea}$), 11.21 (s, 1H, NH$_{Py7}$), 11.41 (s, 1H, NH$_{Py9}$). LC-MS, t$_R$=4.80 minutes, m/z: 502.20 (M+H)$^+$, calculated for C$_{26}$H$_{25}$N$_7$O$_3$F. HRMS (EI): m/z [M+H] calculated for C$_{26}$H$_{25}$N$_7$O$_3$F: 502.2003; found: 502.2011.

(XIII) Synthesis of Amides

1. Amides from Pyridoimidazolone Intermediates (According to Scheme 3)

Synthesis 66

4-Chloro-N-(3-(2-oxo-2,3-dihydro-1H-imidazo[4,5-b]pyridin-7-yloxy)phenyl)-3-(trifluoromethyl)benzamide (CJS 3685)

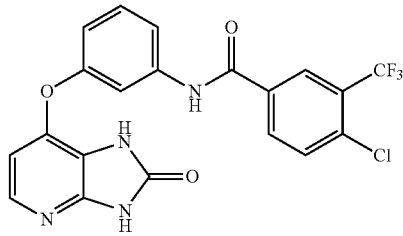

Method H: 7-(3-Aminophenoxy)-1H-imidazo[4,5-b]pyridin-2(3H)-one (30 mg, 0.13 mmol) and triethylamine (22.3 µL, 0.16 mmol) were mixed in dry THF (5 mL) and 4-chloro-3-(trifluoromethyl)benzoyl chloride (39.0 mg, 0.16 mmol) was added. This mixture was heated to reflux for 20 h and subsequently the solvent was removed in vacuo. The obtained residue was dissolved in acetone (2 mL) and upon addition of water a solid precipitated. This solid was collected, washed with water (2×2 mL) and Et$_2$O (2×2 mL) and dried to afford the title compound as a light brown solid (26 mg, 45%). $^1$H-NMR ($\delta$, ppm, DMSO-d$_6$): $^1$H-NMR ($\delta$, ppm, DMSO-d$_6$): 6.50 (d, 1H, H$_{Py,5}$, J=5.5 Hz), 6.94 (d, 1H, H$_{arom}$, J=7.5 Hz), 7.45 (ps t, 1H, H$_{arom}$, J=8.0 Hz), 7.57-7.67 (m, 2H, H$_{arom}$), 7.81 (d, 1H, H$_{Py,6}$, J=5.5 Hz), 7.88-7.93 (m, 1H, H$_{arom}$), 8.24 (d, 1H, H$_{arom}$, J=7.5 Hz), 8.36 (s, 1H, H$_{arom}$), 10.60 (s, 1H, NH$_{amide}$), 11.20 (s, 1H, NH$_{Py3}$), 11.40 (s, 1H, NH$_{Py2}$). $^{13}$C-NMR ($\delta$, ppm, DMSO-d$_6$): 106.65, 110.85, 113.82, 114.85, 116.40, 122.61, 126.66, 127.07, 130.28, 131.95, 133.39, 133.92, 134.03, 140.33, 141.35, 144.50, 147.18, 154.21, 154.81, 163.32. HRMS (EI): m/z [M+H] calcd for C$_{20}$H$_{13}$ClF$_3$N$_4$O$_3$: 449.0628; found: 444.0627.

Synthesis 67

3-Fluoro-5-morpholino-N-(3-(2-oxo-2,3-dihydro-1H-imidazo[4,5-b]pyridin-7-yloxy)phenyl)benzamide (CJS 3686)

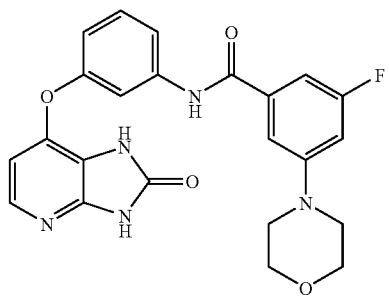

Method H was used with 7-(3-aminophenoxy)-1H-imidazo[4,5-b]pyridin-2(3H)-one and 3-fluoro-5-morpholinobenzoyl chloride to afford the title compound as a light brown solid (38 mg, 65%). $^1$H-NMR (δ, ppm, DMSO-$d_6$): 3.22 (m, 4H, $CH_2N$), 3.74 (m, 4H, $CH_2O$), 6.48 (d, 1H, $H_{Py,5}$, J=6.0 Hz), 6.91 (d, 1H, $H_{arom}$, J=8.0 Hz), 6.98 (d, 1H, $H_{arom}$, J=10.5 Hz), 7.11 (d, 1H, $H_{arom}$, J=9.0 Hz), 7.26 (s, 1H, $H_{arom,Ph'}$), 7.42 (ps t, 1H, $H_{arom}$, J=8.5 Hz), 7.61-7.64 (m, 2H, $H_{arom}$), 7.81 (d, 2H, $H_{Py,6}$, J=6.0 Hz), 10.28 (s, 1H, $NH_{amide}$), 11.19 (s, 1H, $NH_{Py3}$), 11.38 (s, 1H, $NH_{Py2}$). $^{13}$C-NMR (δ, ppm, DMSO-$d_6$): 47.76, 65.85, 104.17, 104.41, 106.58, 109.73, 110.86, 113.75, 114.57, 116.35, 130.16, 137.05, 140.61, 141.35, 144.60, 147.15, 152.65, 154.21, 154.73, 162.98, 164.81. HRMS (EI): m/z [M+H] calcd for $C_{23}H_{21}FN_5O_4$: 450.1578; found: 450.1571.

Synthesis 68

N-(3-(2-oxo-2,3-dihydro-1H-imidazo[4,5-b]pyridin-7-yloxy)phenyl)-3-(trifluoromethyl)benzamide (CJS 3687)

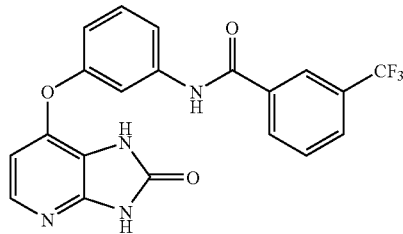

Method H was used with 7-(3-aminophenoxy)-1H-imidazo[4,5-b]pyridin-2(3H)-one and 3-(trifluoromethyl)benzoyl chloride to afford the title compound as an off-white solid (17 mg, 32%). $^1$H-NMR (δ, ppm, DMSO-$d_6$): 6.50 (d, 1H, $H_{Py,5}$, J=6.0 Hz), 6.94 (d, 1H, $H_{arom}$, J=8.0 Hz), 7.44 (ps t, 1H, $H_{arom}$, J=8.0 Hz), 7.62 (s, 1H, $H_{arom}$), 7.66 (d, 1H, $H_{arom}$, J=7.5 Hz), 7.72-7.82 (m, 2H, $H_{arom+Py,6}$), 7.96 (d, 1H, $H_{arom}$, J=8.0 Hz), 8.24 (d, 1H, $H_{arom}$, J=7.5 Hz), 8.26 (s, 1H, $H_{arom}$), 10.55 (s, 1H, $NH_{amide}$), 11.20 (s, 1H, $NH_{Py3}$), 11.39 (s, 1H, $NH_{Py2}$). $^{13}$C-NMR (δ, ppm, DMSO-$d_6$): 106.62, 110.87, 113.79, 114.73, 116.37, 123.93, 124.26, 128.28, 129.19, 129.75, 130.25, 131.85, 135.54, 140.48, 141.35, 144.55, 147.17, 154.21, 154.78, 164.22. HRMS (EI): m/z [M+H] calcd for $C_{20}H_{14}F_3N_4O_3$: 415.1018; found: 415.1010.

Synthesis 69

3-Methoxy-N-(3-(2-oxo-2,3-dihydro-1H-imidazo[4,5-b]pyridin-7-yloxy)phenyl)benzamide (CJS 3688)

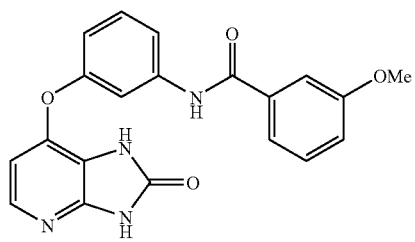

Method H was used with 7-(3-aminophenoxy)-1H-imidazo[4,5-b]pyridin-2(3H)-one and 3-methoxy-benzoyl chloride to afford the title compound as a brown solid (21 mg, 40%). $^1$H-NMR (δ, ppm, DMSO-$d_6$): 3.83 (s, 3H, OMe), 6.49 (d, 1H, $H_{Py,5}$, J=5.8 Hz), 6.90 (d, 1H, $H_{arom}$, J=7.48 Hz), 7.16 (d, 1H, $H_{arom}$, J=6.52 Hz), 7.39-7.49 (m, 3H, $H_{arom}$), 7.52 (d, 1H, $H_{arom}$, J=7.61 Hz), 7.62-7.68 (m, 2H, $H_{arom}$), 7.81 (d, 1H, $H_{Py,6}$, J=5.44 Hz), 10.31 (s, 1H, $NH_{amide}$), 11.19 (s, 1H, $NH_{Py3}$), 11.39 (s, 1H, $NH_{Py2}$).

Synthesis 70

N-(3-(2-oxo-2,3-dihydro-1H-imidazo[4,5-b]pyridin-7-yloxy)phenyl)benzamide (CJS 3689)

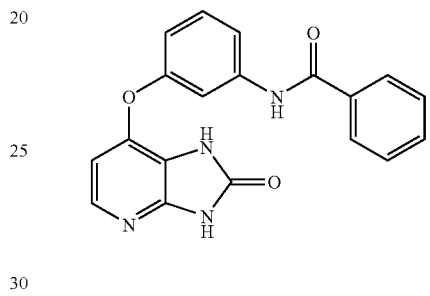

Method H was used with 7-(3-aminophenoxy)-1H-imidazo[4,5-b]pyridin-2(3H)-one and benzoyl chloride to afford the title compound as an off-white solid (37 mg, 82%). $^1$H-NMR (□, ppm, DMSO-$d_6$): 6.49 (d, 1H, $H_{Py,5}$, J=6.0 Hz), 6.90 (d, 1H, $H_{arom}$, J=8.0 Hz), 7.42 (ps t, 1H, $H_{arom}$, J=8.0 Hz), 7.51-7.68 (m, 5H, $H_{arom}$), 7.81 (d, 1H, $H_{Py,6}$, J=6.0 Hz), 7.93 (d, 2H, $H_{arom}$, J=7.5 Hz), 10.35 (s, 1H, $NH_{amide}$), 11.20 (s, 1H, $NH_{Py3}$), 11.40 (s, 1H, $NH_{Py2}$). $^{13}$C-NMR (□, ppm, DMSO-$d_6$): 106.56, 110.71, 114.34, 116.20, 127.64, 128.37, 129.32, 130.13, 131.69, 134.68, 140.88, 141.26, 144.65, 147.10, 154.19, 154.69, 165.72. HRMS (EI): m/z [M+H] calcd for $C_{19}H_{15}N_4O_3$: 347.1144; found: 347.1140.

Synthesis 71

3-Bromo-N-(3-(2-oxo-2,3-dihydro-1H-imidazo[4,5-b]pyridin-7-yloxy)phenyl)benzamide (CJS 3690)

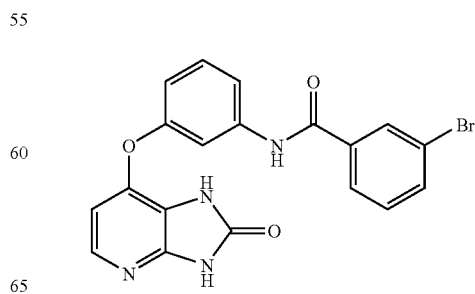

Method H was used with 7-(3-aminophenoxy)-1H-imidazo[4,5-b]pyridin-2(3H)-one and 3-bromo-benzoyl chloride to afford the title compound as a light brown solid (50 mg, 73%). $^1$H-NMR (δ, ppm, DMSO-d$_6$): 6.50 (d, 1H, H$_{Py,5}$, J=6.0 Hz), 6.92 (d, 1H, H$_{arom}$, J=8.0 Hz), 7.43 (ps t, 1H, H$_{arom}$, J=8.0 Hz), 7.48 (m, 1H, H$_{arom}$), 7.62 (s, 1H, H$_{arom}$), 7.66 (d, 1H, H$_{arom}$, J=8.0 Hz), 7.78-7.84 (m, 2H, H$_{arom+Py,6}$), 7.93 (d, 1H, H$_{arom}$, J=8.0 Hz), 8.12 (s, 1H, H$_{arom}$), 10.45 (s, 1H, NH$_{amide}$), 11.23 (s, 1H, NH$_{Py3}$), 11.44 (s, 1H, NH$_{Py2}$). $^{13}$C-NMR (δ, ppm, DMSO-d$_6$): 106.58, 110.82, 113.83, 114.62, 116.32, 121.66, 126.87, 128.24, 130.65, 130.87, 131.71, 136.80, 140.56, 141.08, 144.67, 147.00, 154.17, 154.68, 164.13. HRMS (EI): m/z [M+H] calcd for C$_{19}$H$_{14}$BrN$_4$O$_3$: 425.0249; found: 425.0248.

Synthesis 72

N-(3-(2-oxo-2,3-dihydro-1H-imidazo[4,5-b]pyridin-7-yloxy)phenyl)-3-(trifluoromethoxy)benzamide (CJS 3695)

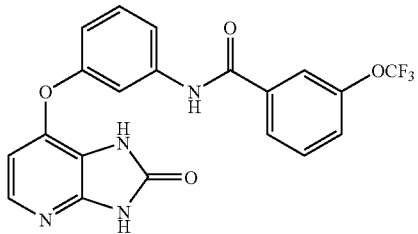

Method H was used with 7-(3-aminophenoxy)-1H-imidazo[4,5-b]pyridin-2(3H)-one and 3-(trifluoromethoxy)benzoyl chloride to afford the title compound as an off-white solid (36 mg, 64%). $^1$H-NMR (δ, ppm, DMSO-d$_6$): 6.50 (d, 1H, H$_{Py,5}$, J=6.0 Hz), 6.93 (d, 1H, H$_{arom}$, J=7.0 Hz), 7.44 (ps t, 1H, H$_{arom}$, J=8.0 Hz), 7.62 (s, 1H, H$_{arom}$), 7.64-7.69 (m, 3H, H$_{arom}$), 7.81 (d, 1H, H$_{Py,6}$, J=6.0 Hz), 7.88 (s, 1H, H$_{arom}$), 7.99 (d, 1H, H$_{arom}$, J=8.0 Hz), 10.47 (s, 1H, NH$_{amide}$), 11.20 (s, 1H, NH$_{Py3}$), 11.39 (s, 1H, NH$_{Py2}$). $^{13}$C-NMR (δ, ppm, DMSO-d$_6$): 106.61, 110.86, 113.78, 114.72, 116.36, 120.05, 121.07, 124.17, 126.80, 130.23, 130.64, 136.83, 140.47, 141.35, 144.55, 147.17, 148.28, 154.21, 154.76, 164.03. HRMS (EI): m/z [M+H] calcd for C$_{20}$H$_{14}$F$_3$N$_4$O$_4$: 431.0967; found: 431.0968.

Synthesis 73

4-Fluoro-N-(3-(2-oxo-2,3-dihydro-1H-imidazo[4,5-b]pyridin-7-yloxy)phenyl)-3-(trifluoromethoxy)benzamide (CJS 3696)

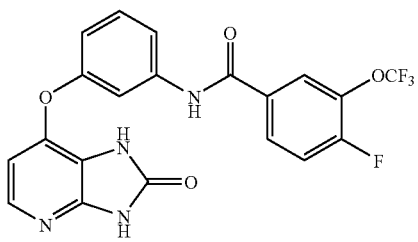

Method H was used with 7-(3-aminophenoxy)-1H-imidazo[4,5-b]pyridin-2(3H)-one and 4-fluoro-3-(trifluoromethoxy)benzoyl chloride to afford the title compound as a brown solid (25 mg, 43%). $^1$H-NMR (δ, ppm, DMSO-d$_6$): 6.49 (d, 1H, H$_{Py,5}$, J=6.0 Hz), 6.93 (d, 1H, H$_{arom}$, J=8.0 Hz), 7.44 (t, 1H, H$_{arom}$, J=8.0 Hz), 7.59 (s, 1H, H$_{arom}$), 7.63 (d, 1H, H$_{arom}$, J=9.0 Hz), 7.70 (t, 1H, H$_{arom}$, J=9.0 Hz), 7.81 (d, 1H, H$_{Py,6}$, J=6.0 Hz), 8.06-8.13 (m, 2H, H$_{arom}$), 10.47 (s, 1H, NH$_{amide}$), 11.20 (s, 1H, NH$_{Py3}$), 11.39 (s, 1H, NH$_{Py2}$).

Synthesis 74

N-(3-(2-oxo-2,3-dihydro-1H-imidazo[4,5-b]pyridin-7-yloxy)phenyl)-4-(trifluoromethyl)benzamide (CJS 3697)

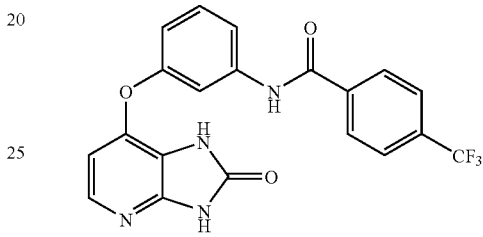

Method H was used with 7-(3-aminophenoxy)-1H-imidazo[4,5-b]pyridin-2(3H)-one and 4-(trifluoromethyl)benzoyl chloride to afford the title compound as a brown solid (33 mg, 61%). $^1$H-NMR (δ, ppm, DMSO-d$_6$): 6.50 (d, 1H, H$_{Py,5}$, J=6.0 Hz), 6.93 (d, 1H, H$_{arom}$, J=7.0 Hz), 7.44 (t, 1H, H$_{arom}$, J=8.0 Hz), 7.63 (s, 1H, H$_{arom}$), 7.64-7.68 (m, 1H, H$_{arom}$), 7.82 (d, 1H, H$_{Py,6}$, J=6.0 Hz), 7.91 (d, 2H, H$_{arom}$, J=8.0 Hz), 8.12 (d, 2H, H$_{arom}$, J=8.0 Hz), 10.55 (s, 1H, NH$_{amide}$), 11.20 (s, 1H, NH$_{Py3}$), 11.38 (s, 1H, NH$_{Py2}$).

Synthesis 75

5-tert-Butyl-2-methyl-N-(3-(2-oxo-2,3-dihydro-1H-imidazo[4,5-b]pyridin-7-yloxy)phenyl) furan-3-carboxamide (CJS 3722)

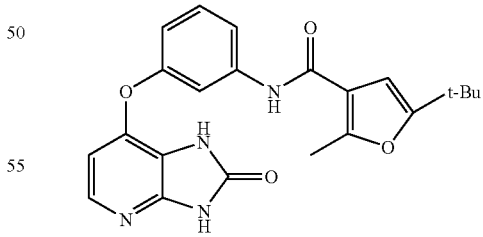

Method H was used with 7-(3-aminophenoxy)-1H-imidazo[4,5-b]pyridin-2(3H)-one and 5-tert-butyl-2-methylfuran-3-carbonyl chloride to afford the title compound (25 mg, 29%). $^1$H-NMR (δ, ppm, DMSO-d$_6$): 1.25 (s, 9H, t-Bu), 3.29 (s, 3H, Me), 6.47 (d, 1H, H$_{Py,5}$, J=6.0 Hz), 6.64 (s, 1H, H$_{fur}$), 6.86 (d, 1H, H$_{arom}$, J=8.0 Hz), 7.38 (t, 1H, H$_{arom}$, J=8.0 Hz), 7.57 (t, 1H, H$_{arom}$, J=2.2 Hz), 7.61 (d, 1H, H$_{arom}$, J=8.0 Hz), 7.79 (d, 1H, H$_{Py,6}$, J=6.0 Hz), 9.68 (s, 1H, NH$_{amide}$), 11.18 (s, 1H, NH$_{Py3}$), 11.37 (s, 1H, NH$_{Py2}$). HRMS (EI): m/z [M+H] calcd for C$_{22}$H$_{23}$N$_4$O$_4$: 407.1719; found: 407.1721.

Synthesis 76

1,3-Dimethyl-N-(3-(2-oxo-2,3-dihydro-1H-imidazo[4,5-b]pyridin-7-yloxy)phenyl)-1H-pyrazole-5-carboxamide (CJS 3724)

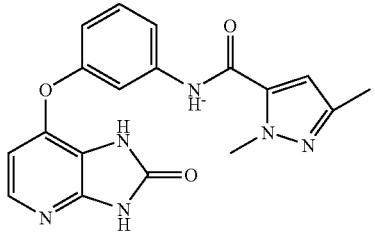

Method H was used with 7-(3-aminophenoxy)-1H-imidazo[4,5-b]pyridin-2(3H)-one and 1,3-dimethyl-1H-pyrazole-5-carbonyl chloride to afford the title compound (20 mg, 26%). $^1$H-NMR (δ, ppm, DMSO-d$_6$): 2.19 (s, 3H, Me$_{pyrrazole,3}$), 3.98 (s, 3H, Me$_{pyrrazole,1}$), 6.48 (d, 1H, H$_{Py,5}$, J=6.0 Hz), 6.81 (s, 1H, H$_{pyrrazole}$), 6.91 (d, 1H, H$_{arom}$, J=8.0 Hz), 7.41 (t, 1H, H$_{arom}$, J=8.0 Hz), 7.56 (s, 1H, H$_{arom}$), 7.61 (d, 1H, H$_{arom}$, J=8.0 Hz), 7.80 (d, 1H, H$_{Py,6}$, J=6.0 Hz), 10.19 (s, 1H, NH$_{amide}$), 11.19 (s, 1H, NH$_{Py3}$), 11.39 (s, 1H, NH$_{Py2}$). HRMS (EI): m/z [M+H] calcd for C$_{18}$H$_{17}$N$_6$O$_3$: 365.1362; found: 365.1356.

Synthesis 77

N-(3-(2-oxo-2,3-dihydro-1H-imidazo[4,5-b]pyridin-7-yloxy)phenyl)-1-phenyl-1H-pyrazole-5-carboxamide (CJS 3725)

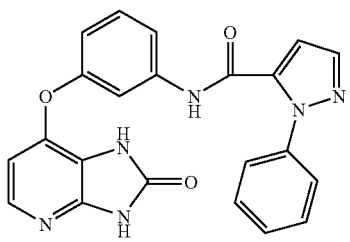

Method H was used with 7-(3-aminophenoxy)-1H-imidazo[4,5-b]pyridin-2(3H)-one and 1-phenyl-1H-pyrazole-5-carbonyl chloride to afford the title compound (15 mg, 17%). $^1$H-NMR (δ, ppm, DMSO-d$_6$): 6.47 (d, 1H, H$_{Py,5}$, J=6.0 Hz), 6.89 (d, 1H, H$_{arom}$, J=8.0 Hz), 7.06 (d, 1H, H$_{pyrrazole}$, J=2.1 Hz), 7.37-7.49 (m, 7H, H$_{arom}$), 7.53 (d, 1H, H$_{arom}$, J=8.0 Hz), 7.78-7.81 (m, 2H, H$_{pyrrazole+Py,6}$), 10.64 (s, 1H, NH$_{amide}$), 11.16 (s, 1H, NH$_{Py3}$), 11.37 (s, 1H, NH$_{Py2}$). HRMS (EI): m/z [M+H] calcd for C$_{22}$H$_{17}$N$_6$O$_3$: 413.1362; found: 413.1366.

Synthesis 78

N-(3-(2-oxo-2,3-dihydro-1H-imidazo[4,5-b]pyridin-7-yloxy)phenyl)-1-phenyl-5-(trifluoromethyl)-1H-pyrazole-4-carboxamide (CJS 3726)

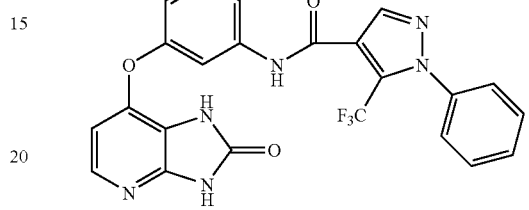

Method H was used with 7-(3-aminophenoxy)-1H-imidazo[4,5-b]pyridin-2(3H)-one and 1-phenyl-5-(trifluoromethyl)-1H-pyrazole-4-carbonyl chloride to afford the title compound (28 mg, 28%). $^1$H-NMR (δ, ppm, DMSO-d$_6$): 6.50 (d, 1H, H$_{Py,5}$, J=6.0 Hz), 6.92 (d, 1H, H$_{arom}$, J=8.0 Hz), 7.43 (t, 1H, H$_{arom}$, J=8.0 Hz), 7.51-7.63 (m, 7H, H$_{arom}$), 7.81 (d, 1H, H$_{Py,6}$, J=6.0 Hz), 8.29 (s, 1H, H$_{pyrrazole}$), 10.63 (s, 1H, NH$_{amide}$), 11.19 (s, 1H, NH$_{Py3}$), 11.39 (s, 1H, NH$_{Py2}$). HRMS (EI): m/z [M+H] calcd for C$_{23}$H$_{16}$N$_6$O$_3$F$_3$: 481.1236; found: 481.1229.

Synthesis 79

1-Benzyl-3-tert-butyl-N-(3-(2-oxo-2,3-dihydro-1H-imidazo[4,5-b]pyridin-7-yloxy)phenyl)-1H-pyrazole-5-carboxamide (CJS 3727)

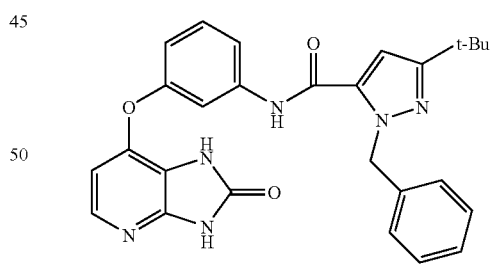

Method H was used with 7-(3-aminophenoxy)-1H-imidazo[4,5-b]pyridin-2(3H)-one and 1-benzyl-3-tert-butyl-1H-pyrazole-5-carbonyl chloride to afford the title compound (40 mg, 39%). $^1$H-NMR (δ, ppm, DMSO-d$_6$): 1.29 (s, 9H, t-Bu), 5.67 (s, 2H, CH$_2$), 6.47 (d, 1H, H$_{Py,5}$, J=6.0 Hz), 6.89 (d, 1H, H$_{arom}$, J=8.0 Hz), 7.00 (s, 1H, H$_{pyrrazole}$), 7.11 (d, 2H, H$_{arom}$, J=8.0 Hz), 7.22 (t, 1H, H$_{arom}$, J=7.0 Hz), 7.11 (t, 2H, H$_{arom}$, J=8.0 Hz), 7.40 (t, 1H, H$_{arom}$, J=8.0 Hz), 7.48-7.51 (m, 1H, H$_{arom}$), 7.60 (d, 1H, H$_{arom}$, J=8.0 Hz), 7.79 (d, 1H, H$_{Py,6}$, J=6.0 Hz), 10.23 (s, 1H, NH$_{amide}$), 11.18 (s, 1H, NH$_{Py3}$), 11.38 (s, 1H, NH$_{Py2}$). HRMS (EI): m/z [M+H] calcd for C$_{27}$H$_{27}$N$_6$O$_3$: 483.2145; found: 483.2145.

Synthesis 80

N-(3-(2-oxo-2,3-dihydro-1H-imidazo[4,5-b]pyridin-7-yloxy)phenyl)benzo[b]thiophene-5-carboxamide (CJS 3728)

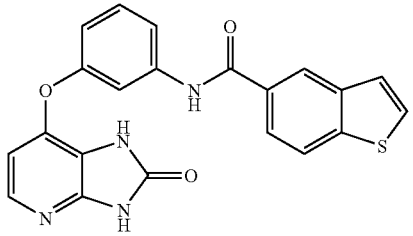

Method H was used with 7-(3-aminophenoxy)-1H-imidazo[4,5-b]pyridin-2(3H)-one and benzo[b]thiophene-5-carbonyl chloride to afford the title compound (25 mg, 30%). $^1$H-NMR (δ, ppm, DMSO-d$_6$): 6.50 (d, 1H, H$_{Py,5}$, J=6.0 Hz), 6.91 (d, 1H, H$_{arom}$, J=7.0 Hz), 7.43 (t, 1H, H$_{arom}$, J=8.0 Hz), 7.60 (d, 1H, H$_{arom}$, J=5.0 Hz), 7.67 (t, 1H, H$_{arom}$, J=2.5 Hz), 7.81 (d, 1H, H$_{Py,6}$, J=6.0 Hz), 7.89 (d, 1H, H$_{arom}$, J=6.0 Hz), 7.91 (d, 1H, H$_{arom}$, J=8.0 Hz), 8.15 (d, 1H, H$_{arom}$, J=8.5 Hz), 8.49 (d, 1H, H$_{arom}$, J=1.5 Hz), 10.44 (s, 1H, NH$_{amide}$), 11.20 (s, 1H, NH$_{Py3}$), 11.39 (s, 1H, NH$_{Py2}$). HRMS (EI): m/z [M+H] calcd for C$_{21}$H$_{15}$N$_4$O$_3$: 403.0865; found: 403.0867.

Synthesis 81

N-(3-(2-oxo-2,3-dihydro-1H-imidazo[4,5-b]pyridin-7-yloxy)phenyl)benzo[c][1,2,5]thiadiazole-5-carboxamide (CJS 3729)

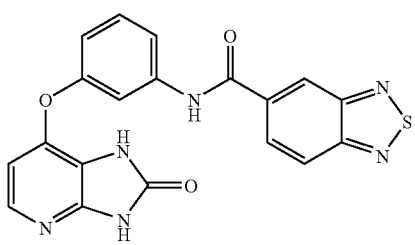

Method H was used with 7-(3-aminophenoxy)-1H-imidazo[4,5-b]pyridin-2(3H)-one and benzo[c][1,2,5]thiadiazole-5-carbonyl chloride to afford the title compound (28 mg, 33%). $^1$H-NMR (δ, ppm, DMSO-d$_6$): 6.51 (d, 1H, H$_{Py,5}$, J=6.0 Hz), 6.95 (d, 1H, H$_{arom}$, J=8.0 Hz), 7.46 (t, 1H, H$_{arom}$, J=8.0 Hz), 7.68 (t, 1H, H$_{arom}$, J=2.0 Hz), 7.71 (d, 1H, H$_{arom}$, J=8.0 Hz), 7.82 (d, 1H, H$_{Py,6}$, J=6.0 Hz), 7.91 (d, 1H, H$_{arom}$, J=8.0 Hz), 8.15-8.23 (m, 2H, H$_{arom}$), 8.73 (s, 1H, H$_{arom}$), 10.68 (s, 1H, NH$_{amide}$), 11.21 (s, 1H, NH$_{Py3}$), 11.39 (s, 1H, NH$_{Py2}$). HRMS (EI): m/z [M+H] calcd for C$_{19}$H$_{13}$N$_6$O$_3$S: 405.0770; found: 405.0772.

Synthesis 82

4-Chloro-N-(3-(2-oxo-2,3-dihydro-1H-imidazo[4,5-b]pyridin-7-yloxy)phenyl)benzamide (CJS 3730)

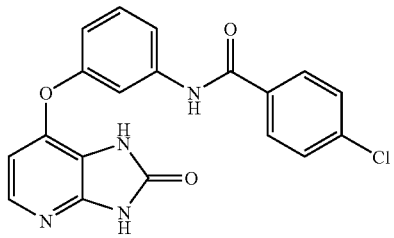

Method H was used with 7-(3-aminophenoxy)-1H-imidazo[4,5-b]pyridin-2(3H)-one and 4-chlorobenzoyl chloride to afford the title compound (11 mg, 15%). $^1$H-NMR (δ, ppm, DMSO-d$_6$): 6.49 (d, 1H, H$_{Py,5}$, J=6.0 Hz), 6.91 (d, 1H, H$_{arom}$, J=8.0 Hz), 7.42 (t, 1H, H$_{arom}$, J=8.0 Hz), 7.59-7.63 (m, 3H, H$_{arom}$), 7.65 (d, 1H, H$_{arom}$, J=8.0 Hz), 7.80 (d, 1H, H$_{Py,6}$, J=6.0 Hz), 7.96 (d, 2H, H$_{arom}$, J=9.0 Hz), 10.40 (s, 1H, NH$_{amide}$), 11.19 (s, 1H, NH$_{Py3}$), 11.38 (s, 1H, NH$_{Py2}$). HRMS (EI): m/z [M+H] calcd for C$_{19}$H$_{14}$N$_4$O$_3$Cl: 381.0754; found: 381.0753.

Synthesis 83

2-Chloro-N-(3-(2-oxo-2,3-dihydro-1H-imidazo[4,5-b]pyridin-7-yloxy)phenyl) isonicotinamide (CJS 3731)

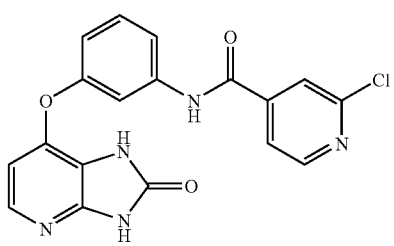

Method H was used with 7-(3-aminophenoxy)-1H-imidazo[4,5-b]pyridin-2(3H)-one and 2-chloroisonicotinoyl chloride to afford the title compound (39 mg, 49%). $^1$H-NMR (δ, ppm, DMSO-d$_6$): 6.50 (d, 1H, H$_{Py,5}$, J=6.0 Hz), 6.96 (d, 1H, H$_{arom}$, J=8.0 Hz), 7.45 (t, 1H, H$_{arom}$, J=8.0 Hz), 7.59 (t, 1H, H$_{arom}$, J=2.0 Hz), 7.64 (d, 1H, H$_{arom}$, J=8.0 Hz), 7.82 (d, 1H, H$_{Py,6}$, J=6.0 Hz), 7.85 (d, 1H, H$_{arom}$, J=5.0 Hz), 7.97 (s, 1H, H$_{arom}$), 7.61 (d, 1H, H$_{arom}$, J=5.0 Hz), 10.66 (s, 1H, NH$_{amide}$), 11.21 (s, 1H, NH$_{Py3}$), 11.42 (s, 1H, NH$_{Py2}$). HRMS (EI): m/z [M+H] calcd for C$_{18}$H$_{13}$N$_5$O$_3$Cl: 382.0707; found: 382.0702.

Synthesis 84

N-(3-(2-oxo-2,3-dihydro-1H-imidazo[4,5-b]pyridin-7-yloxy)phenyl)-2-phenylacetamide (CJS 3732)

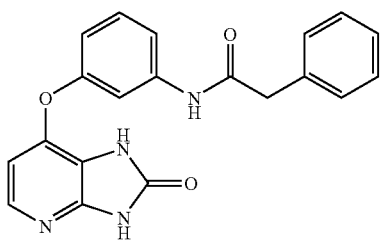

Method H was used with 7-(3-aminophenoxy)-1H-imidazo[4,5-b]pyridin-2(3H)-one and 2-phenylacetyl chloride to afford the title compound (11 mg, 15%). $^1$H-NMR (δ, ppm, DMSO-d$_6$): 3.62 (s, 2H, CH$_2$), 6.45 (d, 1H, H$_{Py,5}$, J=6.0 Hz), 6.83 (d, 1H, H$_{arom}$, J=8.0 Hz), 7.22-7.47 (m, 8H, H$_{arom}$), 7.78 (d, 1H, H$_{Py,6}$, J=6.0 Hz), 10.28 (s, 1H, NH$_{amide}$), 11.15 (s, 1H, NH$_{Py3}$), 11.37 (s, 1H, NH$_{Py2}$). HRMS (EI): m/z [M+H] calcd for C$_{20}$H$_{17}$N$_4$O$_3$: 361.1301; found: 361.1299.

Synthesis 85

N-(3-(2-oxo-2,3-dihydro-1H-imidazo[4,5-b]pyridin-7-yloxy)phenyl)-3-phenyl propanamide (CJS 3733)

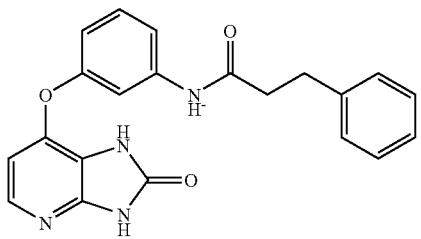

Method H was used with 7-(3-aminophenoxy)-1H-imidazo[4,5-b]pyridin-2(3H)-one and 3-phenylpropanoyl chloride to afford the title compound (15 mg, 19%). $^1$H-NMR (δ, ppm, DMSO-d$_6$): 2.61 (t, 2H, CH$_2$, J=8.0 Hz), 2.89 (t, 2H, CH$_2$, J=8.0 Hz), 6.45 (d, 1H, H$_{Py,5}$, J=6.0 Hz), 6.82 (d, 1H, H$_{arom}$, J=8.0 Hz), 7.16-7.44 (m, 8H, H$_{arom}$), 7.79 (d, 1H, H$_{Py,6}$, J=6.0 Hz), 10.02 (s, 1H, NH$_{amide}$), 11.16 (s, 1H, NH$_{Py3}$), 11.37 (s, 1H, NH$_{Py2}$). HRMS (EI): m/z[M+H] calcd for C$_{21}$H$_{19}$N$_4$O$_3$: 375.1457; found: 375.1469.

Synthesis 86

N-(3-(2-oxo-2,3-dihydro-1H-imidazo[4,5-b]pyridin-7-yloxy)phenyl)-2-(3-trifluoromethoxyphenyl)acetamide (CJS 3735)

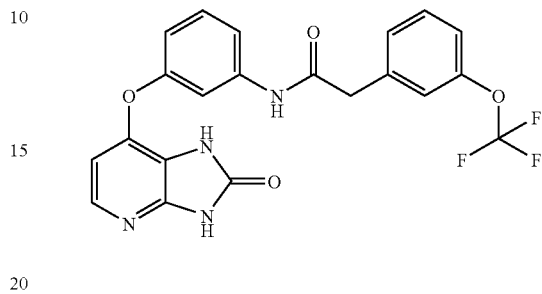

Method H was used with 7-(3-aminophenoxy)-1H-imidazo[4,5-b]-pyridin-2(3H)-one and 2-(3-trifluoromethoxyphenyl)-acetyl chloride to afford the title compound (22 mg, 23.5%). $^1$H-NMR (δ, ppm, DMSO-d$_6$): 3.71 (s, 2H, CH$_2$), 6.43 (d, 1H, H$_{Py,5}$, J=5.9 Hz), 6.83-6.86 (m, 1H, H$_{arom}$), 7.24-7.47 (m, 8H, H$_{arom}$), 7.78 (d, 1H, H$_{Py,6}$, J=5.9 Hz), 10.37 (s, 1H, NH$_{amide}$), 11.21 (s, 1H, NH$_{Py7}$), 11.42 (s, 1H, NH$_{Py9}$). LC-MS, t$_R$=4.65 minutes, m/z: 445.04 (M+H)+, calculated for C$_{21}$H$_{16}$N$_4$O$_4$F$_3$. HRMS (EI): m/z [M+H] calculated for C$_{21}$H$_{16}$N$_4$O$_4$F$_3$: 445.1124; found: 445.1107.

Synthesis 87

N-(3-(2-oxo-2,3-dihydro-1H-imidazo[4,5-b]pyridin-7-yloxy)phenyl)-2-(3-trifluoromethylphenyl)acetamide (CJS 3736)

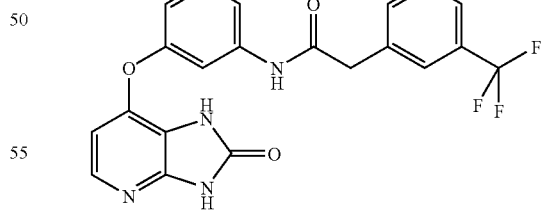

Method H was used with 7-(3-aminophenoxy)-1H-imidazo[4,5-b]-pyridin-2(3H)-one and 2-(3-trifluoromethylphenyl)-acetyl chloride to afford the title compound (30 mg, 33.3%). $^1$H-NMR (δ, ppm, DMSO-d$_6$): 3.77 (s, 2H, CH$_2$), 6.43 (d, 1H, H$_{Py,5}$, J=5.9 Hz), 6.83-6.86 (m, 1H, H$_{arom}$), 7.34-7.64 (m, 7H, H$_{arom}$), 7.67 (s, 1H, H$_{arom}$), 7.78 (d, 1H, H$_{Py,6}$, J=5.9 Hz), 10.39 (s, 1H, NH$_{amide}$), 11.21 (s, 1H, NH$_{Py7}$), 11.42 (s, 1H, NH$_{Py9}$). LC-MS, t$_R$=4.56 minutes, m/z:

429.05 (M+H)+, calculated for C21H16N4O3F3. HRMS (EI): m/z [M+H] calculated for C21H16N3O4F3: 429.1175; found: 429.1175.

Synthesis 88

N-(3-(2-oxo-2,3-dihydro-1H-imidazo[4,5-b]pyridin-7-yloxy)phenyl)-3-trifluoromethyl-5-chloro-benzamide (CJS 3743)

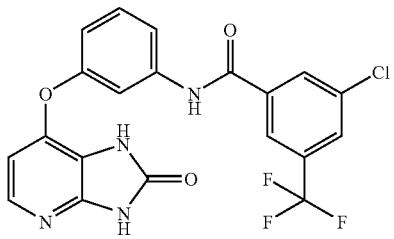

Method H was used with 7-(3-aminophenoxy)-1H-imidazo[4,5-b]-pyridin-2(3H)-one and 3-trifluoromethyl-5-chlorobenzoyl chloride to afford the title compound (28 mg, 29.8%). $^1$H-NMR (δ, ppm, DMSO-d$_6$): 6.50 (d, 1H, H$_{Py,5}$, J=5.9 Hz), 6.94-6.96 (m, 1H, H$_{arom}$), 7.45 (t, 1H, H$_{arom-5}$, J=8.2 Hz), 7.59 (s, 1H, H$_{arom-2}$), 7.63-7.65 (m, 1H, H$_{arom}$), 7.81 (d, 1H, H$_{Py,6}$, J=5.9 Hz), 8.12 (s, 1H, H$_{arom'}$), 8.22 (s, 1H, H$_{arom'}$), 8.30 (s, 1H, H$_{arom'}$), 10.60 (s, 1H, NH$_{amide}$), 11.20 (s, 1H, NH$_{Py7}$), 11.39 (s, 1H, NH$_{Py9}$). LC-MS, t$_R$=5.07 minutes, m/z: 448.06 (M+H)+, calculated for C20H13N4O3F3Cl. HRMS (EI): m/z [M+H] calculated for C20H13N4O3F3Cl: 449.0628; found: 449.0619.

Synthesis 89

N-(3-(2-oxo-2,3-dihydro-1H-imidazo[4,5-b]pyridin-7-yloxy)phenyl)-2-fluoro-3-trifluoromethyl-5-chloro-benzamide (CJS 3744)

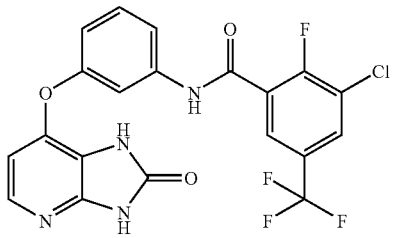

Method H was used with 7-(3-aminophenoxy)-1H-imidazo[4,5-b]-pyridin-2(3H)-one and 2-fluoro-3-chloro-5-trifluoromethyl-benzoyl chloride to afford the title compound (17 mg, 17.3%). $^1$H-NMR (δ, ppm, DMSO-d$_6$): 6.51 (d, 1H, H$_{Py,5}$, J=5.9 Hz), 6.94-6.96 (m, 1H, H$_{arom}$), 7.45 (t, 1H, H$_{arom-5}$, J=8.1 Hz), 7.59 (s, 1H, H$_{arom-2}$), 7.51-7.53 (m, 2H, H$_{arom}$), 7.81 (d, 1H, H$_{Py,6}$, J=5.9 Hz), 8.05-8.06 (m, 1H, H$_{arom2'\ or\ 4'}$), 8.28-8.30 (m, 1H, H$_{arom\ 4'\ or\ 2'}$), 10.79 (s, 1H, NH$_{amide}$), 11.19 (s, 1H, NH$_{Py7}$), 11.39 (s, 1H, NH$_{Py9}$). LC-MS, t$_R$=4.89 minutes, m/z: 467.05 (M+H)+, calculated for C20H12N4O3F4Cl. HRMS (EI): m/z [M+H] calculated for C20H12N4O3F4Cl: 467.0536; found: 467.0537.

Synthesis 90

N-(3-(2-oxo-2,3-dihydro-1H-imidazo[4,5-b]pyridin-7-yloxy)phenyl)-3-trifluoromethoxy-5-chloro-benzamide (CJS 3745)

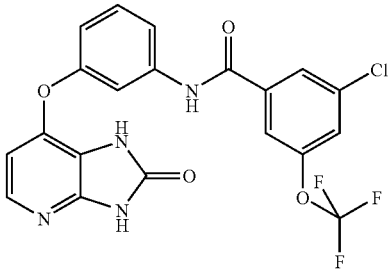

Method H was used with 7-(3-aminophenoxy)-1H-imidazo[4,5-b]-pyridin-2(3H)-one and 3-trifluoromethoxy-5-chlorobenzoyl chloride to afford the title compound (38 mg, 38.9%). $^1$H-NMR (δ, ppm, DMSO-d$_6$): 6.49 (d, 1H, H$_{Py,5}$, J=5.9 Hz), 6.93-6.96 (m, 1H, H$_{arom}$), 7.44 (t, 1H, H$_{arom-5}$, J=8.0 Hz), 7.58 (s, 1H, H$_{arom-2}$), 7.63-7.65 (m, 1H, H$_{arom}$), 7.81 (d, 1H, H$_{Py,6}$, J=5.9 Hz), 7.82 (m, 1H, H$_{arom'}$), 7.86 (m, 1H, H$_{arom'}$), 8.08 (t, 1H, H$_{arom'}$, J=1.6 Hz), 10.53 (s, 1H, NH$_{amide}$), 11.20 (s, 1H, NH$_{Py7}$), 11.40 (s, 1H, NH$_{Py9}$). LC-MS, t$_R$=5.13 minutes, m/z: 467.05 (M+H)+, calculated for C20H13N4O4F3Cl. HRMS (EI): m/z [M+H] calculated for C20H13N4O4F3Cl: 465.0585; found: 465.0583.

Synthesis 91

N-(3-(2-oxo-2,3-dihydro-1H-imidazo[4,5-b]pyridin-7-yloxy)phenyl)-1-naphtoyl-amide (CJS 3747)

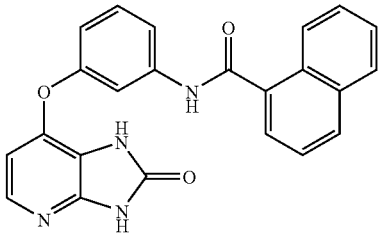

Method H was used with 7-(3-aminophenoxy)-1H-imidazo[4,5-b]-pyridin-2(3H)-one and 1-naphtoyl chloride to afford the title compound (37 mg, 44.4%). $^1$H-NMR (δ, ppm, DMSO-d$_6$): 6.41 (d, 1H, H$_{Py,5}$, J=5.9 Hz), 6.52 (d, 1H, H$_{arom}$), 6.90-6.92 (m, 1H, H$_{arom'}$), 7.05 (t, 1H, H$_{arom'}$, J=8.0 Hz), 7.43 (t, 1H, H$_{arom-5}$, J=8.4 Hz), 7.56-7.62 (m, 2H, H$_{arom}$), 7.67 (m, 1H, H$_{arom}$), 7.74-7.76 (m, 1H, H$_{arom}$), 7.81 (d, 1H, H$_{Py,6}$, J=5.9 Hz), 8.00-8.02 (m, 1H, H$_{arom'}$), 8.08 (d, 1H, H$_{arom'}$, J=8.3 Hz), 8.15-8.18 (m, 1H, H$_{arom'}$), 10.68 (s, 1H, NH$_{amide}$), 11.19 (s, 1H, NH$_{Py7}$), 11.39 (s, 1H, NH$_{Py9}$).

LC-MS, $t_R$=4.36 minutes, m/z: 397.13 (M+H)⁺, calculated for $C_{23}H_{17}N_4O_3$. HRMS (EI): m/z [M+H] calculated for $C_{23}H_{17}N_4O_3$: 397.1301; found: 397.1300.

Synthesis 92

N-(3-(2-oxo-2,3-dihydro-1H-imidazo[4,5-b]pyridin-7-yloxy)phenyl)-5-(2,3-dihydrobenzo[b]1,4-dioxinoyl) amide (CJS 3748)

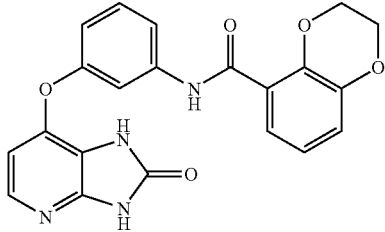

Method H was used with 7-(3-aminophenoxy)-1H-imidazo[4,5-b]pyridin-2(3H)-one and 2,3-dihydrobenzo-[b]-1,4-dioxine-5-carbonyl chloride to afford the title compound (21 mg, 24.7%). ¹H-NMR (δ, ppm, DMSO-$d_6$): 4.29 (t, 2H, CH₂, J=2.6 Hz), 4.35 (t, 2H, CH₂), 6.47 (d, 1H, $H_{Py,5}$, J=5.9 Hz), 6.88-6.89 (m, 1H, $H_{arom'}$), 6.90-6.92 (m, 1H, $H_{arom'}$), 6.99-7.01 (m, 1H, $H_{arom'}$), 7.10-7.12 (m, 1H, $H_{arom}$), 7.39 (t, 1H, $H_{arom-5}$, J=8.2 Hz), 7.61 (m, 1H, $H_{arom-2}$), 7.80 (d, 1H, $H_{Py,6}$, J=5.9 Hz), 10.21 (s, 1H, $NH_{amide}$), 11.18 (s, 1H, $NH_{Py7}$), 11.37 (s, 1H, $NH_{Py9}$). LC-MS, $t_R$=4.17 minutes, m/z: 405.12 (M+H)⁺, calculated for $C_{21}H_{17}N_4O_5$. HRMS (EI): m/z [M+H] calculated for $C_{21}H_{17}N_4O_5$: 405.1199; found: 404.1203.

Synthesis 93

N-(3-(2-oxo-2,3-dihydro-1H-imidazo[4,5-b]pyridin-7-yloxy)phenyl)-6-(3,4-dihydro-2H-benzo[b][1,4]-dioxepinoyl) amide (CJS 3749)

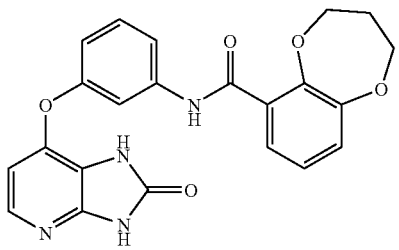

Method H was used with 7-(3-aminophenoxy)-1H-imidazo[4,5-b]pyridin-2(3H)-one and 3,4-dihydro-2H-benzo-[b][1,4]-dioxepine-6-carbonyl chloride to afford the title compound (26 mg, 29.5%). ¹H-NMR (δ, ppm, DMSO-$d_6$): 4.01 (m, 2H, CH₂), 4.29 (t, 2H, CH₂, J=5.3 Hz), 4.35 (t, 2H, CH₂), 6.48 (d, 1H, $H_{Py,5}$, J=5.9 Hz), 6.86-6.88 (m, 1H, $H_{arom}$), 7.04 (t, 1H, $H_{arom3''}$, J=6.5 Hz), 7.09-7.11 (m, 1H, $H_{arom}$), 7.16-7.18 (m, 1H, $H_{arom'}$), 7.39 (t, 1H, $H_{arom-5}$, J=8.2 Hz), 7.54-7.56 (m, 1H, $H_{arom}$), 7.61 (m, 1H, $H_{arom-2}$), 7.80 (d, 1H, $H_{Py,6}$, J=5.9 Hz), 10.31 (s, 1H, $NH_{amide}$), 11.18 (s, 1H, $NH_{Py7}$), 11.37 (s, 1H, $NH_{Py9}$). LC-MS, $t_R$=4.26 minutes, m/z: 419.13 (M+H)⁺, calculated for $C_{22}H_{19}N_4O_5$. HRMS (EI): m/z [M+H] calculated for $C_{22}H_{19}N_4O_5$: 419.1355; found: 419.1353.

Synthesis 94

N-(3-(2-oxo-2,3-dihydro-1H-imidazo[4,5-b]pyridin-7-yloxy)phenyl)-2-trifluoro-methoxy-benzamide (CJS 3751)

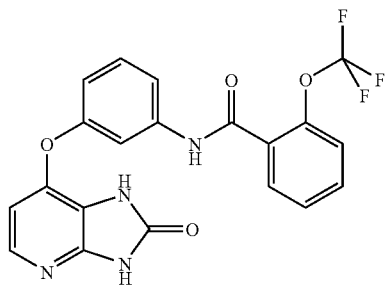

Method H was used with 7-(3-aminophenoxy)-1H-imidazo[4,5-b]pyridin-2(3H)-one and 2-trifluoromethoxy-benzoyl chloride to afford the title compound (24 mg, 22.2%). ¹H-NMR (δ, ppm, DMSO-$d_6$): 6.50 (d, 1H, $H_{Py,5}$, J=5.9 Hz), 6.88-6.90 (m, 1H, $H_{arom}$), 7.48-7.71 (m, 6H, $H_{arom}$), 7.80 (d, 1H, $H_{Py,6}$, J=5.9 Hz), 10.59 (s, 1H, $NH_{amide}$), 11.18 (s, 1H, $NH_{Py7}$), 11.38 (s, 1H, $NH_{Py9}$). LC-MS, $t_R$=4.24 minutes, m/z: 431.09 (M+H)⁺, calculated for $C_{20}H_{14}N_4O_4F_3$. HRMS (EI): m/z [M+H] calculated for $C_{20}H_{14}N_4O_4F_3$: 431.0967; found: 431.0966.

Synthesis 95

N-(3-(2-oxo-2,3-dihydro-1H-imidazo[4,5-b]pyridin-7-yloxy)phenyl)-3-N-pyrolyl-benzamide (CJS 3752)

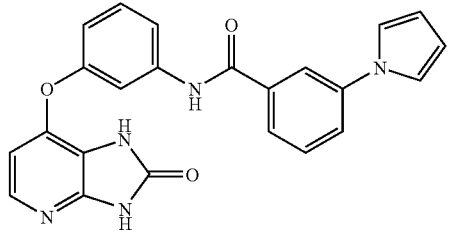

Method H was used with 7-(3-aminophenoxy)-1H-imidazo[4,5-b]pyridin-2(3H)-one and 3-N-pyrolyl-benzoyl chloride to afford the title compound (24 mg, 23.3%). ¹H-NMR (δ, ppm, DMSO-$d_6$): 6.50 (d, 1H, $H_{Py,5}$, J=5.9 Hz), 6.91-6.93 (m, 1H, $H_{arom}$), 7.42-7.46 (m, 3H, $H_{arom}$), 7.60-7.65 (m, 4H, $H_{arom}$), 7.67-8.05 (m, 3H, $H_{arom}$), 7.81 (d, 1H, $H_{Py,6}$, J=5.9 Hz), 8.06 (d, 1H, $H_{arom}$, J=1.7 Hz), 10.41 (s, 1H, $NH_{amide}$), 11.20 (s, 1H, $NH_{Py7}$), 11.39 (s, 1H, $NH_{Py9}$). LC-MS, $t_R$=4.33 minutes, m/z: 412.14 (M+H)⁺, calculated for $C_{23}H_{18}N_5O_3$. HRMS (EI): m/z [M+H] calculated for $C_{23}H_{18}N_5O_3$: 412.1410; found: 412.1404.

Synthesis 96

N-(3-(2-oxo-2,3-dihydro-1H-imidazo[4,5-b]pyridin-7-yloxy)phenyl)-3-N-pyrolidyl-benzamide (CJS 3753)

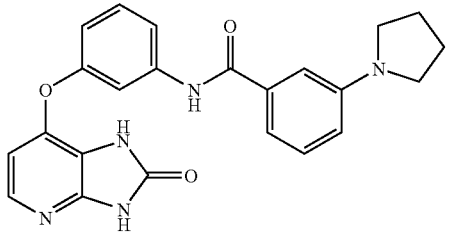

Method H was used with 7-(3-aminophenoxy)-1H-imidazo[4,5-b]pyridin-2(3H)-one and 3-N-pyrolidyl-benzoyl chloride to afford the title compound (22 mg, 25.1%). $^1$H-NMR (δ, ppm, DMSO-d$_6$): 1.96-1.99 (m, 4H, CH$_2$), 3.27-3.29 (m, 4H, CH$_2$), 6.48 (d, 1H, H$_{Py,5}$, J=5.9 Hz), 6.71-6.73 (m, 1H, H$_{arom}$), 6.87-6.89 (m, 1H, H$_{arom}$), 7.06 (m, 1H, H$_{arom}$), 7.12-7.14 (m, 1H, H$_{arom}$), 7.28 (t, 1H, H$_{arom}$, J=7.9 Hz), 7.40 (t, 1H, H$_{arom}$, J=8.5 Hz), 7.64 (m, 2H, H$_{arom}$), 7.80 (d, 1H, H$_{Py,6}$, J=5.9 Hz), 10.20 (s, 1H, NH$_{amide}$), 11.18 (s, 1H, NH$_{Py7}$), 11.37 (s, 1H, NH$_{Py9}$). LC-MS, t$_R$=4.72 minutes, m/z: 416.17 (M+H)$^+$, calculated for $C_{23}H_{22}N_5O_3$. HRMS (EI): m/z [M+H] calculated for $C_{23}H_{22}N_5O_3$: 416.1723; found: 416.1720.

Synthesis 97

N-(3-(2-oxo-2,3-dihydro-1H-imidazo[4,5-b]pyridin-7-yloxy)phenyl)-3-N-piperidinyl-benzamide (CJS 3754)

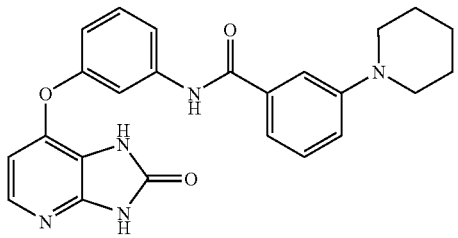

Method H was used with 7-(3-aminophenoxy)-1H-imidazo[4,5-b]pyridin-2(3H)-one and 3-N-piperidinyl-benzoyl chloride to afford the title compound (23 mg, 25.5%). $^1$H-NMR (δ, ppm, DMSO-d$_6$): 1.61-1.63 (m, 4H, CH$_2$), 3.07-3.09 (m, 2H, CH$_2$), 3.19-3.22 (m, 4H, CH$_2$), 6.48 (d, 1H, H$_{Py,5}$, J=5.9 Hz), 6.87-6.90 (m, 1H, H$_{arom}$), 7.12-7.14 (m, 1H, H$_{arom}$), 7.28-7.33 (m, 2H, H$_{arom}$), 7.39-7.44 (m, 2H, H$_{arom}$), 7.64-7.66 (m, 2H, H$_{arom}$), 7.80 (d, 1H, H$_{Py,6}$, J=5.9 Hz), 10.23 (s, 1H, NH$_{amide}$), 11.19 (s, 1H, NH$_{Py7}$), 11.38 (s, 1H, NH$_{Py9}$). LC-MS, t$_R$=3.84 minutes, m/z: 430.18 (M+H)$^+$, calculated for $C_{24}H_{24}N_5O_3$. HRMS (EI): m/z [M+H] calculated for $C_{24}H_{24}N_5O_3$: 430.1884; found: 430.1887.

Synthesis 98

N-(3-(2-oxo-2,3-dihydro-1H-imidazo[4,5-b]pyridin-7-yloxy)phenyl)-3-trifluoromethylthio-benzamide (CJS 3756)

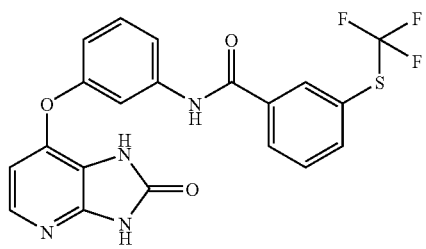

Method H was used with 7-(3-aminophenoxy)-1H-imidazo[4,5-b]pyridin-2(3H)-one and 3-trifluoromethylthio-benzoyl chloride to afford the title compound (16 mg, 17.0%). $^1$H-NMR (δ, ppm, DMSO-d$_6$): 6.49 (d, 1H, H$_{Py,5}$, J=5.9 Hz), 6.93 (ddd, 1H, H$_{arom}$, J=0.6 Hz, J=2.4 Hz, J=8.2 Hz), 7.44 (t, 1H, H$_{arom}$, J=8.2 Hz), 7.62 (t, 1H, H$_{arom}$, J=2.1 Hz), 7.66 (dd, 1H, H$_{arom}$, J=1.1 Hz, J=8.2 Hz), 7.71 (t, 1H, H$_{arom}$, J=7.8 Hz), 7.81 (d, 1H, H$_{Py,5}$, J=5.9 Hz), 7.94 (d, 1H, H$_{arom}$, J=7.8 Hz), 8.16 (m, 1H, H$_{arom}$), 8.26 (s, 1H, H$_{arom}$), 10.50 (s, 1H, NH$_{amide}$), 11.19 (s, 1H, NH$_{Py7}$), 11.39 (s, 1H, NH$_{Py9}$). LC-MS, t$_R$=4.87 minutes, m/z: 447.07 (M+H)$^+$, calculated for $C_{20}H_{14}N_4O_3SF_3$. HRMS (EI): m/z [M+H] calculated for $C_{20}H_{14}N_4O_3SF_3$: 447.0739; found: 447.0743.

Synthesis 99

N-(3-(2-oxo-2,3-dihydro-1H-imidazo[4,5-b]pyridin-7-yloxy)phenyl)-5-(1-N-phenyl-3-tert-butyl)-pyrazolyl-amide (CJS 3757)

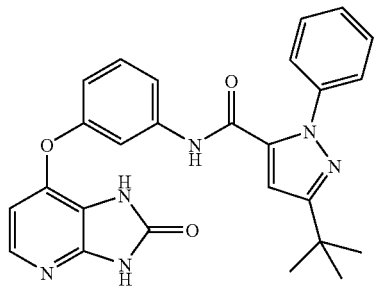

Method H was used with 7-(3-aminophenoxy)-1H-imidazo[4,5-b]pyridin-2(3H)-one and 5-(1-N-phenyl-3-tertbutyl)-pyrazolyl carbonyl chloride to afford the title compound (19 mg, 19.3%). $^1$H-NMR (δ, ppm, DMSO-d$_6$): 1.16 (s, 9H, 3×CH$_3$), 6.47 (d, 1H, H$_{Py,5}$, J=5.9 Hz), 6.75 (s, 1H, H$_{pyrazol}$), 6.84 (dd, 1H, H$_{arom}$, J=2.0 Hz, J=8.2 Hz), 7.36 (t, 1H, H$_{arom}$, J=8.2 Hz), 7.50-7.57 (m, 5H, H$_{arom}$), 7.67 (m, 1H, H$_{arom}$), 7.70-7.72 (m, 1H, H$_{arom}$), 7.78 (d, 1H, H$_{Py,6}$, J=5.9 Hz), 10.18 (s, 1H, NH$_{amide}$), 11.16 (s, 1H, NH$_{Py7}$), 11.37 (s, 1H, NH$_{Py9}$).

LC-MS, $t_R$=7.80 minutes, m/z: 469.19 (M+H)$^+$, calculated for $C_{26}H_{25}N_6O_3$.

Synthesis 100

N-(3-(2-oxo-2,3-dihydro-1H-imidazo[4,5-b]pyridin-7-yloxy)phenyl)-5-(1-N-phenyl-3-isopropyl)-pyrazolyl-amide (CJS 3758)

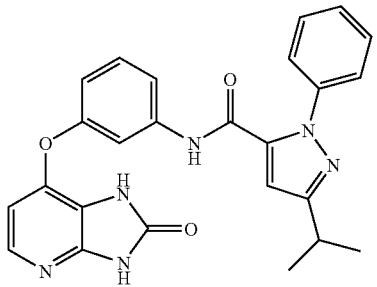

Method H was used with 7-(3-aminophenoxy)-1H-imidazo[4,5-b]pyridin-2(3H)-one and 5-(1-N-phenyl-3-isopropyl)-pyrazolyl carbonyl chloride to afford the title compound (11 mg, 11.5%). $^1$H-NMR (δ, ppm, DMSO-d$_6$): 1.14 (s, 3H, CH$_3$), 1.15 (s, 3H, CH$_3$), 2.99 (t, 1H, CH), 6.48 (d, 1H, H$_{Py,5}$, J=5.9 Hz), 6.81 (s, 1H, H$_{pyrrazole}$), 6.84-6.87 (m, 1H, H$_{arom}$), 7.38 (t, 1H, H$_{arom}$, J=8.2 Hz), 7.54-7.60 (m, 5H, H$_{arom}$), 7.68 (s, 1H, H$_{arom}$), 7.70-7.72 (m, 1H, H$_{arom}$), 7.81 (d, 1H, H$_{Py,6}$, J=5.9 Hz), 10.18 (s, 1H, NH$_{amide}$), 11.17 (s, 1H, NH$_{Py7}$), 11.37 (s, 1H, NH$_{Py9}$). LC-MS, $t_R$=4.91 minutes, m/z: 455.18 (M+H)$^+$, calculated for $C_{25}H_{23}N_6O_3$. HRMS (EI): m/z [M+H] calculated for $C_{25}H_{23}N_6O_3$: 455.1832; found: 455.1832.

Synthesis 101

N-(3-(2-oxo-2,3-dihydro-1H-imidazo[4,5-b]pyridin-7-yloxy)phenyl)-2-fluoro-3-trifluoromethoxy-benzamide (CJS 3759)

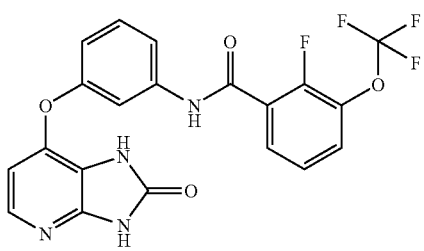

Method H was used with 7-(3-aminophenoxy)-1H-imidazo[4,5-b]pyridin-2(3H)-one and 2-fluoro-3-trifluoromethoxy-benzoyl chloride to afford the title compound (11 mg, 11.7%). $^1$H-NMR (δ, ppm, DMSO-d$_6$): 6.50 (d, 1H, H$_{Py,5}$, J=5.9 Hz), 6.91-6.94 (m, 1H, H$_{arom}$), 7.43-7.46 (m, 3H, H$_{arom}$), 7.53-7.55 (m, 2H, H$_{arom}$), 7.70-7.74 (m, 1H, H$_{arom}$), 7.81 (d, 1H, H$_{Py,6}$, J=5.9 Hz), 10.70 (s, 1H, NH$_{amide}$), 11.18 (s, 1H, NH$_{Py7}$), 11.39 (s, 1H, NH$_{Py9}$). LC-MS, $t_R$=4.62 minutes, m/z: 449.08 (M+H)$^+$, calculated for $C_{20}H_{13}N_4O_4F_4$. HRMS (EI): m/z [M+H] calculated for $C_{20}H_{13}N_4O_4F_4$: 449.0873; found: 449.0879.

Synthesis 102

N-(3-(2-oxo-2,3-dihydro-1H-imidazo[4,5-b]pyridin-7-yloxy)phenyl)-2-fluoro-5-trifluoromethoxy-benzamide (CJS 3760)

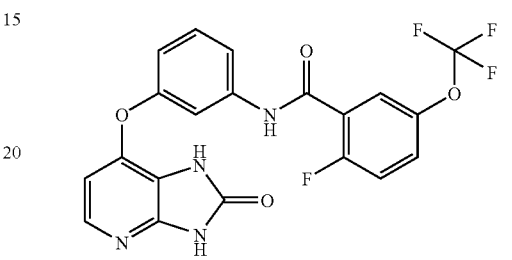

Method H was used with 7-(3-aminophenoxy)-1H-imidazo[4,5-b]pyridin-2(3H)-one and 2-fluoro-5-trifluoromethoxy-benzoyl chloride to afford the title compound (11 mg, 11.7%). $^1$H-NMR (δ, ppm, DMSO-d$_6$): 6.50 (d, 1H, H$_{Py,5}$, J=5.9 Hz), 6.91-6.94 (m, 1H, H$_{arom}$), 7.41-7.44 (m, 2H, H$_{arom}$), 7.50-7.53 (m, 2H, H$_{arom}$), 7.67-7.69 (m, 1H, H$_{arom}$), 7.81 (d, 1H, H$_{Py,6}$, J=5.9 Hz), 10.65 (s, 1H, NH$_{amide}$), 11.18 (s, 1H, NH$_{Py7}$), 11.39 (s, 1H, NH$_{Py9}$). LC-MS, $t_R$=4.65 minutes, m/z: 449.08 (M+H)$^+$, calculated for $C_{20}H_{13}N_4O_4F_4$. HRMS (EI): m/z [M+H] calculated for $C_{20}H_{13}N_4O_4F_4$: 449.0873; found: 449.0873.

Synthesis 103

N-(3-(1-methyl-2-oxo-2,3-dihydro-1H-imidazo[4,5-b]pyridin-7-yloxy)phenyl)-3-trifluoromethylthio-benzamide (CJS 3767)

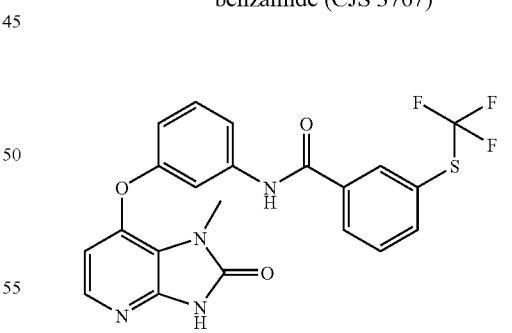

Method H was used with 7-(3-aminophenoxy)-1H-imidazo[4,5-b]pyridin-1-methyl-2(3H)-one and 3-trifluoromethylthio-benzoyl chloride to afford the title compound (21 mg, 25.4%). $^1$H-NMR (δ, ppm, DMSO-d$_6$): 3.42 (s, 1H, CH$_3$N), 6.57 (d, 1H, H$_{Py,5}$, J=5.9 Hz), 6.49 (ddd, 1H, H$_{arom}$, J=0.9 Hz, J=2.4 Hz, J=8.7 Hz), 7.45 (t, 1H, H$_{arom}$, J=8.4 Hz), 7.63-7.65 (m, 2H, H$_{arom}$), 7.71 (t, 1H, H$_{arom}$, J=7.8 Hz), 7.86 (d, 1H, H$_{Py,6}$, J=5.9 Hz), 7.94 (d, 1H, H$_{arom}$, J=7.9 Hz), 8.16 (d, 1H, H$_{arom}$, J=8.3 Hz), 8.26 (s, 1H, H$_{arom}$), 10.51 (s, 1H, NH$_{amide}$), 11.66 (s, 1H, NH$_{Py9}$). LC-MS, t$_R$=5.16 minutes, m/z: 460.08 (M+H)$^+$, calculated for C$_{21}$H$_{16}$N$_4$O$_3$S.

Synthesis 104

N-(3-(1-methyl-2-oxo-2,3-dihydro-1H-imidazo[4,5-b]pyridin-7-yloxy)phenyl)-3-trifluoromethoxy-benzamide (CJS 3768)

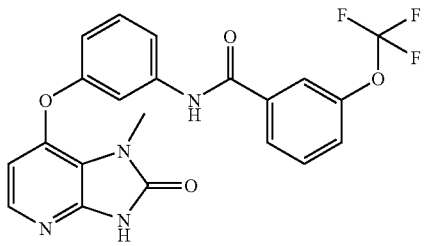

Method H was used with 7-(3-aminophenoxy)-1H-imidazo[4,5-b]-pyridin-1-methyl-2(3H)-one and 3-trifluoromethoxy-benzoyl chloride to afford the title compound (32 mg, 40.0%). $^1$H-NMR (δ, ppm, DMSO-d$_6$): 3.41 (s, 1H, CH$_3$N), 6.57 (d, 1H, H$_{Py,5}$, J=5.9 Hz), 6.49 (ddd, 1H, H$_{arom}$, J=0.8 Hz, J=2.3 Hz, J=8.2 Hz), 7.44 (t, 1H, H$_{arom}$, J=8.4 Hz), 7.58-7.61 (m, 2H, H$_{arom}$), 7.68 (t, 1H, H$_{arom}$, J=8.0 Hz), 7.85 (d, 1H, H$_{Py,6}$, J=5.9 Hz), 7.88 (s, 1H, H$_{arom}$), 7.99 (d, 1H, H$_{arom}$, J=7.8 Hz), 10.47 (s, 1H, NH$_{amide}$), 11.66 (s, 1H, NH$_{Py9}$). LC-MS, t$_R$=5.16 minutes, m/z: 445.11 (M+H)$^+$, calculated for C$_{21}$H$_{16}$N$_4$O$_4$F$_3$. HRMS (EI): m/z [M+H] calculated for C$_{21}$H$_{16}$N$_4$O$_4$F$_3$: 445.1124; found: 445.1135.

Synthesis 105

3-tert-butyl-N-(3-(2-oxo-2,3-dihydro-1H-imidazo[4,5-b]pyridin-7-yloxy)phenyl)benzamide (CJS 3902)

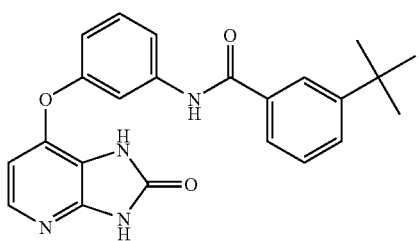

Method H was used Method H was used with 7-(3-Aminophenoxy)-1H-imidazo[4,5-b]pyridin-2(3H)-one and 3-tert-butylbenzoyl chloride to afford the title compound as a light pink solid (90 mg, 54%). $^1$H-NMR (δ, ppm, DMSO-d$_6$): 1.32 (s, 9H, $^t$Bu), 6.49 (d, 1H, H$_{Py,5}$, J=5.9 Hz), 6.91 (d, 1H, H$_{arom}$, J=6.7 Hz), 7.41-7.46 (m, 2H, H$_{arom}$), 7.62-7.66 (m, 3H, H$_{arom}$), 7.75 (d, 1H, H$_{arom}$, J=7.6 Hz), 7.81 (d, 1H, H$_{Py,6}$, J=5.9 Hz), 7.89 (s, 1H, H$_{arom}$,), 10.35 (s, 1H, NH$_{amide}$), 11.26 (s, 1H, NH$_{urea}$), 11.44 (s, 1H, NH$_{urea}$). $^{13}$C-NMR (δ, ppm, DMSO-d$_6$): 30.98 (C(CH$_3$)$_3$), 34.55 (C(CH$_3$)$_3$), 106.41, 110.83, 113.60, 114.40, 116.31, 124.30, 124.78, 128.09, 128.67, 130.11, 134.42, 140.84, 141.31, 144.67, 147.06, 150.90, 154.17, 154.58, 166.06. HRMS (EI): m/z [M+H] calculated for C$_{23}$H$_{22}$N$_4$O$_3$: 403.1765; found: 403.1762.

Synthesis 106

3-(1H-imidazol-1-yl)-N-(3-(2-oxo-2,3-dihydro-1H-imidazo[4,5-b]pyridin-7-yloxy)phenyl)benzamide (CJS 3900)

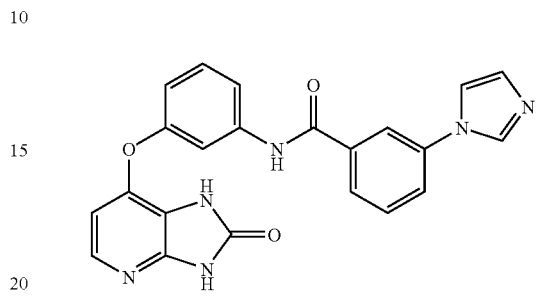

Method H2: 7-(3-Aminophenoxy)-1H-imidazo[4,5-b]pyridin-2(3H)-one (100 mg, 0.413 mmol) and diisopropylethylamine (71 µL, 0.413 mmol) were mixed in dry DMF (3.3 mL). Then, this solution was added to the mixture of 3-(1H-imidazol-1-yl)benzoic acid (71 mg, 0.375 mmol), 1-hydroxybenzotriazole (64 mg, 0.413 mmol) and diisopropylcarbodiimide (65 µL, 0.413 mmol) in dry DMF (7.5 mL) under stirring. This mixture was stirred for 60 hours and the solvent was removed in vacuo. The obtained residue was chromatographied (eluent: EtOAc/EtOH 1/0 toward 95/5) and the title compound was obtained as a white solid (21 mg, 14%). $^1$H-NMR (δ, ppm, DMSO-d$_6$): 6.50 (d, 1H, H$_{Py,5}$, J=5.9 Hz), 6.93 (ddd, 1H, H$_{arom}$, J=8.1 Hz, J=2.4 Hz, J=0.7 Hz), 7.15 (s, 1H, H$_{arom}$), 7.45 (t, 1H, H$_{arom}$, J=8.2 Hz), 7.63-7.67 (m, 3H, H$_{arom}$), 7.81-7.84 (m, 2H, H$_{arom}$), 7.87-7.90 (m, 2H, H$_{arom}$), 8.15 (s, 1H, H$_{arom}$), 8.34 (s, 1H, H$_{arom}$,), 10.43 (s, 1H, NH$_{amide}$), 11.20 (s, 1H, NH$_{urea}$), 11.39 (s, 1H, NH$_{urea}$). HRMS (EI): m/z [M+H] calculated for C$_{22}$H$_{16}$N$_6$O$_3$: 413.1357, found: 413.1357.

Synthesis 107

N-(3-(2-oxo-2,3-dihydro-1H-imidazo[4,5-b]pyridin-7-yloxy)phenyl)-2-thiomorpholinoisonicotinamide (CJS 3901)

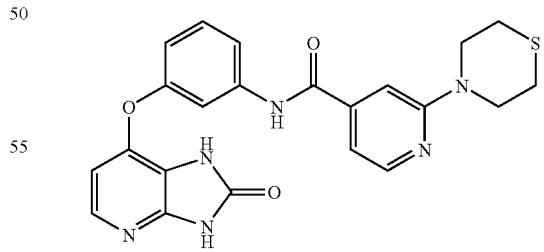

Method Method H2 was used with 7-(3-aminophenoxy)-1H-imidazo[4,5-b]pyridin-2(3H)-one and 2-thiomorpholinoisonicotinic acid to afford the title compound as a light pink solid (93 mg, 50%). $^1$H-NMR (δ, ppm, DMSO-d$_6$): 2.62 (d, 4H, H$_{Thiomorph}$, J=7.2 Hz), 3.96 (d, 4H, H$_{Thiomorph}$, J=7.2 Hz), 6.49 (d, 1H, H$_{Py,5}$, J=5.9 Hz), 6.93 (dd, 1H, H$_{arom}$, J=7.9 Hz, J=1.8 Hz), 7.01 (d, 1H, H$_{arom}$, J=5.1 Hz), 7.19 (s, 1H, H$_{arom}$), 7.43 (t, 1H, H$_{arom}$, J=8.2 Hz), 7.60-7.64 (m, 2H, H$_{arom}$), 7.81 (d, 1H, H$_{Py,6}$, J=5.9 Hz), 8.25 (d, 1H, H$_{arom}$, J=5.1 Hz), 10.39 (s, 1H, NH$_{amide}$), 11.19 (s, 1H, NH$_{urea}$), 11.39 (s, 1H, NH$_{urea}$). $^{13}$C-NMR (δ, ppm, DMSO-d$_6$): 25.18 (C$_{Thiomorph}$), 47.14 (C$_{Thiomorph}$), 105.01, 106.50, 110.05, 110.75, 113.67, 114.63, 116.26, 130.08, 140.24, 141.28, 143.63, 144.42, 147.04, 148.30, 154.08, 154.64, 158.13, 164.81. HRMS (EI): m/z [M+H] calculated for C$_{22}$H$_{20}$N$_6$O$_3$S: 449.1390, found: 449.1396.

Synthesis 108

N-(3-(2-oxo-2,3-dihydro-1H-imidazo[4,5-b]pyridin-7-yloxy)phenyl)-3-tert-pentylbenzamide (CJS 3903)

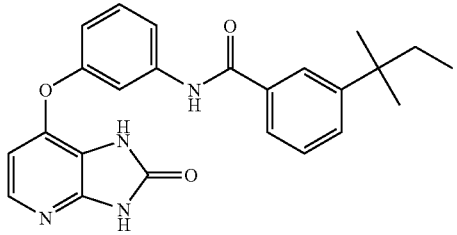

Method H2 was used with 7-(3-aminophenoxy)-1H-imidazo[4,5-b]pyridin-2(3H)-one and 3-tert-pentylbenzoic acid to afford the title compound as a light pink solid (54 mg, 31%). $^1$H-NMR (δ, ppm, DMSO-d$_6$): 0.63 (t, 3H, CH$_{3Et}$, J=7.4 Hz), 1.29 (s, 6H, CH$_{3Me}$), 1.66 (q, 2H, CH$_{2Et}$, J=7.4 Hz), 6.49 (d, 1H, H$_{Py,5}$, J=5.9 Hz), 6.90 (dd, 1H, H$_{arom}$, J=7.4 Hz, J=1.7 Hz), 7.41-7.47 (m, 2H, H$_{arom}$), 7.56 (d, 1H, H$_{arom}$, J=7.8 Hz), 7.65-7.66 (m, 2H, H$_{arom}$), 7.75 (d, 1H, H$_{arom}$, J=7.7 Hz) 7.81 (d, 1H, H$_{Py,6}$, J=5.9 Hz), 7.84 (s, 1H, H$_{arom}$), 10.30 (s, 1H, NH$_{amide}$), 11.21 (s, 1H, NH$_{urea}$), 11.39 (s, 1H, NH$_{urea}$). $^{13}$C-NMR (δ, ppm, DMSO-d$_6$): 8.89 (CH$_{3Et}$), 28.03 (CH$_3$), 35.90 (C(CH$_3$)$_3$Et,) 37.66 (CH$_{2Et}$), 106.38, 110.81, 113.58, 114.28, 116.27, 124.61, 124.89, 127.91, 129.16, 129.98, 134.30, 140.76, 141.22, 144.57, 147.02, 149.24, 154.09, 154.56, 165.97. HRMS (EI): m/z [M+H] calculated for C$_{24}$H$_{24}$N$_4$O$_3$: 417.1921, found: 417.1923.

Synthesis 109

N-(3-(2-oxo-2,3-dihydro-1H-imidazo[4,5-b]pyridin-7-yloxy)phenyl)-3-(1,1,2,2-tetrafluoroethoxy)benzamide (CJS 3904)

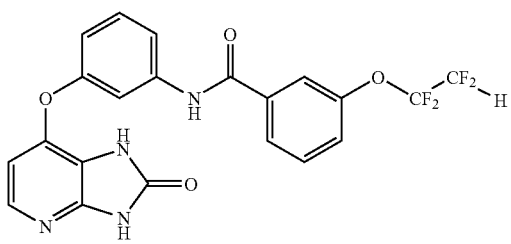

Method H2 was used with 7-(3-aminophenoxy)-1H-imidazo[4,5-b]pyridin-2(3H)-one and 3-(1,1,2,2-tetrafluoroethoxy)benzoic acid to afford the title compound as a light pink solid (69 mg, 36%). $^1$H-NMR (δ, ppm, DMSO-d$_6$): 6.49 (d, 1H, H$_{Py,5}$, J=5.8 Hz), 6.86 (t, 1H, CF$_2$H, J=51.7 Hz), 6.94 (d, 1H, H$_{arom}$, J=7.2 Hz), 7.44 (t, 1H, H$_{arom}$, J=8.2 Hz), 7.54 (d, 1H, H$_{arom}$, J=7.6 Hz), 7.62-7.67 (m, 3H, H$_{arom}$), 7.80-7.82 (m, 2H, H$_{arom}$), 7.95 (d, 1H, H$_{arom}$, J=7.8 Hz) 10.49 (s, 1H, NH$_{amide}$), 11.25 (s, 1H, NH$_{urea}$), 11.44 (s, 1H, NH$_{urea}$). $^{13}$C-NMR (δ, ppm, DMSO-d$_6$): 105.81 (CF$_2$), 106.61, 107.79 (CF$_2$) 110.90, 113.78, 114.68, 116.38, 120.76, 124.77, 126.26, 130.2, 130.40, 136.62, 140.51, 141.35, 144.60, 147.17, 148.04, 154.22, 154.75, 164.17. HRMS (EI): m/z [M+H] calcd for C$_{21}$H$_{14}$F$_4$N$_4$O$_4$: 463.1024, found: 463.1022.

(XIV) Synthesis of Amides

2. Amides from 2-Amino-3-nitropyridine Intermediates (According to Scheme 5)

Synthesis 110

N-(3-(2-amino-3-nitropyridin-4-yloxy)-4-methoxyphenyl)-3-(trifluoromethoxy)benzamide

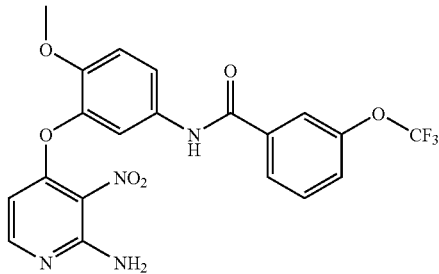

Method H was used with 4-(5-amino-2-methoxyphenoxy)-3-nitropyridin-2-amine (438 mg, 1.6 mmol), to afford the title compound as a yellow oil (348 mg, 47%). $^1$H-NMR (δ, ppm, DMSO-d$_6$): 3.76 (s, 3H, CH$_3$), 5.89 (d, 1H, H$_{Py,5}$, J=5.7 Hz), 7.12 (bs, 2H, NH$_2$), 7.24 (d, 1H, H$_{arom}$, J=9.6 Hz), 7.59 (d, 1H, H$_{arom}$, J=8.2 Hz), 7.66-7.69 (m, 3H, H$_{arom}$), 7.89 (s, 1H, H$_{arom}$), 7.96 (d, 1H, H$_{Py,6}$, J=5.7 Hz), 7.99 (d, 1H, H$_{arom}$, J=7.8 Hz), 10.39 (bs, 1H, NH$_{amide}$). $^{13}$C-NMR (δ, ppm, DMSO-d$_6$): 56.0, 99.5, 113.7, 114.7, 119.1, 120.0, 121.0, 121.2, 123.9, 126.6, 130.6, 132.5, 136.7, 140.4, 147.2, 148.2, 152.9, 153.6, 158.7, 163.5. LC-MS (m/z): 465 (M+H, 100).

Synthesis 111

N-(5-(2-amino-3-nitropyridin-4-yloxy)-2,4-dichlorophenyl)-3-(trifluoromethoxy)benzamide

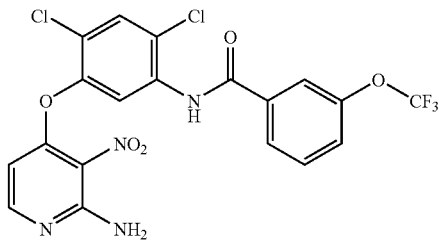

Method H was used with 4-(5-amino-2,4-dichlorophenoxy)-3-nitropyridin-2-amine (1 g, 3.2 mmol), to afford the title compound as a yellow solid (636 mg, 40%). $^1$H-NMR ($\delta$, ppm, DMSO-d$_6$): 6.02 (d, 1H, H$_{Py,5}$, J=5.1 Hz), 6.90 (d, 1H, H$_{arom}$, J=5.5 Hz), 7.70 (m, 2H, H$_{arom}$), 8.01 (m, 3H, H$_{arom}$), 8.56 (d, 1H, H$_{arom}$, J=5.5 Hz), 10.40 (s, 1H, NH$_2$), 10.46 (bs, 1H, NH$_2$), 11.70 (bs, 1H, H$_{amide}$). $^{13}$C-NMR ($\delta$, ppm, DMSO-d$_6$): 99.9, 109.0, 118.9, 120.2, 120.5, 121.4, 123.3, 124.5, 125.2, 126.8, 130.6, 130.8, 135.5, 145.1, 146.8, 147.4, 152.0, 153.9, 157.4, 163.9. LC-MS (m/z): 503 (M, 100).

Synthesis 112

N-(3-(2-amino-3-nitropyridin-4-yloxy)-4-methylphenyl)-3-(trifluoromethoxy)benzamide

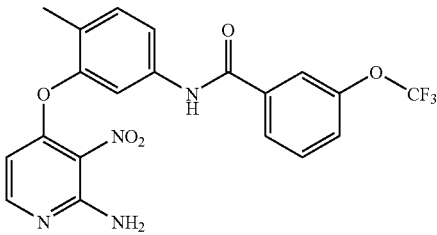

Method H was used with 4-(5-Amino-2-methylphenoxy)-2-amino-3-nitropyridine (990 mg, 3.8 mmol), to afford the title compound as a yellow solid (995 mg, 58%). $^1$H-NMR ($\delta$, ppm, DMSO-d$_6$): 2.22 (s, 3H, CH$_3$), 6.18 (d, 1H, H$_{Py,5}$, J=6.5 Hz), 7.24 (d, 1H, H$_{arom}$, J=7.2 Hz), 7.35 (s, 1H, H$_{arom}$), 7.51 (d, 1H, H$_{arom}$, J=7.6 Hz), 7.80 (m, 3H, H$_{arom}$), 8.02 (s, 1H, H$_{arom}$), 8.20 (d, 1H, H$_{arom}$, J=4.6 Hz), 8.86 (bs, 2H, NH$_2$), 11.05 (s, 1H, NH$_{amide}$). $^{13}$C-NMR ($\delta$, ppm, DMSO-d$_6$): 15.3, 99.9, 115.7, 118.8, 120.3, 120.8, 121.7, 124.3, 126.7, 128.8, 129.7, 130.6, 131.4, 131.8, 135.2, 148.3, 149.1, 151.4, 152.1, 162.6. LC-MS (m/z): 448 (M, 100).

Synthesis 113

N-(3-(2-amino-3-nitropyridin-4-yloxy)-2-methylphenyl)-3-(trifluoromethoxy)benzamide

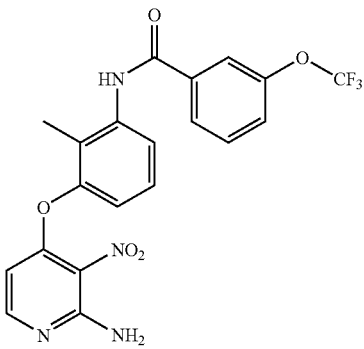

Method H was used with 4-(3-Amino-2-methylphenoxy)-2-amino-3-nitropyridine (500 mg, 1.9 mmol), to afford the title compound as a yellow solid (452 mg, 53%). $^1$H-NMR ($\delta$, ppm, DMSO-d$_6$): 2.04 (s, 3H, CH$_3$), 5.82 (d, 1H, H$_{Py,5}$, J=5.6 Hz), 7.11 (dd, 1H, H$_{arom}$, J=2.4 Hz, J=6.8 Hz), 7.19 (s, 2H, NH$_2$), 7.36 (m, 2H, H$_{arom}$), 7.61 (m, 1H, H$_{arom}$), 7.69 (t, 1H, H$_{arom}$, J=7.9 Hz), 7.93 (s, 1H, H$_{arom}$), 8.01 (d, 1H, H$_{Py,6}$, J=5.6 Hz), 8.04 (d, 1H, H$_{arom}$, J=7.7 Hz), 10.26 (s, 1H, NH$_{amide}$). $^{13}$C-NMR ($\delta$, ppm, DMSO-d$_6$): 10.8, 118.8, 118.9, 120.0, 121.1, 124.0, 124.5, 126.5, 126.6, 126.8, 130.5, 136.2, 138.0, 148.2, 151.2, 153.1, 153.7, 158.4, 163.7. LC-MS (m/z): 449 (M+H, 100).

Synthesis 114

N-(3-(2-amino-3-nitropyridin-4-yloxy)-5-methoxyphenyl)-3-(trifluoromethoxy)benzamide

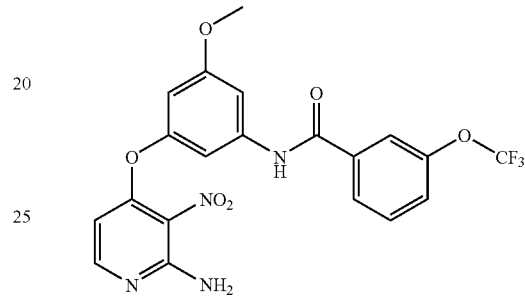

Method H was used with 4-(3-Amino-5-methoxyphenoxy)-2-amino-3-nitropyridine (319 mg, 1.1 mmol), to afford the title compound as a yellow solid (327 mg, 53%). $^1$H-NMR ($\delta$, ppm, DMSO-d$_6$): 3.78 (s, 3H, CH$_3$), 6.14 (d, 1H, H$_{Py,5}$, J=5.6 Hz), 6.60 (t, 1H, H$_{arom}$, J=2.2 Hz), 7.18 (bs, 2H, NH$_2$), 7.27 (t, 1H, H$_{arom}$, J=1.8 Hz), 7.39 (t, 1H, H$_{arom}$, J=1.9 Hz), 7.68 (t, 1H, H$_{arom}$, J=7.9 Hz), 7.61 (m, 1H, H$_{arom}$), 7.89 (s, 1H, H$_{arom}$), 7.99 (m, 1H, H$_{arom}$, J=7.8 Hz), 8.05 (d, 1H, H$_{Py,6}$, J=5.6 Hz), 10.46 (bs, 1H, NH$_{amide}$). $^{13}$C-NMR ($\delta$, ppm, DMSO-d$_6$): 55.4, 101.1, 101.7, 103.2, 103.9, 120.1, 122.0, 124.1, 126.7, 128.2, 130.5, 136.6, 140.9, 148.2, 153.1, 153.7, 154.4, 158.2, 160.6, 163.9. LC-MS (m/z): 465 (M+H, 100).

Synthesis 115

N-(5-(2-amino-3-nitropyridin-4-yloxy)-2-methylphenyl)-3-(trifluoromethoxy)benzamide

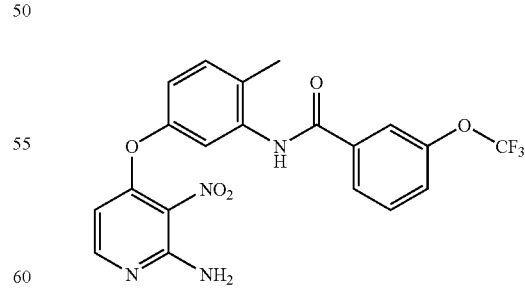

Method H was used with 4-(3-amino-4-methylphenoxy)-3-nitropyridin-2-amine (500 mg, 1.9 mmol), to afford the title compound as a dark solid (781 mg, 92%). $^1$H-NMR ($\delta$, ppm, DMSO-d$_6$): 2.27 (s, 3H, CH$_3$), 6.01 (d, 1H, H$_{Py,5}$, J=5.6 Hz), 7.04 (dd, 1H, H$_{arom}$, J=8.3 Hz and J=2.6 Hz), 7.16 (s, 2H, H$_{arom}$), 7.28 (d, 1H, H$_{arom}$, J=2.4 Hz), 7.38 (d, 1H, H$_{arom}$, J=8.4 Hz), 7.62 (m, 2H, H$_{arom}$), 7.68 (m, 1H, H$_{arom}$), 7.91 (s, 1H, H$_{arom}$), 8.02 (d, 1H, H$_{arom}$, J=5.7 Hz), 10.12 (s, 1H, NH$_{amide}$). $^{13}$C-NMR (δ, ppm, DMSO-d$_6$): 17.2, 100.5, 117.8, 118.0, 120.0, 120.9, 121.8, 124.0, 126.7, 128.1, 130.6, 131.6, 136.4, 137.3, 148.2, 150.9, 153.0, 153.7, 158.6, 163.7. LC-MS (m/z): 449 (M, 100).

Synthesis 116

N-(5-(2-Amino-3-nitropyridin-4-yloxy)-2,4-difluorophenyl)-3-(trifluoromethoxy)benzamide

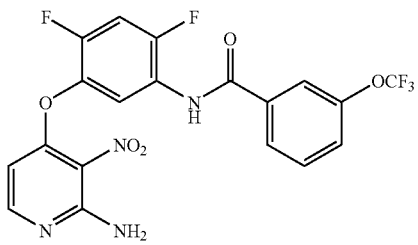

Method H was used with 4-(5-amino-2,4-difluorophenoxy)-3-nitropyridin-2-amine and 3-(trifluoromethoxy)benzoyl chloride to afford the title compound as a yellow solid (0.33 g, 88%). $^1$H NMR δ (DMSO): 6.09 (d, 1H, H$_{py,5}$, J=5.5 Hz), 7.26 (bs, 2H, NH$_2$), 7.7 (m, 3H, H$_{arom}$), 7.90 (s, 1H, H$_{arom,2'}$), 8.0 (d, 1H, H$_{arom}$), 8.06 (d, 1H, H$_{py,6}$, J=5.5 Hz), 10.4 (bs, 1H, NH$_{amide}$). $^{19}$F NMR δ (DMSO): −56.78 (s, 1F, CF$_3$), −118.54 (s, 1F, aromF), −129.58 (s, 1F, aromF).

Synthesis 117

N-(5-(2-Amino-3-nitropyridin-4-yloxy)-2,3,4-trifluorophenyl)-3-(trifluoromethoxy)benzamide

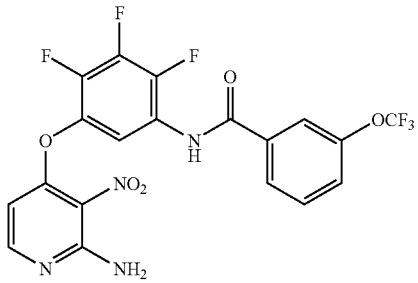

Method H was used with 4-(5-amino-2,3,4-trifluorophenoxy)-3-nitropyridin-2-amine and 3-(trifluoromethoxy)benzoyl chloride to afford the title compound (140 mg, 57%). $^1$H NMR δ (DMSO): 6.26 (d, 1H, H$_{py,5}$, J=5.5 Hz), 7.35 (s, 2H, NH$_2$), 7.55 (t, 1H, H$_{arom,6'}$, J=6.5 Hz), 7.66 (d, 1H, H$_{arom}$), 7.71 (t, 1H, H$_{arom,5'''}$, J=8.0 Hz), 7.91 (s, 1H, H$_{arom,2''}$), 8.00 (d, 1H, H$_{arom}$), 8.08 (d, 1H, H$_{Py,6}$, J=5.5 Hz), 10.63 (s, 1H, NH$_{amide}$). $^{19}$F NMR δ (DMSO): −56.28 (s, 3F, CF$_3$), −141.42 (d, 1F, aromF, J=21.5 Hz), −152.31 (d, 1F, aromF, J=21.5 Hz), −156.04 (t, 1F, F3, J=21.5 Hz).

Synthesis 118

N-(5-(2-Amino-3-nitropyridin-4-yloxy)-2-chlorophenyl)-3-(trifluoromethoxy)benzamide

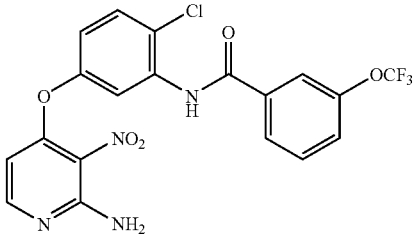

Method H was used with 4-(3-amino-4-chlorophenoxy)-3-nitropyridin-2-amine and 3-(trifluoromethoxy)benzoyl chloride to afford the title compound as a yellow solid (0.153 g, 33%). $^1$H NMR δ (DMSO): 6.11 (d, 1H, H$_{py,5}$, J=5.5 Hz), 7.18 (dd, 1H, H$_{arom,5}$, J=3+9 Hz), 7.23 (s, 2H, NH$_2$), 7.53 (d, 1H, H$_{arom,2}$, J=3 Hz), 7.63 (dt, 1H, H$_{arom}$, J=1+8 Hz), 7.66 (d, 1H, H$_{arom,6}$, J=9 Hz), 7.70 (t, 1H, H$_{arom,5}$, J=8 Hz), 7.91 (s, 1H, H$_{arom,2'}$), 8.02 (dt, 1H, H$_{arom}$, J=1+8 Hz), 8.07 (d, 1H, H$_{py,6}$, J=5.5 Hz), 10.63 (s, 1H, NH$_{amide}$). $^{19}$F NMR δ (DMSO): −56.37 (s, 3F, CF$_3$).

Synthesis 119

N-(3-(2-Amino-3-nitropyridin-4-yloxy)-5-chlorophenyl)-3-(trifluoromethoxy)benzamide

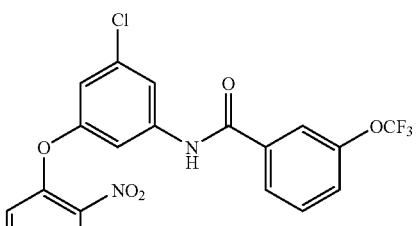

Method H was used with 4-(3-Amino-5-chlorophenoxy)-3-nitropyridin-2-amine and 3-(trifluoromethoxy)benzoyl chloride to afford the title compound as a yellow solid (0.155 g, 74%). $^1$H NMR δ (DMSO): 6.21 (d, 1H, H$_{py,5}$, J=5.5 Hz), 7.13 (t, 1H, H$_{arom}$, J=2 Hz), 7.25 (s, 2H, NH$_2$), 7.58 (t, 1H, H$_{arom}$, J=2 Hz), 7.63 (dt, 1H, H$_{arom}$, J=1+8 Hz), 7.70 (t, 1H, H$_{arom,5}$, J=8 Hz), 7.86 (d, 1H, H$_{arom}$, J=2 Hz), 7.89 (s, 1H, H$_{arom,2'}$), 8.02 (dt, 1H, H$_{arom}$, J=1+8 Hz), 8.09 (d, 1H, H$_{py,6}$, J=5.5 Hz), 10.6 (s, 1H, NH$_{amide}$). $^{19}$F NMR δ (DMSO): −56.77 (s, 3F, CF$_3$). MS m/z 469/71(M$^+$+1).

(XV) Synthesis of Sulfonamides from Pyridoimidazolone Intermediates (According to Scheme 3)

Synthesis 120

4-Chloro-N-(3-(2-oxo-2,3-dihydro-1H-imidazo[4,5-b]pyridin-7-yloxy)phenyl)-3-(trifluoromethyl)benzenesulfonamide (CJS 3684)

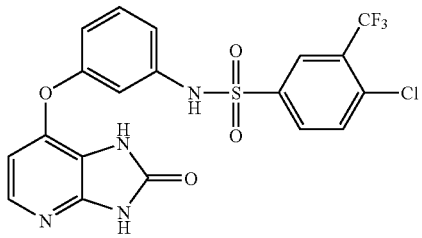

Method K: 7-(3-Aminophenoxy)-1H-imidazo[4,5-b]pyridin-2(3H)-one (30 mg, 0.13 mmol) was suspended in dry pyridine (3 mL) and 4-chloro-3-(trifluoromethyl)-benzene-1-sulfonyl chloride (44.4 mg, 0.16 mmol) in pyridine (2 mL) was added. The resulting solution was stirred at room temperature for 20 h and subsequently the solvent was removed in vacuo. The obtained residue was dissolved in acetone (4 mL) and upon addition of water a solid precipitated. This solid was collected, washed with water (2×2 mL) and Et$_2$O (2×2 mL) and dried to afford the title compound as an off-white solid (38 mg, 60%). $^1$H-NMR (δ, ppm, DMSO-d$_6$): 6.23 (d, 1H, H$_{Py,5}$, J=5.78 Hz), 6.76-6.98 (m, 3H, H$_{arom}$), 7.35 (m, 1H, H$_{arom}$), 7.73 (m, 1H, H$_{arom}$), 7.94-7.96 (m, 2H, H$_{arom}$), 8.05 (d, 1H, H$_{Py,6}$, J=5.78 Hz) 10.62 (s, 1H, NHSO$_2$), 11.13 (s, 1H, NH$_{Py3}$), 11.40 (s, 1H, NH$_{Py2}$). $^{13}$C-NMR (δ, ppm, DMSO-d$_6$): 106.31, 111.11, 113.80, 115.61, 116.73, 121.97, 125.78, 131.10, 132.18, 132.33, 133.22, 135.76, 138.47, 138.57, 141.13, 144.01, 147.23, 154.15, 155.11. HRMS (EI): m/z [M+H] calcd for C$_{19}$H$_{13}$ClF$_3$N$_4$O$_4$S: 485.0298; found: 485.0297.

Synthesis 121

N-(3-(2-oxo-2,3-dihydro-1H-imidazo[4,5-b]pyridin-7-yloxy)phenyl)-3-(trifluoromethoxy)benzenesulfonamide (CJS 3691)

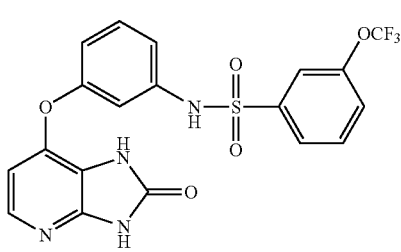

Method K was used with 7-(3-aminophenoxy)-1H-imidazo[4,5-b]pyridin-2(3H)-one and 3-(trifluoromethoxy)benzenesulfonyl chloride to afford the title compound as an off-white solid (51 mg, 84%). $^1$H-NMR (δ, ppm, DMSO-d$_6$): 6.20 (br s, 1H, H$_{Py,5}$), 6.78 (s, 1H, H$_{arom}$), 6.86 (d, 1H, H$_{arom}$, J=7.5 Hz), 6.98 (d, 1H, H$_{arom}$, J=7.4 Hz), 7.31-7.35 (m, 1H, H$_{arom}$), 7.64-7.86 (m, 5H, H$_{arom}$), 10.57 (s, 1H, NHSO$_2$), 11.13 (s, 1H, NH$_{Py3}$), 11.39 (s, 1H, NH$_{Py2}$). $^{13}$C-NMR (δ, ppm, DMSO-d$_6$): 106.18, 110.92, 113.71, 115.35, 116.48, 118.88, 121.88, 125.77, 125.83, 130.96, 131.93, 138.77, 141.03, 141.15, 144.12, 147.19, 148.23, 154.15, 154.99. HRMS (EI): m/z [M+H] calcd for C$_{19}$H$_{14}$F$_3$N$_4$O$_5$S: 467.0637; found: 467.0644.

Synthesis 122

N-(3-(2-oxo-2,3-dihydro-1H-imidazo[4,5-b]pyridin-7-yloxy)phenyl)-3-(trifluoromethyl)benzenesulfonamide (CJS 3692)

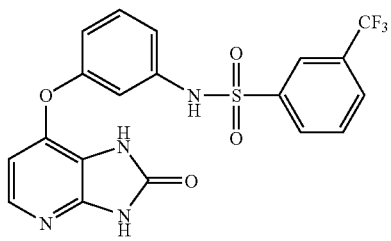

Method K was used with 7-(3-aminophenoxy)-1H-imidazo[4,5-b]pyridin-2(3H)-one and 3-(trifluoromethyl)benzenesulfonyl chloride to afford the title compound as an off-white solid (42 mg, 72%). $^1$H-NMR (δ, ppm, DMSO-d$_6$): 6.19 (d, 1H, H$_{Py,5}$, J=5.5 Hz), 6.78 (s, 1H, H$_{arom}$), 6.86 (d, 1H, H$_{arom}$, J=8.0 Hz), 6.98 (d, 1H, H$_{arom}$, J=7.5 Hz), 7.31-7.35 (m, 1H, H$_{arom}$), 7.74 (d, 1H, H$_{Py,6}$, J=5.5 Hz), 7.82-7.85 (m, 1H, H$_{arom}$), 7.96-8.06 (m, 4H, H$_{arom}$), 10.57 (s, 1H, NHSO$_2$), 11.13 (s, 1H, NH$_{Py3}$), 11.39 (s, 1H, NH$_{Py2}$). $^{13}$C-NMR (δ, ppm, DMSO-d$_6$): 106.21, 110.98, 113.74, 115.45, 116.59, 123.09, 123.24, 129.88, 130.68, 131.02, 131.08, 138.71, 138.72, 140.20, 141.16, 144.09, 147.21, 154.15, 155.04. HRMS (EI): m/z [M+H] calcd for C$_{19}$H$_{14}$F$_3$N$_4$O$_4$S: 451.0688; found: 451.0687.

Synthesis 123

N-(3-(2-oxo-2,3-dihydro-1H-imidazo[4,5-b]pyridin-7-yloxy)phenyl)benzenesulfonamide (CJS 3693)

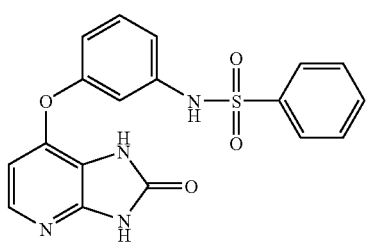

Method K was used with 7-(3-aminophenoxy)-1H-imidazo[4,5-b]pyridin-2(3H)-one and benzenesulfonyl chloride to afford the title compound as a brown solid (25 mg, 50%).

¹H-NMR (δ, ppm, DMSO-d₆): ): 6.21 (s, 1H, H$_{Py,5}$), 6.77 (s, 2H, H$_{arom}$), 6.95 (s, 1H, H$_{arom}$), 7.29 (s, 1H, H$_{arom}$), 7.53-7.86 (m, 6H, H$_{arom}$), 10.44 (s, 1H, NHSO₂), 11.12 (s, 1H, NH$_{Py3}$), 11.39 (s, 1H, NH$_{Py2}$). ¹³C-NMR (δ, ppm, DMSO-d₆): 106.39, 110.14, 113.74, 114.64, 115.83, 126.61, 129.33, 130.82, 133.09, 139.13, 139.36, 141.25, 144.12, 147.16, 154.15, 154.97. HRMS (EI): m/z [M+H] calcd for C₁₈H₁₅N₄O₄S: 383.0814; found: 383.0815.

Synthesis 124

N-(3-(2-oxo-2,3-dihydro-1H-imidazo[4,5-b]pyridin-7-yloxy)phenyl)naphthalene-1-sulfonamide (CJS 3694)

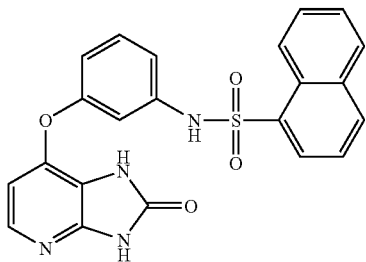

Method K was used with 7-(3-aminophenoxy)-1H-imidazo[4,5-b]pyridin-2(3H)-one and naphthalene-1-sulfonyl chloride to afford the title compound as a brown solid (32 mg, 57%). ¹H-NMR (δ, ppm, DMSO-d₆): 6.09 (d, 1H, H$_{Py,5}$, J=6.0 Hz), 6.68 (m, 2H, H$_{arom}$), 6.87 (d, 1H, H$_{arom}$, J=8.5 Hz), 7.20 (ps t, 1H, H$_{arom}$, J=8.0 Hz), 7.60 (ps t, 1H, H$_{arom}$, J=7.5 Hz), 7.65-7.73 (m, 3H, H$_{arom+Py,6}$), 8.08 (d, 1H, H$_{arom}$, J=8.0 Hz), 8.12 (d, 1H, H$_{arom}$, J=7.5 Hz), 8.23 (d, 1H, H$_{arom}$, J=8.5 Hz), 8.67 (d, 1H, H$_{arom}$, J=8.5 Hz), 10.83 (s, 1H, NHSO₂), 11.08 (s, 1H, NH$_{Py3}$), 11.39 (s, 1H, NH$_{Py2}$). ¹³C-NMR (δ, ppm, DMSO-d₆): 106.48, 108.98, 113.81, 114.02, 114.77, 124.06, 124.40, 127.03, 127.33, 128.21, 129.13, 129.97, 130.73, 133.74, 133.92, 134.60, 139.14, 141.21, 143.88, 147.15, 154.13, 155.01. HRMS (EI): m/z [M+H] calcd for C₂₂H₁₇N₄O₄S: 433.0971; found: 433.0969.

(XVI) Synthesis of Compounds with Reverse Amide Linker

Synthesis 125

Methyl 3-(2-amino-3-nitropyridin-4-yloxy)benzoate

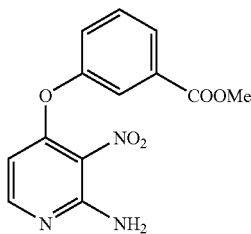

Method A was used with methyl 3-hydroxybenzoate to afford the title compound (760 mg, 53%). ¹H-NMR (DMSO), δ (ppm), J (Hz): 3.86 (s, 3H, Me), 6.04 (d, 1H, H$_{Pyr}$, J=6.0 Hz), 7.23 (s, 2H, NH₂), 7.52 (d, 1H, H$_{arom}$, J=8.0 Hz), 7.63-7.66 (m, 1H, H$_{arom}$), 7.88 (d, 1H, H$_{arom}$, J=8.0 Hz), 8.04 (d, 1H, H$_{Pyr}$); LC-MS m/z: 290 [M⁺+H], 100.

Synthesis 126

Methyl 3-(2,3-diaminopyridin-4-yloxy)benzoate

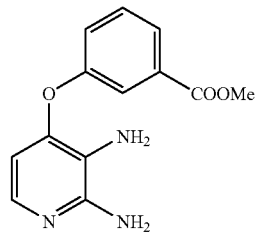

Method D was used with methyl 3-(2-amino-3-nitropyridin-4-yloxy)benzoate to afford the title compound (680 mg, 100%). ¹H-NMR (DMSO), δ (ppm), J (Hz): 3.83 (s, 3H, Me), 4.54 (s, 2H, NH₂), 5.68 (s, 2H, NH₂), 6.12 (d, 1H, H$_{Pyr}$, J=6.0 Hz), 7.27-7.32 (m, 1H, H$_{arom}$), 7.43 (d, 1H, H$_{arom}$, J=1.5 Hz), 7.52 (t, 1H, H$_{arom}$, J=8.0 Hz), 7.69 (d, 1H, H$_{Pyr}$); LC-MS m/z: 260 [M⁺+H], 100.

Synthesis 127

Methyl 3-(2-oxo-2,3-dihydro-1H-imidazo[4,5-b]pyridin-7-yloxy)benzoate

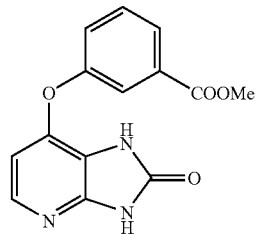

Method E was used with methyl 3-(2,3-diaminopyridin-4-yloxy)benzoate to afford the title compound (52 mg, 7%). ¹H-NMR (DMSO), δ (ppm), J (Hz): 3.85 (s, 3H, Me), 6.51 (d, 1H, H$_{Py,5}$, J=5.9 Hz), 7.42-7.46 (m, 1H, H$_{arom,Ph}$), 7.57-7.62 (m, 2H, H$_{arom,Ph}$), 7.81 (d, 2H, H$_{arom+Py,6}$), 11.19 (s, NH, NH$_{Py}$), 11.41 (s, NH, NH$_{Py}$). LC-MS m/z: 286 [M⁺+H], 100.

Synthesis 128

3-(2-Oxo-2,3-dihydro-1H-imidazo[4,5-b]pyridin-7-yloxy)-N-(3-(trifluoromethoxy)phenyl)benzamide (CJS 3256)

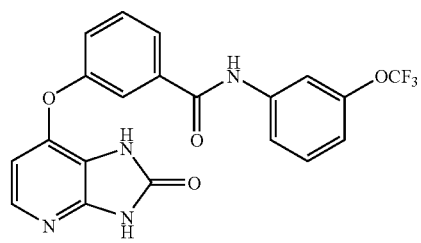

Method L: 3-(Trifluoromethoxy)aniline (40 μL, 0.3 mmol) was dissolved in dry THF, cooled at 0° C. and NaHMDS (0.3 mL, 1 M solution in THF, 0.3 mmol) was added. Methyl 3-(2-oxo-2,3-dihydro-1H-imidazo[4,5-b]pyridin-7-yloxy)benzoate (30 mg, 0.1 mmol) was added and the reaction mixture stirred at room temperature for 3 hours. The reaction was quenched with saturated NH$_4$Cl solution, and with 1M HCl. The solvents were evaporated, and the residue washed with water and with diethyl ether. The precipitate was collected by filtration, to afford the title compound as an off-white solid (7 mg, 16%). $^1$H-NMR (DMSO), δ (ppm), J (Hz): 6.49 (d, 1H, H$_{Py,5}$, J=5.9 Hz), 7.10 (d, 1H, Harom, J=7.0 Hz), 7.39 (d, 1H, H$_{arom,Ph}$, J=8.0 Hz), 7.48 (t, 1H, H$_{arom,Ph}$, J=8.0 Hz), 7.62 (t, 1H, H$_{arom,Ph}$, J=8.0 Hz), 7.74 (s, 1H, H$_{arom}$), 7.82 (d, 2H, H$_{arom+Py,6}$), 7.48 (d, 1H, H$_{arom,Ph}$, J=8.0 Hz), 7.91 (s, 1H, H$_{arom}$), 10.52 (s, 1H, NH$_{amide}$), 11.24 (s, NH, NH$_{Py}$), 11.44 (s, NH, NH$_{Py}$). LC-MS m/z: 431 [M$^+$+H], 100.

Synthesis 129

N-(3-tert-butyl-1-phenyl-1H-pyrazol-5-yl)-3-(2-oxo-2,3-dihydro-1H-imidazo[4,5-b]pyridin-7-yloxy)benzamide (CJS 3906)

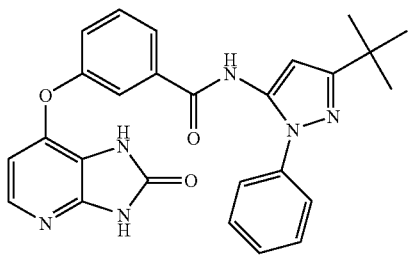

Method L2: A solution of AlMe$_3$ (solution in toluene 2M, 260 μL, 0.527 mmol,) was added dropwise to a cooled (0° C.) solution of 3-tert-butyl-1-phenyl-1H-pyrazol-5-amine (113 mg, 0.527 mmol) in THF (2.5 mL). When the addition was complete, the mixture was allowed to warm to room temperature and stirring was continued for 30 minutes. Then methyl 3-(2-oxo-2,3-dihydro-1H-imidazo[4,5-b]pyridin-7-yloxy)benzoate (100 mg, 0.351 mmol) was added and the mixture was heated under reflux for 19 hours. The mixture was cooled to room temperature and carefully quenched with 5% aq HCl (1 mL). After evaporation of solvent, the residue was retaken in CH$_2$Cl$_2$, washed with saturated solution of NaHCO$_3$ then with brine, dried over MgSO$_4$ and evaporated under vacuum. The obtained residue was chromatographied (eluent: EtOAc) and the title compound was obtained as a light yellow solid (54 mg, 33%). $^1$H-NMR (δ, ppm, DMSO-d$_6$): 1.30 (s, 9H, $^t$Bu), 6.39 (s, 1H, H$_{pyrrazole}$) 6.51 (d, 1H, H$_{Py,5}$, J=5.9 Hz), 7.31 (t, 1H, H$_{arom}$, J=7.4 Hz), 7.37 (dd, 1H, H$_{arom}$, J=8.0 Hz, J=2.3 Hz), 7.41-7.44 (m, 2H, H$_{arom}$), 7.49-7.51 (m, 2H, H$_{arom}$), 7.55-7.62 (m, 2H, H$_{arom}$), 7.71 (d, 1H, H$_{arom}$, J=8.1 Hz), 7.82 (d, 1H, H$_{Py,6}$, J=5.9 Hz), 10.34 (s, 1H, NH$_{amide}$), 11.18 (s, 1H, NH$_{urea}$), 11.42 (s, 1H, NH$_{urea}$). LC-MS (m/z): 469 (M+H).

Biological Methods—Kinase Assay No. 1

Compounds were assessed by a kinase assay performed according to the following protocol.
1. Prepare three stock solutions: AB Solution, Start Mix, and Dilution Buffer.

| AB solution: 1 ml | |
|---|---|
| Tris pH 7.5 (1M) | 50 μL |
| β-Mercaptoethanol | 3 μL |
| EDTA pH 8 (0.5M) | 2 μL |
| Triton (10%) | 10 μL |
| NaF (5 mM) | 30 μL |
| NaVO$_4$ (20 μM) | 25 μL |
| Bovine Serum Albumin (20 mg/ml) | 50 μL |
| *Myelin Basic Protein (30 mg/mL) | 60 μL |
| *MEK (5 mg/ml) | 5 μL |
| *ERK (7.5 mg/ml) | 37.5 μL |
| H$_2$O | 727.5 μL |

*= Added just prior to use

| Start mix: 300 μL | |
|---|---|
| ATP (100 mM) | 1.8 μL |
| MgCl$_2$ (1M) | 14.4 μL |
| H$_2$O | 281.8 μL |
| HOT $^{32}$Pα | 2 μL |

| Dilution buffer: 1 ml | |
|---|---|
| Tris pH 7.5 (1M) | 50 μL |
| EDTA pH 8 (0.5M) | 0.2 μL |
| NaCl (5M) | 20 μL |
| Triton (10%) | 10 μL |
| NaF (5 mM) | 10 μL |
| NaVO$_4$ (20 μM) | 10 μL |
| β-Mercaptoethanol | 3 μL |
| Bovine Serum Albumin (20 mg/mL) | 50 μL |
| H$_2$O | 847 μL |

2. Prepare the B-RAF dilutions:
B-RAF dilution (1)=Mix 7.5 μL $^{V600E}$B-RAF+30 μL dilution buffer. (This is a 1 in 5 dilution.)
B-RAF dilution (0.1)=Mix 20 μL $^{V600E}$B-RAF dilution (1)+1.80 μL dilution buffer. (This is a further 1 in 10 dilution, so the total B-RAF dilution is 50×.)
3. Mix 700 μL AB solution+175 μL B-RAF dilution (0.1). This solution is now referred to as AB0.1.
4. Add 24.5 μL AB0.1 solution into numbered tubes, as indicated below.
(Note: Each Reaction is Tested in Triplicate.)
5. Add 20 μL AB solution to the blowout and empty vector control tubes.
6. Add DMSO, H$_2$O etc. to the control tubes, as below
7. Add 0.5 μL of test compound of the desired concentration (diluted in DMSO) to the appropriate tubes, as below. (Note: stock test compound concentration is 100 mM.)

| Tube | AB0.1 | AB | Test Compound concentration | Controls | Amount of B-RAF per tube |
|---|---|---|---|---|---|
| 1 | 24.5 μL | — | 1000 μM | — | 0.1 μL |
| 2 | 24.5 μL | — | 100 μM | — | 0.1 μL |

-continued

| Tube | AB0.1 | AB | Test Compound concentration | Controls | Amount of B-RAF per tube |
|---|---|---|---|---|---|
| 3 | 24.5 μL | — | 10 μM | — | 0.1 μL |
| 4 | 24.5 μL | — | 1 μM | — | 0.1 μL |
| 5 | 24.5 μL | — | 0.1 μM | — | 0.1 μL |
| 6 | 24.5 μL | — | 0.01 μM | — | 0.1 μL |
| 7 | 24.5 μL | — | — | DMSO 0.5 μL | 0.1 μL |
| 8 | 24.5 μL | — | — | H$_2$O 0.5 μL | 0.1 μL |
| 9 (blowout) | — | 20 μL | — | B-raf dilution (1) 5 μL | 1 μL |
| 10 | — | 20 μL | — | Empty vector 5 μL | 0 μL |
| 11 (positive control) | 24.5 μL | — | — | PD (10 μM) 0.5 μL | 0.1 μL |

8. Incubate the tubes at 30° C. for 10 minutes.
9. Add 5 μL of start mix to each tube in 15-second intervals, gently spinning each tube after adding the start solution, and incubate at 30° C. for 10 minutes.
10. Stop the reaction by placing 20 μL of the reaction solution in the tube onto a small piece of P81 paper (pre-numbered), and drop this paper into 75 mM orthophosphoric acid. Repeat this every 15 seconds with each tube.
11. When all reactions have been stopped, replace the acid with fresh acid.
12. Do two more of these washes every 15 minutes.
13. Remove the paper from the acid and put into pre-numbered tubes.
14. Count the radiation levels using a Packard Cerenkov counter.

Biological Methods—Kinase Assay No. 2 (DELFIA)

Compounds were assessed by a kinase assay performed according to the following protocol.

The following reagents were prepared:
DELFIA Kinase Buffer (DKB):

| Reagent | Stock Concentration | Volume per mL (μL) | Volume per 10 mL plate (μL) |
|---|---|---|---|
| 20 mM MOPS pH 7.2 | 0.2 M | 100 | 1000 |
| 0.5 M EGTA pH 8.0 | 0.5 M | 10 | 100 |
| 10 mM MgCl$_2$ | 1 M | 10 | 100 |
| 0.1% β-mercaptoethanol | | 1 | 10 |
| 25 mM β-glycerophosphate | 0.5 M | 50 | 500 |
| Water | 100% | 829 | 8290 |

MOPS = 3-[N-Morpholino] propanesulfonic acid (Sigma M3183).
EGTA = Ethylene glycol-bis(2-aminoethylether)-N,N,N',N'-tetraacetic acid (Sigma E3889).

DKB1 (DKB with B-RAF and MEK protein):
Combine 4950 μL of DKB and 50 μL of 2.5 mg/ml GST-MEK stock (to give 1 mg of MEK per 40 μL). Then add 22.5 μL of B-RAF to give ~0.2 μL of B-RAF per 40 μL.

DKB2 (DKB with MEK protein):
Combine 4950 μL of DKB and 50 μL of 2.5 mg/ml GST-MEK stock (to give 1 mg of MEK per 40 μL). Use 500 μL of this for the blow out (BO) and the empty vector (EV) control.

ATP:
100 mM stock, dilute to 500 μM to give 100 μM final concentration in assay.

Inhibitors (Test Compounds):
100 mM stock, dilute to 10, 3, 1, 0.3, 0.1, 0.03, 0.01, 0.003, 0.001, 0.0003, 0.0001 mM in DMSO in drug plate, resulting in concentration of 100, 30, 10, 3, 1, 0.3, 0.1, 0.03, 0.01, 0.003, 0.001 μM in the assay.

Primary Antibody:
Phospho-MEK1/2 CST #9121S diluted 1:1000 in DELFIA assay buffer (AB). Preincubate antibody in the AB for 30 minutes at room temperature prior to use.

Secondary Antibody:
Anti-rabbit-Eur labelled secondary Perkin Elmer #AD0105 diluted 1:1000 in DELFIA assay buffer (AB). Preincubate antibody in the AB for 30 minutes at room temperature prior to use. (Primary and secondary antibodies were incubated together.)

Tween:
0.1% Tween 20 in water

Assay Buffer:
DELFIA assay buffer Perkin Elmer #4002-0010

Enhancement Solution:
DELFIA enhancement solution Perkin Elmer #4001-0010

Assay Plates:
96 well glutathione-coated black plate Perbio #15340

Procedure:
1. Preblock wells with 5% milk in TBS for 1 hour.
2. Wash wells with 3× with 200 μL TBS.
3. Plate out 40 μL of DKB1 for all inhibitors (test compounds), DMSO control, and optionally other control compounds.
4. Plate out 40 μL of DKB2 for BO and EV wells.
5. Add inhibitors (test compounds) at 0.5 μL per well according to desired plate layout.
6. Add 0.5 μL DMSO to vehicle control wells.
7. Add 2 μL of B-RAF to BO and EV wells.
8. Pre-incubate with inhibitors (test compounds) for 10 minutes at room temperature with shaking.
9. Add 10 μL of 500 μM ATP stock, in DKB, to give 100 μM assay concentration.
10. Seal plates with TopSeal and incubate at room temperature with shaking for 45 minutes.
11. Wash plates 3× with 200 μL 0.1% Tween20/Water to terminate reaction.
12. Add 50 μL per well of antibody mix and incubate for 1 hour at room temperature with shaking.
13. Wash plates 3× with 200 μL 0.1% Tween20/Water.
14. Add 100 μL DELFIA enhancement solution per well, cover in foil, and incubate at room temperature for 30 minutes with shaking.
15. Read on Victor using Europium protocol.

Biological Methods—Cell Based Assays

Compounds were assessed using cell-based assays which were performed according to the following protocol.

Day 0:
Plate out 16,000 cells/well in 99 μL medium in a 96-well plate.

Day 1:
1. Add 1 μL inhibitor to the cells (total 1 μL solution).
2. Incubate the cells with test compound for 6 hours at 37° C.
3. Aspirate off the solution from all of the wells.
4. Fixate the cells with 100 μL 4% formaldehyde/0.25% Triton X-100 PBS per well.
5. Incubate the plate for 1 hour at 4° C.
6. Aspirate off the fixing solution and add 300 μL TBS per well.
7. Leave the plate overnight at 4° C.

Day 2:
1. Wash the plate 2× with 200 μL PBS per well.
2. Block with 100 μL 5% dried milk in TBS.
3. Incubate the plate for 20 minutes at 37° C.
4. Wash the plate 2× with 0.1% tween/H$_2$O.
5. Add 50 μL of 3 μg/mL primary antibody ppERK (Sigma M8159), diluted in 5% milk powder/TBS, to each well.

6. Incubate the plate for 2 hours at 37° C.
7. Wash the plate 3× with 0.1% tween/$H_2O$.
8. Add 50 µL of 0.45 µg/mL secondary Europium-labelled anti-mouse antibody (Perkin Elmer) to each well.
9. Incubate the plate for 1 hour at 37° C.
10. Wash the plate 3× with 0.1% tween/$H_2O$.
11. Add 100 µL enhancement solution (Perkin Elmer) to each well.
12. Leave the plate for approximately 10 minutes at room temperature before gently shaking the plate.
13. Read Europium Time Resolved Fluorescence in Victor2.
14. Wash the plate 2× with 0.1% tween/$H_2O$.
15. Measure the protein concentration with BCA (Sigma) by adding 200 µL of solution per well.
16. Incubate the plate for 30 minutes at 37° C.
17. Read absorbance levels at 570 nm in a plate reader.
Note that Europium counts are normalised for protein levels by dividing counts by absorbance.

Biological Methods—Cell Proliferation Assay (SRB $IC_{50}$)

Cultures of WM266.4 melanoma cells are routinely cultured in DMEM/10% foetal bovine serum, at 37° C., in 5% $CO_2$ water saturated atmosphere. Cultures are maintained in exponential growth phase by sub-culturing before having become confluent (3-5 day intervals). Single cell suspensions are prepared by harvesting an 80 $cm^2$ tissue culture flask with 5 mL commercial trypsin EDTA. After 5 minutes, the detached cells are mixed with 5 mL fully complemented culture medium and centrifugally pelleted (1000 rpm for 7 minutes). After aspirating the supernatant, the cell pellet is re-suspended in 10 mL fresh medium and the cells fully disaggregated by drawing the whole volume up/down 5 times through a 19-gauge needle. The concentration of the cells is determined using a haemocytometer (1/10 dilution). A suitable volume to give at least a 2-fold excess for the number of tests being conducted, typically 100-200 mL, is prepared by diluting the cell suspension to 10,000/mL, and 100 µL/well dispensed into 96 well plates using a programmable 8-channel peristaltic pump, giving 1000 cells/well, leaving column 12 blank. The plates are returned to the incubator for 24 hours to allow the cells to re-attach. The compounds being tested are prepared at 20 mM in dimethylsulphoxide. Aliquots (200 µL) are diluted into 20 mL culture medium giving 200 µM, and 10 serial dilutions of 3× performed by transferring 5 mL to 10 mL. Aliquots (100 µL) of each dilution are added to the wells, using an 8-channel pipettor, thus performing a final further 2× dilution, and giving doses ranging from 100 µM to 0.005 µM. Column 11 receives plain culture medium only. Each compound is tested in quadruplicate, each replicate being the average of four wells, and two plates per compound. After a further 6 days growth, the plates are emptied, and the cells are fixed in 10% trichloroacteic acid for 10 minutes on ice. After thorough rinsing in running tap water, the plates are dried, and stained by adding 50 µL of a solution of 0.1% sulphorhodamine-B in 1% acetic acid, for 10 minutes at room temperature. The stain is poured out and the plates thoroughly rinsed under a stream of 1% acetic acid, thus removing unbound stain, and dried. The bound stain is taken into solution by addition of 150 µL Tris buffer pH 8, followed by 10 minutes on a plate-shaker (approximately 500 rpm). The absorbance at 540 nm in each well (being proportional to the number of cells present) is determined using a plate reader. After averaging the results in rows A-D and E-H, the blank value (row 12) is subtracted, and results expressed as percentage of the untreated value (row 11). The 10 values so derived (in quadruplicate) are plotted against the logarithm of the drug concentration, and analysed by non-linear regression to a four parameter logistic equation, setting constraints if suggested by inspection. The $IC_{50}$ generated by this procedure is the concentration of the drug that produces a percentage control $A_{540}$ midway between the saturation, and zero-effect plateaus.

Biological Methods—BRAF High Throughput Screen $^{V600E}$BRAF was used in a cascade assay that included MEK1, ERK2 and Elk. Phosphorylation through this cascade was measured using a specific phospho-Elk antibody and a Europium-labelled anti-mouse IgG secondary antibody in a DELFIA ELISA assay.

High-binding 384-well clear polystyrene plates (Greiner 00360148) were coated overnight (4° C.) with 25 µL Elk (2.5 µg/mL in PBS).

The plates were washed three times with PBS and the wells blocked with 5% milk (Marvel) in PBS. After 30 minutes at room temperature, the plates were again washed three times with PBS.

$^{V600E}$BRAF lysate, MEK1 and ERK2 were pre-mixed in BRAF buffer (Tris 50 mM, pH 7.5, containing 10 mM $MgCl_2$, 100 µM EGTA, 0.1% mercaptoethanol, 5 mM sodium fluoride, 200 µM sodium orthovanadate and 0.5 mg/ml BSA) so that the equivalent of 0.05 µL BRAF, 81.25 ng MEK1 and 1 µg ERK2 were added to each well in a total volume of 17 µL. Inhibitors (200 µM) or DMSO control (2%) 3 µL were added to the plates prior to enzyme mix. The enzyme reaction was started by the addition of 5 µL ATP solution (125 µM in BRAF buffer) (final concentration 25 µM) and the reaction stopped by washing the plates three times in 0.1% Tween/water. Anti-phospho Elk (Ser 383 monoclonal antibody) (Cell Signalling Technology #9186) diluted 1/4000 and Eu-labelled anti-mouse IgG (Perkin Elmer Life Sciences, AD0124) diluted to 1/50, were pre-mixed (30 minutes at room temperature) in DELFIA assay buffer (Perkin Elmer Life Sciences 4002-0010) and 25 µL added to each well. After 1.5 hours, the plates were washed again (3×) in 0.1% Tween/water.

35 µL of Enhancement solution (Perkin Elmer Life Sciences 4001-0010) was then added and after 20 minutes at room temperature, the plates were read on a Victor2 at 615 nm (excitation 340 nm in time resolved fluorescence mode). Percent inhibition was calculated in relation to DMSO only controls. Staurosporin was used as a positive control.

In a high throughput screen (HTS) context, hits were identified as compounds that inhibited the enzyme cascade by more than 3 standard deviations of the mean of the compound wells (n=320) on each plate.

Biological Data

Biological data were obtained (using one or more of: BRAF V600E Kinase Assay; Phospho-ERK Cell-based Assay; Cell proliferation (SRB) assay) for the following compounds:

| No. | ID No. |
|---|---|
| 1 | CJS3256 |
| 2 | CJS 3440 |
| 3 | CJS 3441 |
| 4 | CJS3442 |
| 5 | CJS3443 |
| 6 | CJS 3513 |
| 7 | CJS 3517 |
| 8 | CJS 3518 |
| 9 | CJS 3521 |
| 10 | CJS 3522 |
| 11 | CJS 3523 |
| 12 | CJS 3524 |
| 13 | CJS 3525 |
| 14 | CJS 3526 |

-continued

| No. | ID No. |
|---|---|
| 15 | CJS 3678 |
| 16 | CJS 3683 |
| 17 | CJS 3684 |
| 18 | CJS 3685 |
| 19 | CJS 3686 |
| 20 | CJS 3687 |
| 21 | CJS 3688 |
| 22 | CJS 3689 |
| 23 | CJS 3690 |
| 24 | CJS 3691 |
| 25 | CJS 3692 |
| 26 | CJS 3693 |
| 27 | CJS 3695 |
| 28 | CJS 3696 |
| 29 | CJS 3697 |
| 30 | CJS 3717 |
| 31 | CJS 3720 |
| 32 | CJS 3721 |
| 33 | CJS 3722 |
| 34 | CJS 3724 |
| 35 | CJS 3726 |
| 36 | CJS 3694 |
| 37 | CJS 3727 |
| 38 | CJS 3728 |
| 39 | CJS 3729 |
| 40 | CJS 3730 |
| 41 | CJS 3731 |
| 42 | CJS 3732 |
| 43 | CJS 3733 |
| 44 | CJS 3735 |
| 45 | CJS 3736 |
| 46 | CJS 3741 |
| 47 | CJS 3742 |
| 48 | CJS 3743 |
| 49 | CJS 3744 |
| 50 | CJS 3745 |
| 51 | CJS 3747 |
| 52 | CJS 3748 |
| 53 | CJS 3749 |
| 54 | CJS 3725 |
| 55 | CJS 3751 |
| 56 | CJS 3752 |
| 57 | CJS 3753 |
| 58 | CJS 3754 |
| 59 | CJS 3756 |
| 60 | CJS 3757 |
| 61 | CJS 3758 |
| 62 | CJS 3759 |
| 63 | CJS 3760 |
| 64 | CJS 3767 |
| 65 | CJS 3768 |
| 66 | CJS 3779 |
| 67 | CJS 3781 |
| 68 | CJS 3900 |
| 69 | CJS 3901 |
| 70 | CJS 3902 |
| 71 | CJS 3903 |
| 72 | CJS 3904 |
| 73 | CJS 3905 |
| 74 | CJS 3906 |

For CJS 3678, the BRAF V600E Kinase Assay IC50 value is 0.015 µM, the Phospho-ERK Cell-based Assay IC50 value is 10.7 µM, and the Cell proliferation (SRB) assay IC50 value is 4.2 µM.

For the BRAF V600E Kinase Assay, the IC50 (µM) values are as follows:
at least 2 compounds tested have an IC50 of less than 0.01 µM;
at least 24 of the compounds tested have an IC50 of less than 0.1 µM;
at least 40 of the compounds tested have an IC50 of less than 1 µM.
at least 48 of the compounds tested have an IC50 of less than 10 µM.

For the Phospho-ERK Cell-based Assay, the IC50 (µM) values are as follows:
at least 6 of the compounds tested have an IC50 of less than 5 µM;
at least 13 of the compounds tested have an IC50 of less than 10 µM;
at least 38 of the compounds tested have an IC50 of less than 30 µM;
at least 45 of the compounds tested have an IC50 of less than 50 µM.

For the Cell proliferation (SRB) assay, the IC50 (µM) values are as follows:
at least 8 of the compounds tested have an IC50 of less than 1 µM;
at least 50 of the compounds tested have an IC50 of less than 10 µM;
at least 70 of the compounds tested have an IC50 of less than 50 µM.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. A compound selected from compounds of the following formula and pharmaceutically acceptable salts thereof:

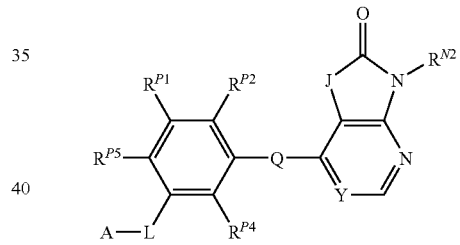

wherein:
J is independently —NR$^{N1}$—;
R$^{N1}$ is independently —H, aliphatic saturated C$_{1-3}$alkyl, or aliphatic C$_{2-3}$alkenyl;
R$^{N2}$ is independently —H, aliphatic saturated C$_{1-3}$alkyl, or aliphatic C$_{2-3}$alkenyl;
Y is independently —CH═;
Q is independently —O—;
each of R$^{P1}$, R$^{P2}$, R$^{P5}$, and R$^{P4}$ is independently —H, -Me, —CF$_3$, —OH, —OMe, —F, or —Cl;
the group A-L- is independently:
A-NR$^N$—C(═O)—NR$^N$—;
A-CH$_2$—NR$^N$—C(═O)—NR$^N$—;
A-NR$^N$—C(═O)—NR$^N$—CH$_2$—;
A-NR$^N$—C(═O)—;
A-CH$_2$—NR$^N$—C(═O)—;
A-NR$^N$—C(═O)—CH$_2$—;
A-CH$_2$—NR$^N$—C(═O)—CH$_2$—;
A-CH$_2$—CH$_2$—NR$^N$—C(═O)—;
A-NR$^N$—C(═O)—CH$_2$—CH$_2$—;
A-NR$^N$—C(═O)—CH$_2$—NR$^N$—;
A-NR$^N$—CH$_2$—NR$^N$—C(═O)—;
A-C(═O)—NR$^N$—;
A-CH$_2$—C(═O)—NR$^N$—;

A-C(=O)—NR$^N$—CH$_2$—;
A-CH$_2$—C(=O)—NR$^N$—CH$_2$—;
A-CH$_2$—CH$_2$—C(=O)—NR$^N$—;
A-C(=O)—NR$^N$—CH$_2$—CH$_2$—;
A-NR$^N$—CH$_2$—C(=O)—NR$^N$—;
A-C(=O)—NR$^N$—CH$_2$—NR$^N$—;
A-C(=O)—CH$_2$—NR$^N$—;
A-C(=O)—CH$_2$—NR$^N$—CH$_2$—;
A-C(=O)—CH$_2$—CH$_2$—NR$^N$—;
A-CH$_2$—C(=O)—CH$_2$—NR$^N$—;
A-NR$^N$—CH$_2$—C(=O)—;
A-NR$^N$—CH$_2$—C(=O)—CH$_2$—;
A-NR$^N$—CH$_2$—CH$_2$—C(=O)—; or
A-CH$_2$—NR$^N$—CH$_2$—C(=O)—;
each R$^N$ is independently —H, saturated aliphatic C$_{1-3}$alkyl, or aliphatic C$_{2-3}$alkenyl;
A is independently C$_{5-14}$heteroaryl, and is independently unsubstituted or substituted with one or more groups selected from: —C(=O)OH, —C(=O)OMe, —C(=O)OEt, —C(=O)O(iPr), —C(=O)O(tBu), —C(=O)O(cPr), —C(=O)OCH$_2$CH$_2$OH, —C(=O)OCH$_2$CH$_2$OMe, —C(=O)OCH$_2$CH$_2$OEt, —C(=O)OPh, —C(=O)OCH$_2$Ph, —(C=O)NH$_2$, —(C=O)NMe$_2$, —(C=O)NEt$_2$, —(C=O)N(iPr)$_2$, —(C=O)N(CH$_2$CH$_2$OH)$_2$, —(C=O)-morpholino, —(C=O)NHPh, —(C=O)NHCH$_2$Ph, —C(=O)H, —(C=O)Me, —(C=O)Et, —(C=O)(tBu), —(C=O)-cHex, —(C=O)Ph, —(C=O)CH$_2$Ph, —F, —Cl, —Br, —I, —CN, —NO$_2$, —OH, —OMe, —OEt, —O(iPr), —O(tBu), —OPh, —OCH$_2$Ph, —OCF$_3$, —OCH$_2$CF$_3$, —OCH$_2$CH$_2$OH, —OCH$_2$CH$_2$OMe, —OCH$_2$CH$_2$OEt, —OCH$_2$CH$_2$NH$_2$, —OCH$_2$CH$_2$NMe$_2$, —OCH$_2$CH$_2$N(iPr)$_2$, —OPh-Me, —OPh-OH, —OPh-OMe, —OPh-F, —OPh-Cl, —OPh-Br, —OPh-I, —SH, —SMe, —SEt, —SPh, —SCH$_2$Ph, —OC(=O)Me, —OC(=O)Et, —OC(=O)(iPr), —OC(=O)(tBu), —OC(=O)(cPr), —OC(=O)CH$_2$CH$_2$OH, —OC(=O)CH$_2$CH$_2$OMe, —OC(=O)CH$_2$CH$_2$OEt, —OC(=O)Ph, —OC(=O)CH$_2$Ph, —OC(=O)NH$_2$, —OC(=O)NHMe, —OC(=O)NMe$_2$, —OC(=O)NHEt, —OC(=O)NEt$_2$, —OC(=O)NHPh, —OC(=O)NCH$_2$Ph, —NH$_2$, —NHMe, —NHEt, —NH(iPr), —NMe$_2$, —NEt$_2$, —N(iPr)$_2$, —N(CH$_2$CH$_2$OH)$_2$, —NHPh, —NHCH$_2$Ph, piperidino, piperazino, morpholino, —NH(C=O)Me, —NHC(=O)Et, —NHC(=O)nPr, —NHC(=O)Ph, —NHC(=O)CH$_2$Ph, —NMe(C=O)Me, —NMe(C=O)Et, —NMe(C=O)Ph, —NMeC(=O)CH$_2$Ph, —NH(C=O)NH$_2$, —NH(C=O)NHMe, —NH(C=O)NHEt, —NH(C=O)NPh, —NH(C=O)NHCH$_2$Ph, —NH(C=S)NH$_2$, —NH(C=S)NHMe, —NH(C=S)NHEt, —NH(C=S)NPh, —NH(C=S)NHCH$_2$Ph, —NHSO$_2$Me, —NHSO$_2$Et, —NHSO$_2$Ph, —NHSO$_2$PhMe, —NHSO$_2$CH$_2$Ph, —NMeSO$_2$Me, —NMeSO$_2$Et, —NMeSO$_2$Ph, —NMeSO$_2$PhMe, —NMeSO$_2$CH$_2$Ph, —SO$_2$Me, —SO$_2$CF$_3$, —SO$_2$Et, —OSO$_2$Ph, —SO$_2$PhMe, —SO$_2$CH$_2$Ph, —OSO$_2$Me, —OSO$_2$CF$_3$, —OSO$_2$Et, —OSO$_2$Ph, —OSO$_2$PhMe, —OSO$_2$CH$_2$Ph, —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph, —CH$_2$Ph, —CH$_2$Ph-Me, —CH$_2$Ph-OH, —CH$_2$Ph-F, —CH$_2$Ph-Cl, -Ph, -Ph-Me, -Ph-OH, -Ph-OMe, -Ph-NH$_2$, -Ph-F, -Ph-Cl, -Ph-Br, -Ph-I, pyridyl, pyrazinyl, pyrimidinyl, pyridazinyl, furanyl, thiophenyl, pyrrolyl, imidazolyl, pyrazolyl, oxazolyl, thiazolyl, thiadiazolyl, pyrrolidinyl, imidazolidinyl, pyrazolidinyl, piperidinyl, piperazinyl, azepinyl, tetrahydrofuranyl, tetrahydropyranyl, morpholinyl, azetidinyl, -Me, -Et, -nPr, -iPr, -nBu, -iBu, -sBu, -tBu, -nPe, -cPr, -cHex, —CH=CH$_2$, —CH$_2$—CH=CH$_2$, —CF$_3$, —CHF$_2$, —CH$_2$F, —CCl$_3$, —CBr$_3$, —CH$_2$CH$_2$F, —CH$_2$CHF$_2$, —CH$_2$CF$_3$, —CH$_2$OH, —CH$_2$OMe, —CH$_2$OEt, —CH$_2$NH$_2$, —CH$_2$NMe$_2$, —CH$_2$CH$_2$OH, —CH$_2$CH$_2$OMe, —CH$_2$CH$_2$OEt, —CH$_2$CH$_2$CH$_2$NH$_2$, and —CH$_2$CH$_2$NMe$_2$.

2. A compound according to claim 1, wherein the group A-L- is independently A-NR$^N$—C(=O)—NR$^N$—, A-C(=O)—NR$^N$—, or A-NR$^N$—C(=O)—.

3. A compound according to claim 1, wherein each of the groups R$^N$ is independently —H or -Me.

4. A compound according to claim 2, wherein each of the groups R$^N$ is independently —H or -Me.

5. A compound according to claim 1, wherein the group A-L- is independently A-NH—C(=O)—NH—, A-C(=O)—NH—, or A-NH—C(=O)—.

6. A compound according to claim 1, wherein the group A-L- is independently A-NH—C(=O)—NH—.

7. A compound according to claim 1, wherein the group A-L- is independently A-C(=O)—NH—.

8. A compound according to claim 1, wherein the group A-L- is independently A-NH—C(=O)—.

9. A compound according to claim 1, wherein R$^{N1}$ is independently —H or -Me; and R$^{N2}$ is independently —H or -Me.

10. A compound according to claim 1, wherein R$^{N1}$ is independently —H; and R$^{N2}$ is independently —H.

11. A compound according to claim 5, wherein R$^{N1}$ is independently —H or -Me; and R$^{N2}$ is independently —H or -Me.

12. A compound according to claim 5, wherein R$^{N1}$ is independently —H; and R$^{N2}$ is independently —H.

13. A compound according to claim 1, wherein each of R$^{P1}$, R$^{P2}$, R$^{P5}$, and R$^{P4}$ is independently —H, -Me, —CF$_3$, —F, or —Cl.

14. A compound according to claim 5, wherein each of R$^{P1}$, R$^{P2}$, R$^{P5}$, and R$^{P4}$ is independently —H, -Me, —CF$_3$, —F, or —Cl.

15. A compound according to claim 11, wherein each of R$^{P1}$, R$^{P2}$, R$^{P5}$, and R$^{P4}$ is independently —H, -Me, —CF$_3$, —F, or —Cl.

16. A compound according to claim 12, wherein each of R$^{P1}$, R$^{P2}$, R$^{P5}$, and R$^{P4}$ is independently —H, -Me, —CF$_3$, —F, or —Cl.

17. A compound according to claim 1, wherein each of R$^{P1}$, R$^{P2}$, R$^{P5}$, and R$^{P4}$ is independently —H.

18. A compound according to claim 5, wherein each of R$^{P1}$, R$^{P2}$, R$^{P5}$, and R$^{P4}$ is independently —H.

19. A compound according to claim 11, wherein each of R$^{P1}$, R$^{P2}$, R$^{P5}$, and R$^{P4}$ is independently —H.

20. A compound according to claim 12, wherein each of R$^{P1}$, R$^{P2}$, R$^{P5}$, and R$^{P4}$ is independently —H.

21. A compound according to claim 1, wherein A is independently monocyclic C$_{5-6}$heteroaryl, and is independently unsubstituted or substituted.

22. A compound according to claim 1, wherein A is independently: pyrrolyl, pyridinyl, furanyl, thienyl, benzothienyl, oxazolyl, isoxazolyl, thiadiazolyl, benzothiadiazolyl, oxadiazolyl, thiazolyl, isothiazolyl, imidazolyl, pyrazolyl, pyridazinyl, pyrimidinyl, pyrazinyl, or tetrazolyl; and is independently unsubstituted or substituted.

23. A compound according to claim 1, wherein A is independently pyrazolyl, and is independently unsubstituted or substituted.

24. A compound according to claim 5, wherein A is independently pyrazolyl, and is independently unsubstituted or substituted.

25. A compound according to claim 11, wherein A is independently pyrazolyl, and is independently unsubstituted or substituted.

26. A compound according to claim 12, wherein A is independently pyrazolyl, and is independently unsubstituted or substituted.

27. A compound according to claim 15, wherein A is independently pyrazolyl, and is independently unsubstituted or substituted.

28. A compound according to claim 16, wherein A is independently pyrazolyl, and is independently unsubstituted or substituted.

29. A compound according to claim 19, wherein A is independently pyrazolyl, and is independently unsubstituted or substituted.

30. A compound according to claim 20, wherein A is independently pyrazolyl, and is independently unsubstituted or substituted.

31. A compound according to claim 1, wherein A is independently unsubstituted or substituted with one or more groups selected from: —C(=O)OH, —C(=O)OMe, —C(=O)OEt, —C(=O)O(iPr), —C(=O)O(tBu), —(C=O)NH$_2$, —(C=O)NMe$_2$, —(C=O)NEt$_2$, —(C=O)N(iPr)$_2$, —(C=O)-morpholino, —F, —Cl, —Br, —I, —CN, —NO$_2$, —OH, —OMe, —OEt, —O(iPr), —O(tBu), —OPh, —OCH$_2$Ph, —OCF$_3$, —OC(=O)Me, —OC(=O)Et, —OC(=O)(iPr), —OC(=O)(tBu), —NH$_2$, —NHMe, —NHEt, —NH(iPr), —NMe$_2$, —NEt$_2$, —N(iPr)$_2$, piperidino, piperazino, morpholino, —NH(C=O)Me, —NH(C=O)Et, —NH(C=O)nPr, —CH$_2$Ph, —CH$_2$Ph-Me, —CH$_2$Ph-OH, —CH$_2$Ph-F, —CH$_2$Ph-Cl, -Ph, -Ph-Me, -Ph-OH, -Ph-OMe, -Ph-NH$_2$, -Ph-F, -Ph-Cl, -Ph-Br, -Ph-I, -Me, -Et, -nPr, -iPr, -nBu, -iBu, -sBu, -tBu, -nPe, and —CF$_3$.

32. A compound according to claim 1, wherein A is:

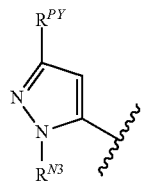

wherein:
R$^{PY}$ is independently saturated C$_{1-7}$alkyl; and
R$^{N3}$ is independently phenyl, and is independently unsubstituted or substituted with one or more groups selected from —F, —Cl, —Br, —I, —OMe, —OCF$_3$, -Me, and —CF$_3$.

33. A compound according to claim 15, wherein A is:

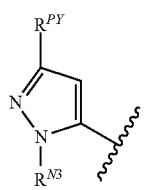

wherein:
R$^{PY}$ is independently saturated C$_{1-7}$alkyl; and
R$^{N3}$ is independently phenyl, and is independently unsubstituted or substituted with one or more groups selected from —F, —Cl, —Br, —I, —OMe, —OCF$_3$, -Me, and —CF$_3$.

34. A compound according to claim 19, wherein A is:

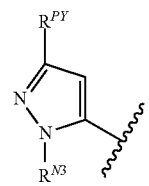

wherein:
R$^{PY}$ is independently saturated C$_{1-7}$alkyl; and
R$^{N3}$ is independently phenyl, and is independently unsubstituted or substituted with one or more groups selected from —F, —Cl, —Br, —I, —OMe, —OCF$_3$, -Me, and —CF$_3$.

35. A compound according to claim 1, wherein A is:

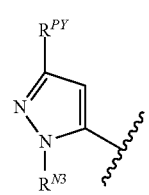

wherein:
R$^{PY}$ is independently -tBu; and
R$^{N3}$ is independently -Ph, -Ph-Me, -Ph-OH, -Ph-OMe, -Ph-NH$_2$, -Ph-F, -Ph-Cl, -Ph-Br, or -Ph-I.

36. A compound according to claim 15, wherein A is:

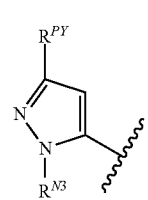

wherein:
R$^{PY}$ is independently -tBu; and
R$^{N3}$ is independently -Ph, -Ph-Me, -Ph-OH, -Ph-OMe, -Ph-NH$_2$, -Ph-F, -Ph-Cl, -Ph-Br, or -Ph-I.

37. A compound according to claim 19, wherein A is:

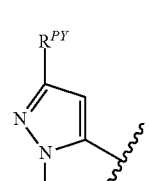

wherein:
R$^{PY}$ is independently -tBu; and
R$^{N3}$ is independently -Ph, -Ph-Me, -Ph-OH, -Ph-OMe, -Ph-NH$_2$, -Ph-F, -Ph-Cl, -Ph-Br, or -Ph-I.

38. A compound according to claim 1, wherein A is:

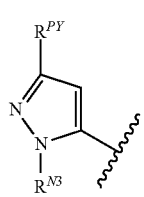

wherein:

R$^{PY}$ is independently -tBu; and

R$^{N3}$ is independently -Ph or -Ph-Me.

39. A compound according to claim 15, wherein A is:

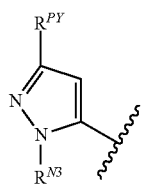

wherein:

R$^{PY}$ is independently -tBu; and

R$^{N3}$ is independently -Ph or -Ph-Me.

40. A compound according to claim 19, wherein A is:

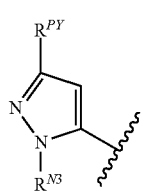

wherein:

R$^{PY}$ is independently -tBu; and

R$^{N3}$ is independently -Ph or -Ph-Me.

41. A compound of the following formula, or a pharmaceutically acceptable salt thereof:

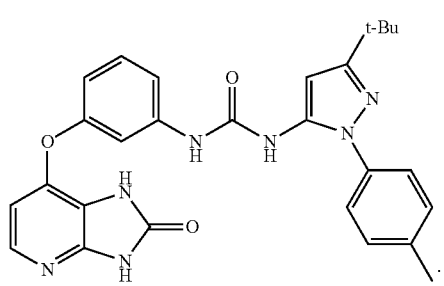

(CJS 3683)

42. A compound of the following formula, or a pharmaceutically acceptable salt thereof:

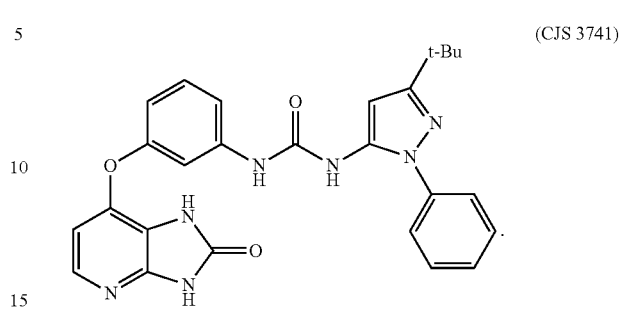

(CJS 3741)

43. A compound of the following formula, or a pharmaceutically acceptable salt thereof:

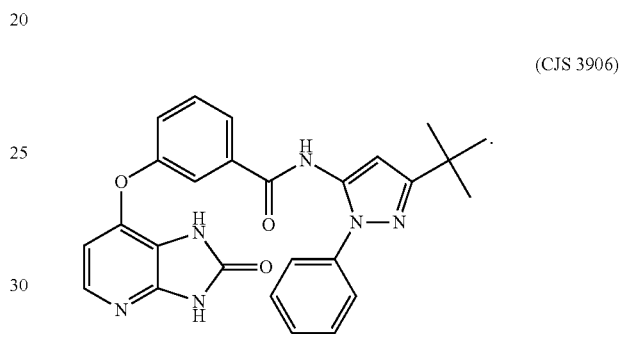

(CJS 3906)

44. A compound of one of the following formulae, or pharmaceutically acceptable salt thereof:

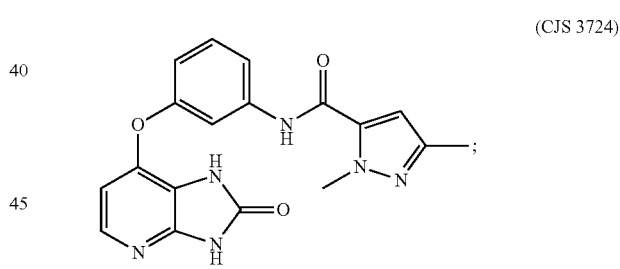

(CJS 3724)

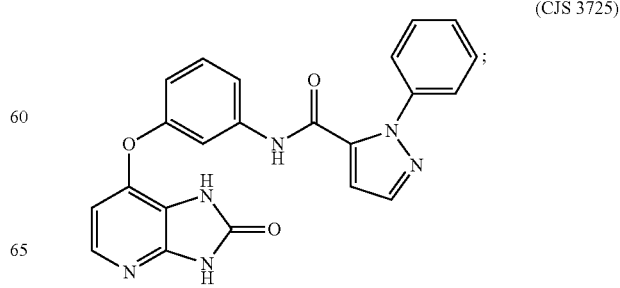

(CJS 3725)

-continued
(CJS 3726)
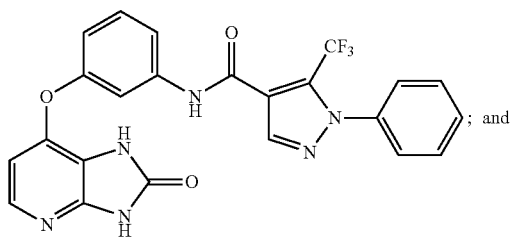
; and
(CJS 3727)
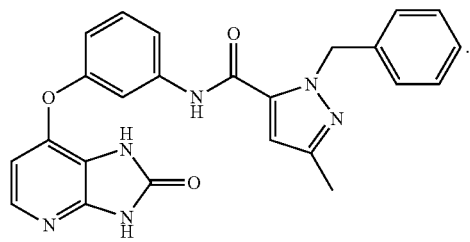
45. A compound of one of the following formulae, or pharmaceutically acceptable salt thereof:
(CJS 3742)
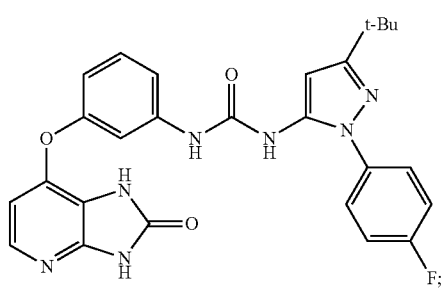
-continued
(CJS 3757)
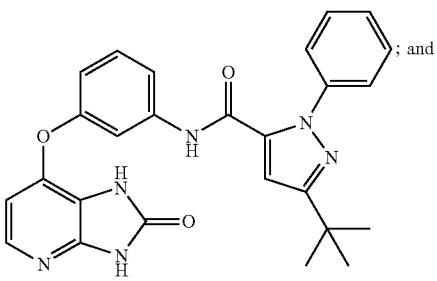
; and
(CJS 3758)
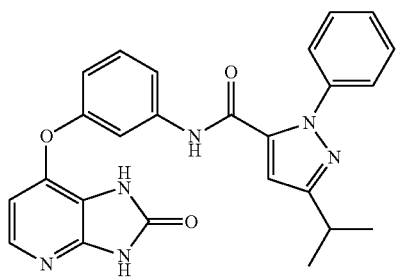
46. A composition comprising a compound according to claim 1, and a pharmaceutically acceptable carrier or diluent.
* * * * *